US012735427B2

(12) United States Patent
Dong et al.

(10) Patent No.: US 12,735,427 B2
(45) Date of Patent: Sep. 15, 2026

(54) SUGAR DERIVED LIPID NANOMATERIALS AND USES THEREOF

(71) Applicant: OHIO STATE INNOVATION FOUNDATION, Columbus, OH (US)

(72) Inventors: Yizhou Dong, Columbus, OH (US); Yuebao Zhang, Columbus, OH (US); Xucheng Hou, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 513 days.

(21) Appl. No.: 18/276,502

(22) PCT Filed: Feb. 11, 2022

(86) PCT No.: PCT/US2022/016137
§ 371 (c)(1),
(2) Date: Aug. 9, 2023

(87) PCT Pub. No.: WO2022/174048
PCT Pub. Date: Aug. 18, 2022

(65) Prior Publication Data

US 2024/0140960 A1 May 2, 2024

Related U.S. Application Data

(60) Provisional application No. 63/148,755, filed on Feb. 12, 2021.

(51) Int. Cl.
*C07D 493/04* (2006.01)
*A61K 47/69* (2017.01)
(Continued)

(52) U.S. Cl.
CPC ........ *C07D 493/04* (2013.01); *A61K 47/6901* (2017.08); *A61P 35/00* (2018.01); *C07K 14/70578* (2013.01)

(58) Field of Classification Search
CPC .. C07D 493/04; A61K 47/6901; A61K 40/19; A61K 40/24; A61K 40/30; A61K 9/5123; A61K 2239/31; A61K 2239/47; A61K 2239/57; A61K 2300/00; A61P 35/00; C07K 14/70578
(Continued)

(56) References Cited

U.S. PATENT DOCUMENTS

| | | | |
|---|---|---|---|
| 4,342,566 | A | 8/1982 | Theofilopoulos et al. |
| 5,674,894 | A | 10/1997 | Currie et al. |

(Continued)

FOREIGN PATENT DOCUMENTS

| | | | |
|---|---|---|---|
| CN | 1189833 | A | 8/1998 |
| CN | 102099367 | A | 6/2011 |

(Continued)

OTHER PUBLICATIONS

International Search Report and Written Opinion in Application No. PCT/US2022/016137, mailed May 4, 2022, 7 pages.

(Continued)

*Primary Examiner* — Taylor V Oh
(74) *Attorney, Agent, or Firm* — Meunier Carlin & Curfman LLC

(57) ABSTRACT

The present disclosure relates to compositions and methods for treating cancers, immune disorders, and other preventive and therapeutic applications.

9 Claims, 74 Drawing Sheets

L-Sorbitol
1
L-Isosorbide
2
3
4
5

(51) Int. Cl.
*A61P 35/00* (2006.01)
*C07K 14/705* (2006.01)

(58) Field of Classification Search
USPC .......................................................... 514/468
See application file for complete search history.

(56) References Cited

U.S. PATENT DOCUMENTS

| | | | |
|---|---|---|---|
| 5,804,440 | A | 9/1998 | Burton et al. |
| 6,096,441 | A | 8/2000 | Hauser et al. |
| 10,392,471 | B2 | 8/2019 | Zenner et al. |
| 2017/0044178 | A1 | 2/2017 | Zenner et al. |
| 2018/0148524 | A1 | 5/2018 | Chen et al. |
| 2018/0298023 | A1 | 10/2018 | Zenner et al. |
| 2019/0314291 | A1 | 10/2019 | Besin et al. |

FOREIGN PATENT DOCUMENTS

| | | | |
|---|---|---|---|
| CN | 103130815 | A | 6/2013 |
| JP | H11505246 | A | 5/1999 |
| JP | 2010525038 | A | 7/2010 |
| JP | 2012508264 | A | 4/2012 |
| WO | 94/29348 | | 12/1994 |

OTHER PUBLICATIONS

Communication under Rule 71(3) EPC for European Application No. 22753419.5, dated Nov. 7, 2025, 8 Pages.
Notice of Reasons for Rejection for Japanese Application No. 2023-548947, dated Nov. 25, 2025, 5 Pages.
Boshart, Michael, et al. "A very strong enhancer is located upstream of an immediate early gene of human cytomegalovirus." cell 41.2 (1985): 521-5.
Takebe, Yutaka, et al. "SR alpha promoter: an efficient and versatile mammalian cDNA expression system composed of the simian virus 40 early promoter and the R-U5 segment of human T-cell leukemia virus type 1 long terminal repeat." Molecular and cellular biology (1988), 466-472.
O'hare, K., C. Benoist, and R. Breathnach. "Transformation of mouse fibroblasts to methotrexate resistance by a recombinant plasmid expressing a prokaryotic dihydrofolate reductase." Proceedings of the National Academy of Sciences 78.3 (1981): 1527-1531.
Altschul, Stephen F., et al. "Gapped BLAST and PSI-BLAST: a new generation of protein database search programs." Nucleic acids research 25.17 (1997): 3389-3402.
Altschul, Stephen F., et al. "Basic local alignment search tool." Journal of molecular biology 215.3 (1990): 403-410.
Karlin, Samuel, and Stephen F. Altschul. "Applications and statistics for multiple high-scoring segments in molecular sequences." Proceedings of the National Academy of Sciences 90.12 (1993): 5873-5877.
Köhler, Georges, and Cesar Milstein. "Continuous cultures of fused cells secreting antibody of predefined specificity." nature 256.5517 (1975): 495-497.
Zoller, Mark J. "New recombinant DNA methodology for protein engineering." Current opinion in biotechnology 3.4 (1992): 348-354.
Sadahira, Yoshito, and Masaharu Mori. "Role of the macrophage in erythropoiesis." Pathology international 49.10 (1999): 841-848.
Takeishi, Toshiyuki, et al. "The role of Kupffer cells in liver regeneration." Archives of histology and cytology 62.5 (1999): 413-422.
Polazzi, Elisabetta, Tatiana Gianni, and Antonio Contestabile. "Microglial cells protect cerebellar granule neurons from apoptosis: evidence for reciprocal signaling." Glia 36.3 (2001): 271-280.
Chen, D. S. & Mellman, I. Oncology meets immunology: the cancer-immunity cycle. Immunity 39, 1-10, doi: 10.1016/j.immuni.2013.07.012 (2013).
Wculek, S. K. et al. Dendritic cells in cancer immunology and immunotherapy. Nature Reviews Immunology 20, 7-24 (2020).
Galluzzi, L., Buqué, A., Kepp, O., Zitvogel, L. & Kroemer, G. Immunogenic cell death in cancer and infectious disease. Nature Reviews Immunology 17, 97-111 (2017).
Kroemer, G., Galluzzi, L., Kepp, O. & Zitvogel, L. Immunogenic cell death in cancer therapy. Annual review of immunology 31, 51-72 (2013).
Li, Y. et al. Multifunctional oncolytic nanoparticles deliver self-replicating IL-12 RNA to eliminate established tumors and prime systemic immunity. Nature Cancer 1, 882-893 (2020).
Vonderheide, R. H. CD40 agonist antibodies in cancer immunotherapy. Annual review of medicine 71, 47-58 (2020).
Melero, I., Castanon, E., Alvarez, M., Champiat, S. & Marabelle, A. Intratumoural administration and tumour tissue targeting of cancer immunotherapies. Nature Reviews Clinical Oncology 18, 558-576 (2021).
Hou, X., Zaks, T., Langer, R. & Dong, Y. Lipid nanoparticles for mRNA delivery. Nature Reviews Materials 6, 1078-1094 (2021).
Zhang, Y., Sun, C., Wang, C., Jankovic, K. E. & Dong, Y. Lipids and lipid derivatives for RNA delivery. Chemical Reviews 121, 12181-12277 (2021).
Hewitt, S. L. et al. Durable anticancer immunity from intratumoral administration of IL-23, IL-36γ, and OX40L mRNAs. Science translational medicine 11, eaat9143 (2019).
Ghosh, S. & Sudha, M. A review on polyols: new frontiers for health-based bakery products. International journal of food sciences and nutrition 63, 372-379 (2012).
Zada, B. et al. Recent advances in catalytic production of sugar alcohols and their applications. Science China Chemistry 60, 853-869 (2017).
Stoss, P. & Hemmer, R. 1, 4: 3, 6-Dianhydrohexitols. Advances in carbohydrate chemistry and biochemistry 49, 93-173 (1991).
Spagnolo, F. et al. Survival of patients with metastatic melanoma and brain metastases in the era of MAP-kinase inhibitors and immunologic checkpoint blockade antibodies: a systematic review. Cancer treatment reviews 45, 38-45 (2016).
Wiggins, L. F. (1950). Anhydrides of the Pentitols and Hexitols. Advances in Carbohydrate Chemistry, 191-228. doi:10.1016/s0096-5332(08)60339-2.
Fenouillot, F., Rousseau, A., Colomines, G., Saint-Loup, R. & Pascault, J.-P. Polymers from renewable 1, 4: 3, 6-dianhydrohexitols (isosorbide, isomannide and isoidide): A review. Progress in Polymer Science 35, 578-622 (2010).
Aricò, F., Tundo, P., Maranzana, A. & Tonachini, G. Synthesis of five-membered cyclic ethers by reaction of 1, 4-Diols with dimethyl carbonate. ChemSusChem 5, 1578-1586 (2012).
Kikuchi, T., Moore, M. A. & Crystal, R. G. Dendritic cells modified to express CD40 ligand elicit therapeutic immunity against preexisting murine tumors. Blood, The Journal of the American Society of Hematology 96, 91-99 (2000).
Li, W. et al. Biomimetic nanoparticles deliver mRNAs encoding costimulatory receptors and enhance T cell mediated cancer immunotherapy. Nature communications 12, 1-12 (2021).
Zeng, C. et al. Leveraging mRNA Sequences and Nanoparticles to Deliver SARS-CoV-2 Antigens In Vivo. Advanced Materials 32, 2004452 (2020).
Hou, X. et al. Vitamin lipid nanoparticles enable adoptive macrophage transfer for the treatment of multidrug-resistant bacterial sepsis. Nature nanotechnology 15, 41-46 (2020).
First Office Action for Chinese Application No. 202280027539.9 dated Jul. 19, 2025, 13 Pages.
European Patent Office. Extended European Search Report. Issued in EP Application No. 22753419.5. Dec. 17, 2024. 6 pages.

L-Sorbitol
1
L-Isosorbide
2
3
4
5

DIS1 $R=R_1$ DIS6 $R=R_6$
DIS2 $R=R_2$ DIS7 $R=R_7$
DIS3 $R=R_3$ DIS8 $R=R_8$
DIS4 $R=R_4$ DIS9 $R=R_9$
DIS5 $R=R_5$ DIS10 $R=R_{10}$

DIM1 $R=R_1$ DIM6 $R=R_6$
DIM2 $R=R_2$ DIM7 $R=R_7$
DIM3 $R=R_3$ DIM8 $R=R_8$
DIM4 $R=R_4$ DIM9 $R=R_9$
DIM5 $R=R_5$ DIM10 $R=R_{10}$

LIS1 $R=R_1$ LIS6 $R=R_6$
LIS2 $R=R_2$ LIS7 $R=R_7$
LIS3 $R=R_3$ LIS8 $R=R_8$
LIS4 $R=R_4$ LIS9 $R=R_9$
LIS5 $R=R_5$ LIS10 $R=R_{10}$

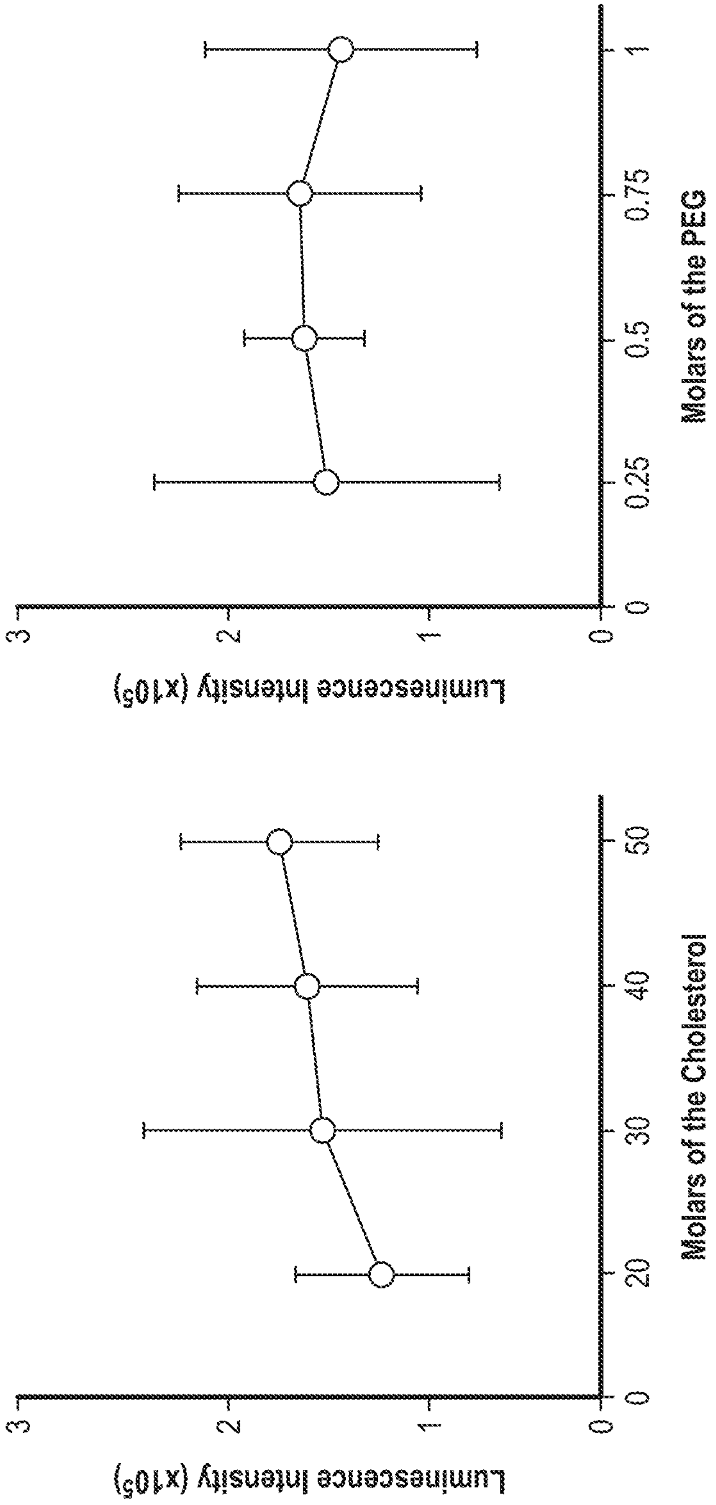
FIG. 2B (con't)

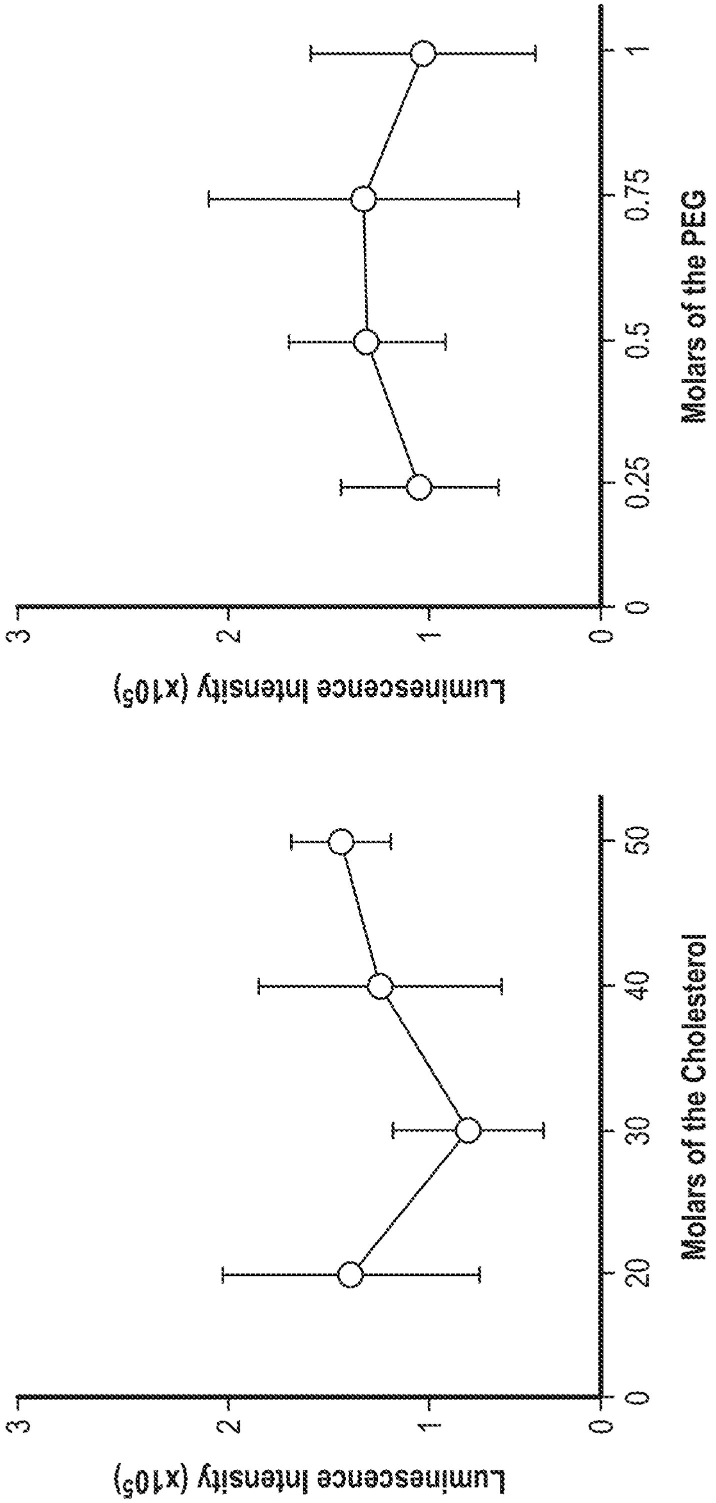
FIG. 2D (con't)

Screening of Optimal Formulations

| Formulation | Factors (Molar Ratio) | | | |
|---|---|---|---|---|
| | Lipid | DOPE | Cholesterol | PEG |
| DIM7Q | 10 | 50 | 50 | 0.5 |
| DIM7R | 10 | 50 | 50 | 0.75 |
| DIM7S | 30 | 50 | 50 | 0.5 |
| DIM7T | 30 | 50 | 50 | 0.75 |
| LIS10Q | 30 | 20 | 20 | 0.5 |
| LIS10R | 30 | 20 | 20 | 0.75 |
| LIS10S | 30 | 20 | 50 | 0.5 |
| LIS10T | 30 | 20 | 50 | 0.75 |
| LIS10U | 30 | 40 | 20 | 0.5 |
| LIS10V | 30 | 40 | 20 | 0.75 |
| LIS10W | 30 | 40 | 50 | 0.5 |
| LIS10X | 30 | 40 | 50 | 0.75 |

FIG. 2F

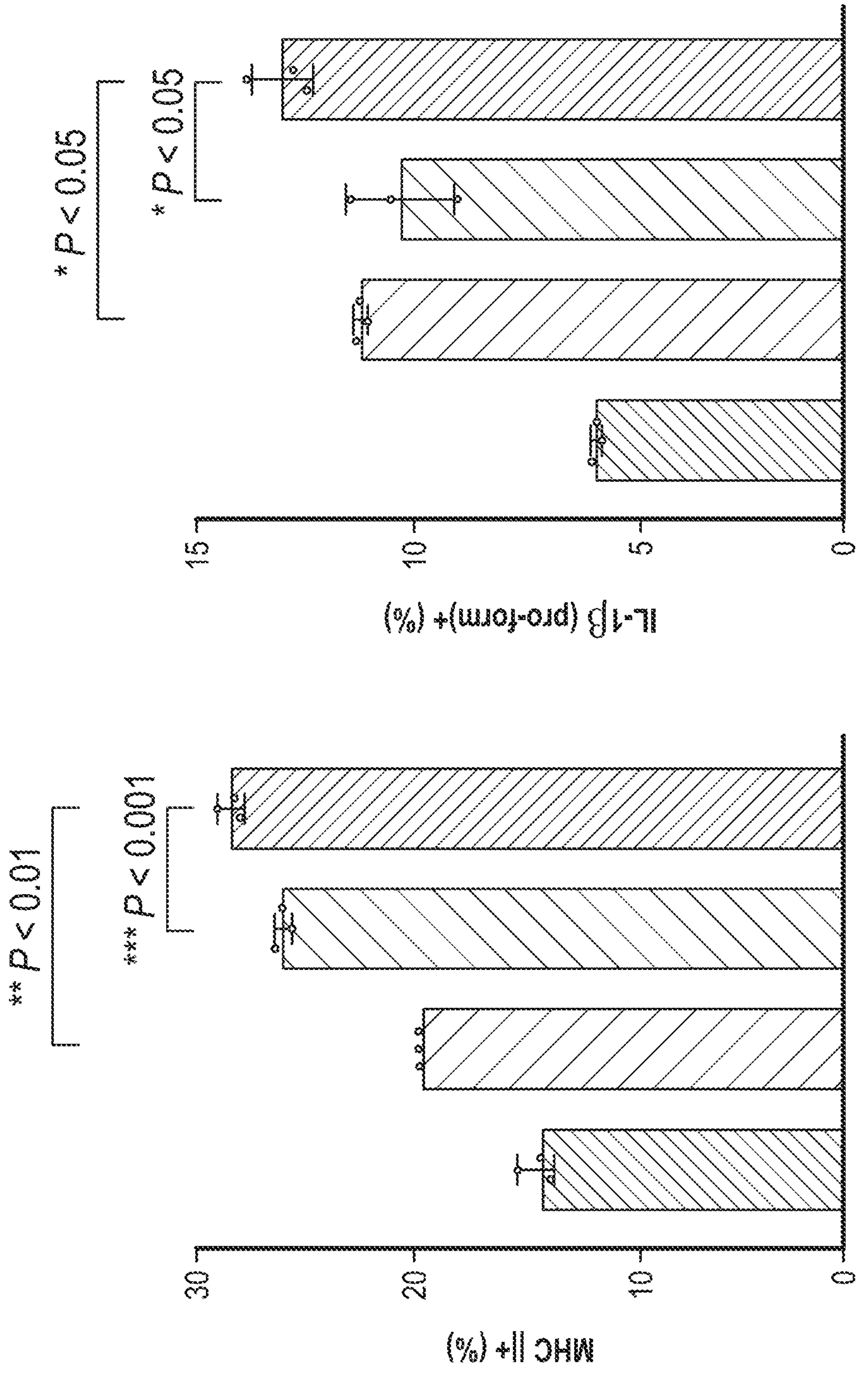
FIG. 3A (con't)

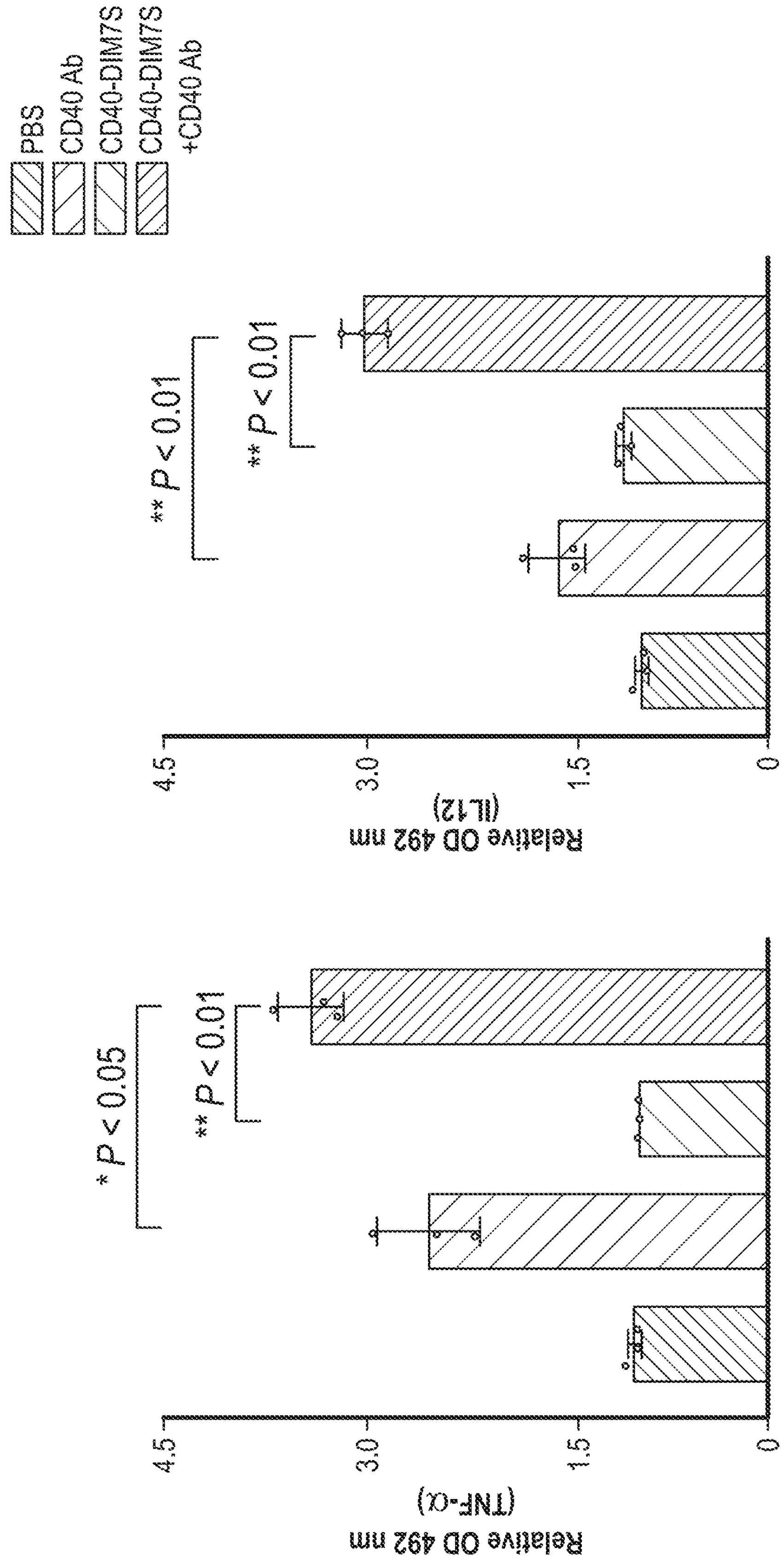
FIG. 3A (con't)

L16 $(4)^4$ Orthogonal Table

| Formulation | Factors (Molar Ratio) | | | |
|---|---|---|---|---|
| | Lipid | DOPE | Cholesterol | PEG |
| A | 10 | 30 | 40 | 0.75 |
| B | 20 | 50 | 20 | 0.75 |
| C | 30 | 50 | 40 | 1 |
| D | 40 | 30 | 20 | 0.25 |
| E | 10 | 40 | 20 | 1 |
| F | 20 | 20 | 40 | 0.25 |
| G | 30 | 20 | 20 | 0.75 |
| H | 40 | 40 | 40 | 0.5 |
| I | 10 | 20 | 50 | 0.5 |
| J | 20 | 40 | 30 | 0.75 |
| K | 30 | 40 | 50 | 0.25 |
| L | 40 | 20 | 30 | 1 |
| M | 10 | 50 | 30 | 0.25 |
| N | 20 | 30 | 50 | 1 |
| O | 30 | 30 | 30 | 0.5 |
| P | 40 | 50 | 50 | 0.75 |

FIG. 7A

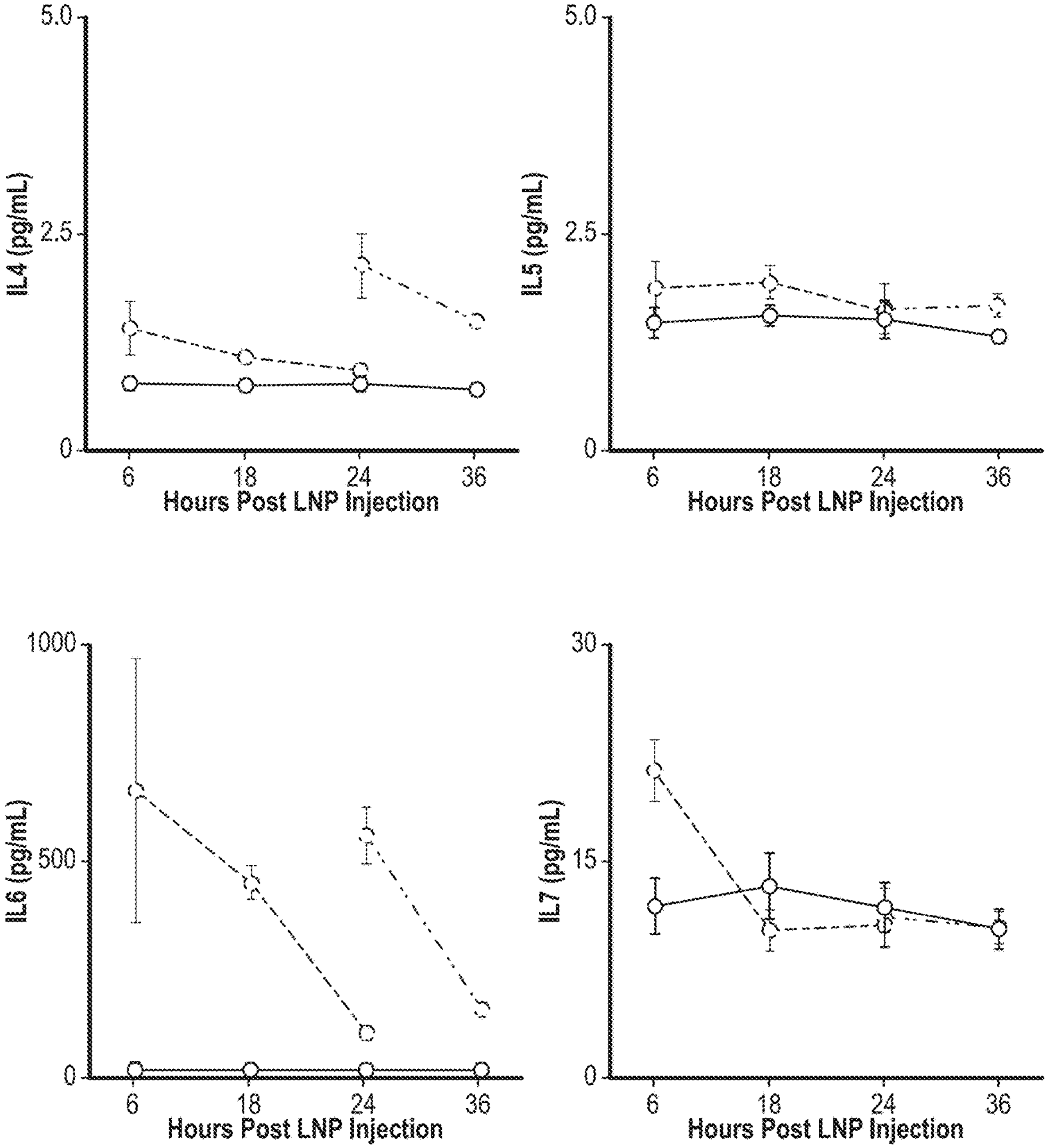
FIG. 12 (con't)

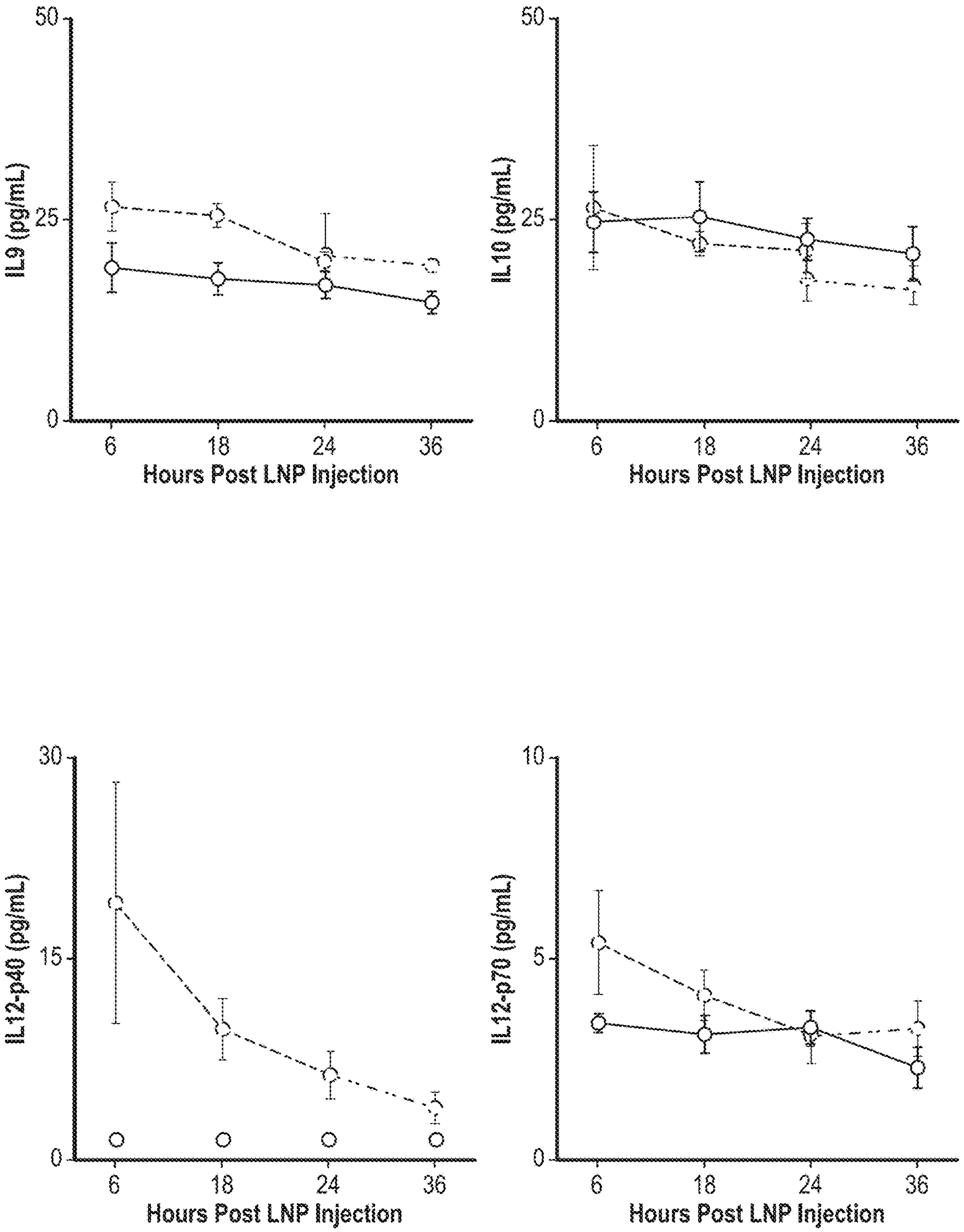
FIG. 12 (con't)

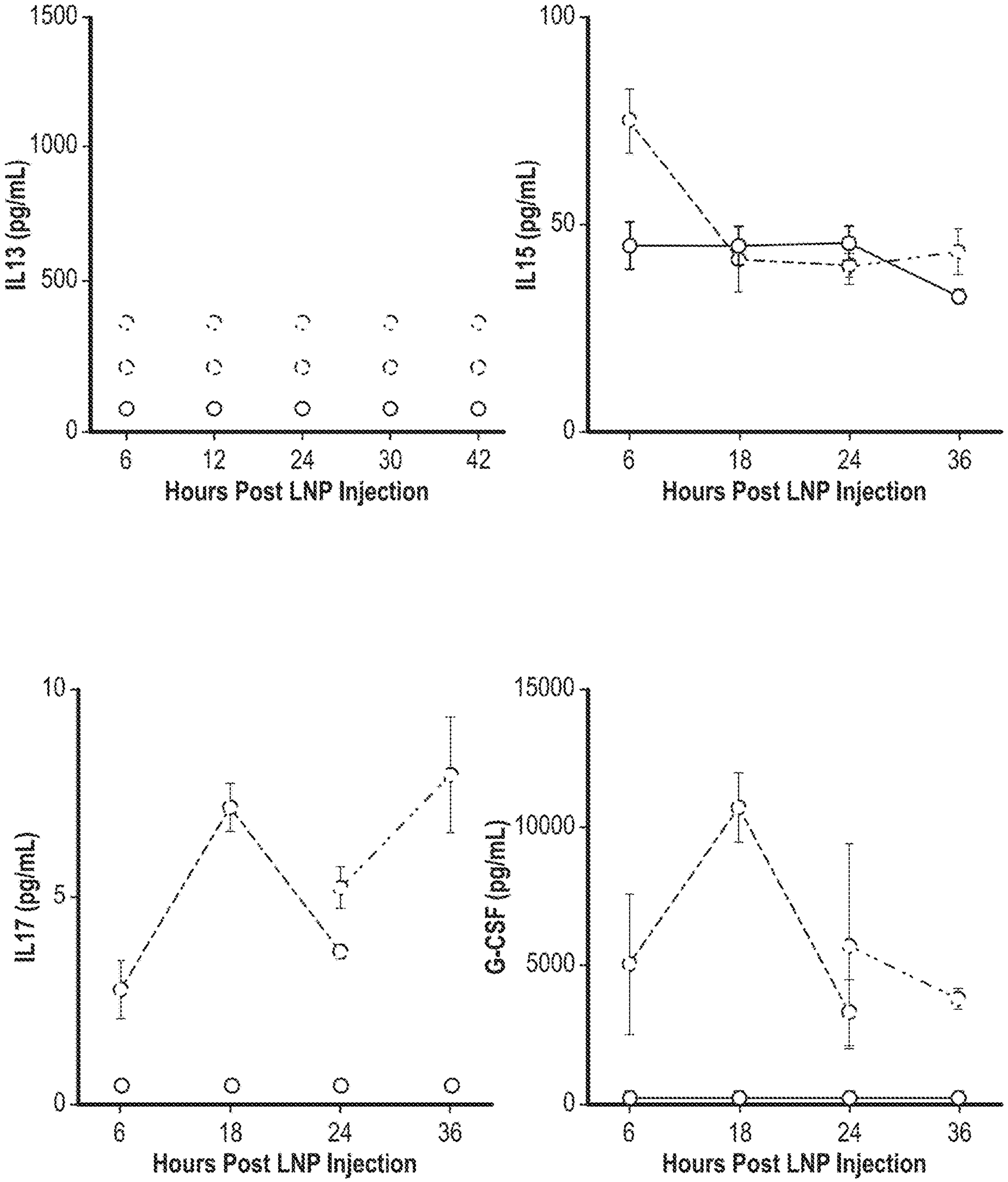
FIG. 12 (con't)

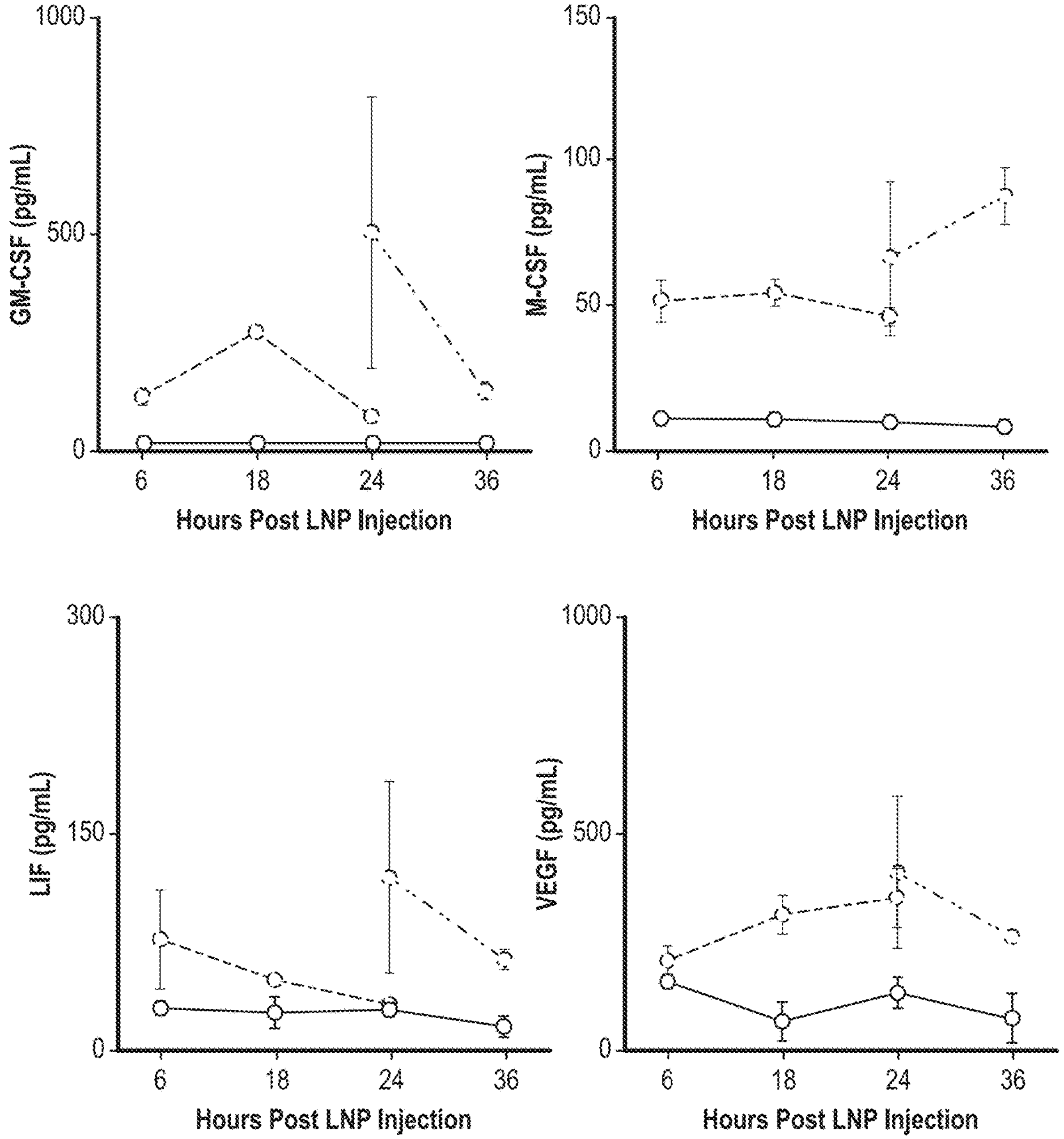
FIG. 12 (con't)

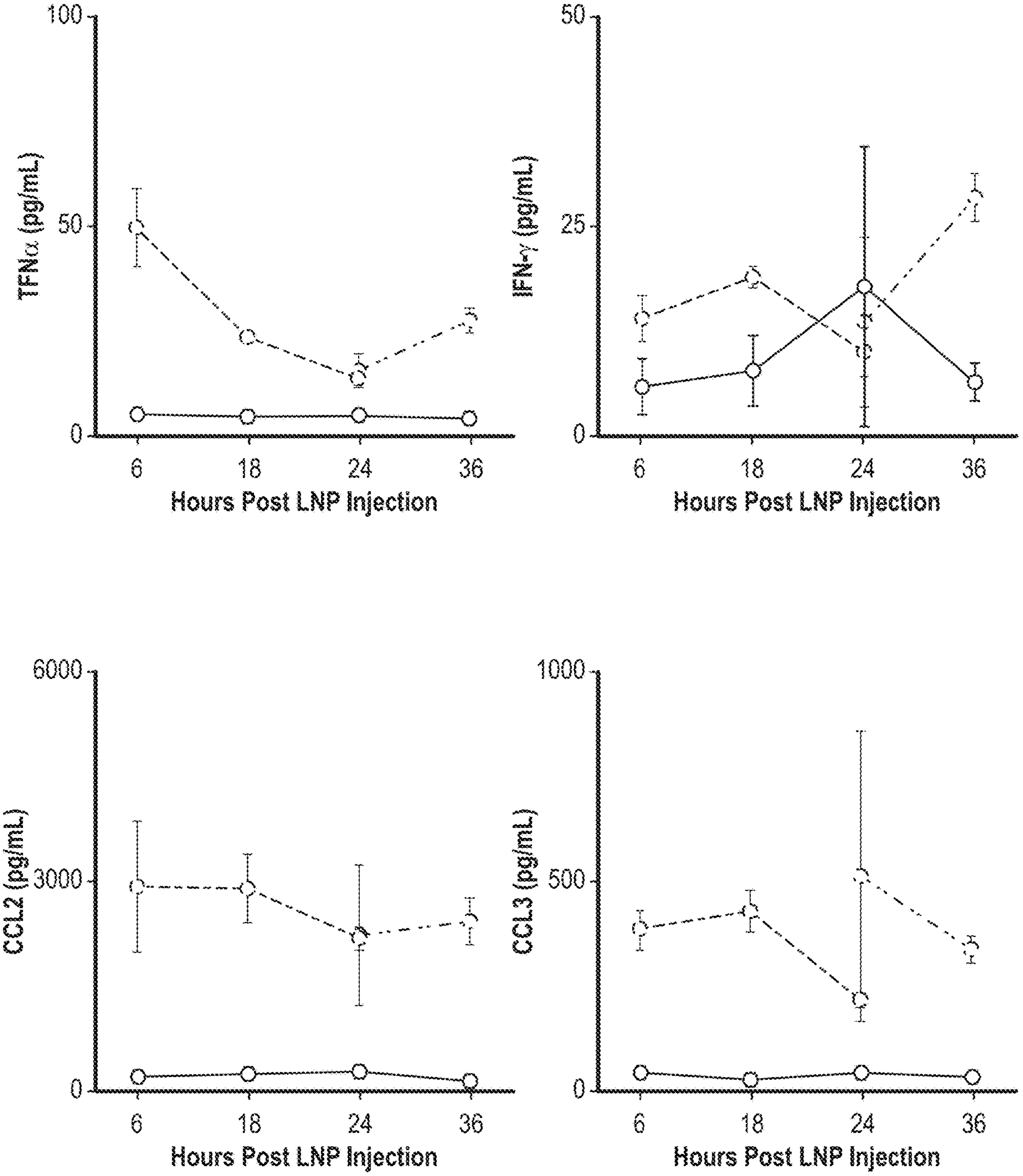
FIG. 12 (con't)

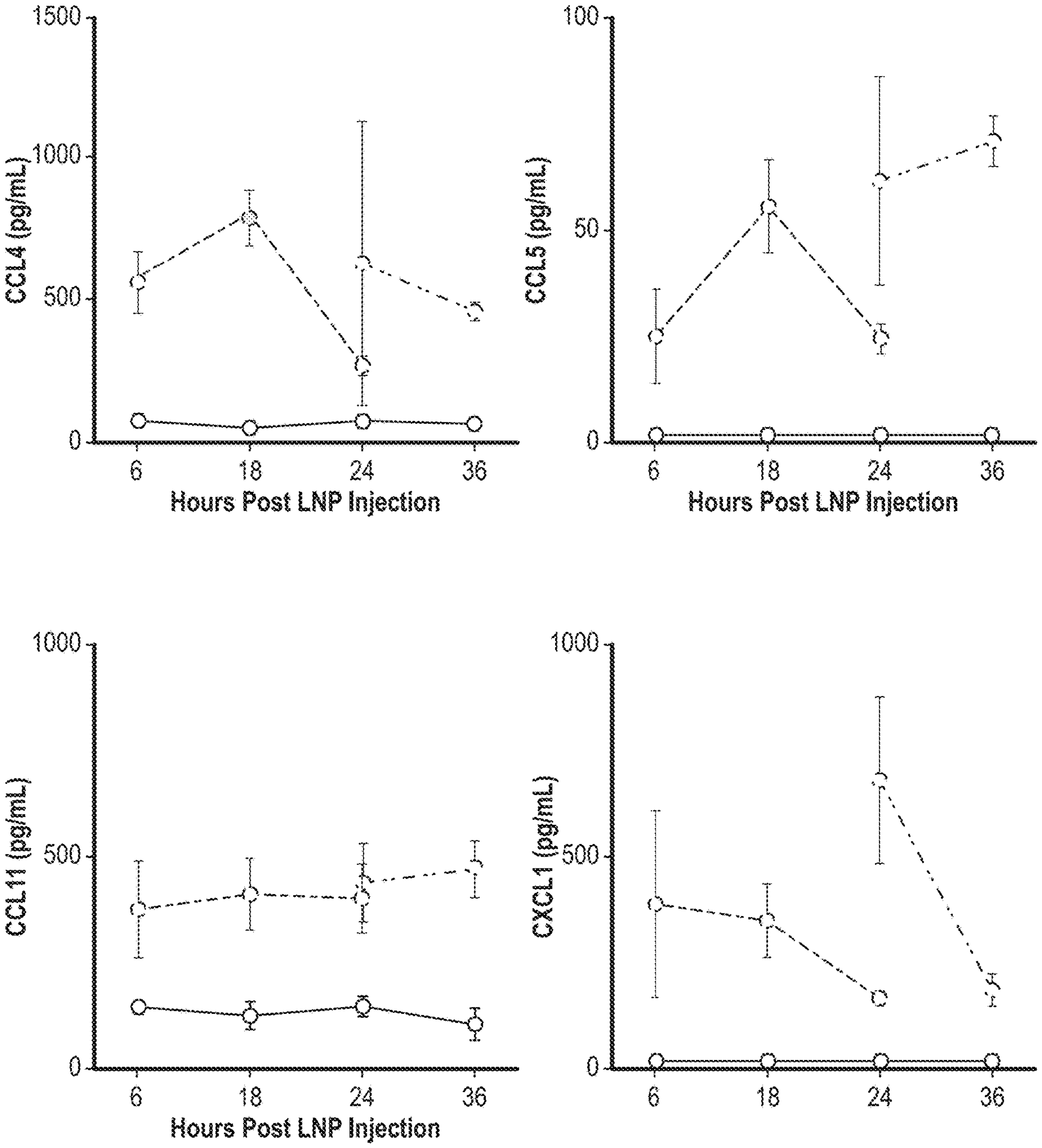
FIG. 12 (con't)

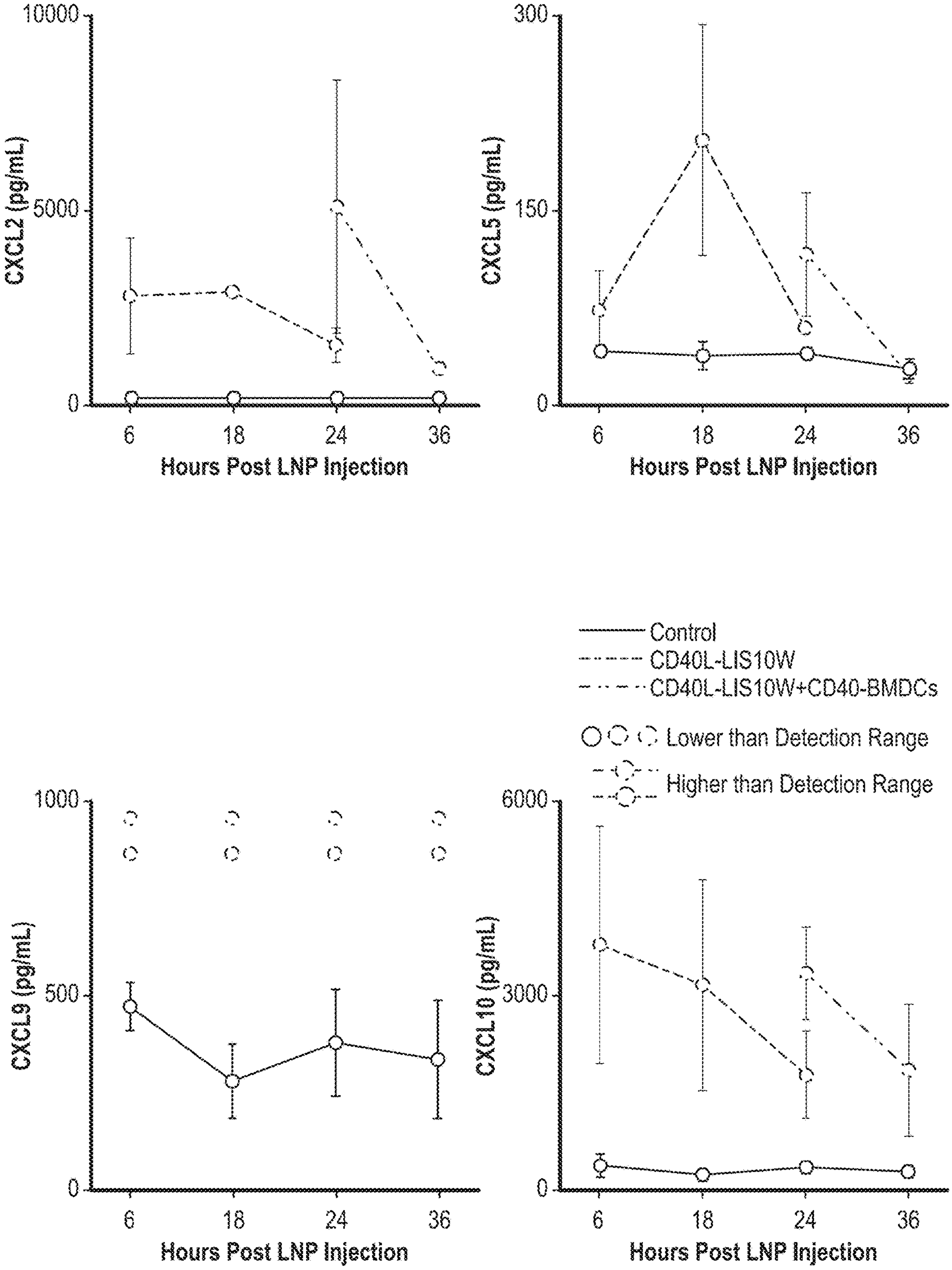
FIG. 12 (con't)

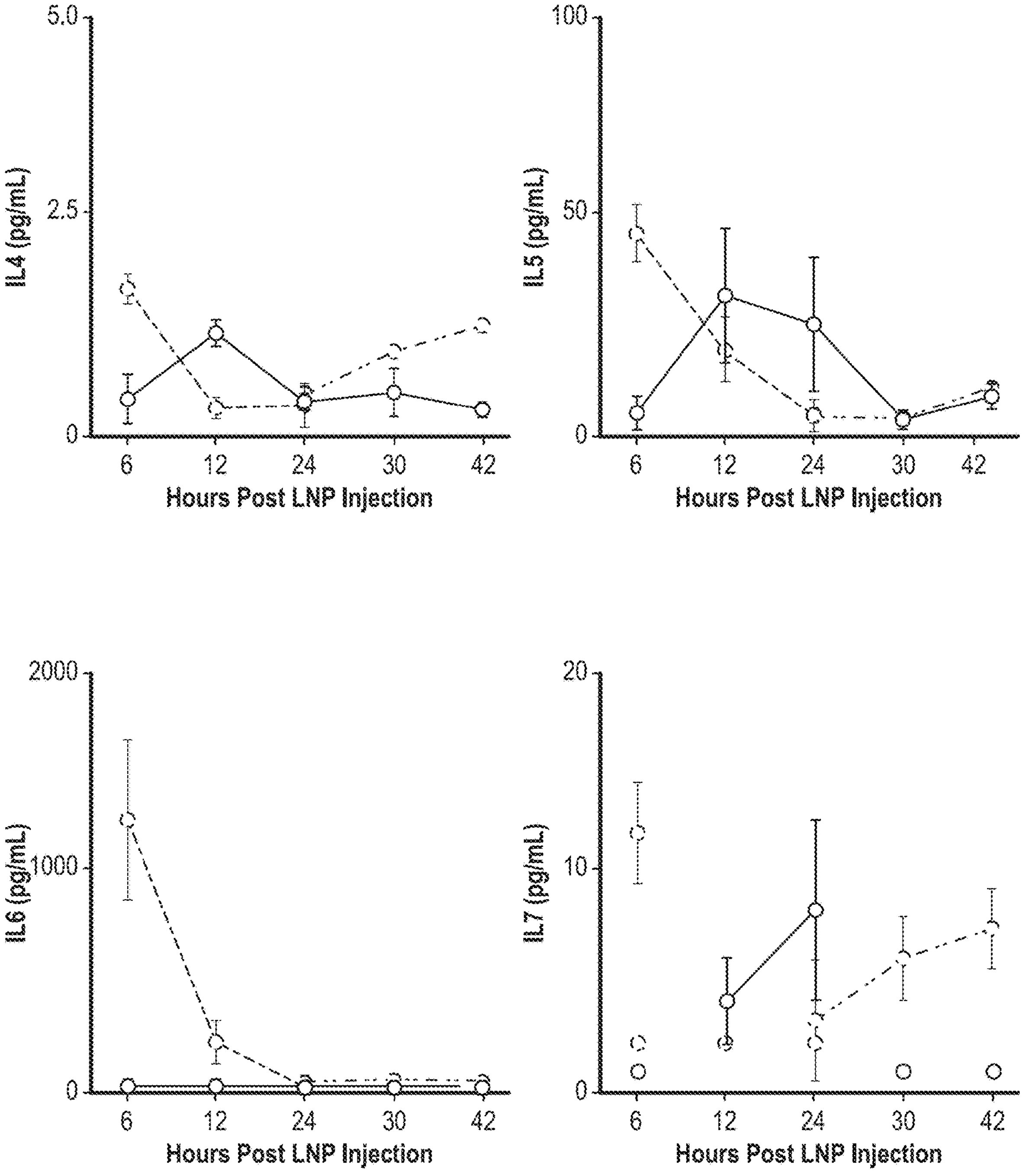
FIG. 13 (con't)

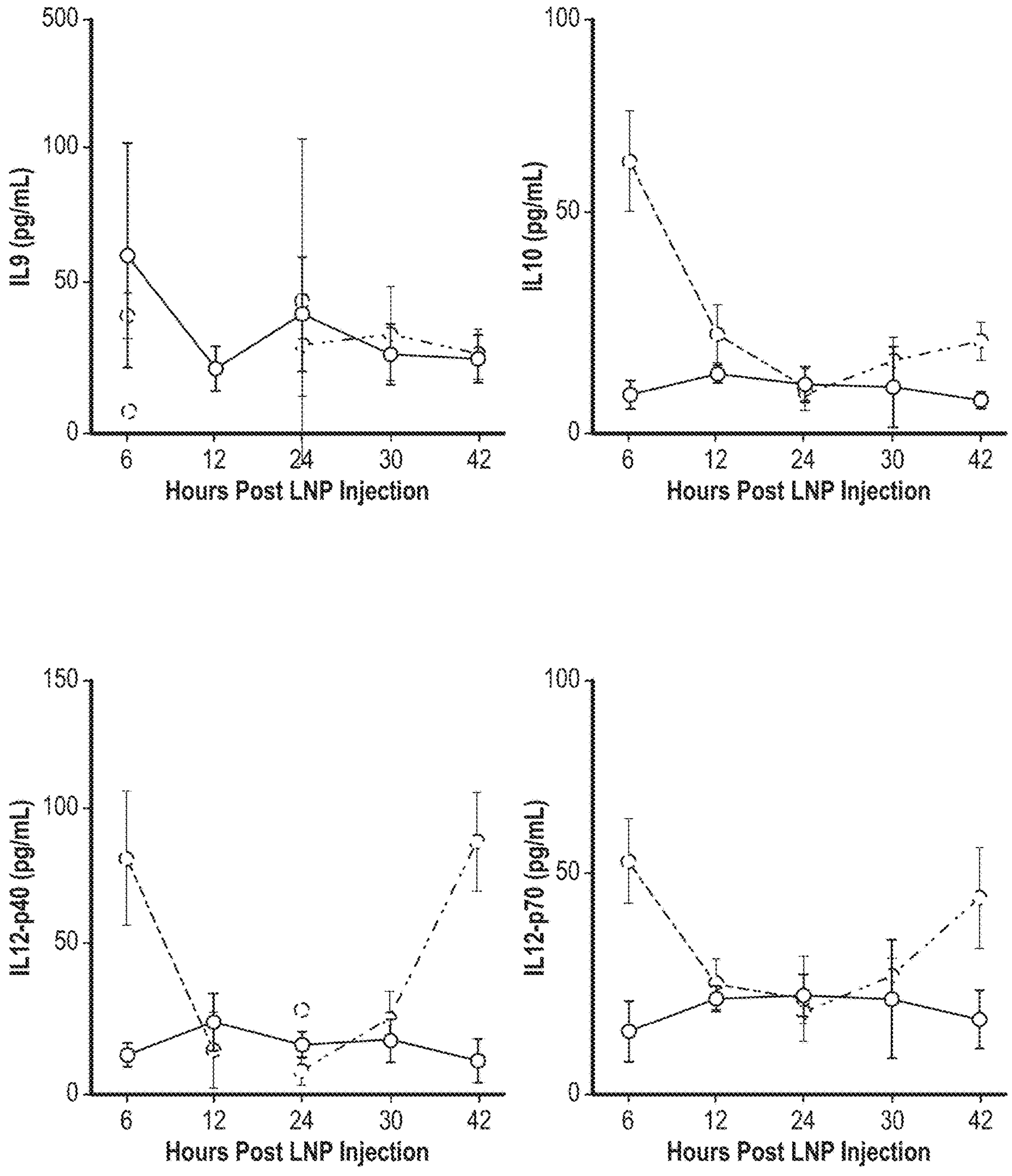
FIG. 13 (con't)

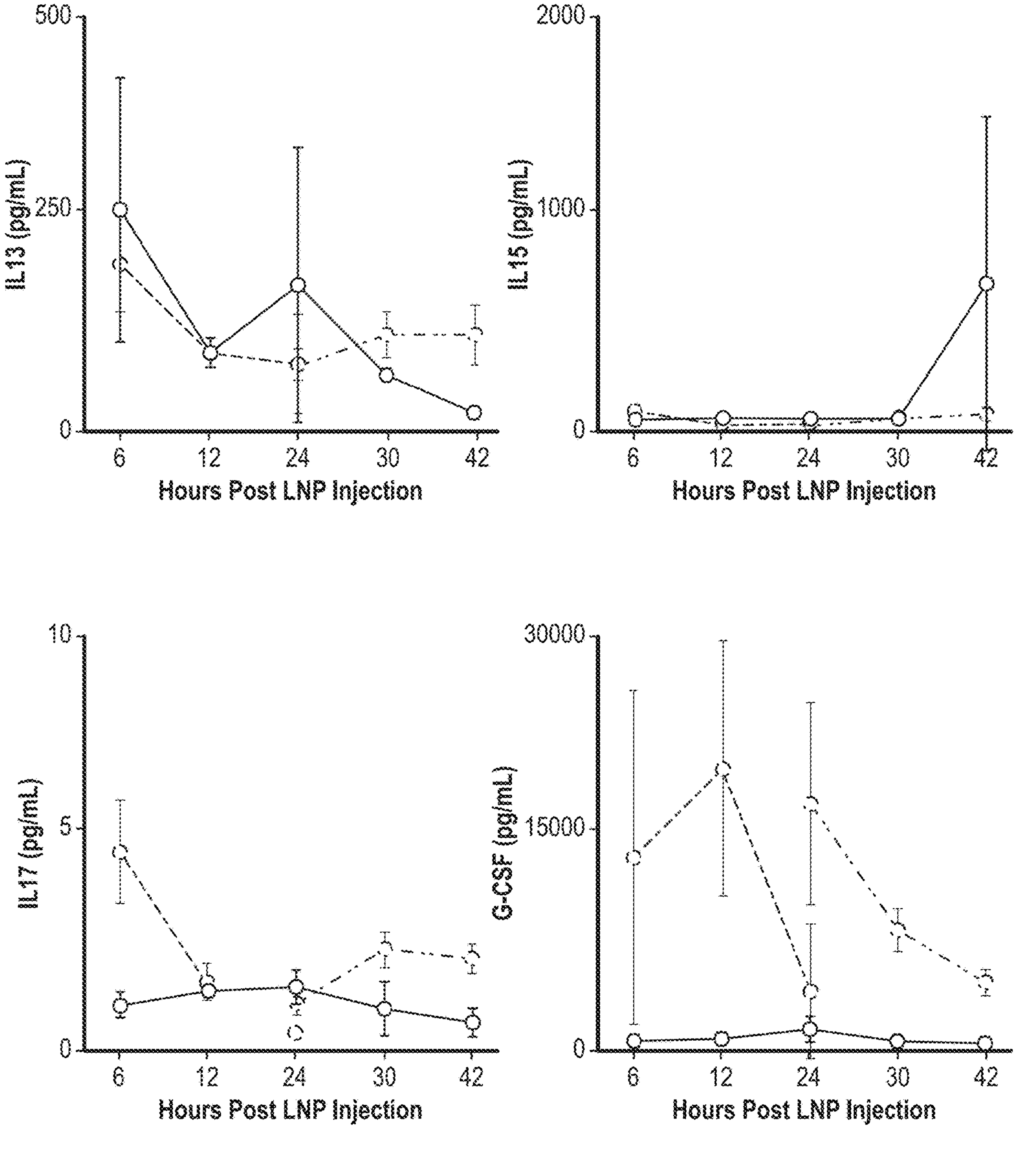
FIG. 13 (con't)

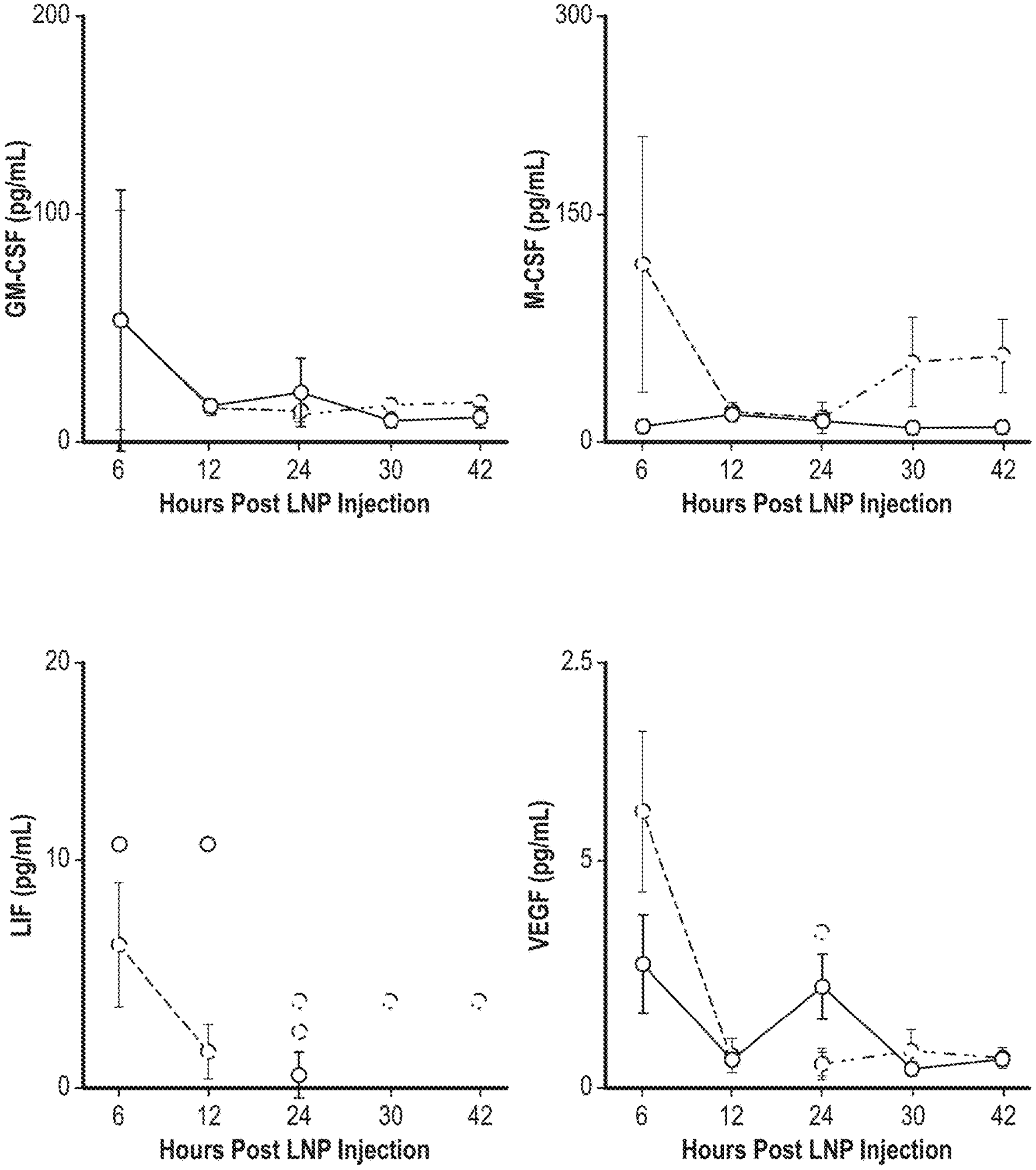
FIG. 13 (con't)

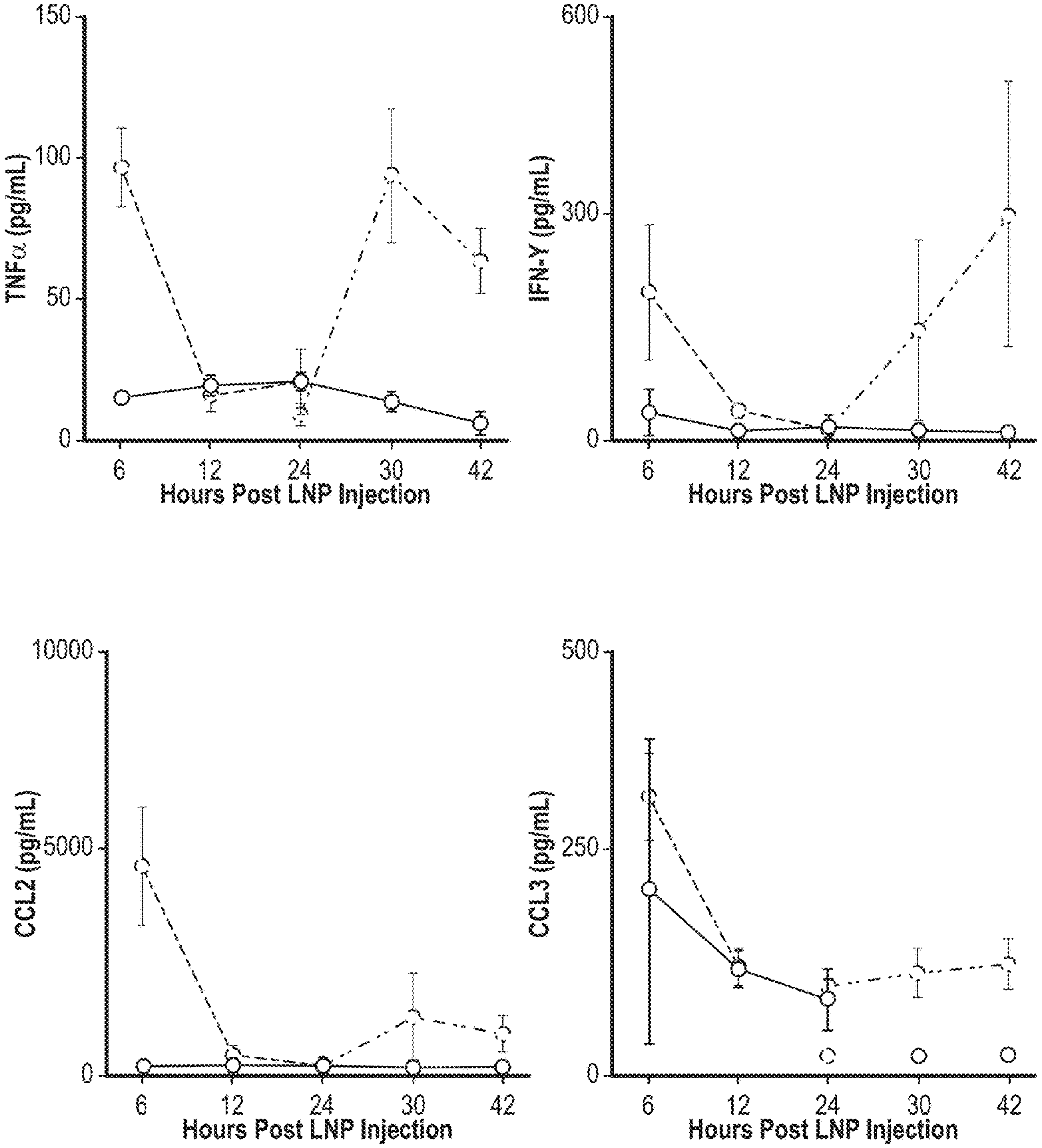
FIG. 13 (con't)

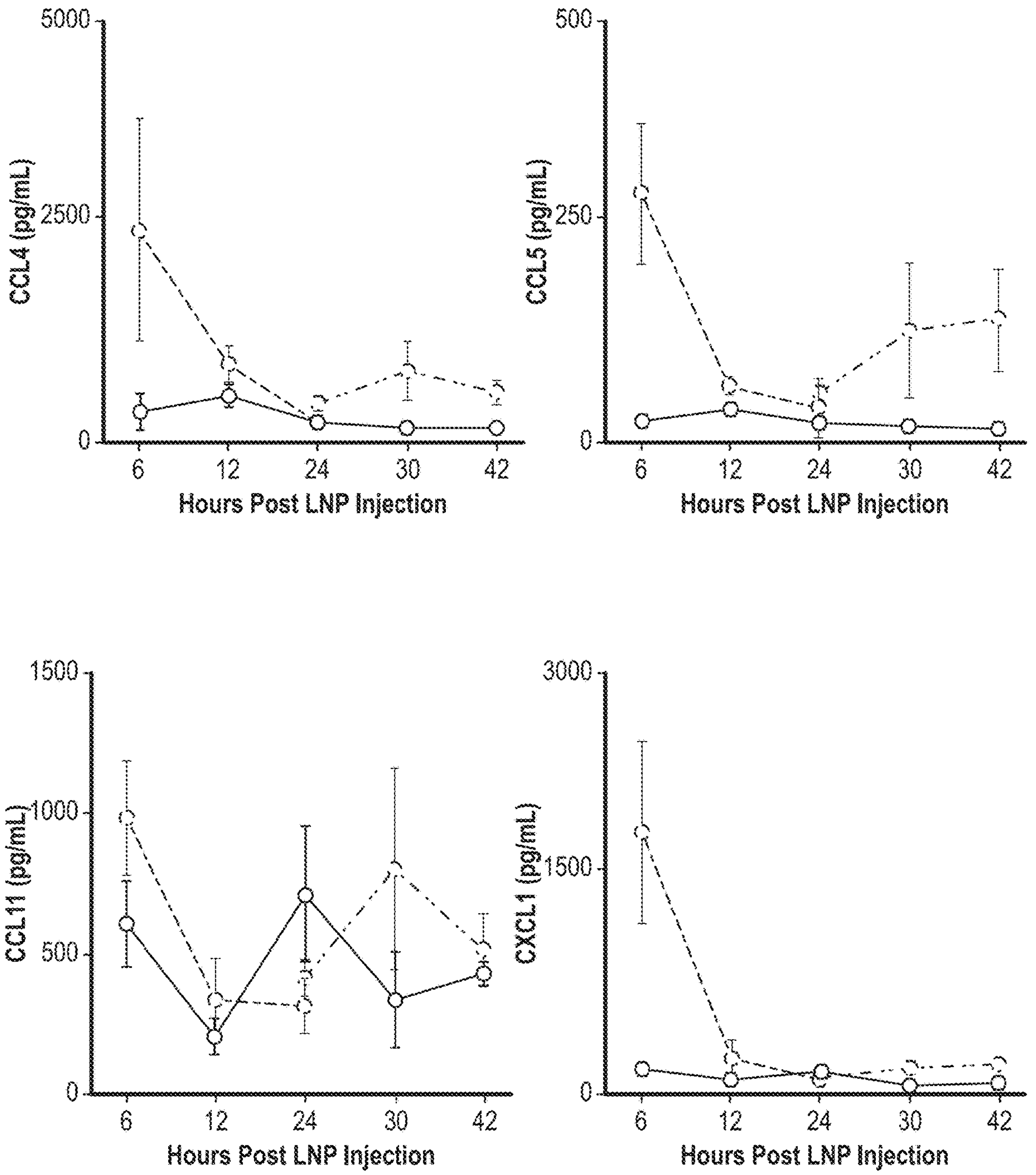
FIG. 13 (con't)

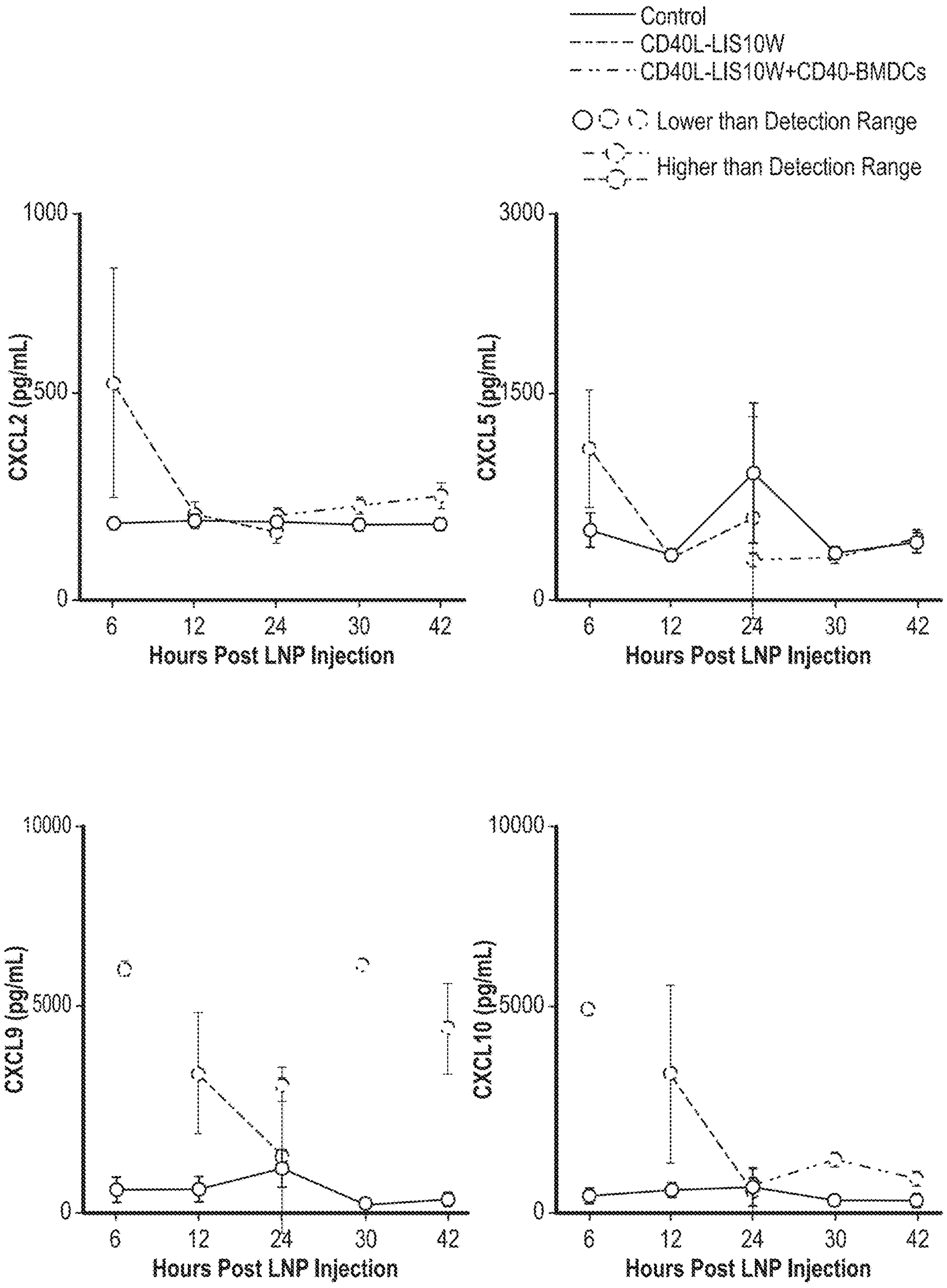
FIG. 13 (con't)

SUGAR DERIVED LIPID NANOMATERIALS AND USES THEREOF

CROSS REFERENCE TO RELATED APPLICATIONS

This application is a United States National Phase Application of International Patent Application Number PCT/US2022/016137, filed on Feb. 11, 2022, which claims the benefit of priority to U.S. Provisional Patent Application Ser. No. 63/148,755 filed Feb. 12, 2021, the disclosures of which are expressly incorporated herein by reference.

STATEMENT REGARDING FEDERALLY SPONSORED RESEARCH

This invention was made with government support under R35 GM119679 awarded by the National Institutes of Health. The government has certain rights in the invention.

FIELD

The present disclosure relates to compositions and methods for treating cancers and other immune disorders.

BACKGROUND

Efficient delivery of mRNA is a key step and challenge for the applicant of mRNA therapeutics. Despite promising data from ongoing clinical trials, the clinical use of mRNA requires the discovery and development of more efficient delivery systems. What is needed are new compositions and methods for delivering mRNA to cells for treating cancers and other immune disorders.

SUMMARY

In some aspects, disclosed herein is a compound having Formula I, II, or III:

Formula I

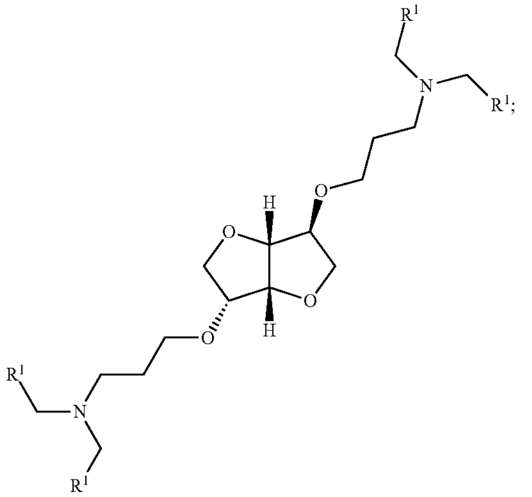

-continued

Formula II

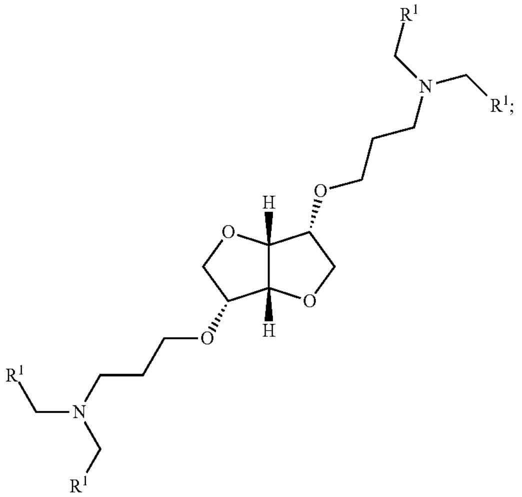

Formula III

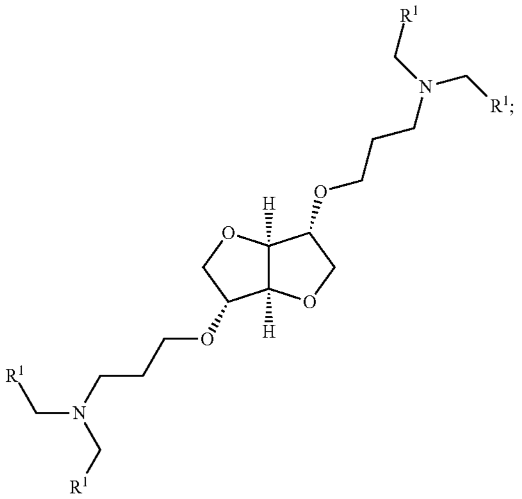

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

In some embodiments, the compound has the formula:

Formula I

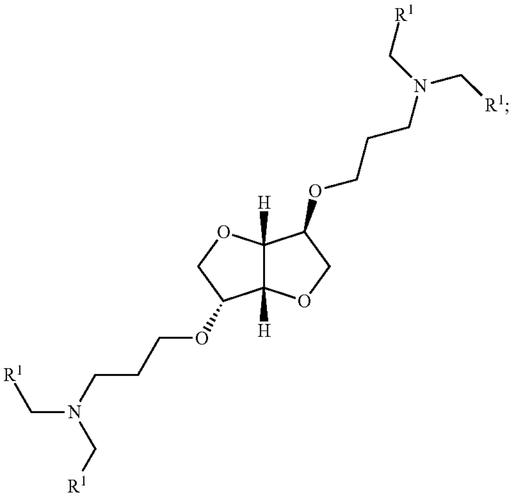

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

In some embodiments, the compound has the formula:

Formula II

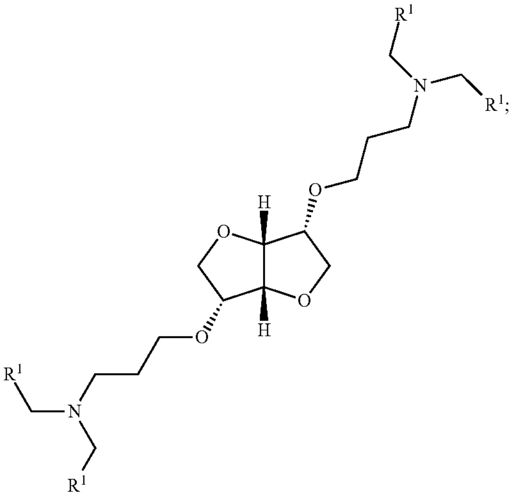

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisuifide, and oxime ether.

In some embodiments, the compound has the formula:

Formula III

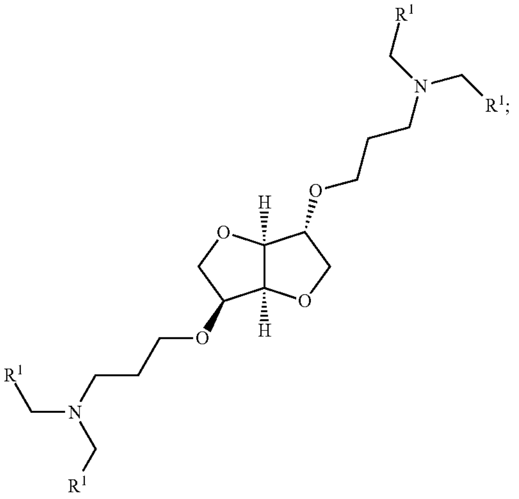

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

In some embodiments, $R^1$ is selected from the following:

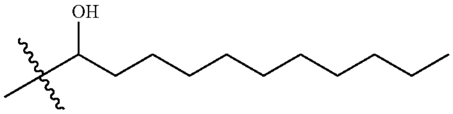,

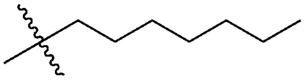,

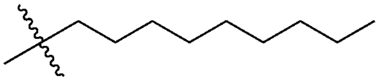,

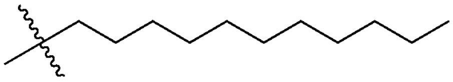,

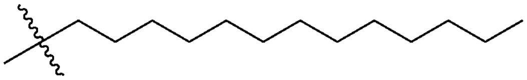,

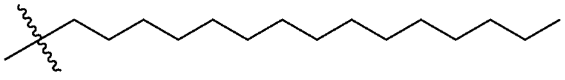,

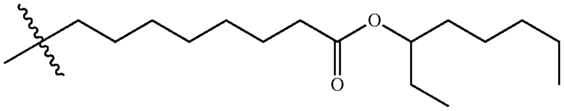,

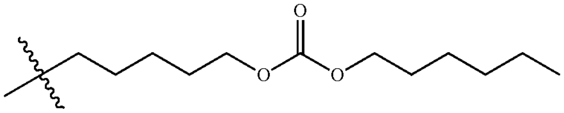,

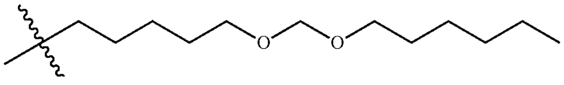,

-continued

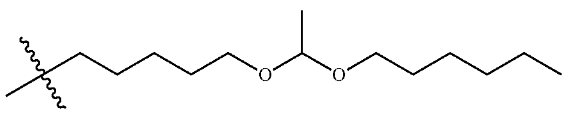

, or a salt thereof

In some embodiments, the compound is

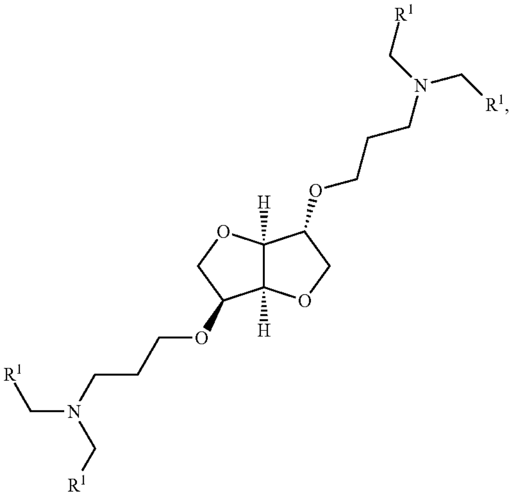

wherein $R^1$ is

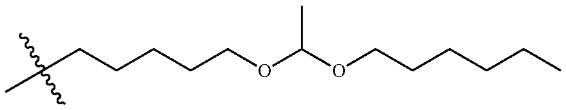

.

In some embodiments, the compound is

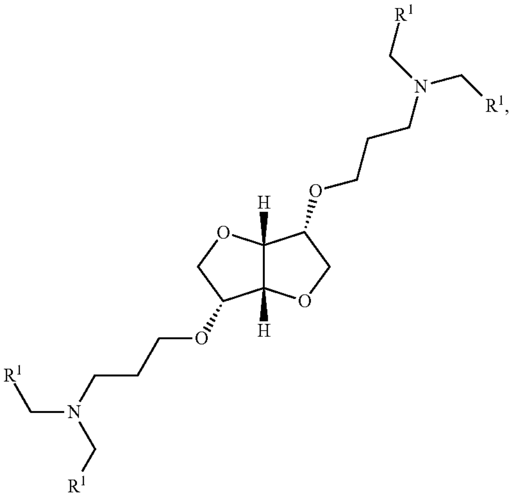

wherein $R^1$ is

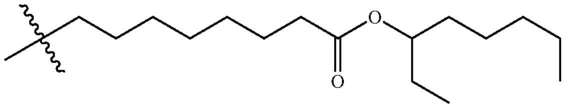

.

In some aspects, disclosed herein is a lipid-based nanoparticle, comprising: the compound of any preceding aspect and a recombinant polynucleotide comprising a nucleic acid encoding a co-stimulatory molecule.

In some aspects, disclosed herein is an antigen presenting cell, comprising: a lipid-based nanoparticle, comprising: the compound of any preceding aspect and a recombinant polynucleotide comprising a nucleic acid encoding a co-stimulatory molecule.

In some embodiments,
the compound is

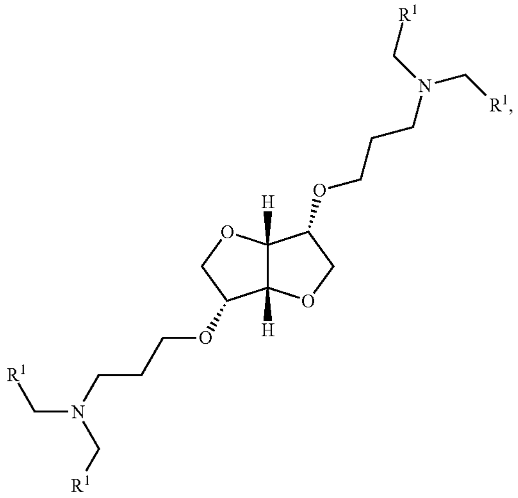

wherein $R^1$ is

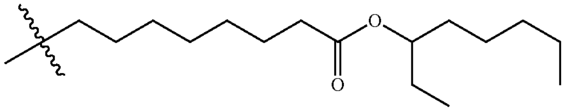

.

In some embodiments, the co-stimulatory molecule is selected from ICOS, CD28, CD27, HVEM, LIGHT, CD40L, 4-1BB, OX40, DR3, GITR, CD30, SLAM, CD2, CD226, Galectin9, TIM1, LFA1, B7-H2, B7-1, B7-2, CD70, LIGHT, HVEM, CD40, 4-1BBL, OX40L, TL1A, GITRL, CD30L, SLAM, CD48, CD58, CD155, CD112, CD80, CD86, ICOSL,, TIM3, TIM4, ICAM1, and LFA3. In some embodiments, the co-stimulatory molecule is CD40.

In some embodiments, the mRNA encoding the co-stimulatory molecule comprises a heterologous 5' untranslated region (5'UTR). In some embodiments, the mRNA encoding the co-stimulatory molecule comprises a heterologous 3' untranslated region (3'UTR). In some embodiments, the mRNA comprises a chemically modified nucleobase. In some embodiments, the chemically modified nucleobase is pseudouridine. In some embodiments, the antigen presenting is a bone marrow-derived dendritic cell.

In some aspects, disclosed herein is a method of treating a cancer comprising administering to a subject in need thereof a therapeutically effective amount of the antigen presenting cell of any preceding aspect and an antibody.

In some embodiments, the antibody is selected from an anti-CD40 antibody, an anti-PDL1 antibody, an anti-PD1 antibody, an anti-CTLA4 antibody, or a combination thereof.

In some embodiments, the antigen presenting cell and the antibody are administered intratumorally.

In some aspects, disclosed herein is a method of treating a cancer comprising administering to a subject in need thereof:

a therapeutically effective amount of the lipid-based nanoparticle of any preceding aspect, and a therapeutically effective amount of the antigen presenting cell of any preceding aspect.

In some embodiments, the lipid-based nanoparticle comprises

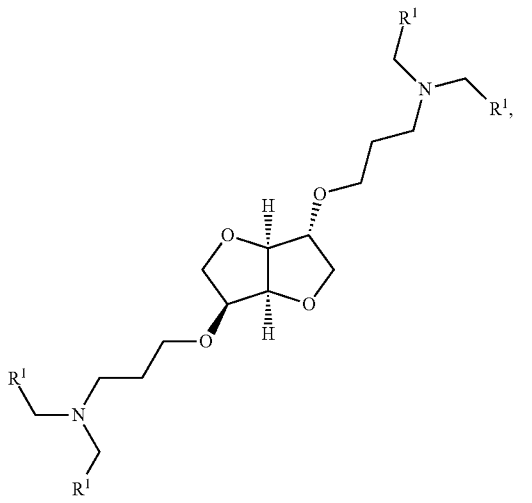

wherein $R^1$ is

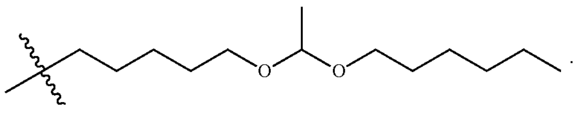 [SMILES: *CCCCCOC(C)OCCCCCC]

In some embodiments, the lipid-based nanoparticle comprises a recombinant polynucleotide comprising a nucleic acid encoding CD40L.

BRIEF DESCRIPTION OF THE DRAWINGS

The accompanying figures, which are incorporated in and constitute a part of this specification, illustrate several aspects described below.

FIGS. 2A-2J. Screening and characterization of lipid nanoparticle (LNP)-mRNA formulations. a, The mRNA delivery efficacy of DIS, DIM, and LIS LNPs in BMDCs. b, The effect of each lipid component at different molar ratios of DIM7 LNPs on mRNA delivery. c, Relative luminescence intensity of DIM7 LNPs' orthogonal formulations and preferred formulations. d, The effect of each lipid component at different molar ratios of LIS10 LNPs on mRNA delivery. e, Relative luminescence intensity of LIS10 LNPs' orthogonal formulations. f, Table for preferred formulations. g, Characterization of DIM7S LNPs, including size, PDI, encapsulation efficiency, and zeta potential. h, Cryo-TEM image of DIM7S (scale bar=50 nm). i, Characterization of LIS10W LNPs, including size, PDI, encapsulation efficiency, and zeta potential. j, Cryo-TEM image of LIS10W (scale bar=50 nm). Data in a, b, c, d, and e are from n=3 biologically independent samples. All data are presented as mean±s.d. Statistical significance was analyzed by two-tailed Student's t-test, *P<0.05, P<0.01, *P<0.001, ****P<0.0001.

FIGS. 7A-7F. Characterization of lipid nanoparticle (LNP)-mRNA formulations. a, L16 $(4)^4$ orthogonal table. b, Cryo-TEM image of DIM7S (scale bar=50 nm). c, Cryo-TEM image of LIS10W (scale bar=50 nm). d, Relative luminescence intensity of electroporation (Electro), DIM7, and DIM7S to Lipofectamine 3000 (Lipo 3K). e, Expression kinetics of mRNA delivered by DIM7S. f, CD40 expression in BMDCs. Data in d, e, and f are from n=3 biologically independent samples and are presented as mean±s.d. Statistical significance in d, e, and f was analyzed by two-tailed Student's t-test. *P<0.05, P0.01, *P<0.001, ****P<0.0001.

DETAILED DESCRIPTION

Figure 1A:
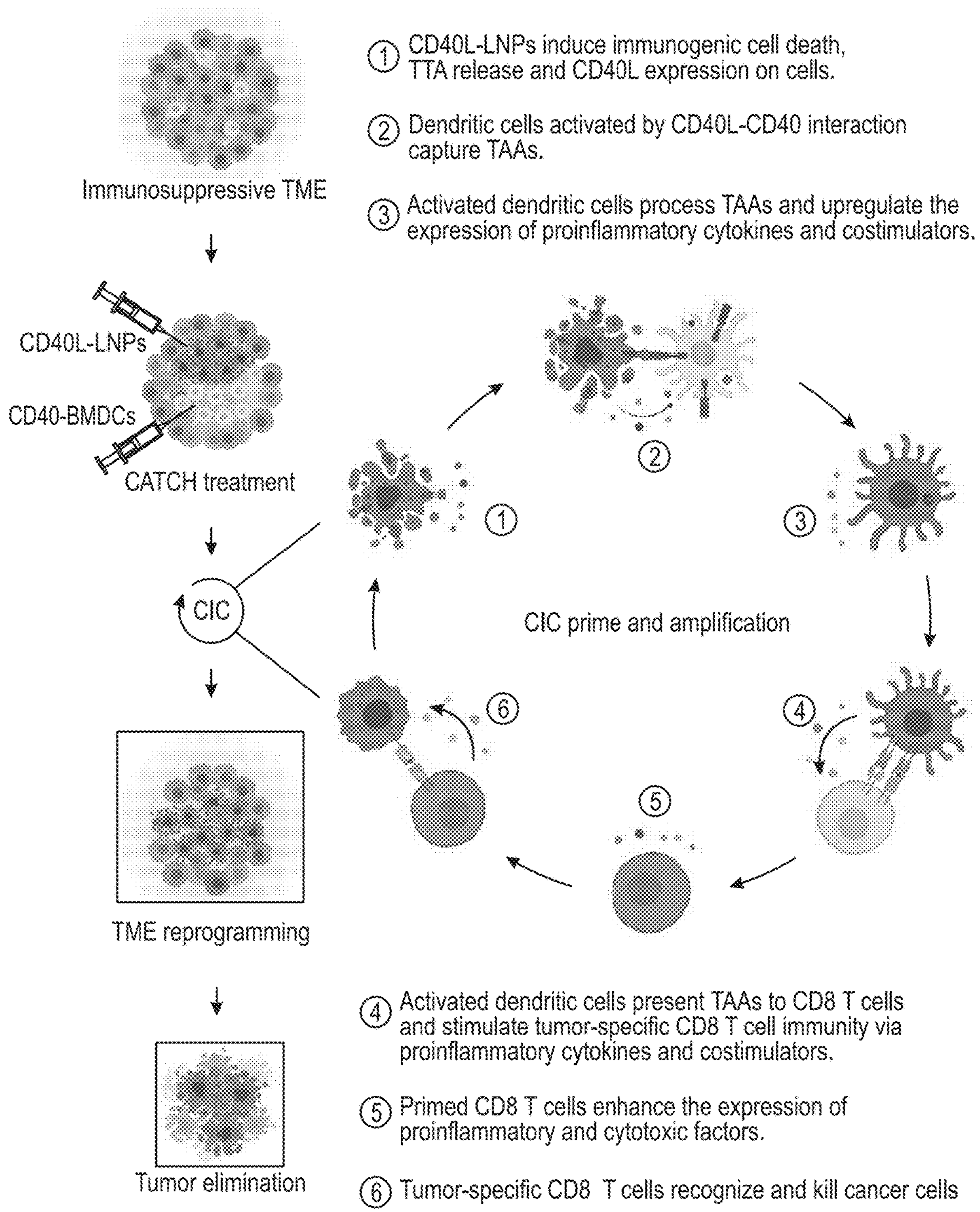
FIGS. 1A-1C. Closing the Cancer Immunity Cycle (CIC) and chemical sythesis of sugar alcohols-derived ionizable lipids. a, Illustration of closing the CIC by integrating lipid nanoparticles and cell therapy (CATCH). b, A representative synthetic route for sugar alcohols-derived ionizable lipids. c Structures of sugar alcohols-derived ionizable lipids (DIS, DIM, and LIS series).

Disclosed herein are compositions and methods which regulate the immune system for treating cancers and other immune disorders.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. in some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK)

promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" or "vector" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%,94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. Administration of the therapeutic agents can be carried out at dosages and for periods of time effective for treatment of a subject.

The term "about" as used herein when referring to a measurable value such as an amount, a percentage, and the like, is meant to encompass variations of ±20%, ±10%, ±5%, or ±1% from the measurable value.

A nucleic acid sequence is "heterologous" to a second nucleic acid sequence if it originates from a foreign species, or, if from the same species, is modified by human action from its original form. For example, a heterologous promoter (or heterologous 5' untranslated region (5' UTR)) operably linked to a coding sequence refers to a coding sequence from a species different from that from which the promoter was derived, or, if from the same species, a coding sequence which is different from naturally occurring allelic variants (for example, the 5' UTR or 3' UTR from a different gene is operably linked to a nucleic acid encoding for a co-stimulatory molecule).

The term "nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. In some embodiments, a nanoparticle typically ranges from about 1 nm to about 1000 nm, from about 50 nm and about 500 nm, from about 50 nm and about 350 nm, from about 100 nm and about 250 nm, or from about 110 nm and about 150 nm.

"Therapeutically effective amount" or "therapeutically effective dose" of a composition refers to an amount that is effective to achieve a desired therapeutic result. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

As used herein, the term "preventing" a disease, a disorder, or unwanted physiological event in a subject refers to the prevention of a disease, a disorder, or unwanted physiological event or prevention of a symptom of a disease, a disorder, or unwanted physiological event "Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the term "therapeutic agent" is used, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

As used herein, the term "controlled-release" or "controlled-release drug delivery" or "extended release" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

The phrases "concurrent administration", "administration in combination", "simultaneous administration" or "administered simultaneously" as used herein, means that the compounds are administered at the same point in time or immediately following one another.

The term "polypeptide" refers to a compound made up of a single chain of D- or L-amino acids or a mixture of D- and L-amino acids joined by peptide bonds.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the att. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or antigen binding fragment thereof" or "antibody or fragments thereof" encompasses chimeric antibodies and hybrid antibodies, with dual or multiple antigen or epitope specificities, and fragments, such as F(ab')2, Fab', Fab, Fv, sFv, scFv and the like, including hybrid fragments. Thus, fragments of the antibodies that retain the ability to bind their specific antigens are provided. For example, fragments of antibodies which maintain binding activity are included within the meaning of the term "antibody or antigen binding fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of "antibody or antigen binding fragment thereof" are conjugates of antibody fragments and antigen binding proteins (single chain antibodies). Also included within the meaning of "antibody or antigen binding fragment thereof" are immunoglobulin single variable domains, such as for example a nanobody.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" refers to a single or double stranded polymer composed of nucleotide monomers.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C{=}C(Z^3Z^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alky, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C═O.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)$O^-$.

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula $—NO_2$.

The term "silyl" as used herein is represented by the formula $—SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula $—S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH—$.

The term "phosphonyl" is used herein to refer to the phospho-oxo group represented by the formula $—P(O)(OZ^1)_2$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

In some aspects, disclosed herein is a compound having Formula I, II, or III:

Formula I

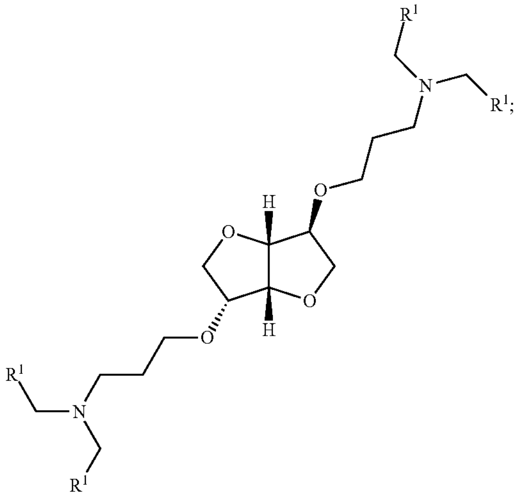

Formula II

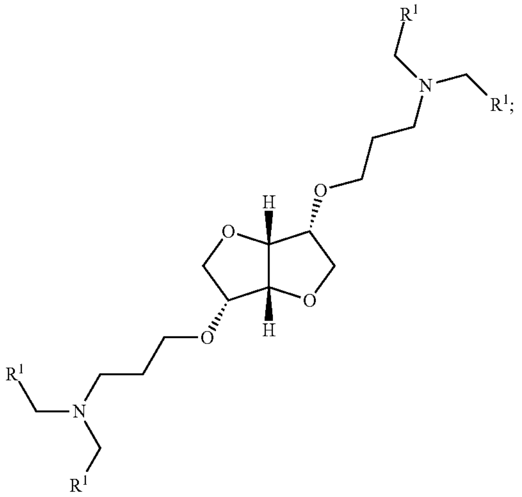

-continued

Formula III

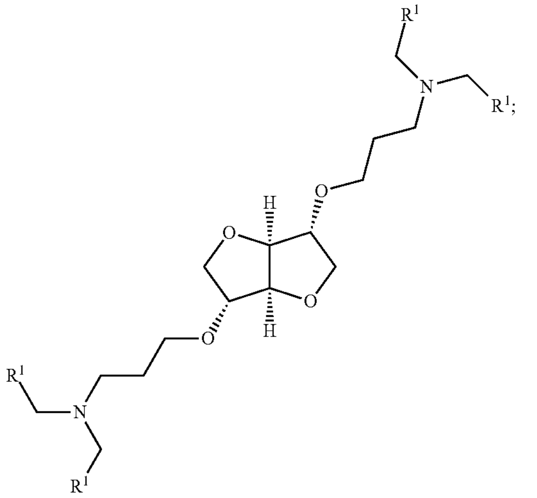

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

In some embodiments, the compound has the formula:

Formula I

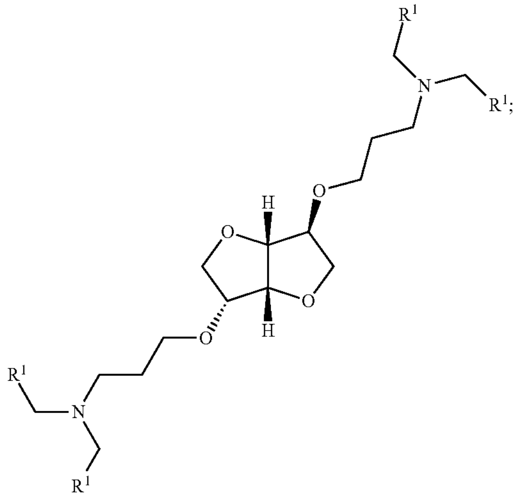

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

In some embodiments, the compound has the formula:

Formula II

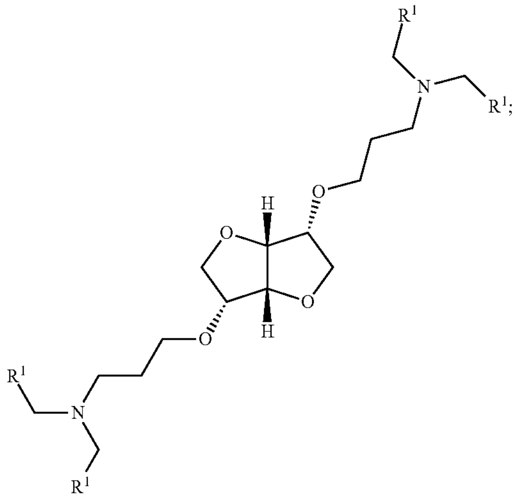

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisuifide, and oxime ether.

In some embodiments, the compound has the formula:

Formula III

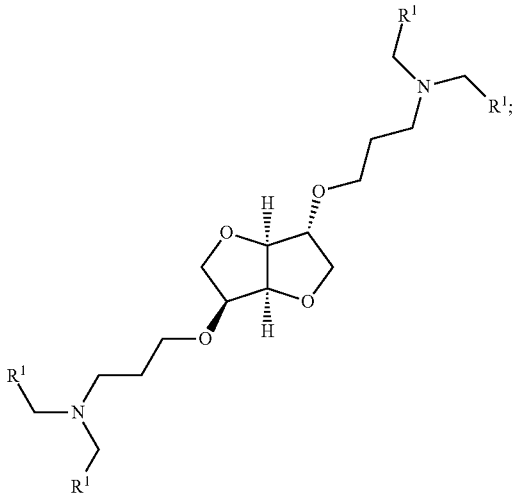

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

In some embodiments, $R^1$ is selected from the following:

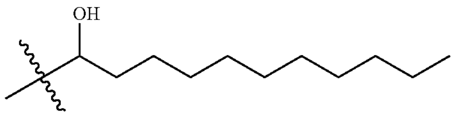

,

-continued
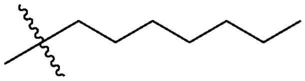
,
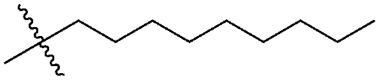
,
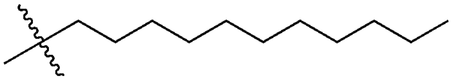
,
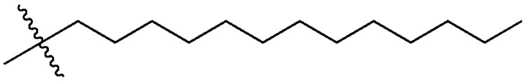
,
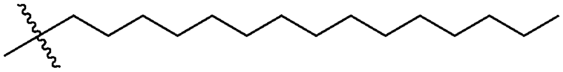
,
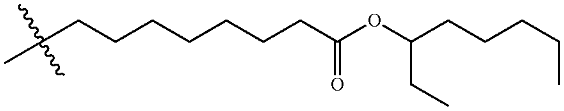
,
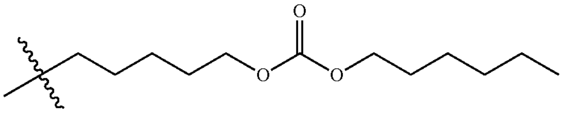
,
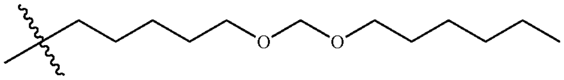
,
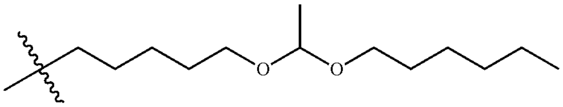
,
or a salt thereof.
In some embodiments, $R^1$ is
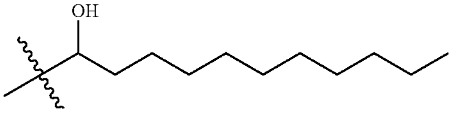
.
In some embodiments, $R^1$ is
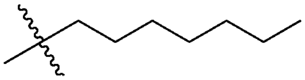
.
In some embodiments, $R^1$ is
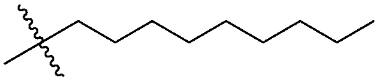
.
In some embodiments, $R^1$ is
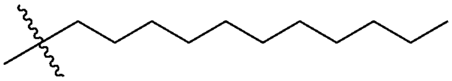
.
In some embodiments, $R^1$ is
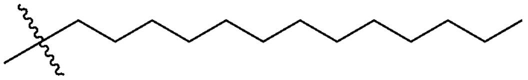
.
In some embodiments, $R^1$ is
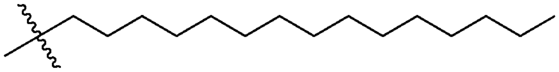
.
In some embodiments, $R^1$ is
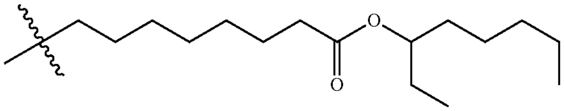
.
In some embodiments, $R^1$ is
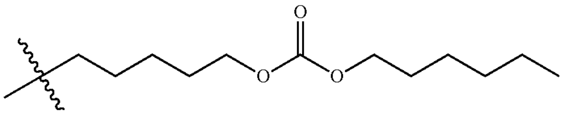
.
In some embodiments, $R^1$ is
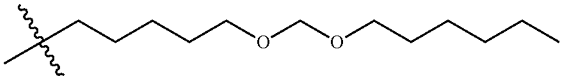
.
In some embodiments, $R^1$ is
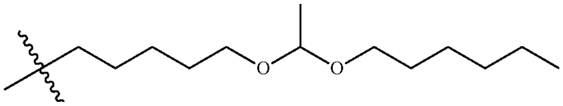
.

In some embodiments, the compound is

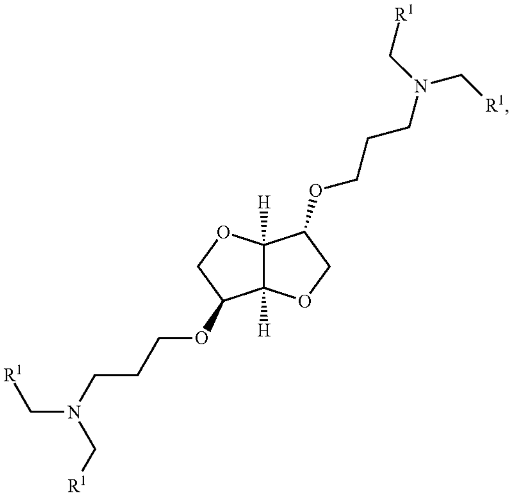

wherein $R^1$ is

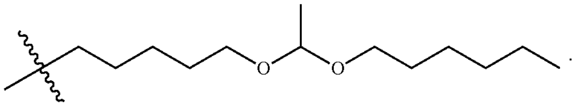 [SMILES: *CCCCCOC(C)OCCCCCC]

In some embodiments, the compound is

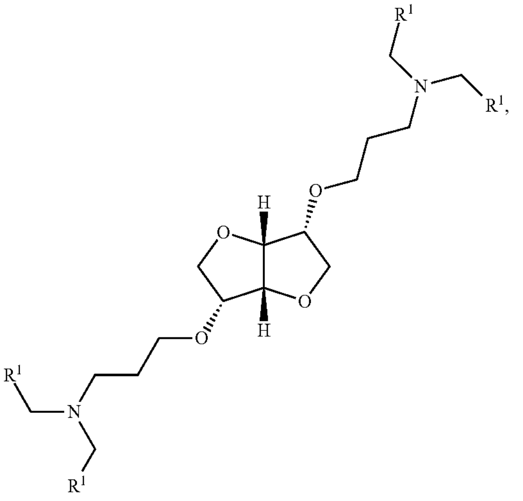

wherein $R^1$ is

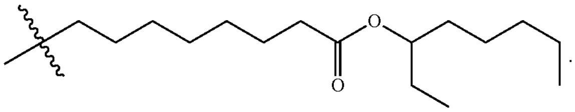 [SMILES: *CCCCCCCC(=O)OC(CC)CCCCC]

In some embodiments, the compound is

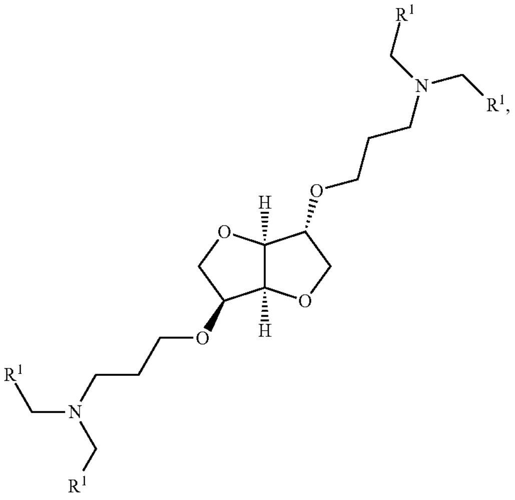

wherein each $R^1$ is

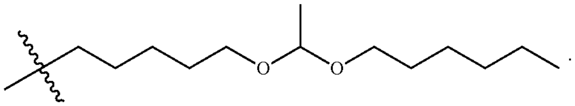 [SMILES: *CCCCCOC(C)OCCCCCC]

In some embodiments, the compound is

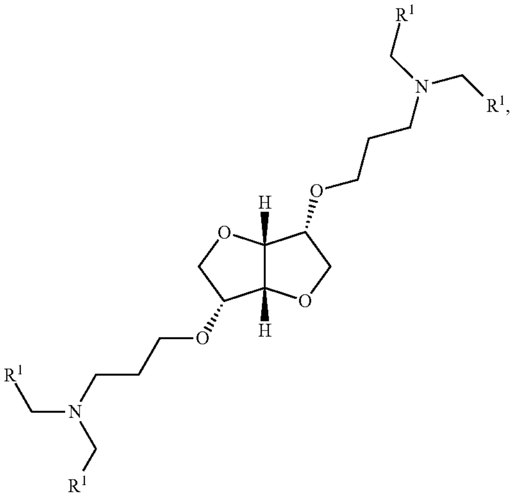

wherein each $R^1$ is

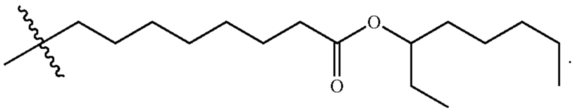 [SMILES: *CCCCCCCC(=O)OC(CC)CCCCC]

In some embodiments, $R^1$ is alkyl. In some embodiments, $R^1$ is alkenyl. In some embodiments, $R^1$ is alkenyl. In some embodiments, $R^1$ is hydroxyl. In some embodiments, $R^1$ is ester. In some embodiments, $R^1$ is ether. In some embodiments, $R^1$ is carbonate. In some embodiments, $R^1$ is alkylalcohol. In some embodiments, $R^1$ is alkylether. In some embodiments, $R^1$ is alkylester. In some embodiments, $R^1$ is carbamate. In some embodiments, $R^1$ is urea. In some embodiments, $R^1$ is guanidine. In some embodiments, $R^1$ is disulfide. In some embodiments, $R^1$ is amide. In some embodiments, $R^1$ is acetal. In some embodiments, $R^1$ is ketal. In some embodiments, $R^1$ is thioketal. In some embodiments, $R^1$ is trisulfide. In some embodiments, $R^1$ is oxime ether.

In some embodiments, each $R^1$ is alkyl. In some embodiments, each $R^1$ is alkenyl. In some embodiments, each $R^1$ is alkynyl. In some embodiments, each $R^1$ is hydroxyl. In some embodiments, each $R^1$ is ester. In some embodiments, each $R^1$ is ether. In some embodiments, each $R^1$ is carbonate. In some embodiments, each $R^1$ is alkylalcohol. In some embodiments, each $R^1$ is alkylether. In some embodiments, each $R^1$ is alkylester. In some embodiments, each $R^1$ is carbamate. In some embodiments, each $R^1$ is urea. In some embodiments, each $R^1$ is guanidine. In some embodiments, each $R^1$ is disulfide. In some embodiments, each $R^1$ is amide. In some embodiments, each $R^1$ is acetal. In some embodiments, each $R^1$ is ketal. In some embodiments, each $R^1$ is thioketal. In some embodiments, each $R^1$ is trisulfide. In some embodiments, each $R^1$ is oxime ether.

In some embodiments, the alkyl is a branched alkyl. In some embodiments, the alkyl is an unbranched alkyl.

In some embodiments, the alkyl is a $C_5$alkyl. In some embodiments, the alkyl is a $C_6$alkyl. In some embodiments, the alkyl is a $C_7$alkyl. In some embodiments, the alkyl is a $C_8$alkyl. In some embodiments, the alkyl is a $C_9$alkyl. In some embodiments, the alkyl is a $C_{10}$alkyl. In some embodiments, the alkyl is a $C_{11}$alkyl. In some embodiments, the alkyl is a $C_{12}$alkyl. In some embodiments, the alkyl is a $C_{13}$alkyl. In some embodiments, the alkyl is a $C_{14}$alkyl. In some embodiments, the alkyl is a $C_{15}$alkyl. In some embodiments, the alkyl is a $C_{16}$alkyl. In some embodiments, the alkyl is a $C_{17}$alkyl. In some embodiments, the alkyl is a $C_{18}$alkyl. In some embodiments, the alkyl is a $C_{19}$alkyl.

Nanoparticles

In one aspect, the disclosure provides a nanoparticle comprising: a compound of Formula I, II, or III described herein.

The various compounds of Formula I, II, or III are described in the Compounds section above. In some embodiments, the nanoparticle comprises a compound of I, II, or III in a molar ratio of about 1% to about 99%. In some embodiments, the nanoparticle comprises a compound of I, II, or III in a molar ratio of about 10% to about 80%. In some embodiments, the nanoparticle comprises a compound of I, II, or III in a molar ratio of about 10% to about 40%. In some embodiments, the nanoparticle comprises a compound of Formula I, II, or III in a molar ratio of about 10%, about 15%, about 20%, about 25%, about 30%, about 35%, or about 40%. In one embodiment, the nanoparticle comprises a compound of Formula I, II, or III in a molar ratio of about 20%.

In some embodiments, the nanoparticle comprises a non-cationic lipid. In some embodiments, the non-cationic lipid interacts with the lipids as a helper lipid. In some embodiments, the non-cationic lipid can include, but is not limited to, 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), DPPC (1,2-dipalmitoyl-sn-glycero-3-phosphocholine), 1,2-dioleyl-sn-glycero-3-phosphotidylcholine (DOPC), 1,2-dipalmitoyl-sn-glycero-3-phosphoethanolamine (DPPE), 1,2-dimyristoyl-sn-glycero-3-phosphoethanolamine (DMPE), 1,2-dioleoyl-5/7-glycero-3-phospho-(1'-rac-glycerol) (DOPG), or combinations thereof. In one embodiment, the non-cationic lipid is 1,2-dioleoyl-sn-glycero-3-phosphoethanolamine (DOPE). In one embodiment, the non-cationic lipid is 1-palmitoyl-2-oleoyl-sn-glycero-3-phosphoethanolamine (POPE), In one embodiment, the non-cationic lipid is 1,2-distearoyl-sn-glycero-3-phosphocholine (DSPC). In one embodiment, the non-cationic lipid is 1-stearoyl-2-oleoyl-sn-glycero-3-phosphoethanolamine (SOPE). While several non-cationic lipids are described here, additional non-cationic lipids can be used in combination with the compounds disclosed herein.

In some embodiments, the nanoparticle comprises a non-cationic lipid in a molar ratio of about 10% to about 80%. In some embodiments, the nanoparticle comprises a non-cationic lipid in a molar ratio of about 10% to about 40%. In some embodiments, the nanoparticle comprises a non-cationic lipid in a molar ratio of about 10%, about 15%, about 20%, about 25%, about 30%, about 35%, or about 40%. In one embodiment, the nanoparticle comprises a non-cationic lipid in a molar ratio of about 30%.

In some embodiments, the nanoparticle includes a polyethylene glycol-lipid (PEG-lipid). PEG-lipid is incorporated to form a hydrophilic outer layer and stabilize the particles. Nonlimiting examples of polyethylene glycol-lipids include PEG-modified lipids such as PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DMG-PEG, DLPE-PEGs, DMPE-PEGs, DPPC-PEGs, and DSPE-PEGs. In one embodiment, the polyethylene glycol-lipid is 1,2-dimyristoyl-sn-glycerol, methoxypolyethylene glycol (DMG-PEG). In one embodiment, the polyethylene glycol-lipid is 1,2-dimyristoyl-sn-glycerol, methoxypolyethylene glycol-2000 (DMG-PEG2000). DMG-PEGXXXX means 1,2-dimyristoyl-sn-glycerol, methoxypolyethylene glycol-XXXX, wherein XXXX signifies the molecular weight of the polyethylene glycol moiety, e.g. DMG-PEG2000 or DIM-PEG5000.

In some embodiments, the nanoparticle comprises a polyethylene glycol-lipid in a molar ratio of about 0% to about 5%. In some embodiments, the nanoparticle comprises a polyethylene glycol-lipid in a molar ratio of about 0%, about 0.25%, about 0.5%, about 0.75%, about 1%, about 1.5%, about 2%, about 3%, about 4%, or about 5%. In one embodiment, the nanoparticle comprises a polyethylene glycol-lipid in a molar ratio of about 0.75%.

In some embodiments, the nanoparticle includes a sterol. Sterols are well known to those skilled in the art and generally refers to those compounds having a perhydrocyclopentanophenanthrene ring system and having one or more OH substituents. Examples of sterols include, but are not limited to, cholesterol, campesterol, ergosterol, sitosterol, and the like.

In some embodiments, the sterol is selected from a cholesterol-based lipid. In some embodiments, the one or more cholesterol-based lipids are selected from cholesterol, PEGylated cholesterol, DC-Choi (N,N-dimethyl-N-ethylcarboxamidocholesterol), 1,4-bis(3-N-oleylamino-propyl) piperazine, or combinations thereof.

The sterol can be used to tune the particle permeability and fluidity base on its function in cell membranes. In one embodiment, the sterol is cholesterol.

In some embodiments, the nanoparticle comprises a sterol in a molar ratio of about 25% to about 50%. In some embodiments, the nanoparticle comprises a sterol in a molar ratio of about 25%, about 30%, about 35%, about 40%, about 45%, or about 50%. In one embodiment, the nanoparticle comprises a sterol in a molar ratio of about 40%.

In one embodiment, the nanoparticle further comprises an agent. In one embodiment, the nanoparticle further comprises a therapeutic agent. In one embodiment, the nanoparticle further comprises a diagnostic agent.

In some embodiments, the nanoparticle comprises one of the formulations as described in FIG. 2F. In some embodiments, the nanoparticle comprises the molar ratios of components (Lipid, DOPE, Cholesterol, and PEG) as disclosed in FIG. 2F. In some embodiments, the nanoparticle comprises one of the formulations as described in FIG. 7A. In some embodiments, the nanoparticle comprises the molar ratios of components (Lipid, DOPE, Cholesterol, and PEG) as disclosed in FIG. 7A.

The agents delivered into cells can be a polynucleotide. Polynucleotides or oligonucleotides that can be introduced according to the methods herein include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA) and combinations thereof. The polynucleotides can also be DNA constructs, such as expression vectors, expression vectors encoding a desired gene product (e.g., a gene product homologous or heterologous to the subject into which it is to be introduced), and the like. In one embodiment, the agent is an mRNA. In some embodiments, the polynucleotide is encapsulated by the nanoparticle.

In some embodiments, polynucleotide comprises a nucleotide acid encoding a co-stimulatory molecule. In some embodiments, the co-stimulatory molecule is selected from ICOS, CD28, CD27, HVEM, LIGHT, CD40L, 4-1BB, OX40, DR3, GITR, CD30, SLAM, CD2, CD226, Galectin9, TIM1, LFA1, B7-H2, B7-1, B7-2, CD70, LIGHT, HVEM, CD40, 4-1BBL, OX40L, TL1A, GITRL, CD30L, SLAM, CD48, CD58, CD155, CD112, CD80 CD86, ICOSL, TIM3, TIM4, ICAM1, and LFA3. In some embodiments, the co-stimulatory molecule is CD40. In some embodiments, the co-stimulatory molecule is CD40L.

The sequences for the co-stimulatory molecules include, for example (for human sequences): ICOS (NCBI Reference Sequence: NM_012092.3), CD28 (NCBI Reference Sequence: NM_006139.4), CD27 (NCBI Reference Sequence: NM_001242.4), HVEM (NCBI Reference Sequence: NM_003820.3), LIGHT (NCBI Reference Sequence: NM_003807.4), CD40L (NCBI Reference Sequence: NM_000074.2), 4-1BB (NCBI Reference Sequence: NM_001561.5), OX40 (NCBI Reference Sequence: NM_003327.4), DR3 (NCBI Reference Sequence: NM_148965.1), GITR (NCBI Reference Sequence: NM_004195.3), CD30 (GenBank: M83554.1), SLAM (NCBI Reference Sequence: NM_003037.4), CD2 (NCBI Reference Sequence: NM_001328609.1), CD226 (NCBI Reference Sequence: NM_006566.3), Galectin-9 (GenBank: AB040130.2), TIM1 (GenBank: U02082.1), B7-H2 (NCBI Reference Sequence: NM_015259.5), B7-1 (NCBI Reference Sequence: NM_005191.4), B7-2 (NCBI Reference Sequence: NM_175862.5), CD70 (NCBI Reference Sequence: NM_001252.5), CD40 (NCBI Reference Sequence: NM_001250.5), 4-1BBL (NCBI Reference Sequence: NM_003811.4), OX40L (NCBI Reference Sequence: NM_003326.5), TL1A (NCBI Reference Sequence: NM_005118.4), GITRL (GenBank: AY358868.1), CD30L (NCBI Reference Sequence: NM_001244.3), SLAM (GenBank: U33017.1), CD48 (NCBI Reference Sequence: NM_001778.4), CD58 (NCBI Reference Sequence: NM_001779.3), CD155 (NCBI Reference Sequence: NM_006505.5), CD112 (NCBI Reference Sequence: NM_001042724.2), TIM3 (GenBank: AF450242.1), TIM4 (NCBI Reference Sequence: NM_138379.3), ICAM1 (NCBI Reference Sequence: NM_00201.3).

In some embodiments, the mRNA encoding the co-stimulatory molecule comprises a heterologous 5' untranslated region (5'UTR). In some embodiments, the mRNA encoding the co-stimulatory molecule comprises a heterologous 3' untranslated region (3'UTR).

In some embodiments, the nucleic acids (for example, the mRNA encoding the co-stimulatory molecule) disclosed herein comprise at least one chemically modified nucleotide. In some embodiments, the at least one chemically modified nucleotide comprises a chemically modified nucleobase, a chemically modified ribose, a chemically modified phosphodiester linkage, or a combination thereof.

In one embodiment, the at least one chemically modified nucleotide is a chemically modified nucleobase.

In one embodiment, the chemically modified nucleobase is selected from 5-formylcytidine (5fC), 5-methylcytidine (5meC), 5-methoxycytidine (5moC), 5-hydroxycytidine (5hoC), 5-hydroxymethylcytidine (5hmC), 5-formyluridine (5fU), 5-methyluridine (5-meU), 5-methoxyuridine (5moU), 5-carboxymethylesteruridine (5camU), pseudouridine (Ψ), $N^1$-methylpseudouridine ($me^1Ψ$), $N^6$-methyladenosine ($me^6A$), or thienoguanosine ($^{th}G$).

In some embodiments, the chemically modified nucleobase is 5-methoxyuridine (5moU). In some embodiments, the chemically modified nucleobase is pseudouridine (Ψ). In some embodiments, the chemically modified nucleobase is $N^1$-methylpseudouridine ($me^1Ψ$).

The structures of these modified nucleobases are shown below:

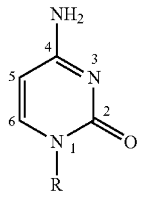

Cytidine
(C)

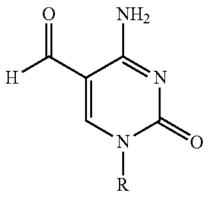

5-formylcytidine
(5fC)

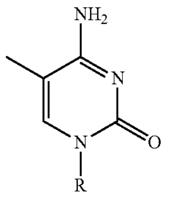

5-methylcytidine
(5meC)

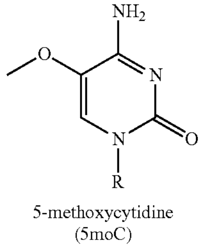

5-methoxycytidine
(5moC)

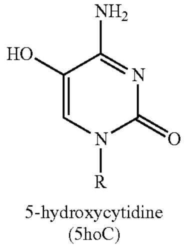

5-hydroxycytidine
(5hoC)

-continued

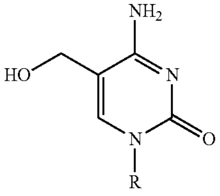

5-hydroxymethyl-cytidine (5hmC)

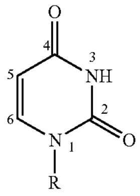

Uridine (U)

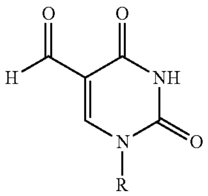

5-formyluridine (5fU)

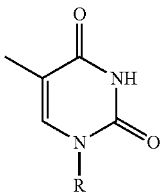

5-methyluridine (5meU)

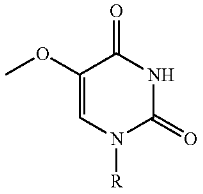

5-methoxy-uridine (5moU)

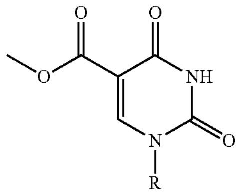

5-carboxy-methyl-esteruridine (5camU)

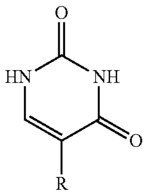

pseudouridine (Ψ)

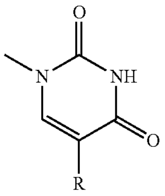

N1-methylpseudo-uridine (me1 Ψ)

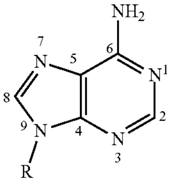

Adenoise (A)

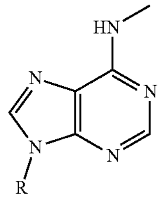

N6 Methyladenosine (me6A)

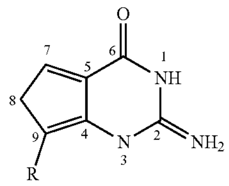

Guanosine (G)

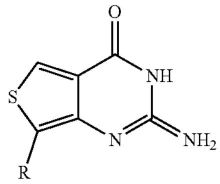

Thienoguanosine (thG)

R = ribose

In one embodiment, the at least one chemically modified nucleotide is a chemically modified ribose.

In one embodiment, the chemically modified ribose is selected from 2'-O-methyl (2'-O-Me), 2'-Fluoro (2'-F), 2'-deoxy-2'-fluoro-beta-D-arabino-nucleic acid (2'F-ANA), 4'-S, 4'-SFANA, 2'-azido, UNA, 2'-O-methoxy-ethyl (2'-O-ME), 2'-O-Allyl, 2'-O-Ethylamine, 2'-O-Cyanoethyl, Locked nucleic acid (LAN), Methylene-cLAN, N-MeO-amino BNA, or N-MeO-aminooxy BNA. In one embodiment, the chemically modified ribose is 2'-O-methyl (2'-O-Me). In one embodiment, the chemically modified ribose is 2'-Fluoro (2'-F).

The structures of these modified riboses are shown below:

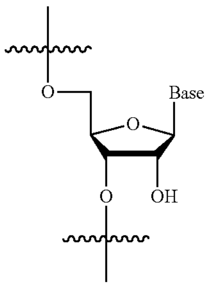

Ribose

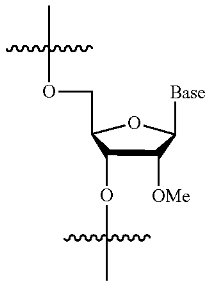

2'-O-methyl (2'-O-Me)

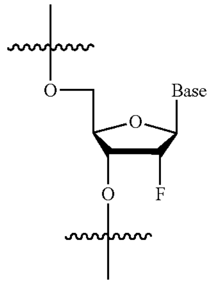

2'-Fluoro (2'-F)

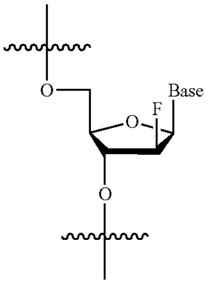

2'-deoxy-2'-fluoro-beta-D-arabino-nucleic acid (2'F-ANA)

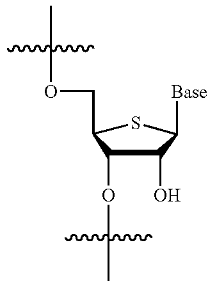

4'-S

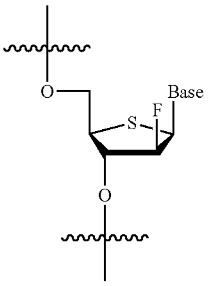

4'-SFANA

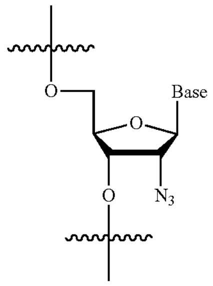

2'-azido

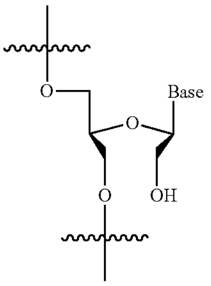

UNA

-continued

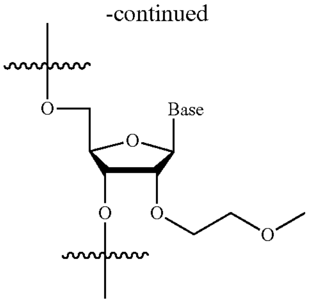

2′-O-methoxy-ethyl
(2′-O-ME)

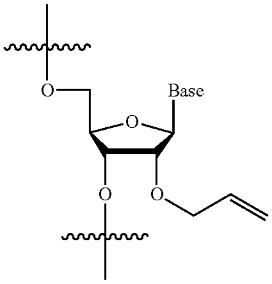

2′-O-Allyl

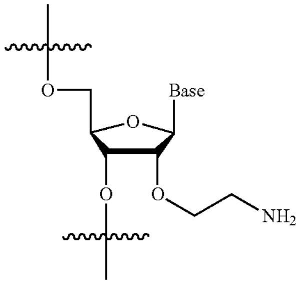

2′-O-Ethylamine

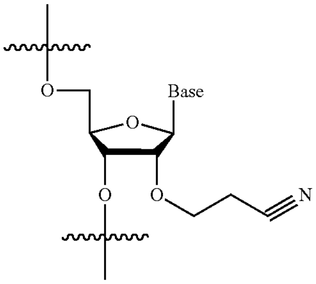

2′-O-Cyanoethyl

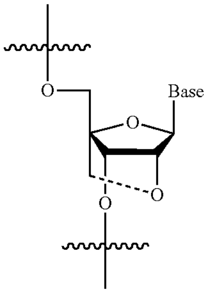

Locked nucleic acid
(LAN)

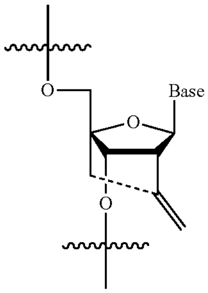

Methylene-cLAN

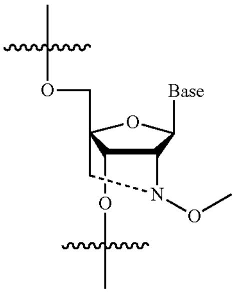

N-MeO-amino
BNA

-continued

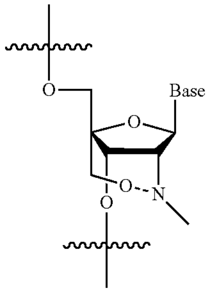

N-MeO-aminooxy
BNA

In one embodiment, the at least one chemically modified nucleotide is a chemically modified phosphodiester linkage.

In one embodiment, the chemically modified phosphodiester linkage is selected from phosphorothioate (PS), boranophosphate, phosphodithioate (PS2), 3',5'-amide, N3'-phosphoramidate (NP), Phosphodiester (PO), or 2',5'-phosphodiester (2',5'-PO). In one embodiment, the chemically modified phosphodiester linkage is phosphorothioate.

The structures of these modified phosphodiester linkages are shown below:

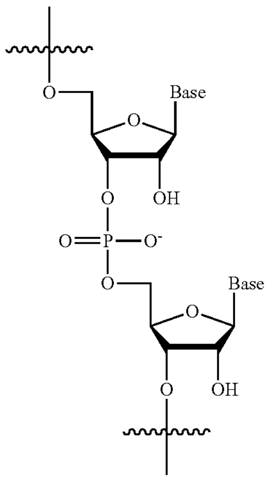

Phosphodiester (PO)

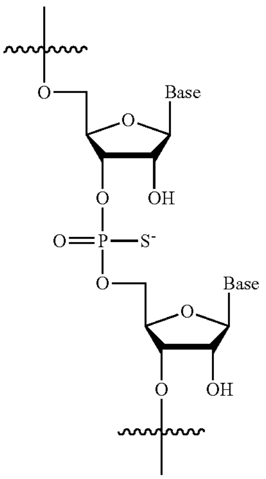

Phosphorothioate (PS)

-continued

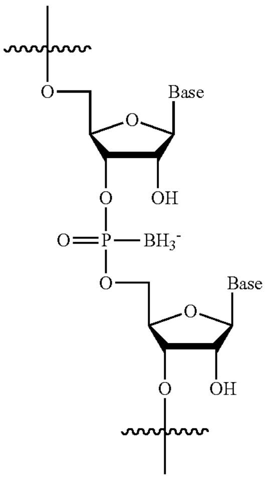

Boranophosphate

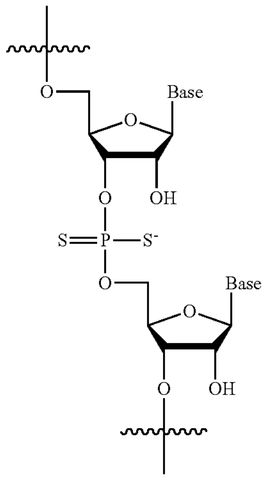

Phosphodithioate (PS)

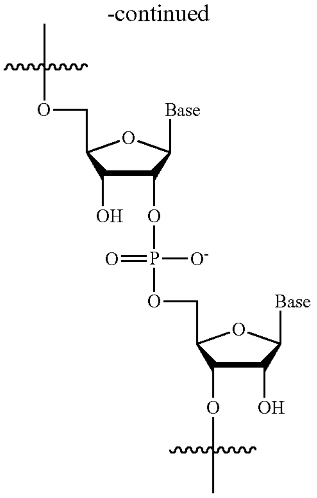

2′,5′-phosphodiester (2′,5′-PO)

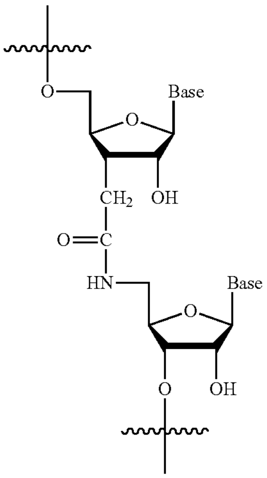

3′,5′-amide

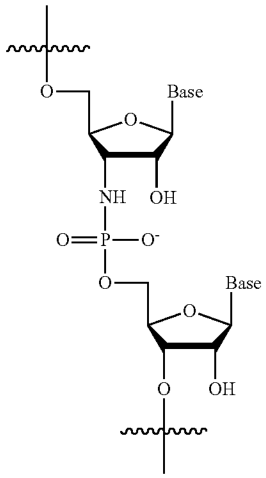

N3′-phosphoramidate (NP)

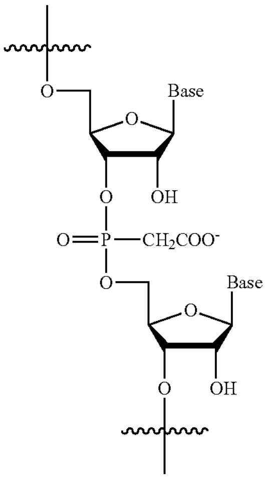

Phosphodiester (PO)

-continued

Antigen Presenting Cells

In some aspects, disclosed herein is an antigen presenting cell, comprising: the lipid-based nanoparticle disclosed herein, comprising: the compound of any preceding aspect and a recombinant polynucleotide comprising a nucleic acid encoding a co-stimulatory molecule.

In some embodiments, the compound is

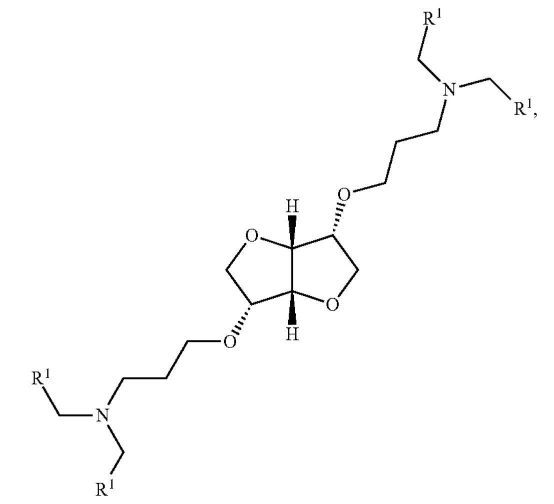

wherein $R^1$ is

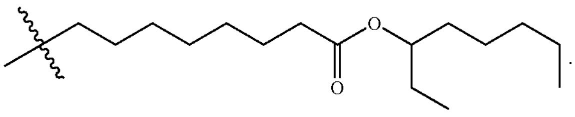 [SMILES: *CCCCCCCC(=O)OC(CC)CCCCC]

In some embodiments, the co-stimulatory molecule is selected from ICOS, CD28, CD27, HVEM, LIGHT, CD40L, 4-1BB, OX40, DR3, CD30, SLAM, CD2, CD226, Galectin9, TIM1, LFA1, B7-H2, B7-1, B7-2, CD70, LIGHT, HVEM, CD40, 4-1BBL, OX40L, TL1A, GITRL, CD30L, SLAM, CD48, CD58, CD155, CD112, CD80, CD86, ICOSL, TIM3, TIM4, ICAM1, and LFA3. In some embodiments, the co-stimulatory molecule is CD40.

In some embodiments, the antigen presenting cell comprises a macrophage or a dendritic cell.

It should be understood that the term "antigen presenting cells" or "APCs" used herein refers to a heterologous group of immune cells that can process and present antigens for stimulating responses of certain lymphocytes (e.g., T cells and B cells). Classical APCs include, for example, dendritic cells, macrophages, B cells, and neutrophils.

It is understood herein that macrophages are commonly known as phagocytosing immune cells (Meszaros et al, 1999). They also secrete factors such as chemokines or cytokines. In addition to phagocytosis and antigen presentation, these cells may play a supportive role through a varied repertoire of plasma membrane and secreted molecules (Gordon 1995, *BioEssays*, Volume 17, Issue 11), as previously shown for erythroblasts, hepatocytes and neurons (Sadahira & Morr, *Pathol Int.* 1999 October; 49(10):841-8,) (Takeishi, Hirano, et al. *Arch Histol Cytol.* 1999 December; 62(5):413-22.) (Polazzi, Gianni, et al. *Glia.* 2001 December; 36(3):271-80.). By "macrophages" is meant cells exhibiting properties usually described for macrophages, including phagocytosis, expression of defined cell surface markers such as CD64, CD14 and HLA-DR antigen expression. Macrophages according to the invention can be isolated from tissues or preferentially by ex vivo differentiation from blood monocytes (also referred herein as "monocyte-derived macrophage"), bone marrow precursor cells (also referred herein as "bone marrow-derived macrophage") or from any other possible precursor, and by using any differentiation method, precursors and methods being known by any person skilled in the art. Accordingly, in some embodiments, the macrophage comprises a bone marrow-derived macrophage. In some embodiments, the macrophage comprises a monocyte-derived. macrophage. In some embodiments, the macrophage comprises an iPSC-derived macrophage. In some embodiments, the macrophage comprises a macrophage cell line, including, for example, RAW264.7, THP-1, U937, IC-21, J774A.1, MV-4-11, or KG1.

It should be also understood herein that "dendritic cell" or "DC", as used herein, refers to a type of antigen presenting cell, which is typically identified by the expression of one or more of the following markers on its cell surface: CD1a, CD1b, and CD1c, CD4, CD11c, CD33, CD40, CD80, CD86, CD83 and HLA-DR. In some embodiments, the dendritic cell is a mature DC. In some embodiments, the dendritic cell is an immature DC. DCs according to the invention can be isolated from tissues or preferentially by ex vivo differentiation from blood monocytes (also referred herein as "monocyte-derived dendritic cell"), bone marrow precursor cells (also referred herein as "bone marrow-derived dendritic cell") or from any other possible precursor, and by using any differentiation method, precursors and methods being known by any person skilled in the art. Accordingly, in some embodiments, the dendritic cell comprises a bone marrow-derived dendritic cell, In some embodiments, the dendritic cell comprises a monocyte-derived dendritic cell. In some embodiments, the dendritic cell comprises an iPSC-derived dendritic cell. In some embodiments, the dendritic cell is a conventional dendritic cell 1 (or cDC1, lymphoid DC), which is typically identified by the expression of one or more of the following markers on its cell surface: CD141, CLEC9A, and XCR1. In some embodiments, the dendritic cell is a conventional dendritic cell 2 (or cDC2, myeloid DC), which is typically identified by the expression of one or more of the following markers on its cell surface: CD1c and CD172a. In some embodiments, the dendritic cell is plasmacytoid DC (or pDC), which is typically identified by the expression of one or more of the following markers on its cell surface: CD123, CD303, and CD304.

In some aspects, disclosed herein is method of expressing a polypeptide in an antigen presenting, comprising administering an effective amount of the nanoparticle disclosed herein to an antigen presenting cell, wherein the nanoparticle comprises a recombinant polynucleotide comprising a nucleic acid encoding the polypeptide.

Compositions and Methods

In some aspects, disclosed herein is a method of treating a cancer comprising administering to a subject in need thereof a therapeutically effective amount of the antigen presenting cell disclosed herein and an antibody.

In some embodiments, the antibody is selected from an anti-CD40 antibody, an anti-PDL1 antibody, an anti-PD1 antibody, an anti-CTLA4 antibody, or a combination thereof.

In some embodiments, the antibody or antigen binding fragment thereof that specifically binds a co-stimulatory molecule is BMS 986178. In some embodiments, the antibody or antigen binding fragment thereof that specifically binds a co-stimulatory molecule is GSK3174998. In sonic embodiments, the antibody or antigen binding fragment thereof that specifically binds a co-stimulatory molecule is PF-04518600. In some embodiments, the antibody or antigen binding fragment thereof that specifically binds a co-stimulatory molecule is MOXR0916. In some embodiments, the antibody or antigen binding fragment thereof that specifically binds a co-stimulatory molecule is PF-04518600. In some embodiments, the antibody or antigen binding fragment thereof that specifically binds a co-stimulatory molecule is MEDI6383. In some embodiments, the antibody or antigen binding fragment thereof that specifically binds a co-stimulatory molecule is MEDI0562. In sonic embodiments, the antibody or antigen binding fragment thereof that specifically binds a co-stimulatory molecule is INCAGN01949. In some embodiments, the antibody or antigen binding fragment thereof that specifically binds a co-stimulatory molecule is InVivoPlus anti-mouse OX40 (done OX-86) (Company: BioXcell, Catalog: BP0031).

Additional antibodies or antigen binding fragments thereof that specifically bind a co-stimulatory molecule can include, for example: for mouse, InVivoPlus anti-mouse 4-1BB (CD137) (clone LOB12.3) (Company: BioXcell, Catalog: BP0169), InVivoPlus anti-mouse CD40 (clone FGK4.5/FGK45) (Company: BioXcell, Catalog: BP0016-2); for human, anti-human OX40, BMS 986178, GSK3174998, PF-04518600, MOXR0916, PF-04518600, MEDI6383, MFDI0562, INCAGN01949; anti-human 4-1BB, Utomilumab, Urelumab; anti-human CD40, CP-870893, APX005M, ADC-1013, JNJ-64457107, SEA-CD40, RO7009789.

In some embodiments, the antigen presenting cell and the antibody are administered intratumorally.

In some aspects, disclosed herein is a method of treating a cancer comprising administering to a subject in need thereof:

a therapeutically effective amount of the lipid-based nanoparticle disclosed herein, and a therapeutically effective amount of the antigen presenting cell disclosed herein.

In some embodiments, the lipid-based nanoparticle comprises

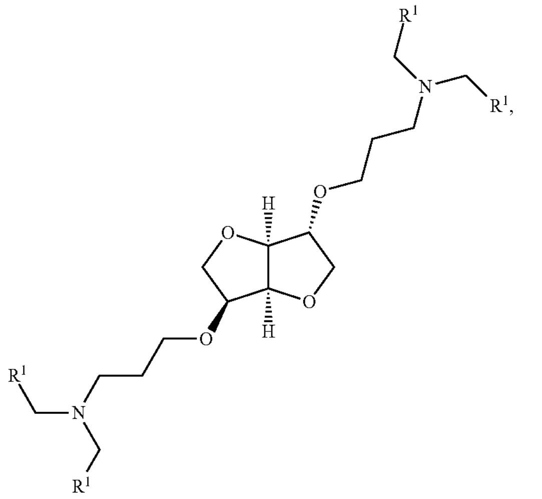

wherein $R^1$ is

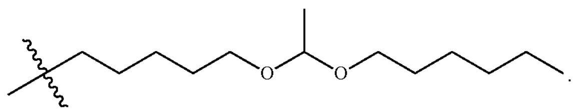 [SMILES: *CCCCCOC(C)OCCCCCC]

In some embodiments, the lipid-based nanoparticle comprises a recombinant polynucleotide comprising a nucleic acid encoding CD40L.

In one aspect, the methods described herein are used to treat cancer, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Sugar Derived Lipid Nanoparticles

Effective cancer immunotherapy depends on the initiation, procession, and amplification of the Cancer-Immunity Cycle (CIC). However, the CIC is usually blocked by the immunosuppressive factors in the tumor microenvironment (TME), resulting in tumor promotion, metastasis, and recurrence. Here, lipid nanoparticle-mRNA formulations and dendritic cell therapy were combined to sufficiently boost the CIC via multiple steps. First, lipid nanoparticles containing CD40 ligand (CD40L) mRNA induce robust immunogenic cell death in tumoral tissues, leading to the release of tumor-associated antigens (TAAs) and the expression of CD40L. Next, CD40-overexpressed dendritic cells are adoptively transferred, which are then activated by the CD40L molecules in tumoral tissues. This promotes the secretion of pro-inflammatory cytokines and chemokines, and the upregulation of costimulatory molecules on dendritic cells, which are crucial for reprogramming the TME and priming T cell responses. After dendritic cells present TAAs to T cells, all the above stepwise events contribute to boosting a potent cancer-specific T cell immunity that eradicates established cutaneous tumors, suppresses distal lesions, and prevents tumor rechallenge. Overall, this work provides closure of the Cancer-Immunity Cycle (CIC) in mouse melanoma models by integrating lipid nanoparticles and cell therapy (CATCH) and to promote tumor elimination and construct long-term antitumor immunity.

Introduction

The development of immunotherapy has made significant breakthroughs for the clinical outcomes of cancer treatment. Effective antitumor immunity depends on appropriately activating a series of responses in the Cancer-Immunity Cycle (CIC)[1]. Firstly, dying cancer cells release tumor-associated antigens (TAAs) that are captured and processed by antigen presenting cells (APCs) such as dendritic cells[1]. Next, APCs present the antigens to T cells, leading to the priming of effector T cell responses against TAAs[1]. The activated effector T cells infiltrate into tumoral tissues and mediate the killing of cancer cells[1]. Lastly, dead cancer cells further release antigens to increase the breadth and depth of these immune responses in the CIC[1]. However, these stepwise events are usually dampened by the immunosuppressive tumor microenvironment (TME), resulting in uncontrollable tumor growth, metastasis, and recurrence[1,2]. For example, the immunosuppressive TME can inhibit dendritic cell recruitment, infiltration, and maturation[1,2]. This reduces dendritic cells' secretion of cytokines and expression of costimulators that are crucial for priming T-cell immunity[1,2].

Here, it was investigated whether synergistically inducing the death of cancer cells to release TAAs and improving the number and maturation of dendritic cells in tumoral tissues have the potential to appropriately boost the CIC. This may further prime systemic and memory antitumor immunity, leading to the eradication of primary tumor, inhibition of tumor metastasis, and prevention of tumor relapse. Immunogenic cell death (ICD), a cell death modality, is accompanied by the emission of damage-associated molecular patterns (DAMPs) and TAAs[3,4]. Recent studies have revealed that lipid nanoparticles (LNPs) with the ability to induce ICD can remodel the TME, resulting in enhanced antitumor immunity[5]. CD40 and CD40 ligand (CD40L) are a pair of costimulatory molecules that belong to the tumor necrosis factor/tumor necrosis factor receptor family[6]. The interaction between CD40 on dendritic cells and CD40L oil CD4 T cells is crucial for dendritic cell maturation, which promotes the secretion of proinflammatory cytokines and the upregulation of other costimulatory molecules[6]. These play central roles in triggering CD8 T cells to develop cytotoxic and memory responses[6]. A few CD40 agonist antibodies have been investigated in clinical trials[6]. Additionally, intratumoural (i.t.) administration of immunotherapeutic agents can improve the in situ bioavailability and, thus, the therapeutic efficiency[7]. Correspondingly, several LNP-mRNA formulations and immune cells delivered via i.t. injection are ongoing in clinical trials[7-10]. In this study, LNPs were utilized containing CD40L mRNA (CD40L-LNPs) to simultaneously induce ICD and CD40L expression in tumoral tissues. Then, i.t. adoptive transfer was performed of CD40-overexpressed bone marrow derived dendritic cells (CD40-BMDCs) that capture TAAs and become matured by the stimulation of CD40L. These activated dendritic cells further present the antigens to T cells, leading to the priming of effector T cell responses against cancer cells (FIG. 1A).

To test this concept, effective delivery of mRNA was needed into tumor cells and primary dendritic cells. Sugar alcohols are carbohydrates that are widely used as sugar substitutes in the food industry, which provide sweet tastes, contain fewer calories, and don't cause blood sugar spikes as compared to regular sugars such as glucose[11]. These compounds are naturally occurring or derived from sugars via the reduction of the carbonyl group to a hydroxy group[12]. Particularly, hexitols, such as sorbitol and mannitol, are six-carbon sugar alcohols that can be double dehydrated to yield dianhydrohexitols, a series of unique cyclic ethers that act as important chemical scaffolds and starting materials[13]. Thus, three sets of sugar alcohols-derived ionizable lipids were designed and synthesized to prepare LNPs for mRNA delivery. To examine these LNPs in bioassays, melanoma was chosen as a disease model. Melanoma is one of the most aggressive skin cancers with an increased morbidity[14]. The main cause of death in melanoma patients is widespread metastasis, such as skin and brain metastasis[14]. Thus, two melanoma cell lines were selected to construct mouse tumor models in this study. After systematic screening and characterization of the sugar alcohols-derived ionizable lipids, two preferred LNP formulations were identified for mRNA delivery. One formulation induced robust ICD in melanoma tumoral tissues, and in the meantime effectively delivered CD40L mRNA into cancer cells. The other formulation showed dramatically higher CD40mRNA delivery efficacy in mouse bone marrow derived dendritic cells (BMDCs) compared with Lipofectamine 3000 (Lipo 3K) and electroporation (Electro). The combination of CD40L-LNP treatment and adoptive CD40-BMDC transfer resulted in more than 80% complete response rate in subcutaneous (s.c.) melanoma tumor models. Moreover, the local treatment enabled the inhibition or elimination of skin and brain tumor metastasis. Importantly, these responder mice were resistant to s.c. rechallenge and showed delayed tumor growth after intracranial rechallenge. In summary, two types of LNP-mRNA formulations were utilized to boost the CIC via inducing ICD and adaptive dendritic cell transfer. This work presents an important immunotherapy strategy that enables broadly efficacious treatment of primary tumor, tumor metastasis, and tumor recurrence.

Results

Figure 1B:
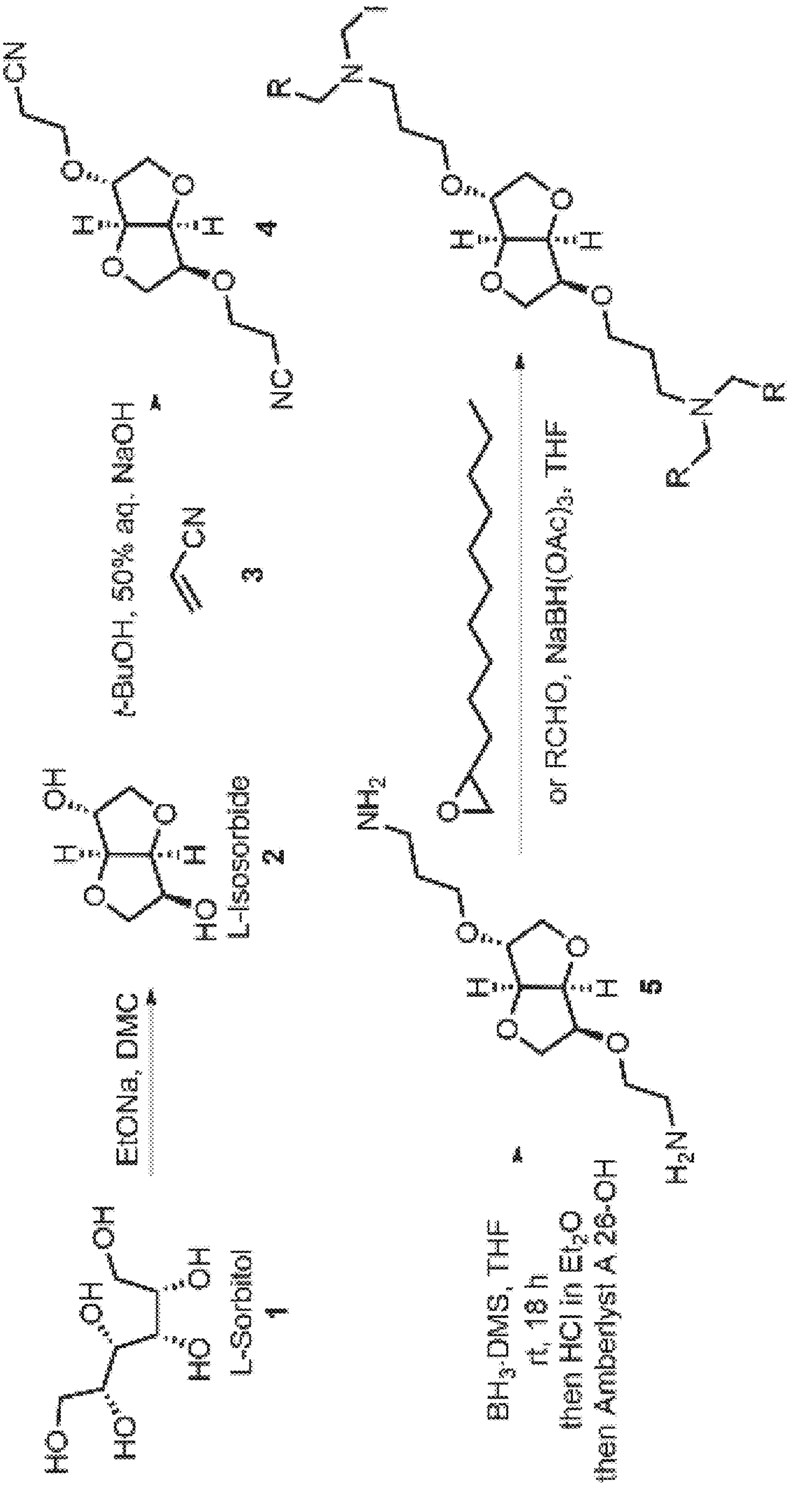
Figure 1C:
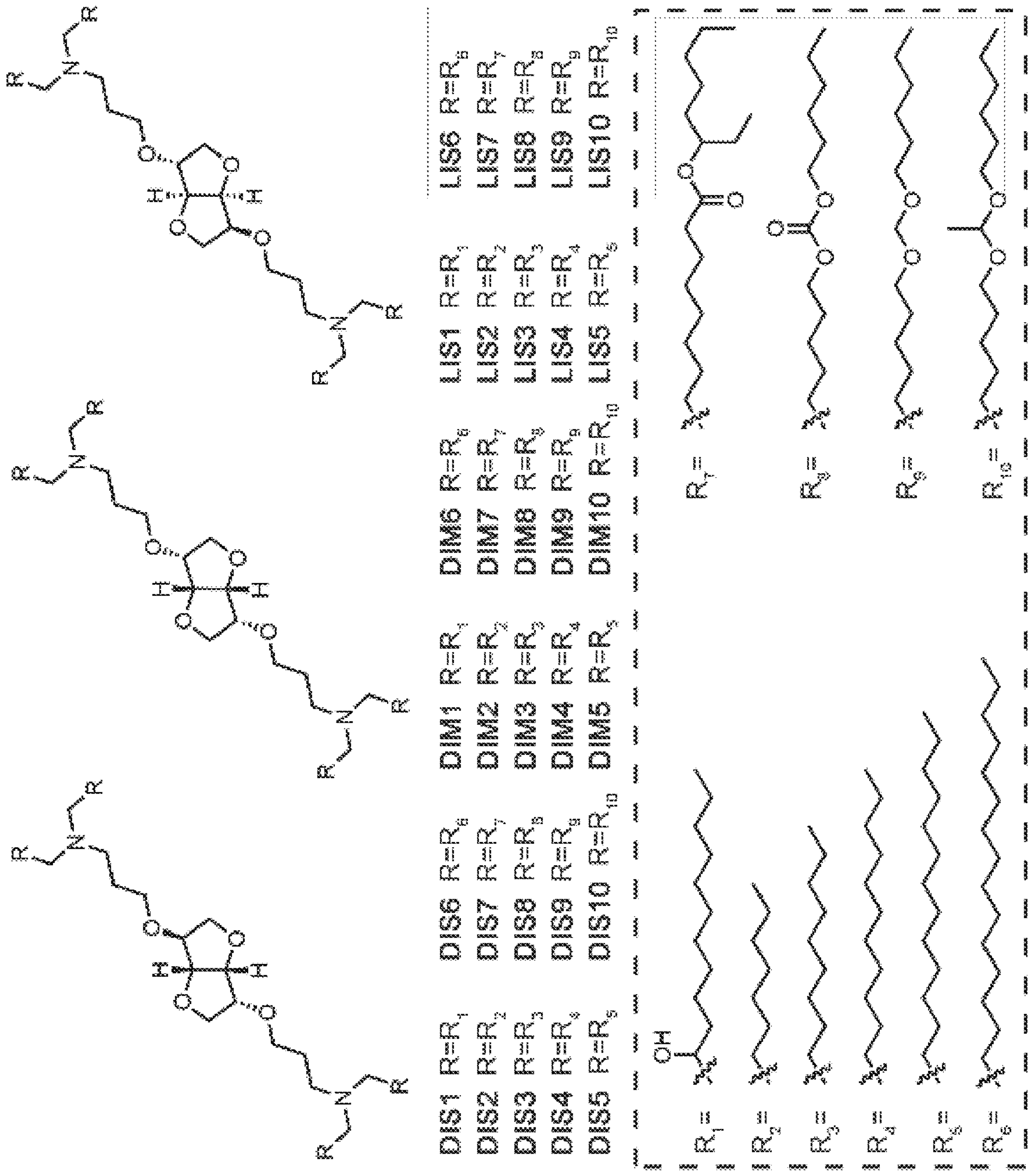

Dianhydrohexitols, such as isosorbide and isomannide, are a series of biologically derived bicyclic compounds prepared by double dehydration of six-carbon sugar alcohols[15]. They are composed of two cis-fused tetrahydrofuran rings with two secondary hydroxy groups situated at the 2- and 5-positions[13]. The different configurations of the two hydroxy groups lead to different reaction reactivities and steric hindrance toward functionalization, thus making dianhydrohexitols versatile bio-based building blocks for the synthesis of pharmaceutically important compounds and polymers[16]. Based on their unique chirality and rigidity, three sets of sugar alcohols-derived ionizable lipids (DIS, DIM, and LIS) were designed and synthesized with sorbitol, mannitol, and L-sorbitol as the precursors, respectively (FIG. 1B, 1C). As a representative synthetic route for LIS lipids (FIG. 1B), L-isosorbide, the enantiomer of isosorbide, was prepared from L-sorbitol in the presence of dimethyl carbonate and sodium ethoxide according to the previously reported dehydration procedure[17]. Then, double Michael addition reaction of L-isosorbide with acrylonitrile followed by reduction of the nitrile groups with borane gave the core amine. Lastly, hydrophobic tails with different functional groups such as hydroxyl (LIS1), hydrocarbon LIS2 to LIS6), ester (LIS7), carbonate ester (LIS8), and acetal (LIS9 and LIS10), were installed via reductive amination reactions or epoxide ring-opening reactions to afford the corresponding ionizable lipids. These diverse hydrophobic domains in lipids affect the formulation of LNPs and their interactions with cell membrane, resulting in different mRNA delivery efficiency. Following similar synthetic routes, DIS and DIM lipids were synthesized, and their structures were confirmed by $^1H$ nuclear magnetic resonance and mass spectroscopy (see methods).

Figure 2A:
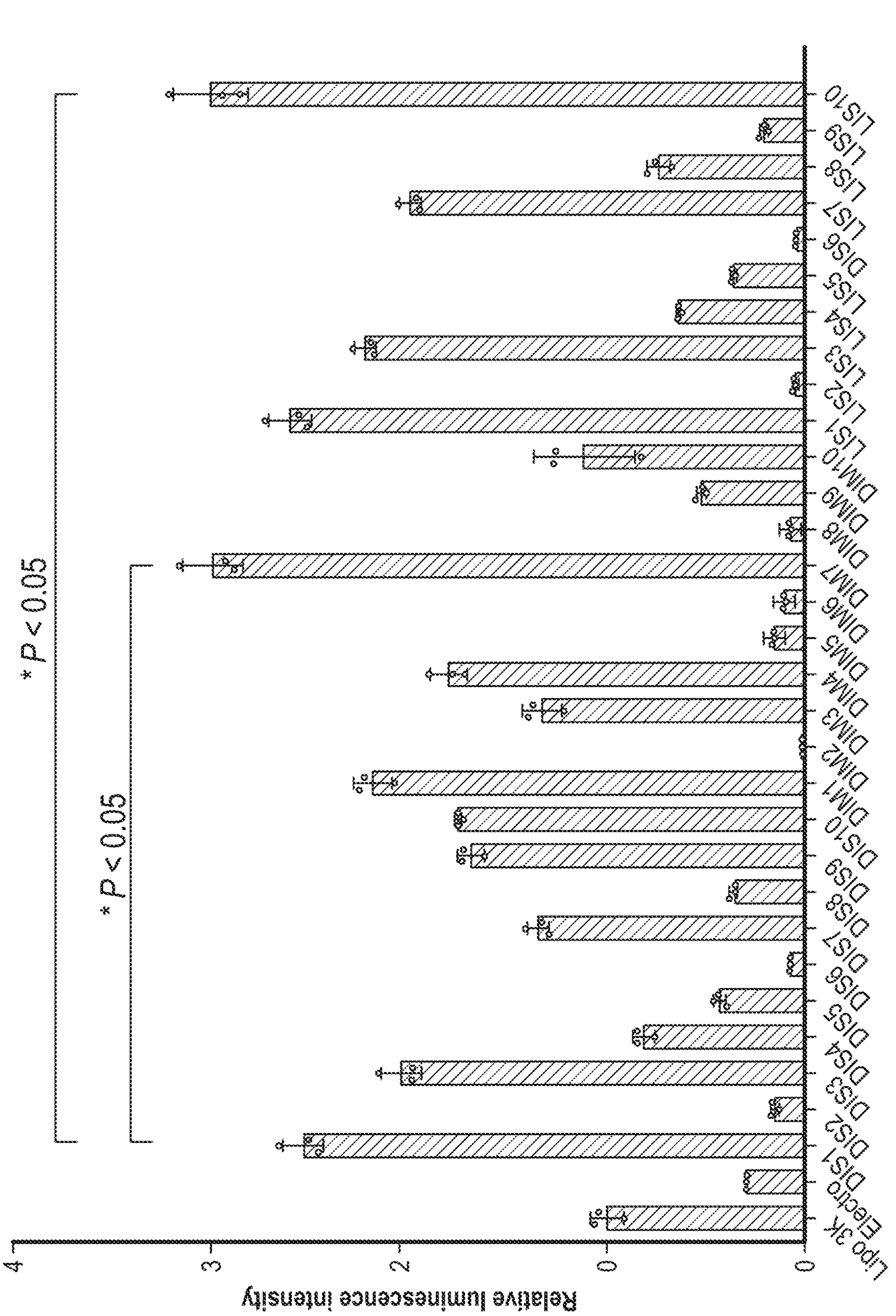
Figure 2B:
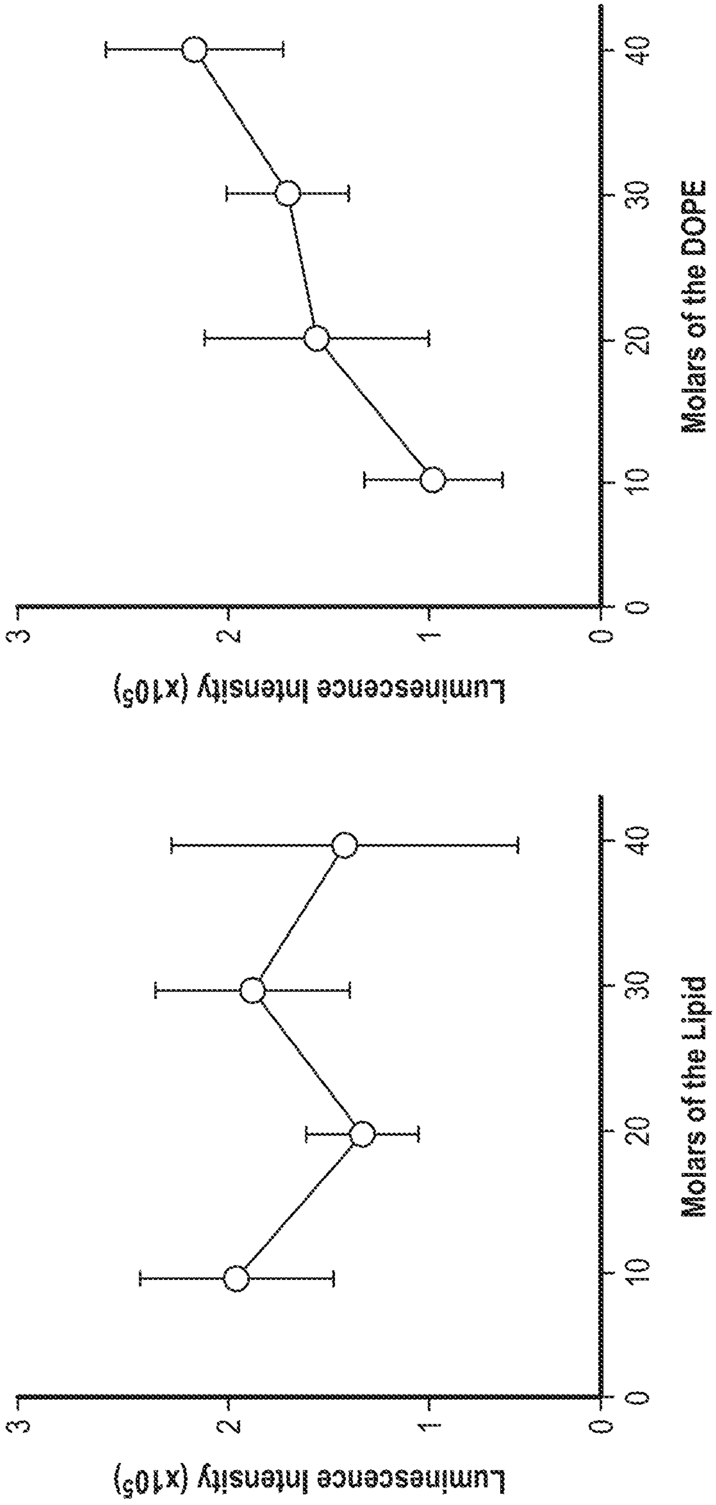
Figure 2C:
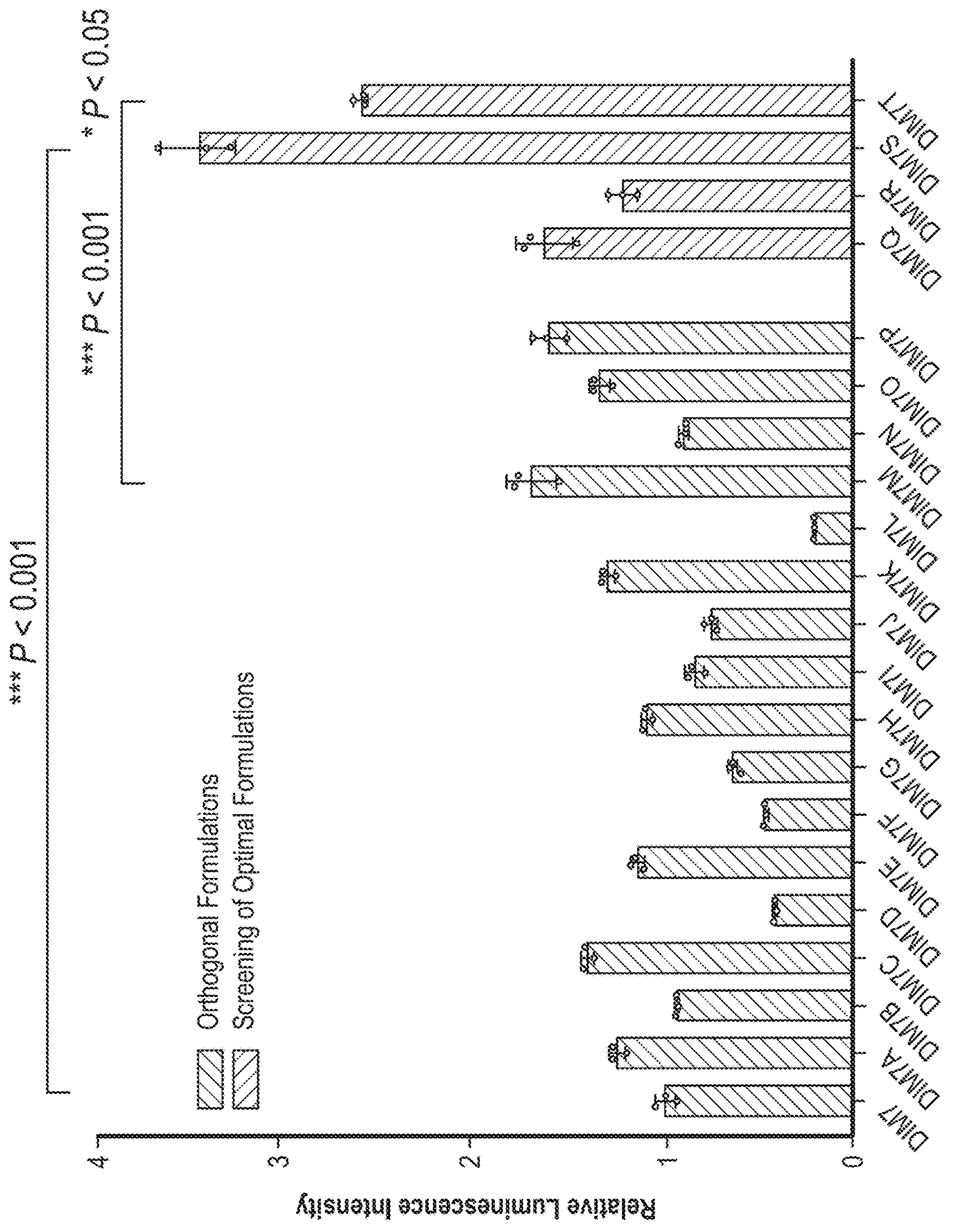
Figure 2D:
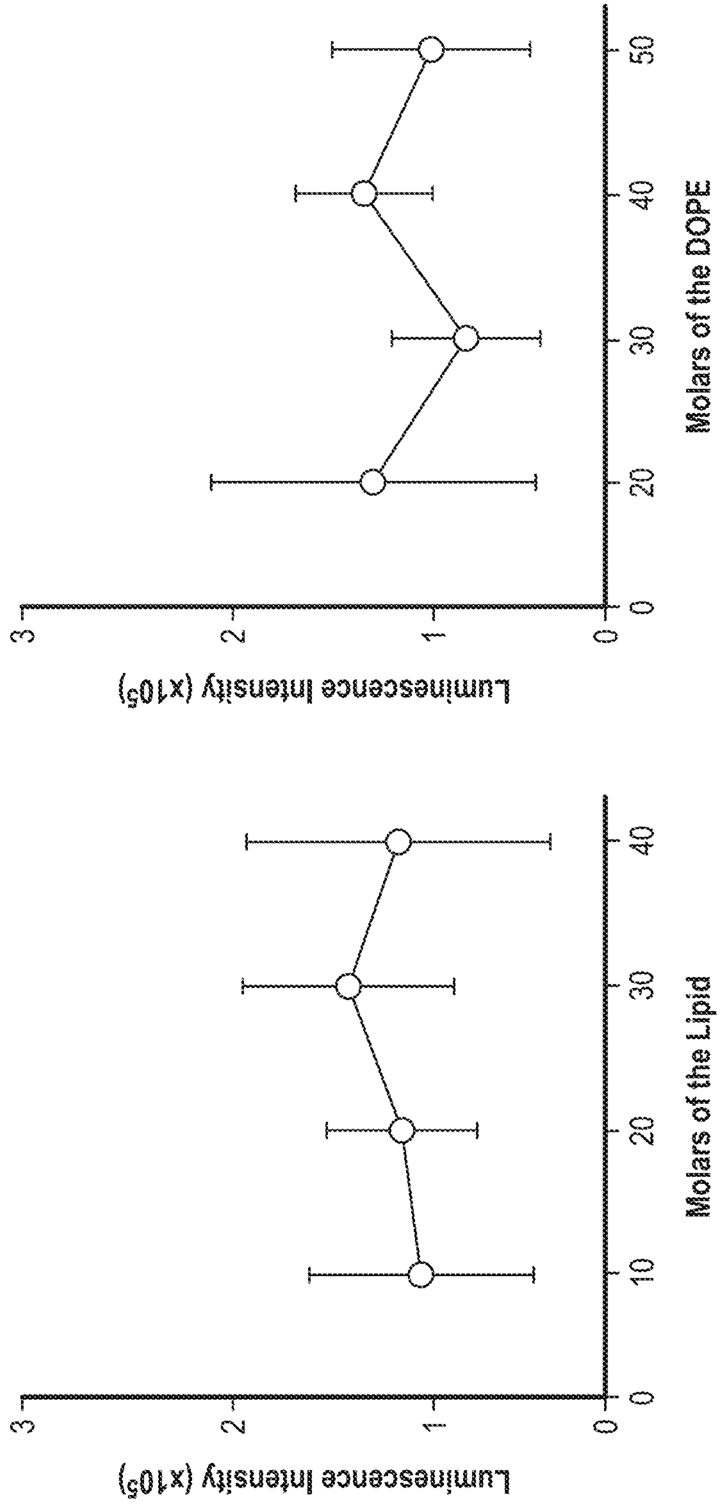
Figure 2E:
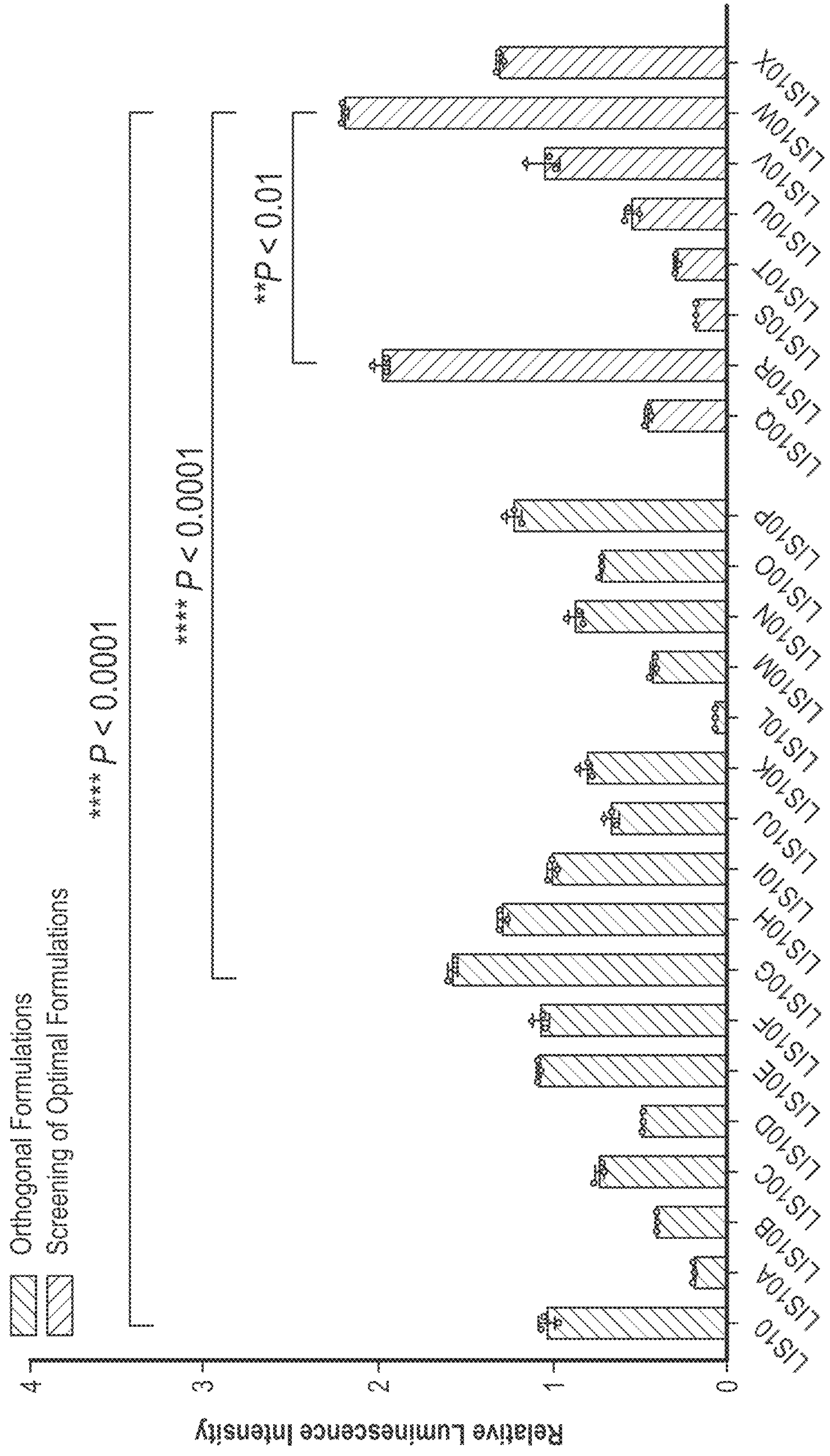
Figure 2G:
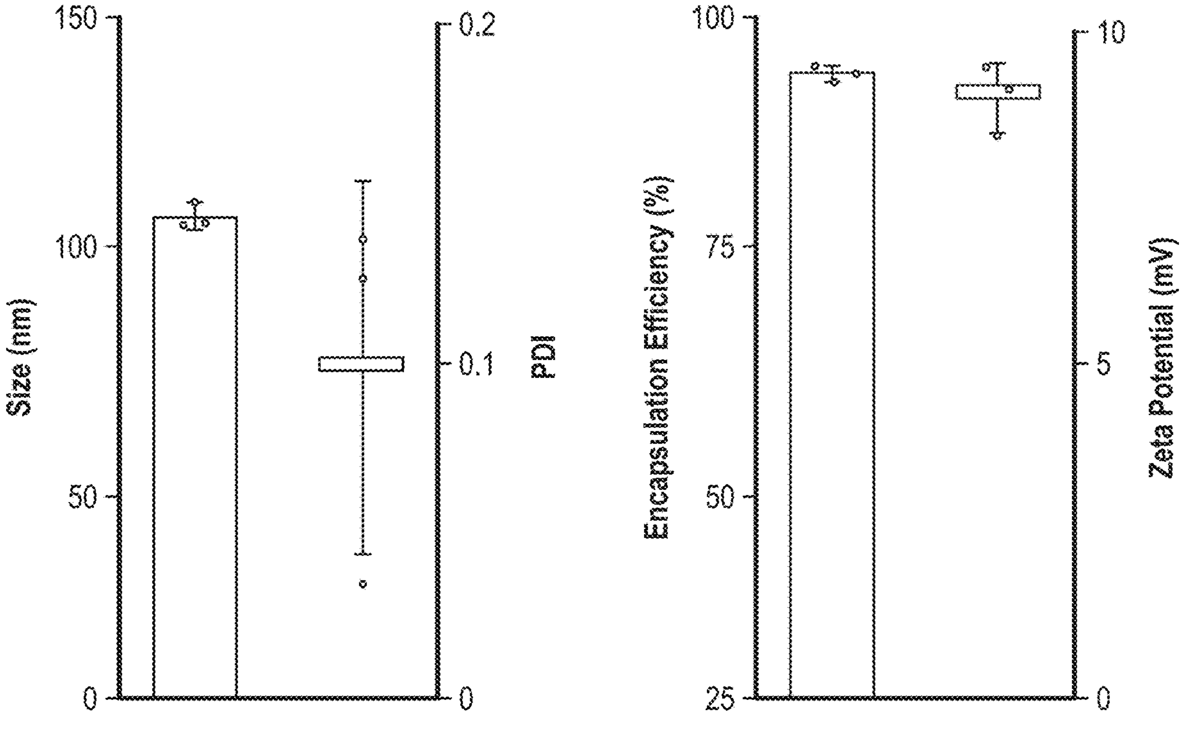
Figure 2H:
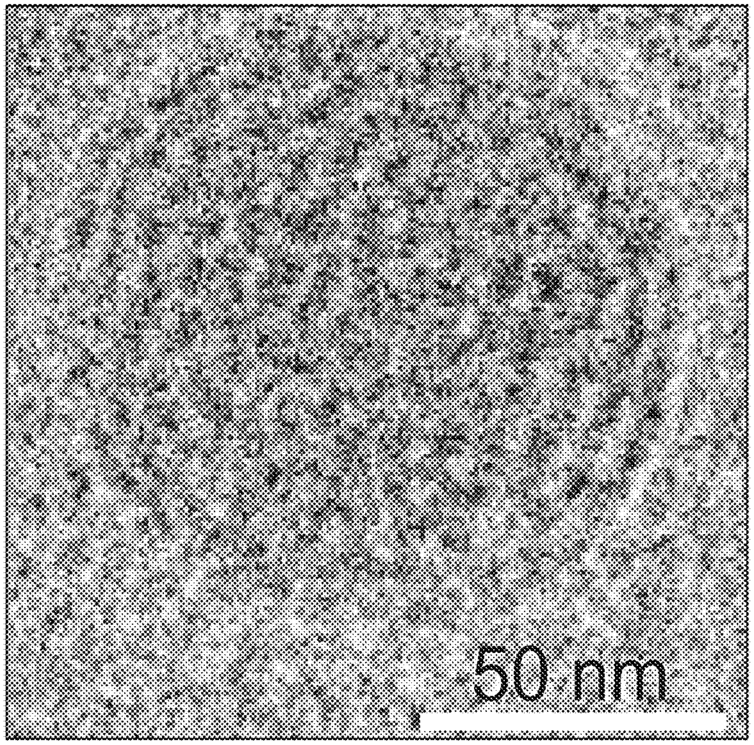
Figure 2I:
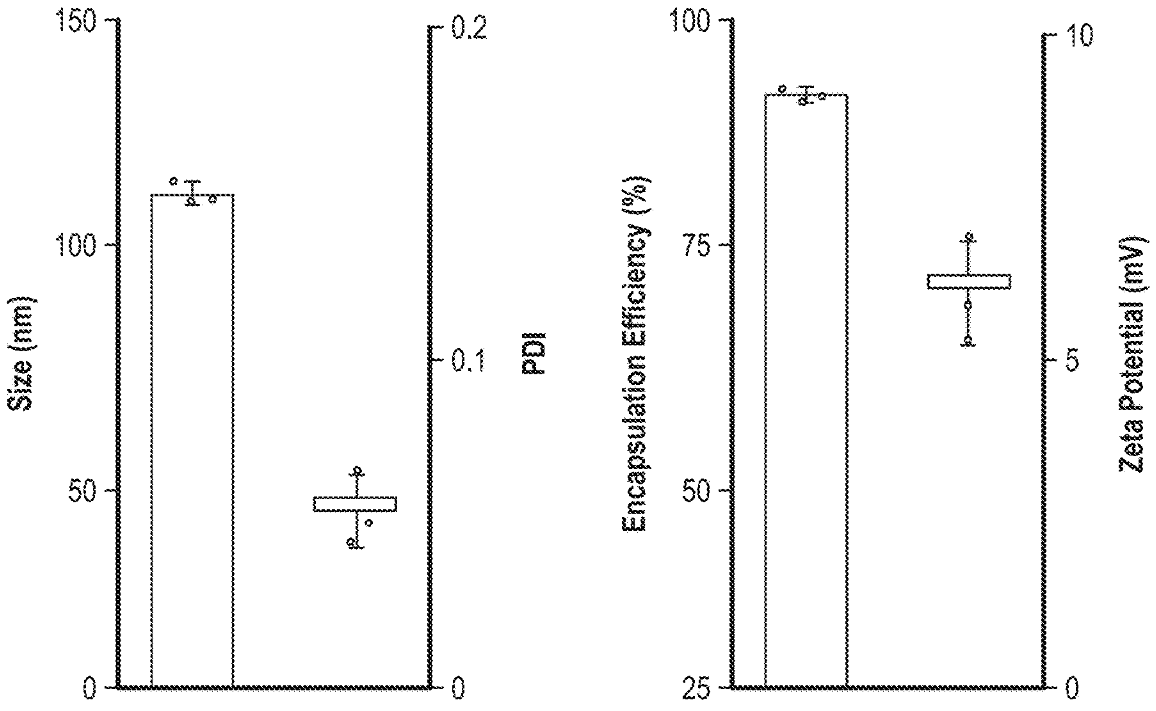
Figure 2J:
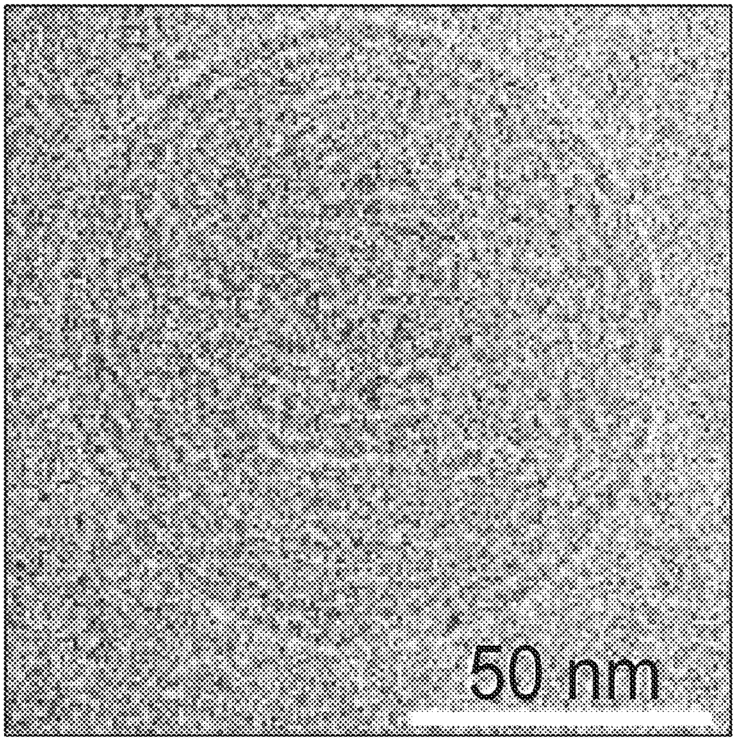
Figure 6A:
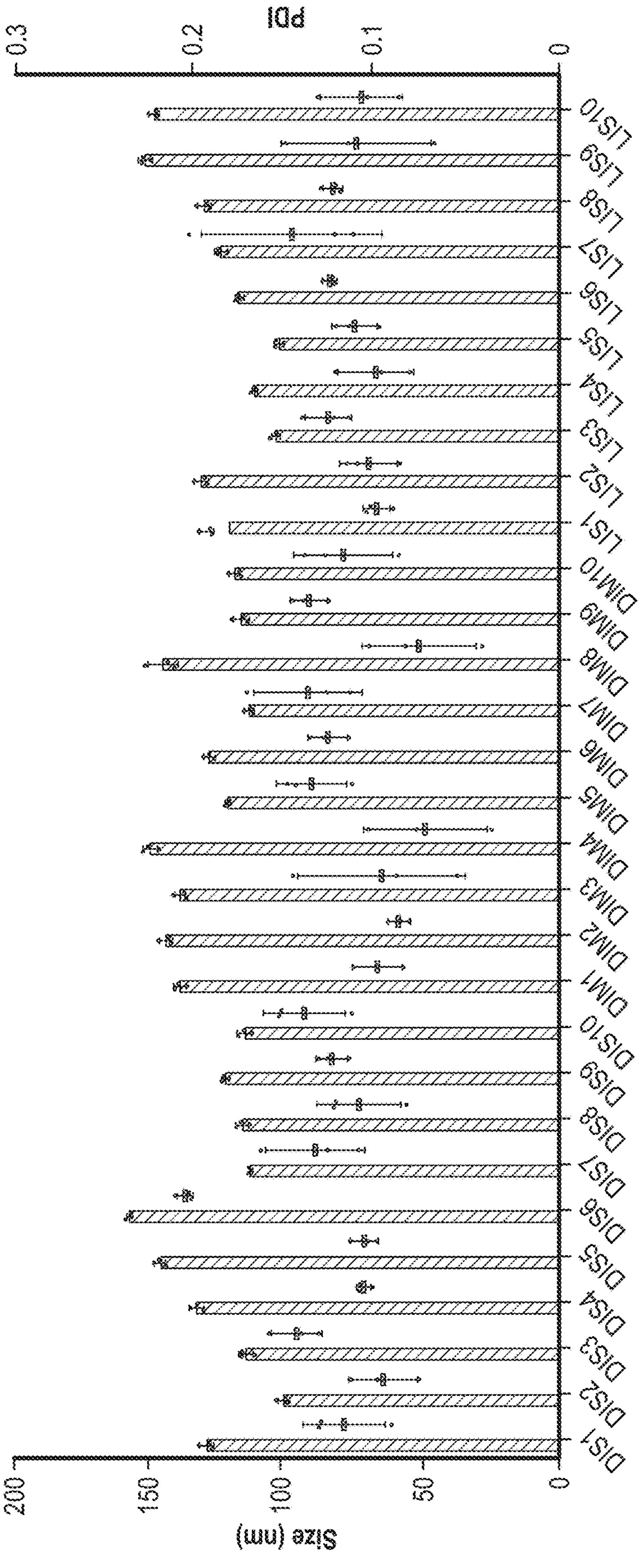
FIGS. 6A-6B. Characterizations of lipid nanoparticle (LNP)-mRNA formulations. a, Nanoparticle size and polydispersity index (PDI). b, Entrapment efficiency and zeta potential. All data are presented as mean±s.d.
Figure 6B:
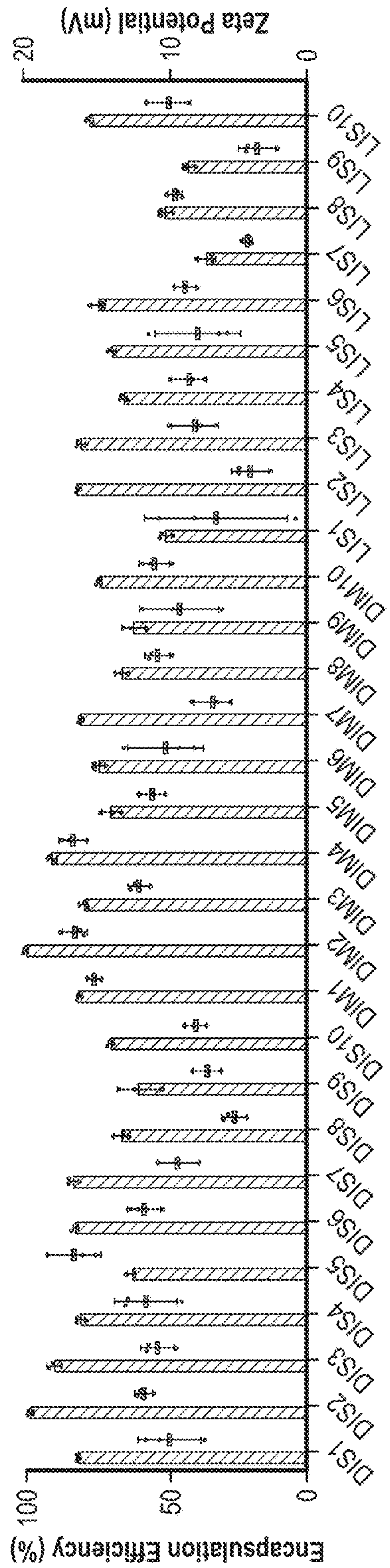
Figure 7B:
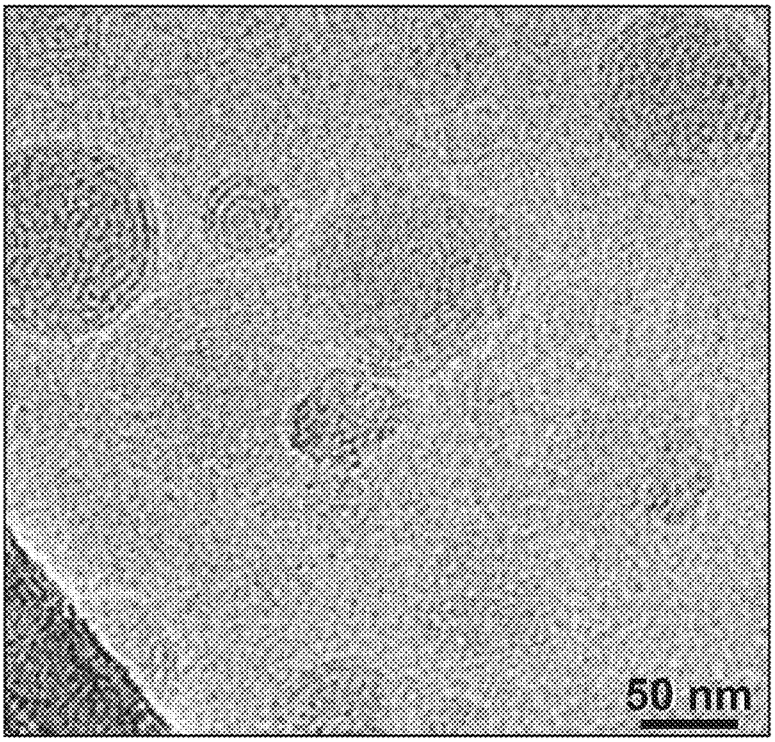
Figure 7C:
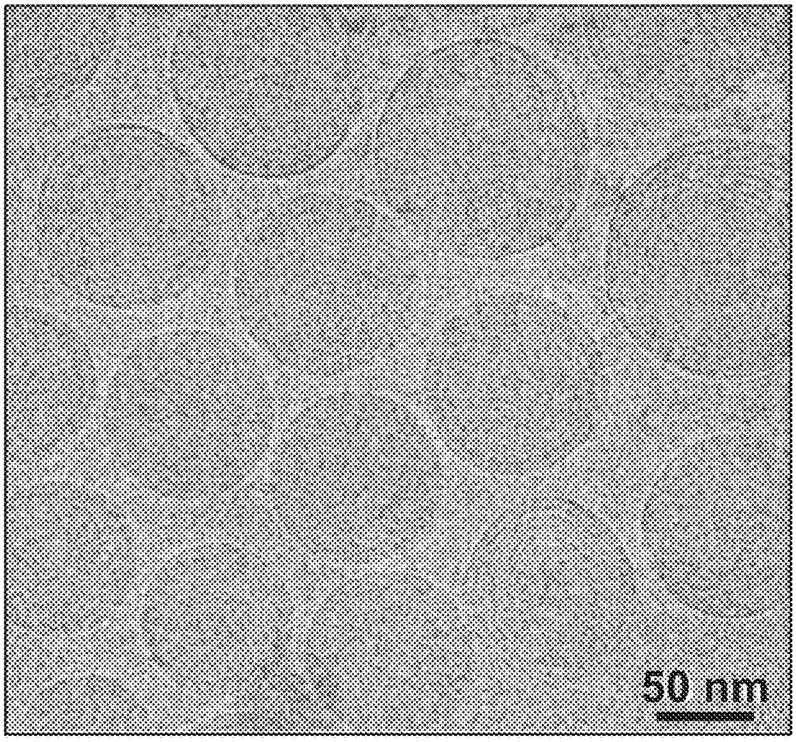
Figure 7F:
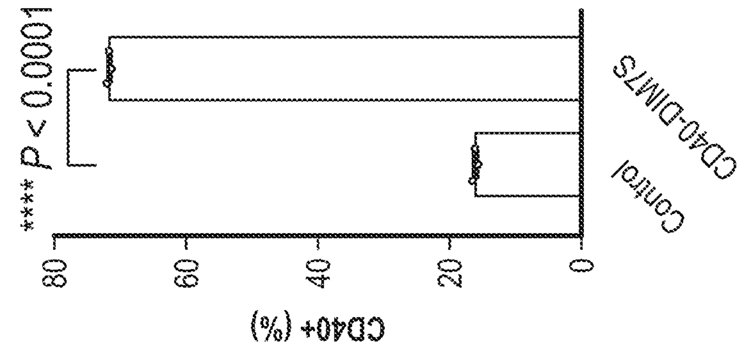
Figure 7E:
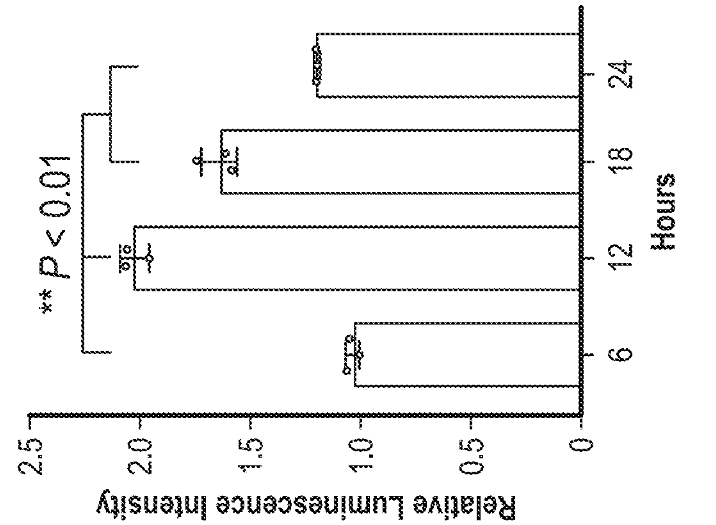
Figure 7D:
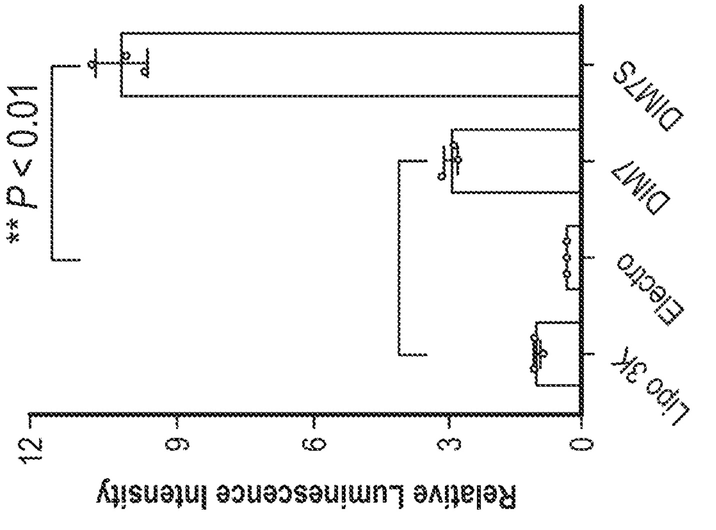
Figure 8A:
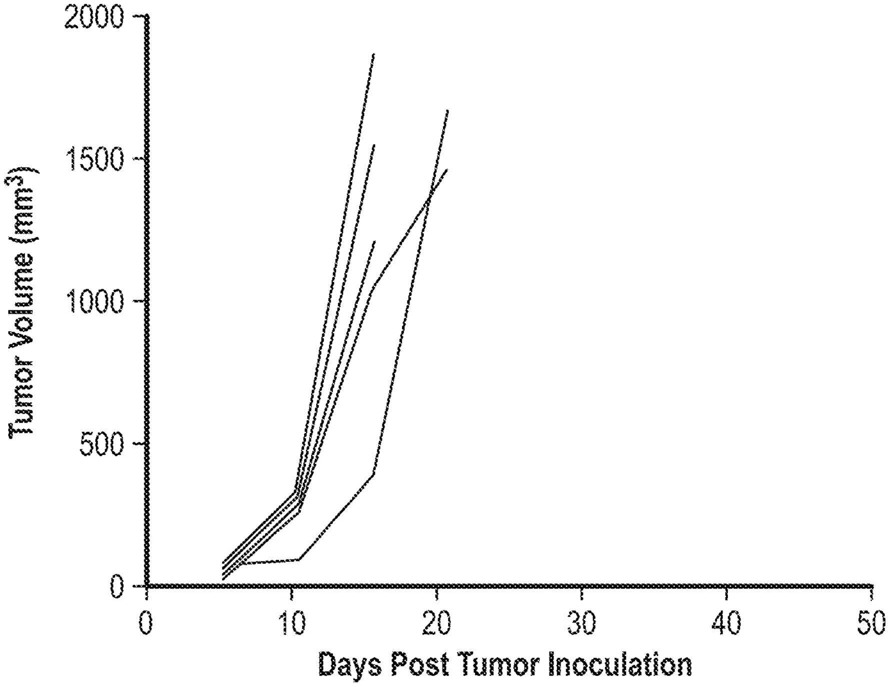
FIG. 8. Tumor volume of individual mice; n=6 or 7.
Figure 8B:
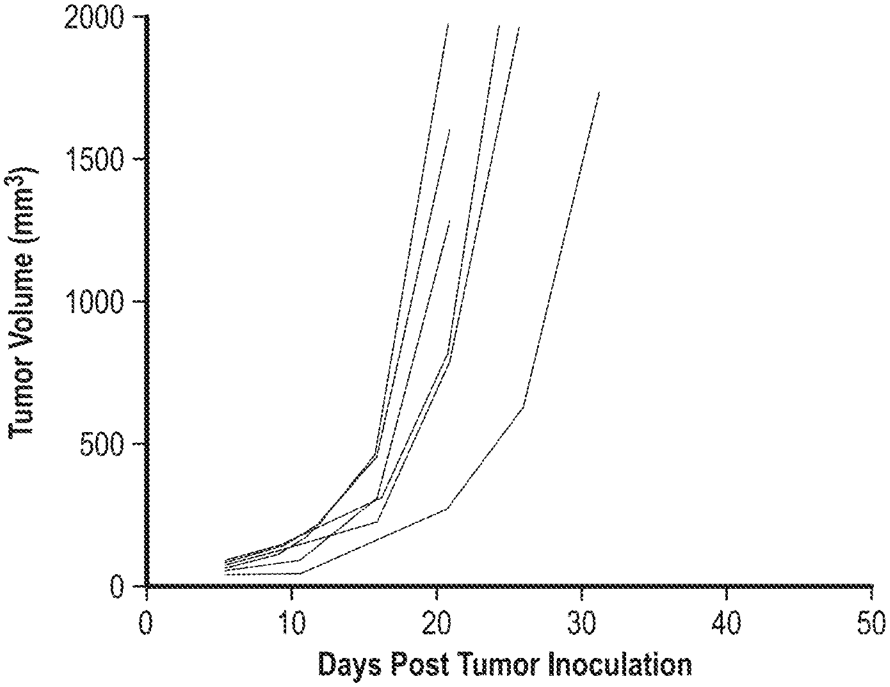
Figure 8C:
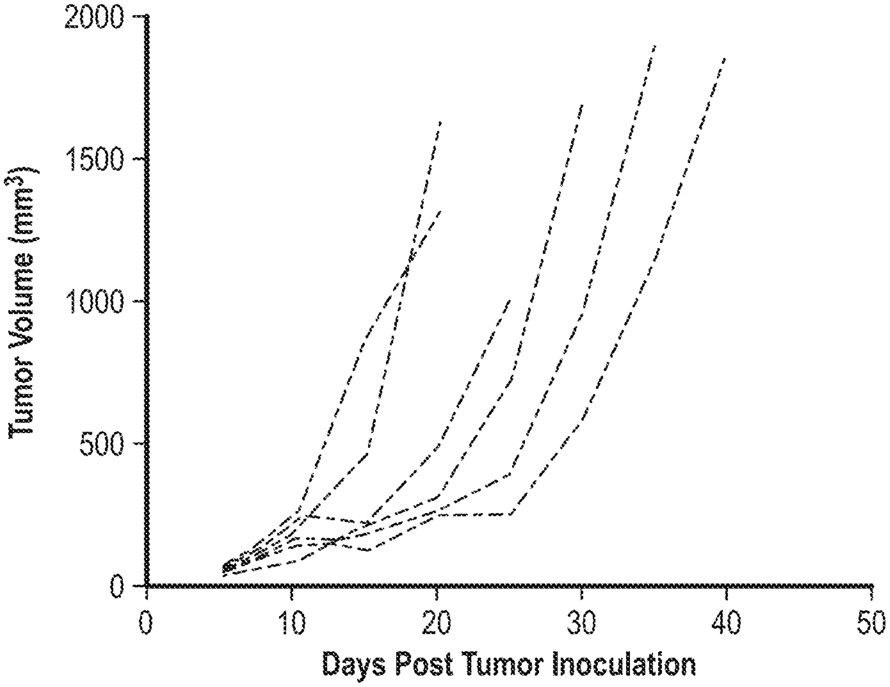
Figure 8D:
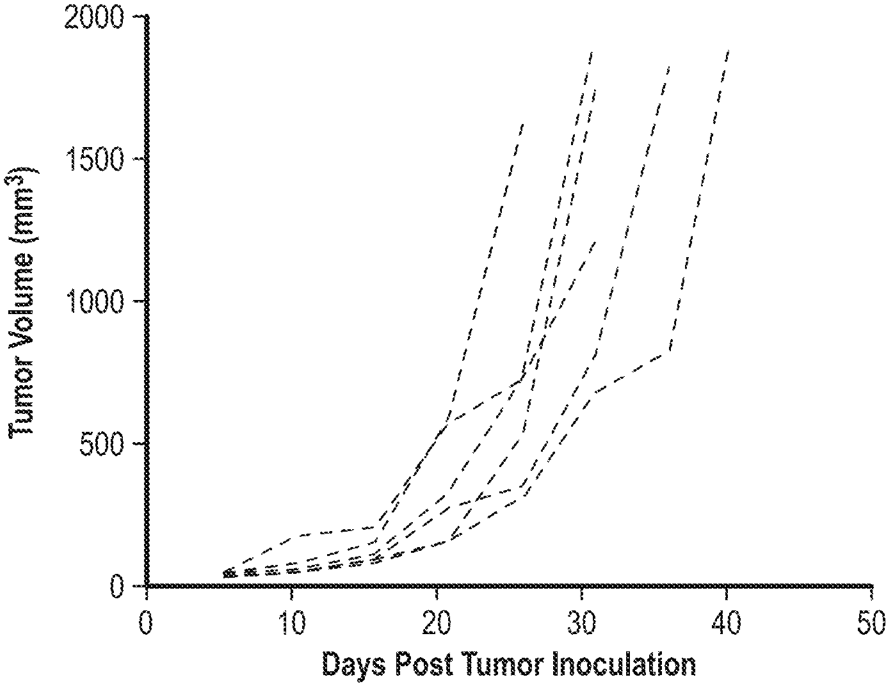
Figure 8E:
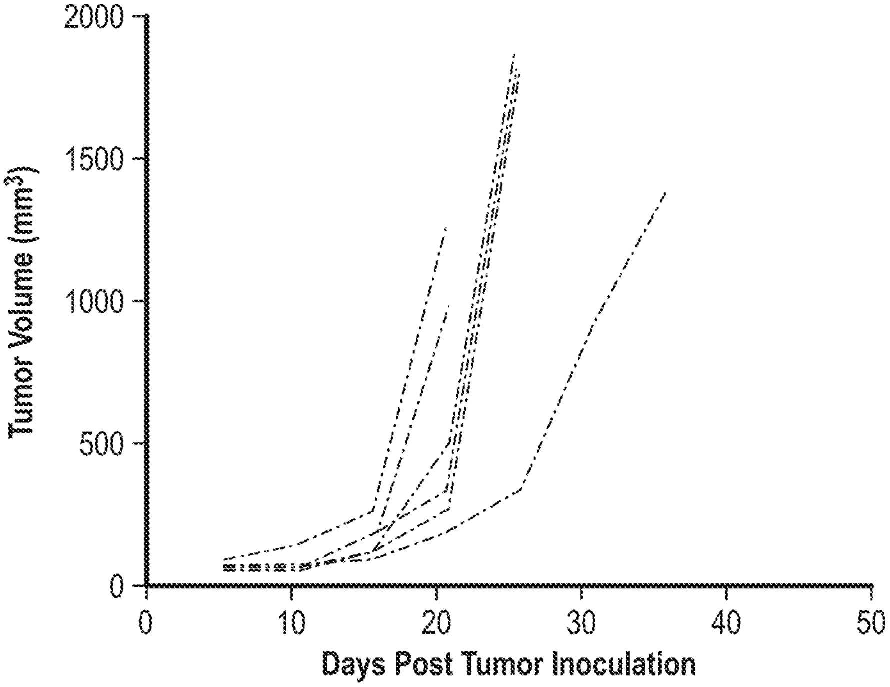
Figure 8F:
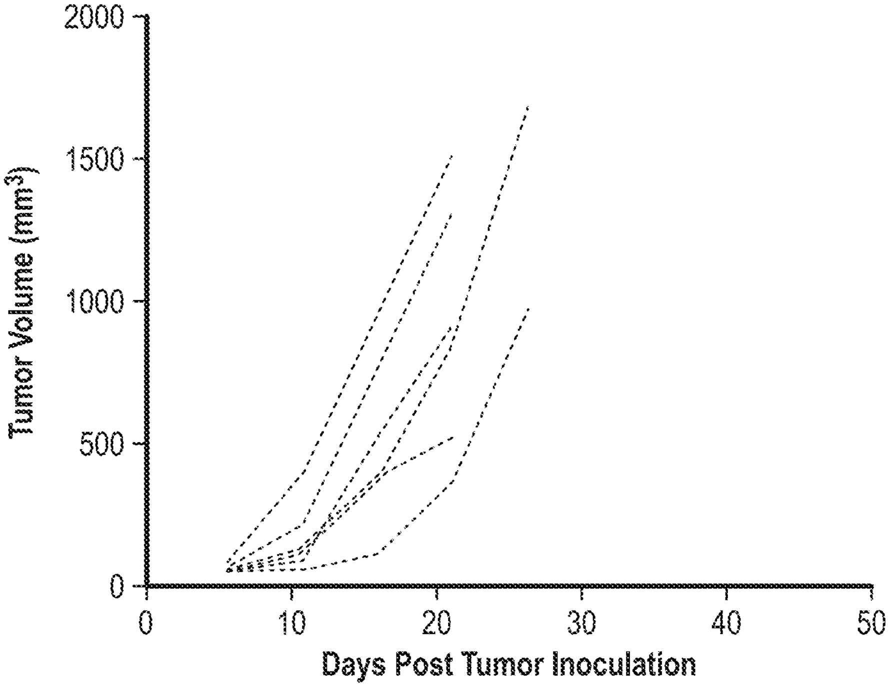
Figure 8G:
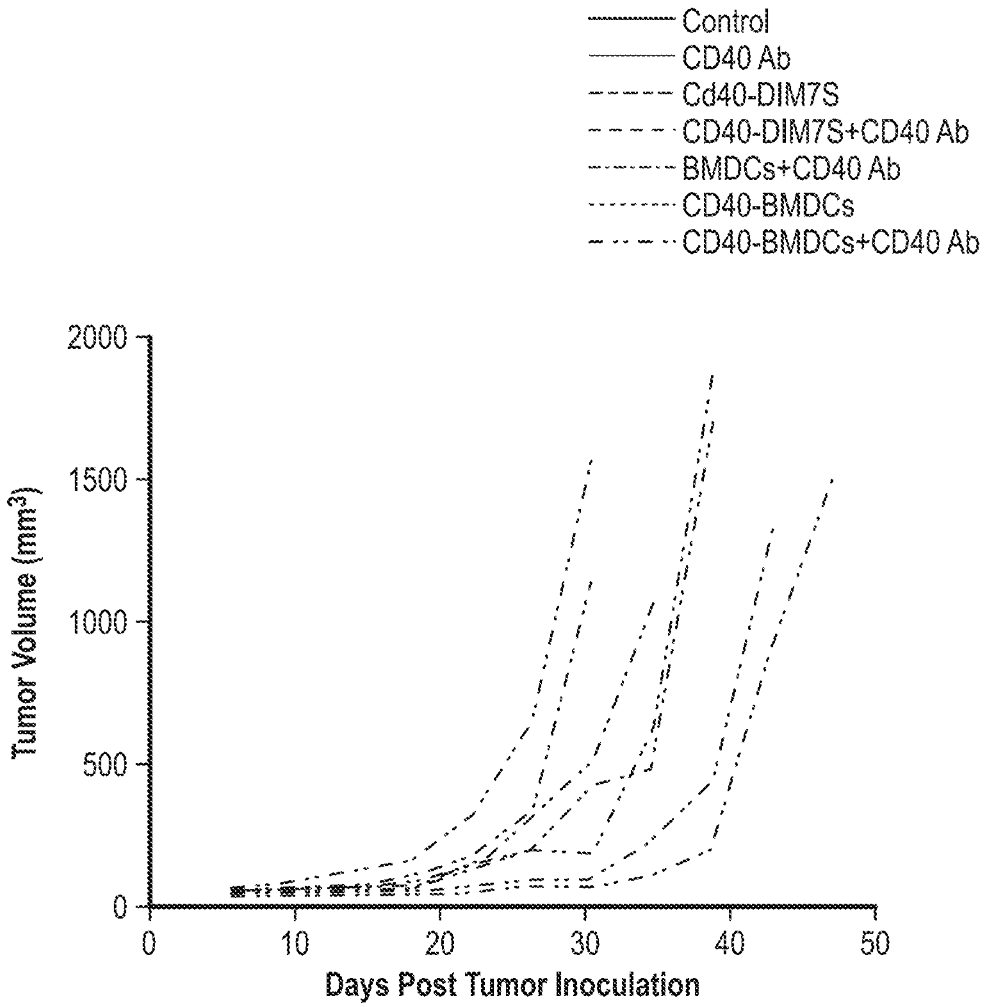

Next, LNPs were formulated containing firefly luciferase (FLuc) MRNA (FLuc-LNPs) and characterized their sizes, surface charges, and mRNA encapsulation efficiency (FIG. 6A-6C). By quantifying the luminescence intensity in bone marrow derived dendritic cells (BMDCs), structure-activity relationship of sugar alcohols-derived ionizable lipids were generalized. Chirality of the amine cores can affect mRNA delivery efficiency of the formulated LNPs. The amine cores of DIS and LIS lipids were a pair of enantiomers and they showed similar mRNA delivery capacity, especially DIS-1 to 8 and LIS-1 to 8). Lipids with C10 hydrocarbon tails induced more effective mRNA delivery than lipids containing other hydrocarbon tails. On the other hand, the DIM series displayed a different trend. Among the DIM series, DIM-7 was most effective in mRNA delivery. Lipids containing carbonate ester linkers (DIS8, DIM8, and LIS8) in the hydrophobic domains showed weak Fluc mRNA delivery ability. Among all these LNPs, DIM7 and LIS10 showed highest mRNA delivery efficiency than other LNPs, which were 3-fold and 10-fold more effective for mRNA delivery than Lipo 3K and Electro, respectively (FIG. 2A). To further investigate the formulations of DIM7 and LIS10, an orthogonal screening assay was performed based on an L16 $(4)^4$ orthogonal table (FIG. 7A). According to the luminescence intensity of the 16 orthogonal formulations of DIM7 or LIS10 (FIG. 2C, 2E), the effect of each lipid component was profiled with different molar ratios on mRNA delivery (FIG. 2B, 2D) and predicted several preferred formulations (FIG. 2B). Then, their mRNA delivery efficacy was validated by comparing with the corresponding top formulations from the orthogonal screening assay, DIM7M and LIS10G (FIG. 2C, 2E). For DIM7, the preferred formulation DMUS resulted in a 2-fold ($P<0.001$) and a 3.5-fold ($P<0.001$) higher luminescence signal than the top orthogonal formulation DIM7M and the initial formulation DIM7, respectively (FIG. 2C). For LIS10, the preferred formulation LIS10W resulted in a 1.2-fold ($P<0.0001$) higher luminescence signal compared with the top orthogonal formulation LIS10G and a 2.3-fold ($P<0.0001$) higher luminescence intensity than the initial formulation LIS10 (FIG. 2E). Formulation DIM7S and formulation LIS10W showed similar characteristics. Their particle sizes were about 110 nm with polydispersity index (PDI)<0.2 (FIG. 2G, 2I). Their encapsulation efficiency of mRNA was around 90% and they were slightly positively charged (FIG. 2G, 2I). Moreover, they both exhibited spherical morphology when visualized by Cryo-TEM (FIG. 2H, 2J, FIG. 7B, 7C). As a result, formulation DIM7S was chosen to ex vivo deliver mRNA into BMDCs for the following studies. With the same mRNA concentration, formulation DIM7S was 10-fold and 30-fold superior in mRNA delivery than Lipo 3K and Electro, respectively (FIG. 7D). The maximal luminescence intensity of formulation DIM7S was observed at 12 h from 6 to 24 h time course (FIG. 7E). Significantly, formulation DIM7S encapsulating CD40mRNA (CD40-DIM7S) led to over 70% CD40 expression in BMDCs compared to about 17% of untreated BMDCs ($P<0.0001$, FIG. 7F).

Figure 3A:
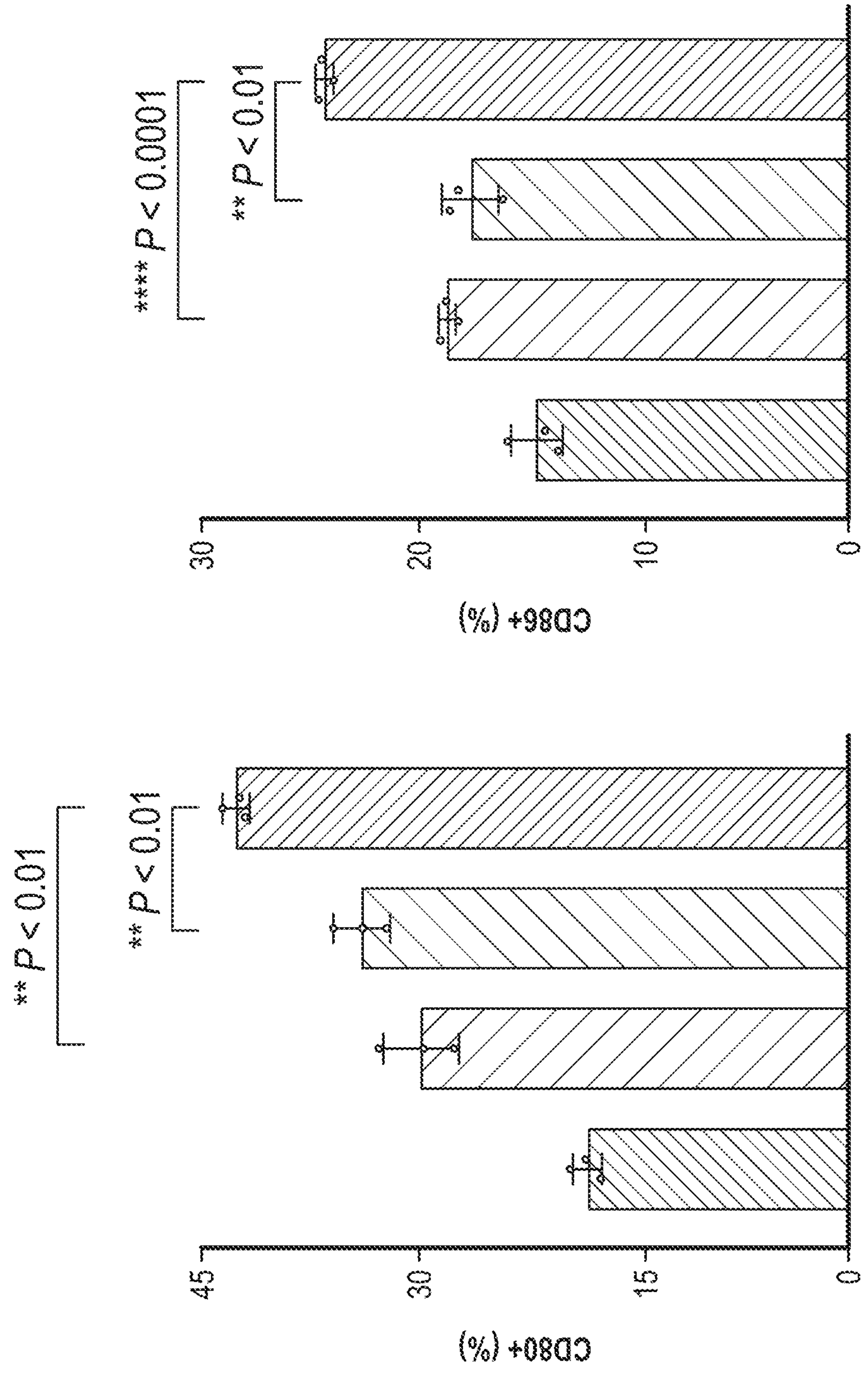
FIGS. 3A-3O. Dendritic cell activation, lipid nanoparticle (LNP)-induced immunogenic cell death (ICD), and therapeutic effects on primary tumor and rechallenged tumor. a, Expression of dendritic cell activation markers, including CD80, CD86, MHC-II, IL1-β (pro-form), TNF-α and IL12. b, Schematic illustration of the B16F10 tumor model and the treatment regimen. c, d, Tumor volumes (c) and mouse survival (d) over time; n=6 or 7. e, f, LNP-induced ICD markers in vitro (e) and in vivo (f), including extracellular HMGB1, extracellular ATP, and cellular surface calreticulin. g, Schematic illustration of the B16F10 tumor model and the treatment regimen. h, Mouse survival over time; n=6. i, Survival of the responder mice in CD40L-LIS10W+CD40-BMDCs group post s.c. tumor rechallenge; n=5 or 6. j, Schematic illustration of the B16F10 tumor model and the treatment regimen. k, Mouse survival over time; n=6. l, Survival of the responder mice in CD40L-LIS10W±CD40-BMDCs group post s.c. tumor rechallenge; n=5 or 6. m, Schematic illustration of the B16F10-Luc2 tumor model and the treatment regimen. n, Mouse survival over time; n=9. o, Survival of the responder mice in CD40L-LIS10W+CD40-BMDCs group post i.e. tumor rechallenge; n=5 or 8. Data in a, e, and f are from n=3 biologically independent samples and are presented as mean±s.d. Data in c are presented as mean±s.e.m. Statistical significance in a, c, e and f was analyzed by two-tailed Student's t-test. Statistical significance in d, h, i, k, l, n, and o was analyzed by log-rank (Mantel-Cox) test. *P<0.05, P<0.01,*P<0.001, ****P<0.0001.
Figure 3B:
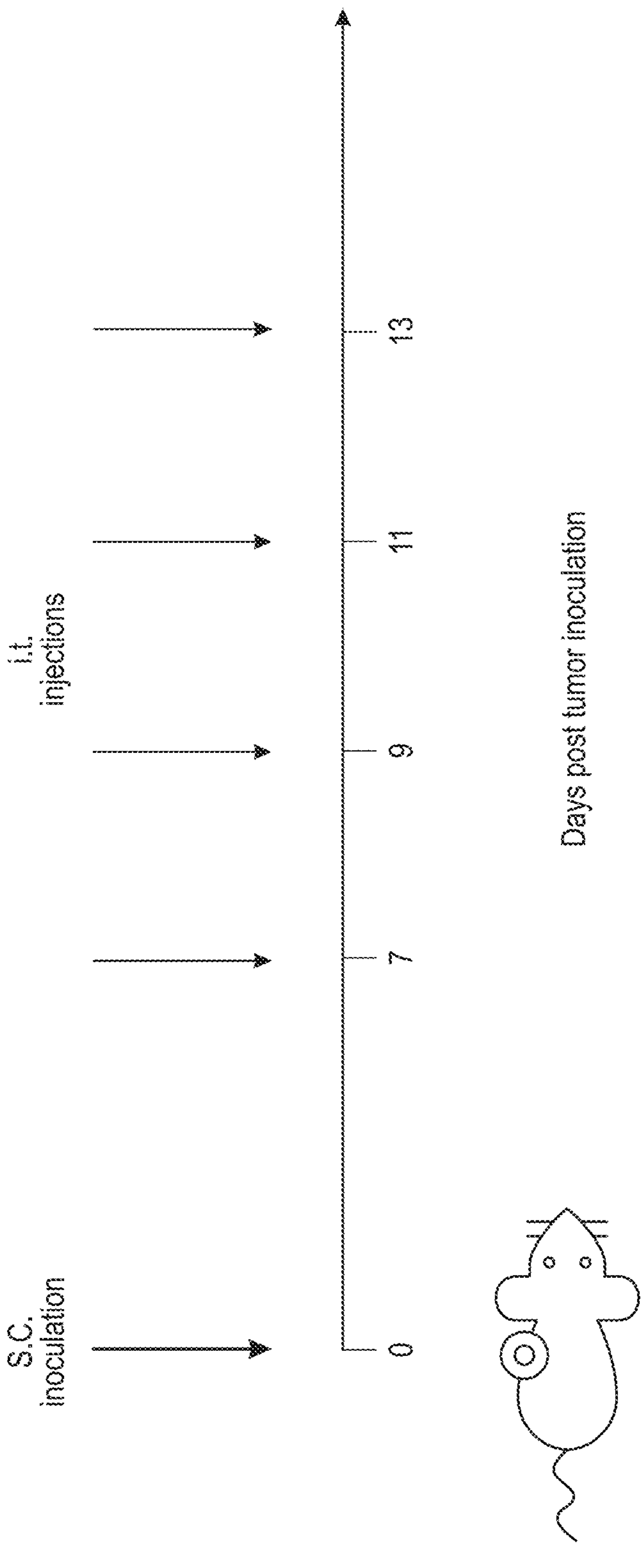
Figure 3C:
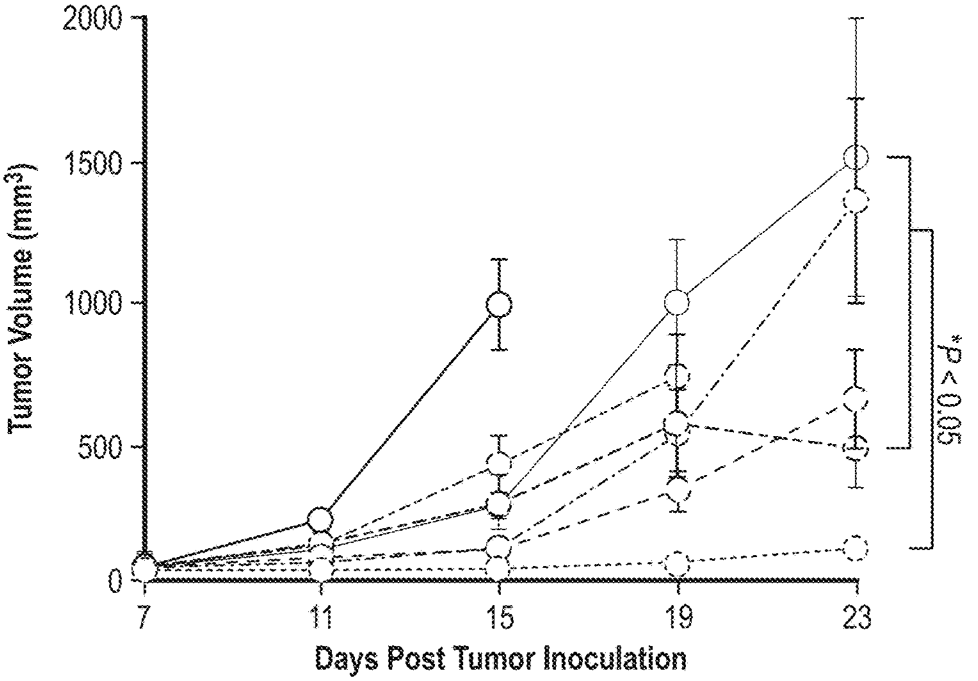
Figure 3D:
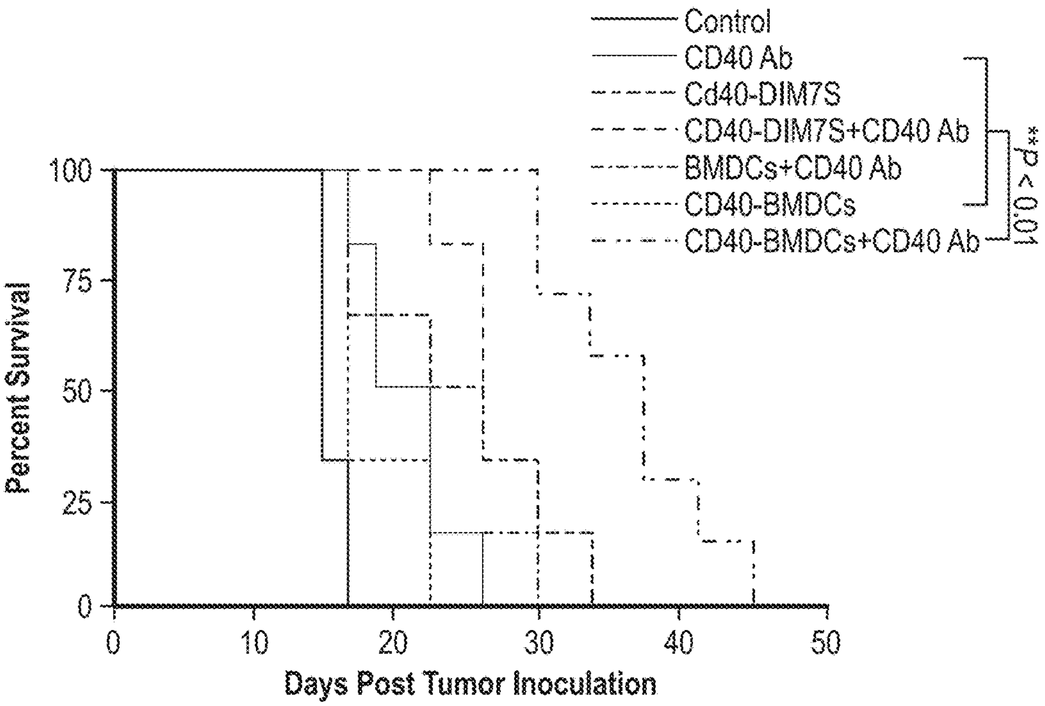
Figure 9A:
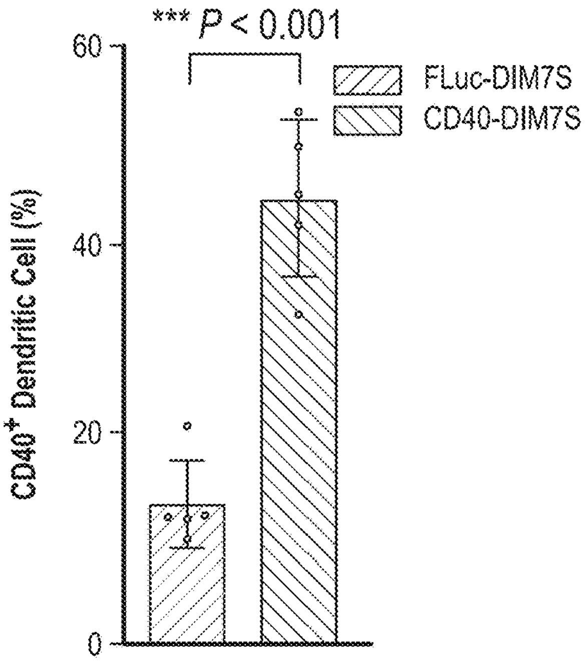
FIGS. 9A-9E. Lipid nanoparticle (LNP)-induced cytotoxicity and expression of CD40 and CD40L. a, In vivo CD40expression mediated by CD40-DIM7S in dendritic cells; n=5. b, In vitro cytotoxicity induced by CD40L-DIM7S and CD40L-LIS10W. c, In vitro CD40L expression in B16F10 melanoma cells mediated by CD40L-DIM7S and CD40L-LIS10W. d, e, In vivo CD40L expression mediated by CD40L-LIS10W in tumor cells (d) and immune cells (e) including macrophages, dendritic cells, CD8 T cells, and CD4 T cells; n=3 or 5. Data in b and c are from n=3 biologically independent samples. All data are presented as mean±s.d. Statistical significance was analyzed by two-tailed Student't-test. *P<0.05, P<0.01, *P<0.001, ****P<0.0001.

The activation of dendritic cell is an essential step for priming T cell responses in the CIC[1]. Thus, it was next tested whether CD40 overexpression facilitates BMDC activation in the presence of anti-CD40 agonist antibodies (CD40 Ab). Compared with PBS, CD40 Ab, and CD40-DIM7S treatments, the combination of CD40-DIM7S and CD40Ab (CD40-DIM7S+CD40 Ab) stimulated higher levels of dendritic cell activation markers (FIG. 3A), including CD80 ($P<0.01$), CD86 ($P<0.01$), MHC-II ($P<0.01$), IL1-β (pro-form, $P<0.05$), TNF-α ($P<0.05$), and IL12 ($P<0.01$), indicating a stronger capacity for dendritic cell activation. To evaluate whether the enhanced activation of dendritic cells improves the in vivo antitumor effects, intratumoral (i.t) injection was performed for multiple treatments every other day for 4 doses in a B16F10 melanoma mouse model (FIG. 3B). The treatment strategy included various combinations including CD40 Ab, CD40-DIM7S, CD40-DIM7S+CD40 Ab, BMDCs+CD40 Ab, CD40-BMDCs, and CD40-BMDCs+CD40 Ab. Compared to all other treatments, CD40-BMDCs+CD40Ab significantly suppressed tumor growth by 5 to 15 folds (23 d post inoculation, $P<0.05$, FIG. 3C, FIG. 8) and markedly extended the overall survival time (FIG. 3D, $P<0.01$). Indeed, CD40-DIM7S can in situ engineer dendritic cells to increase the expression of CD40 receptors (FIG. 9A). However, CD40-DIM7S+CD40 Ab exhibited limited therapeutic effects compared with CD40-BMDCs+CD40 Ab (FIG. 3C, 3D, FIG. 8). This may be partly attributed to the lack of infiltrated dendritic cells in the immunosuppressive TME[1,2]. Although BMDCs+CD40 Ab supplemented dendritic cells in tumoral tissues, the inadequate activation of BMDCs may be responsible for the weak antitumor effects[1,2]. Collectively, these results revealed the importance of adequate dendritic cell infiltration, CD40 overexpression on BMDCs, and CD40 agonism for the antitumor activities of CD40-BMDCs+CD40 Ab treatment.

Figure 3E:
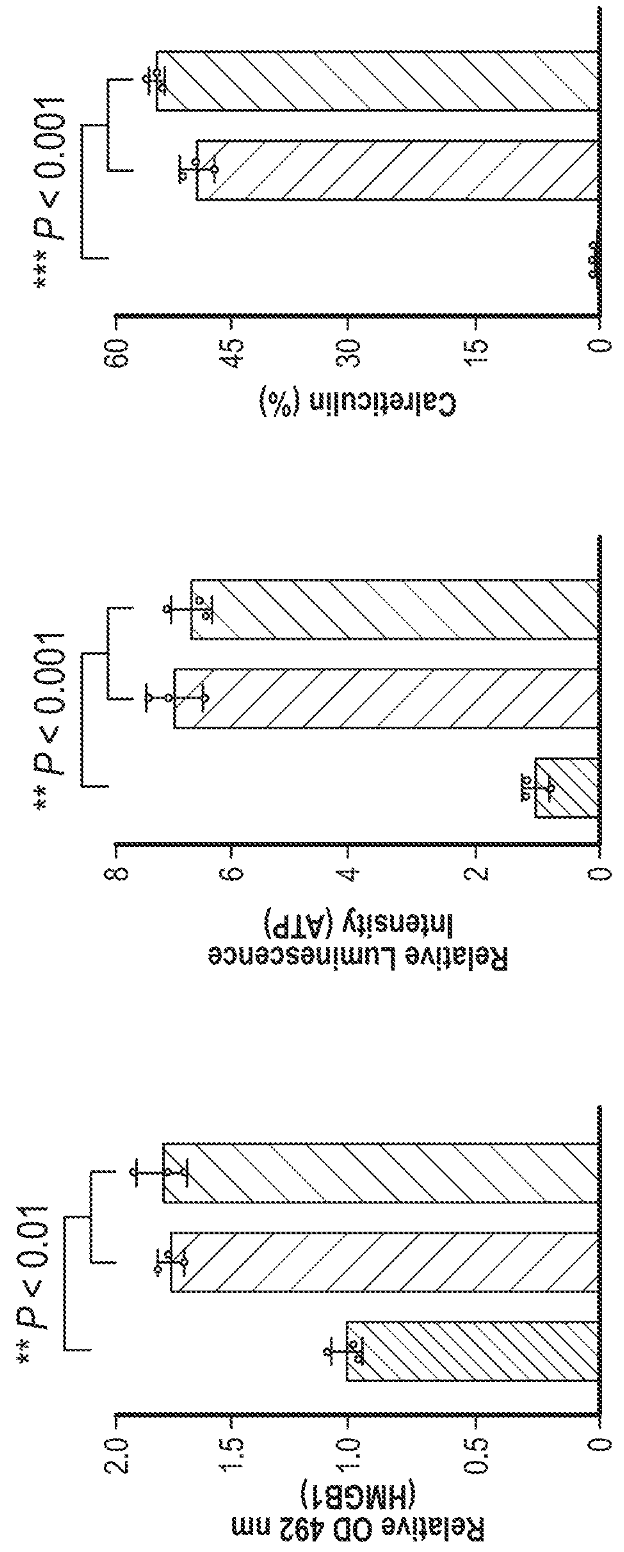
Figure 3F:
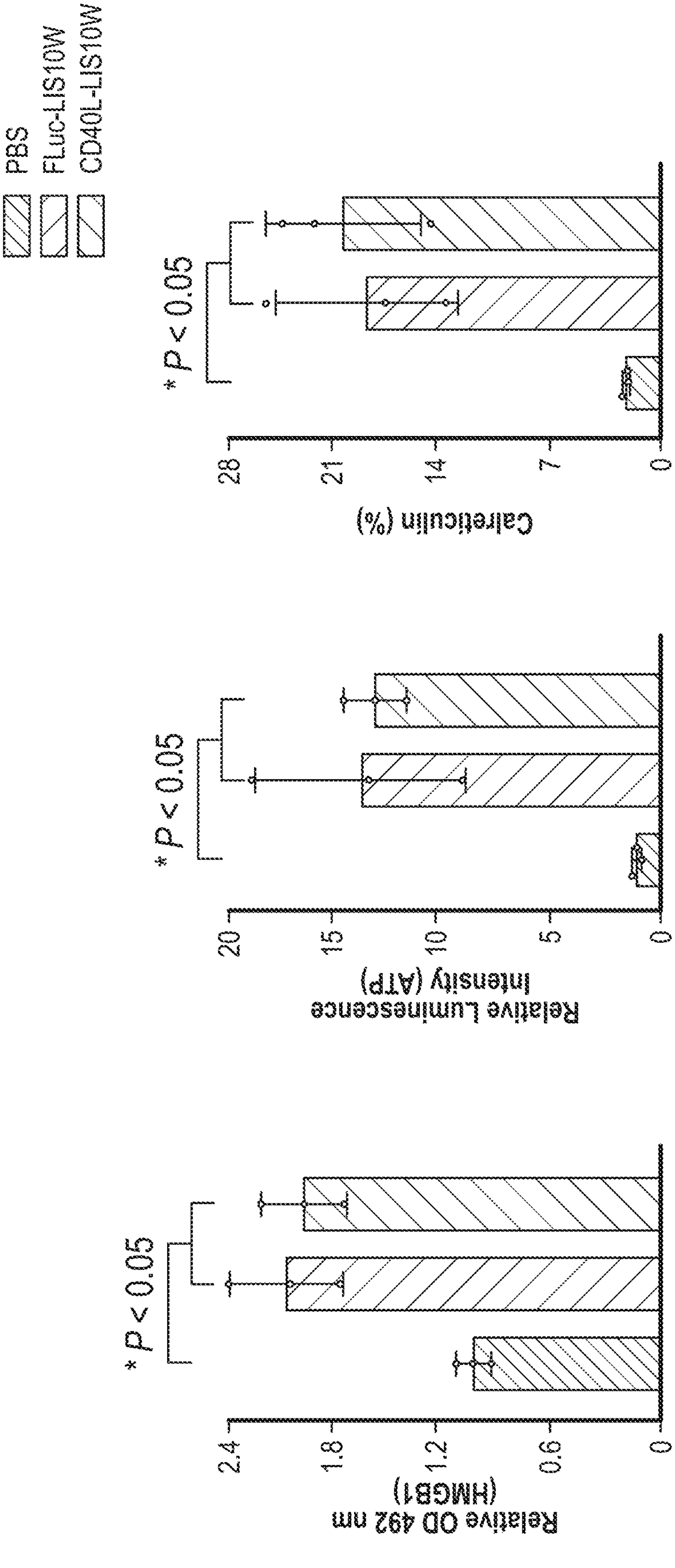
Figure 9B:
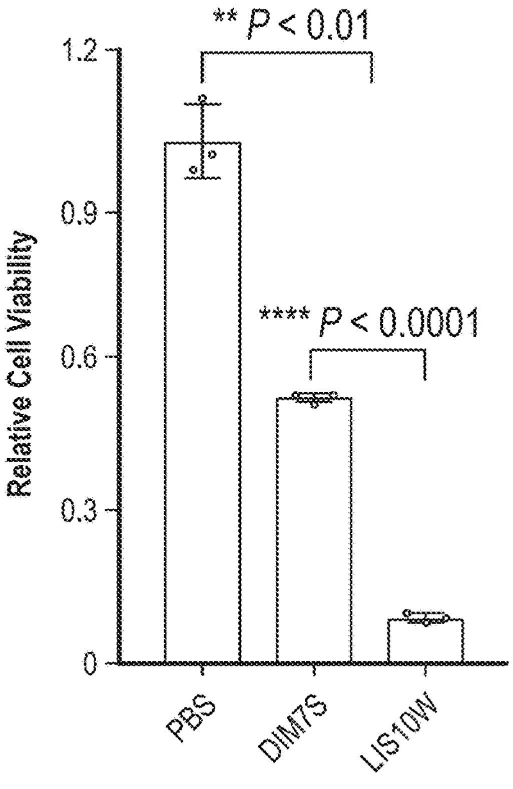

Although CD40-BMDCs+CD40 Ab showed promising antitumor effects, no complete eradication of tumor burden indicated insufficient proceeding of the CIC. Cancer cell death, as the initial step in the CIC, enables the release of TAAs that are presented by dendritic cells and prime tumor-specific T cell responses[1,3-5]. Furthermore, clinical studies have revealed that cancer cell ICD benefits the antitumor effects of immunotherapeutics[3,4]. Therefore, it was investigated whether cancer cell ICD induced by LNPs may promote the antitumor effects of CD40-BMDC therapy. LNP-mediated expression of CD40L was also investigated in tumoral tissues whether it could activate the adoptively transferred CD40-BMDCs. As a result, the combination of cancer cell ICD induced by CD40L-LNPs and adoptive CD40-BMDC transfer may effectively boost the CIC and thereby eliminate tumoral lesions (FIG. 1A). The cytotoxicity of DIM7S and LIS10W containing CD40L mRNA (CD40L-DIM7S and CD40L-LIS10W) was investigated in B16F10 melanoma cells. The LIS10W induced potent cytotoxicity (85%) after 18 h treatment (FIG. 9B). Because both CD40L-DIM7S and CD40L-LIS10W resulted in nearly 100% CD40L expression in B16F10 melanoma cells post 18 h incubation (FIG. 9C), LIS10W was selected to evaluate the ability to induce ICD markers in B6F10 melanoma cells, including extracellular high mobility group box 1 (HMGB1), extracellular ATP, and cellular surface calreticulin. Compared with PBS treatment, FLuc-LIS10W or CD40L-LIS10W induced about 1.7-fold ($P<0.01$), 7-fold ($P<0.001$), and 45-fold ($P<0.001$) higher levels of cell extracellular HMGB1, extracellular ATP, and cellular surface calreticulin in vitro, respectively (FIG. 3E). Consistently, ICD induced by FLuc-LIS10W or CD40L-LIS10W was observed in mouse B16F10 melanoma tissues in vivo (FIG. 3F), suggesting that LIS10W LNP other than the mRNA cargo contributed to the ICD effects.

Figure 9C:
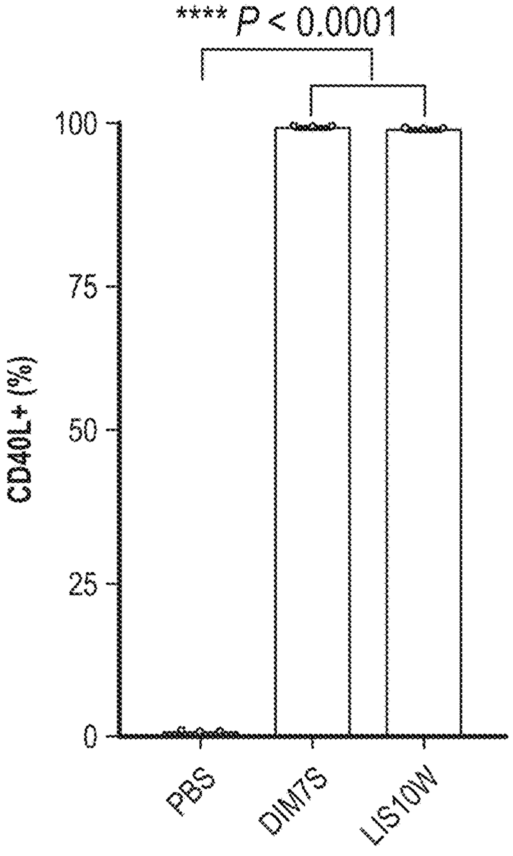
Figure 9D:
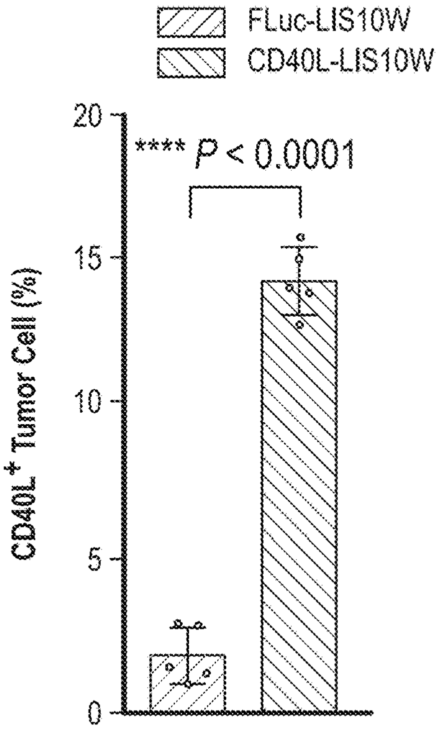
Figure 9E:
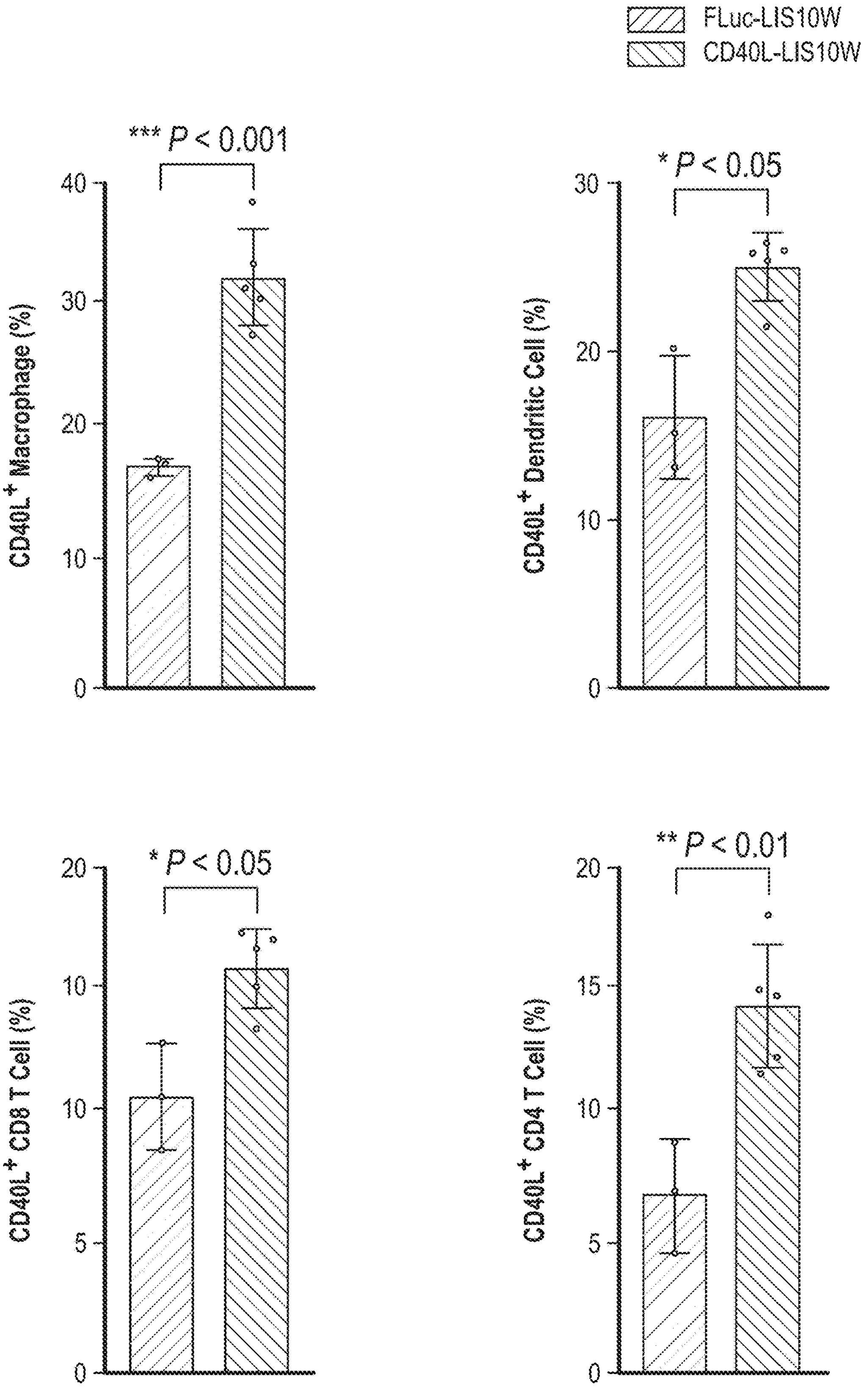

Because the expression profile of CD40L in tumoral tissues may affect its bioactivity, its biodistribution was studied at a cellular level by flow cytometry. A single injection of CD40L-LIS10W led to about 15% of CD40L positive B16F10 cells in tumoral tissues (FIG. 9D). In addition, immune cells in tumoral tissues, including macrophages, dendritic cells, CD4 T cells, and CD8 T cells, exhibited about 1.5 to 2-fold increased expression of CD40L (FIG. 9E), Both the expression of CD40L in cancer cells and immune cells may contribute to CD40-BMDC activation[18].

Figure 3G:
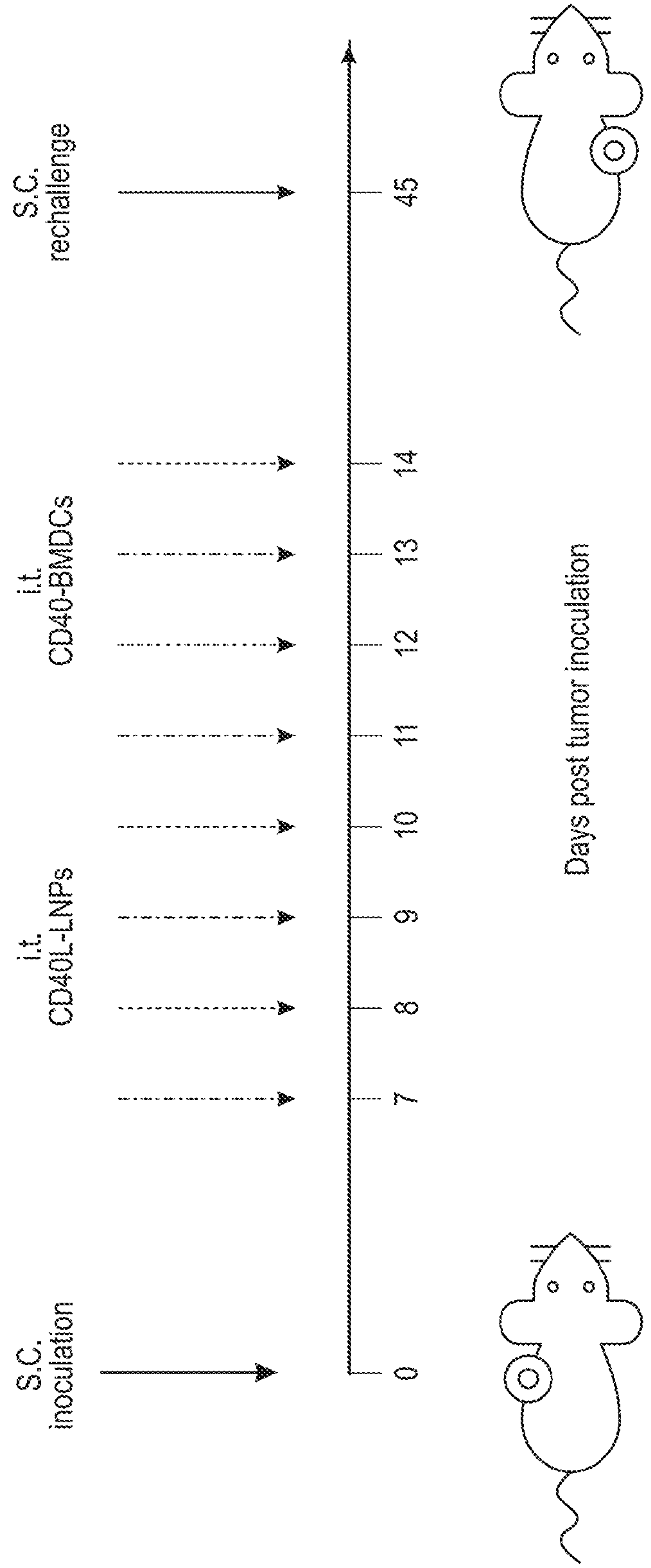
Figure 3H:
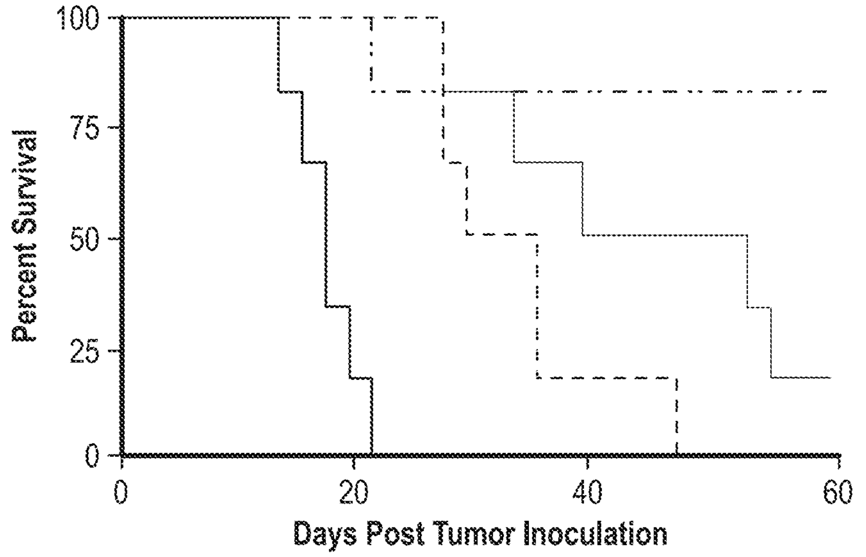
Figure 3I:
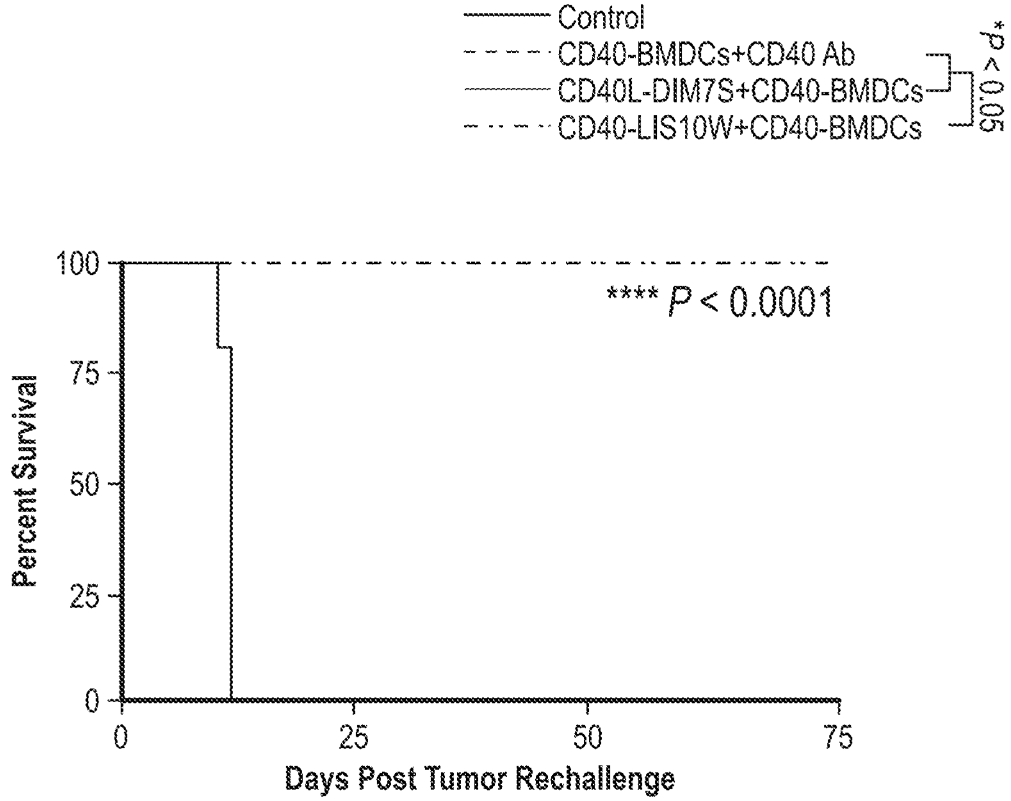
Figure 3J:
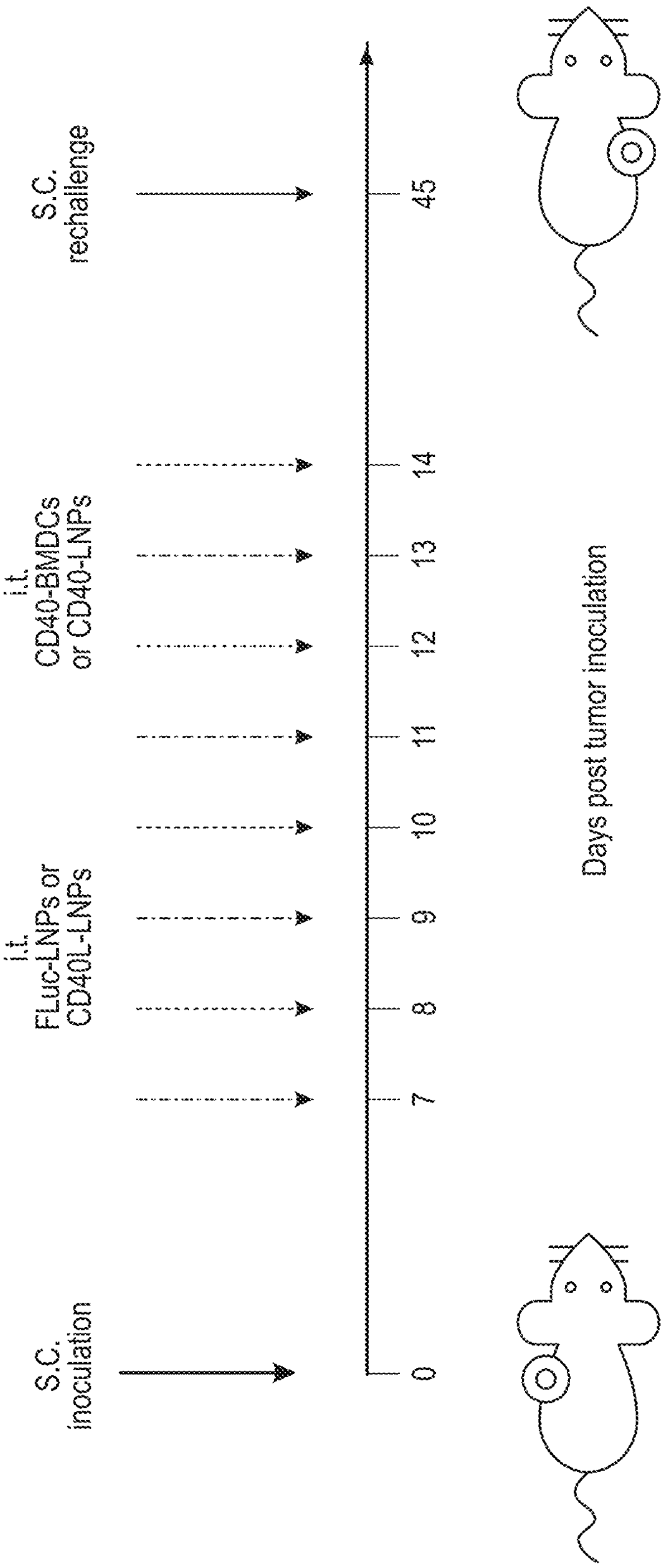
Figure 3K:
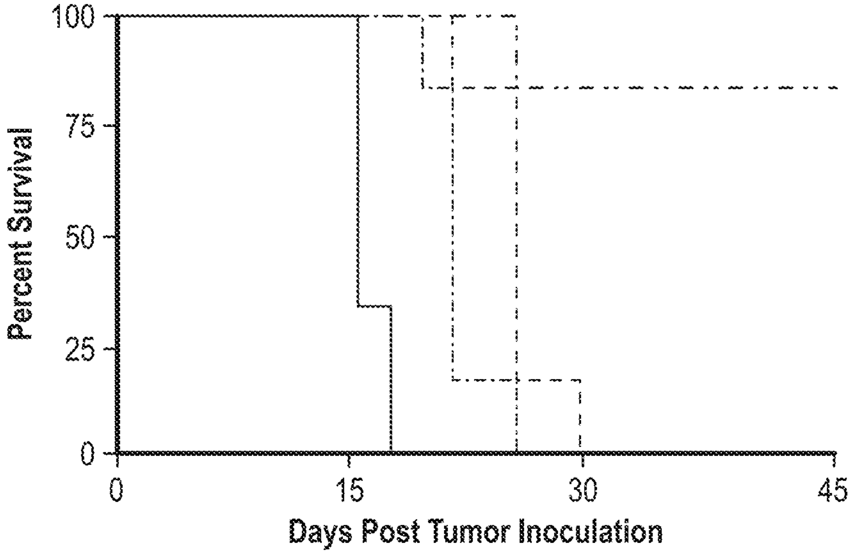
Figure 3L:
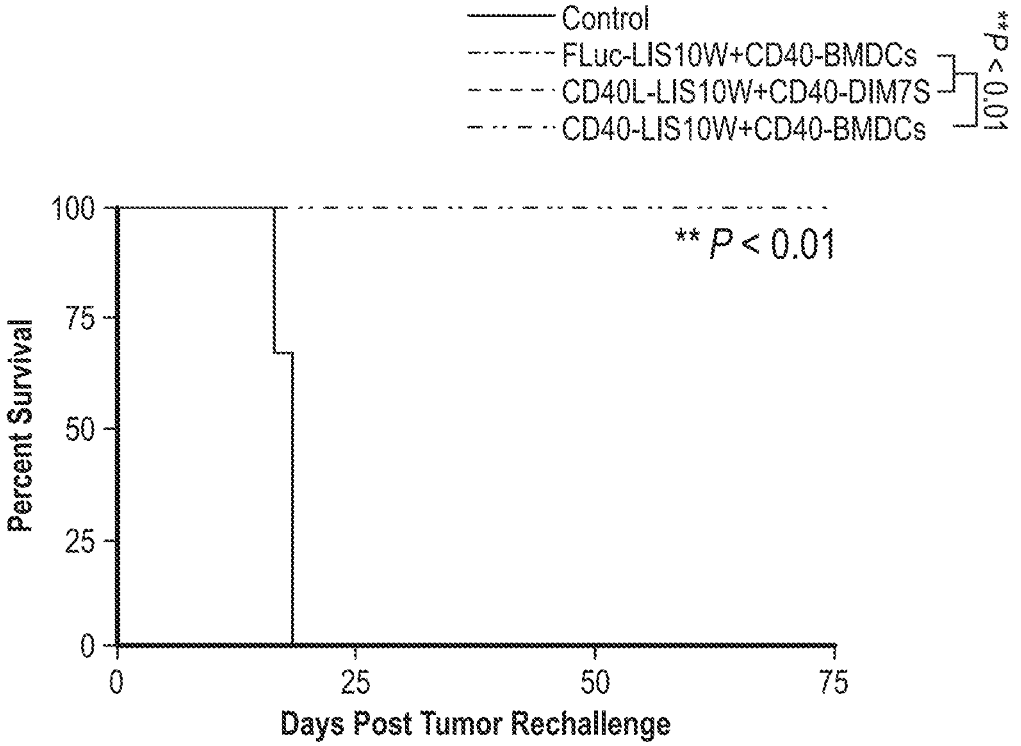
Figure 3M:
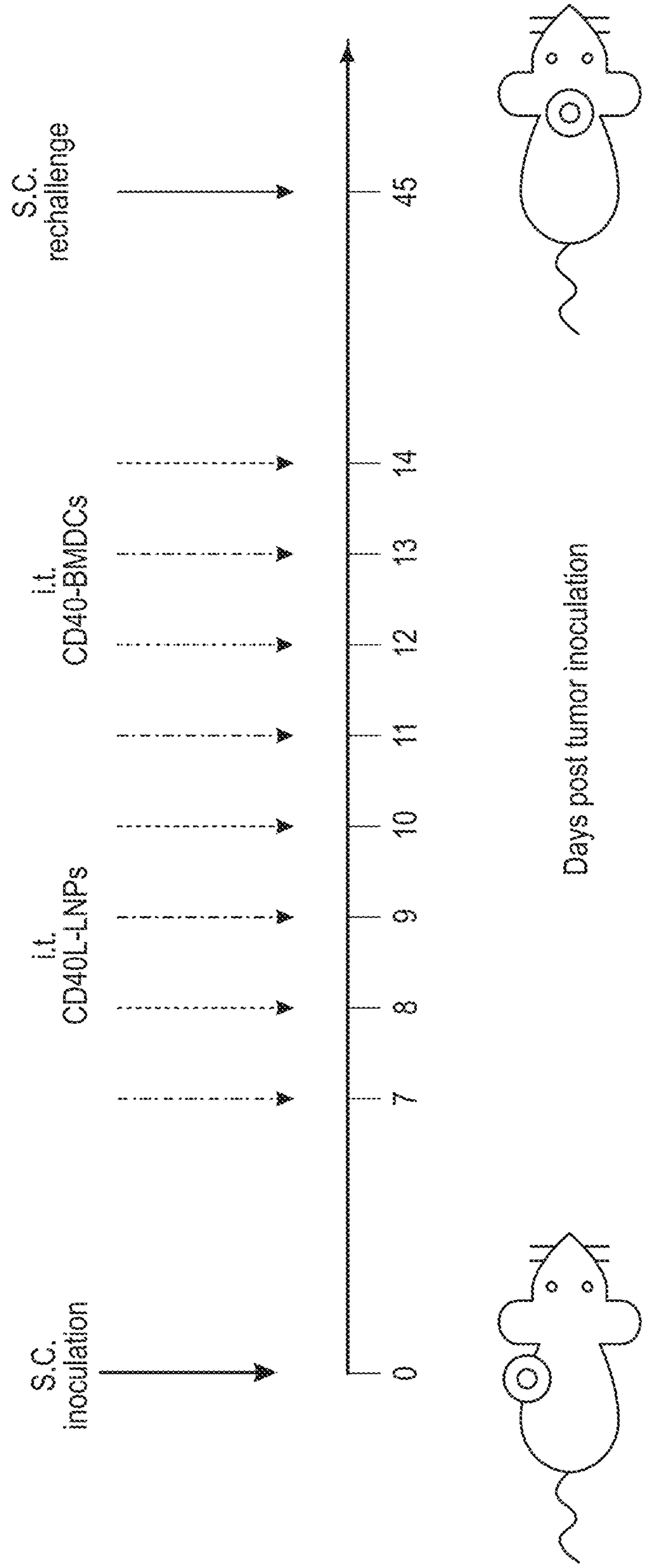
Figure 3N:
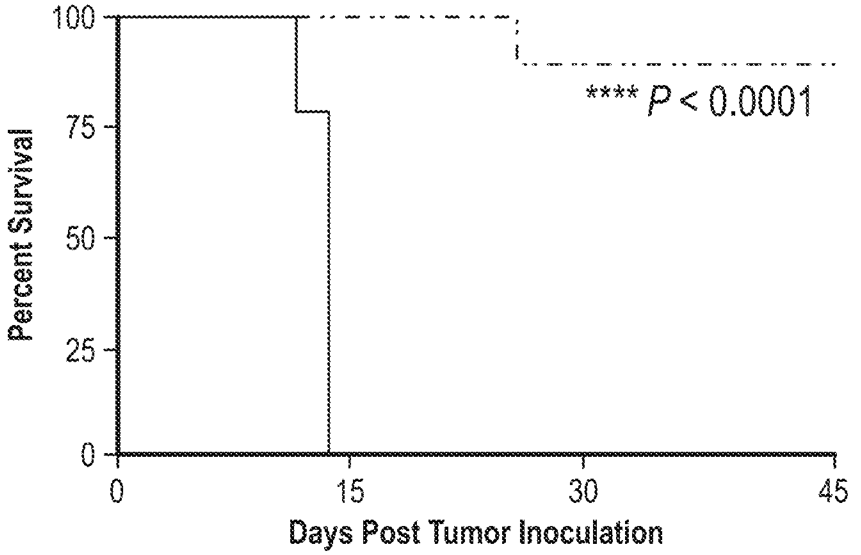
Figure 10A:
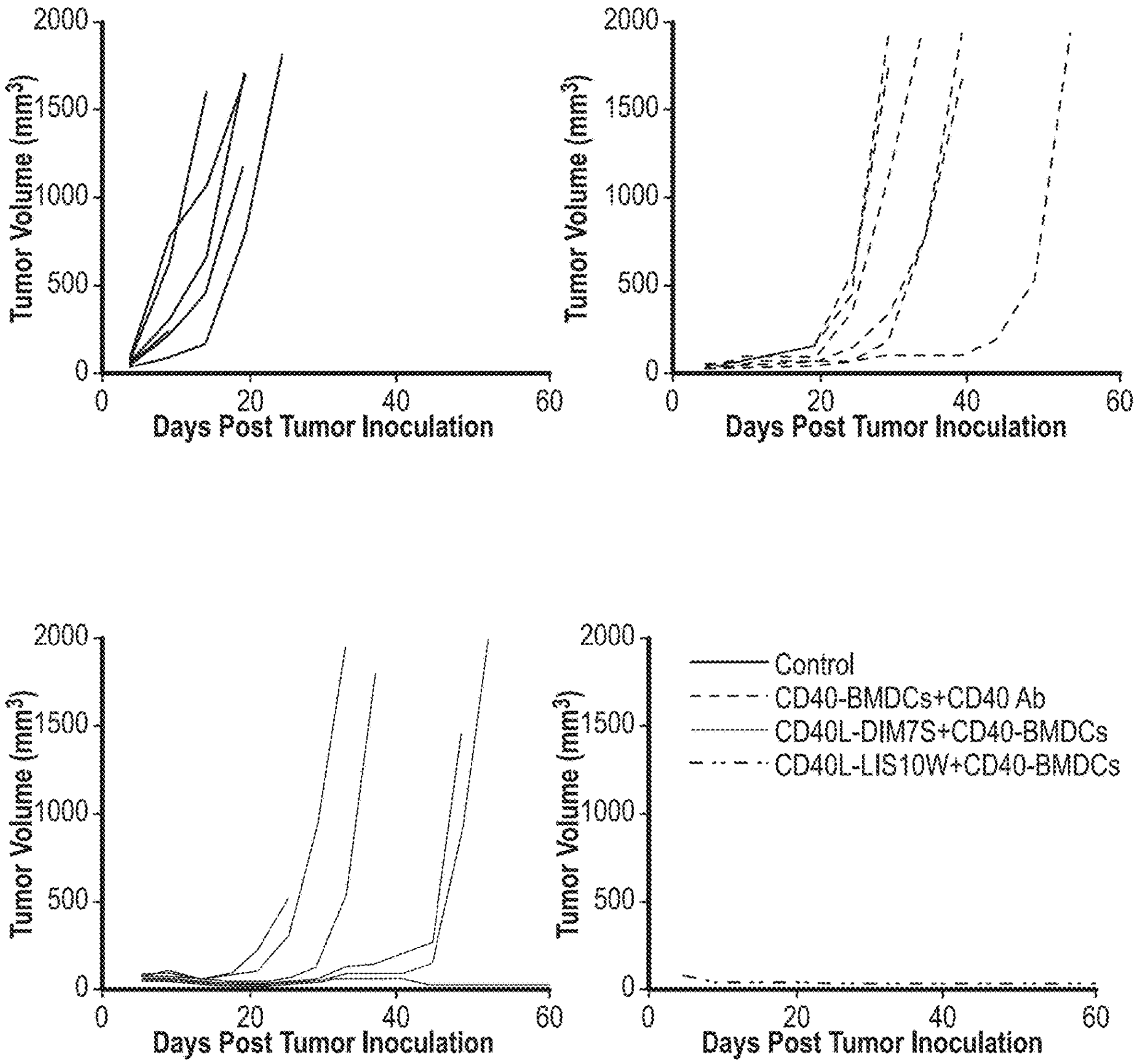
FIGS. 10A-10G. Tumor volumes of individual mice. a, Primary tumor volume of individual mice; n=6. b, Rechallenged s.c. tumor volume of individual mice; n=5 or 6. c, d Tumor volume over time (c) and primary tumor volume of individual mice (d); n=6. e, Rechallenged s.c. tumor volumes of individual mice; n=5 or 6. f, Primary tumor volumes of individual mice; n=9. g, Brain tumor volume over time; n=5 or 8. Data in c and g are presented as mean±s.e.m. Statistical significance was analyzed by two-tailed Student's t-test. *P<0.05, P<0.01, *P<0.001, ****P<0.0001.
Figure 10B:
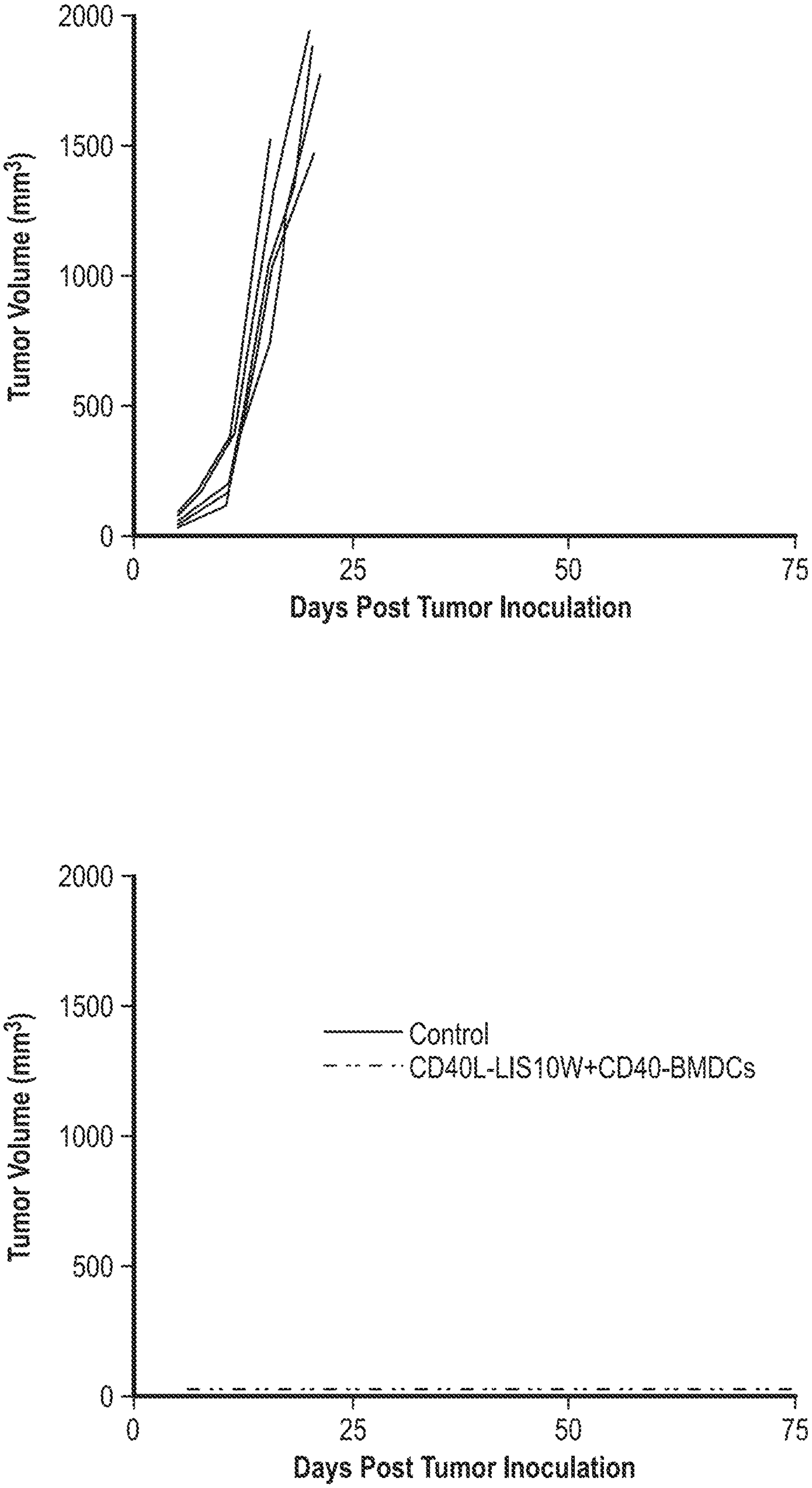
Figure 10C:
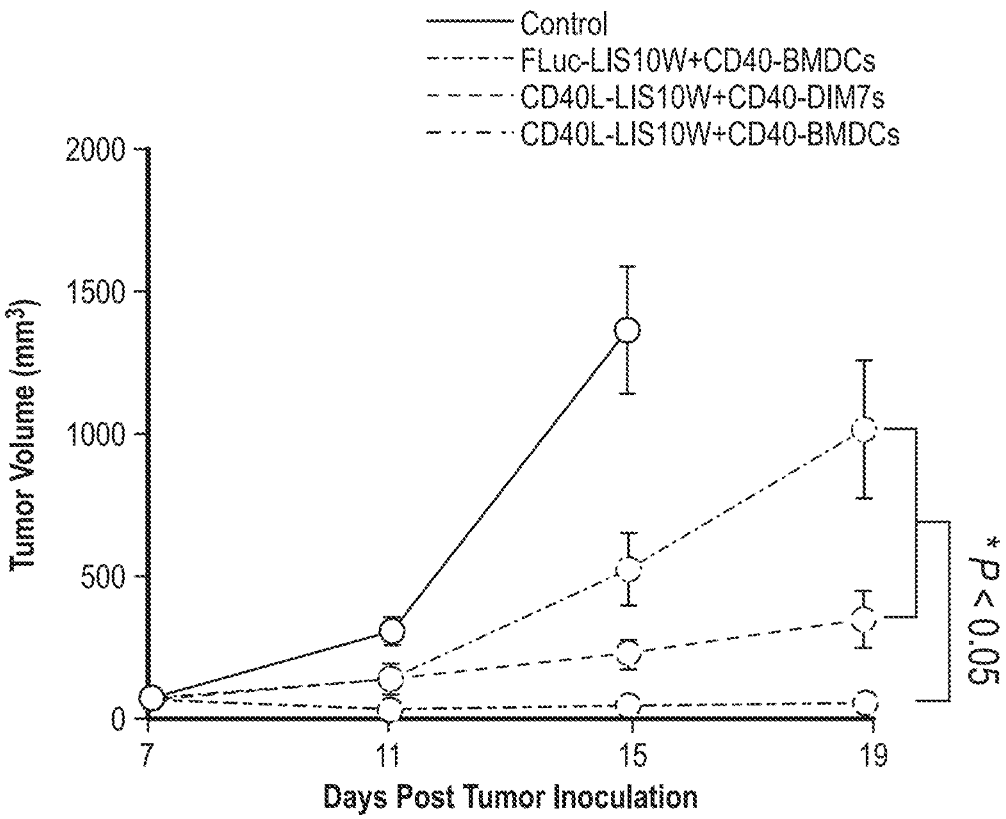
Figure 10D:
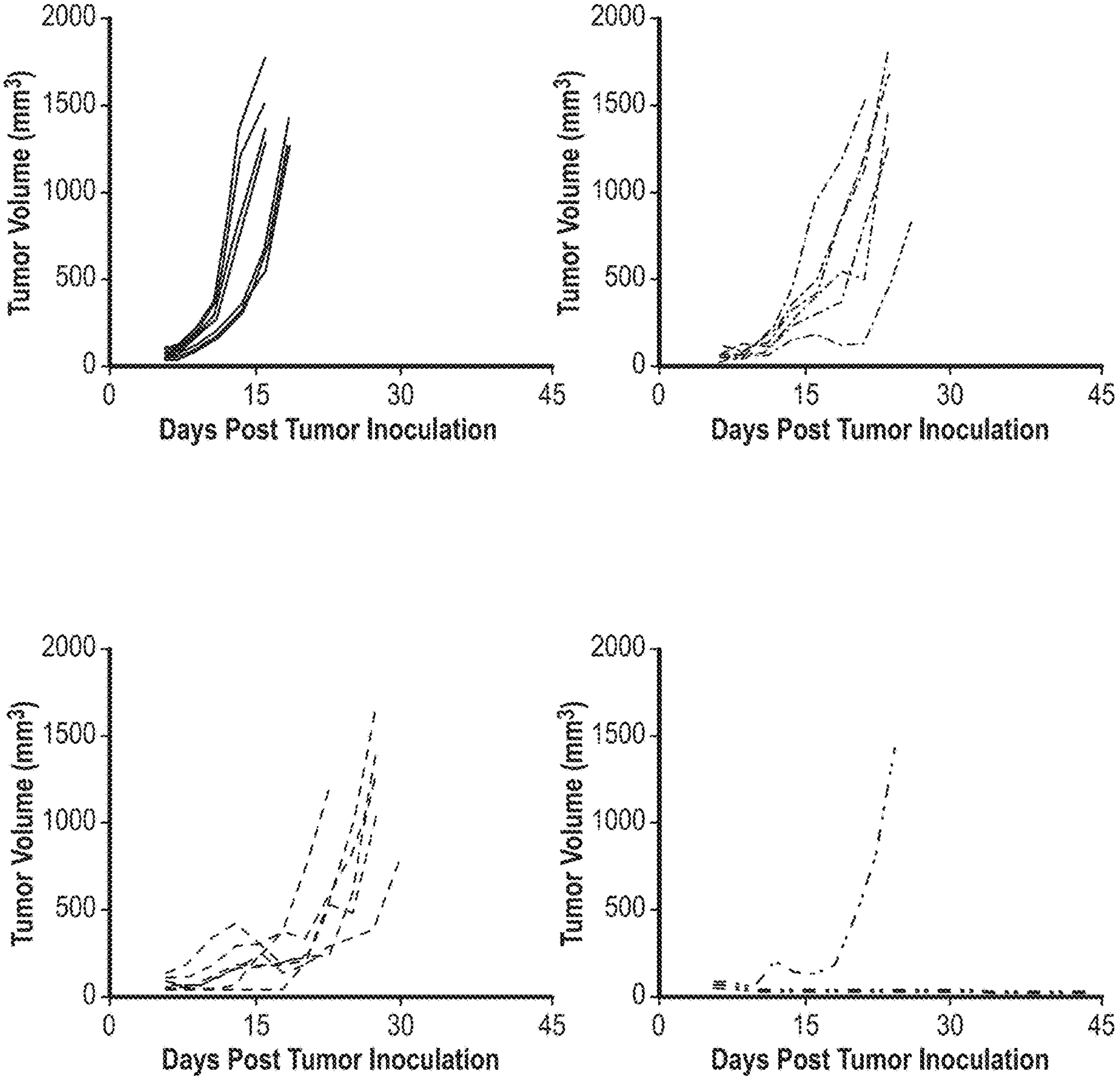
Figure 10E:
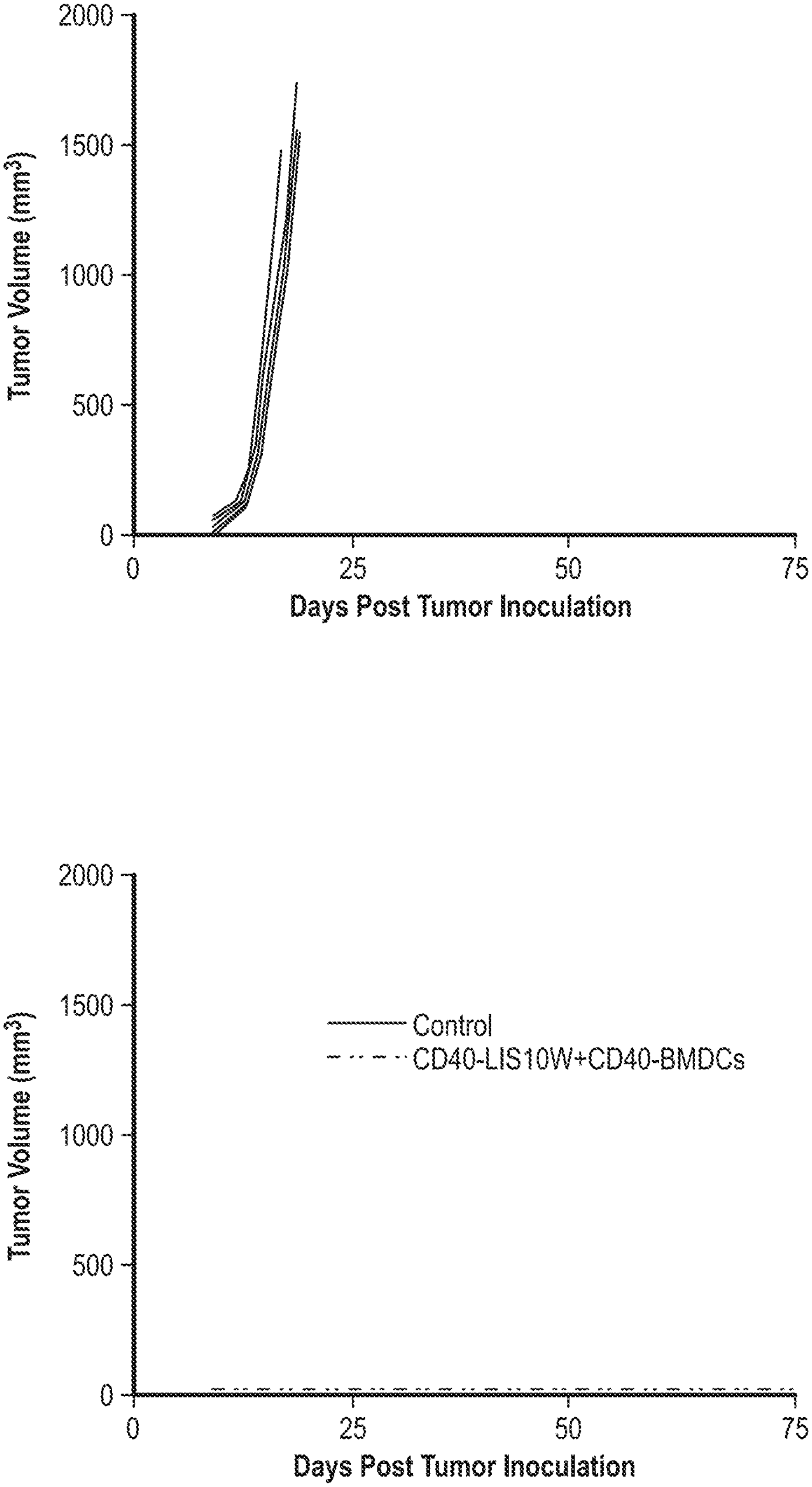
Figure 10F:
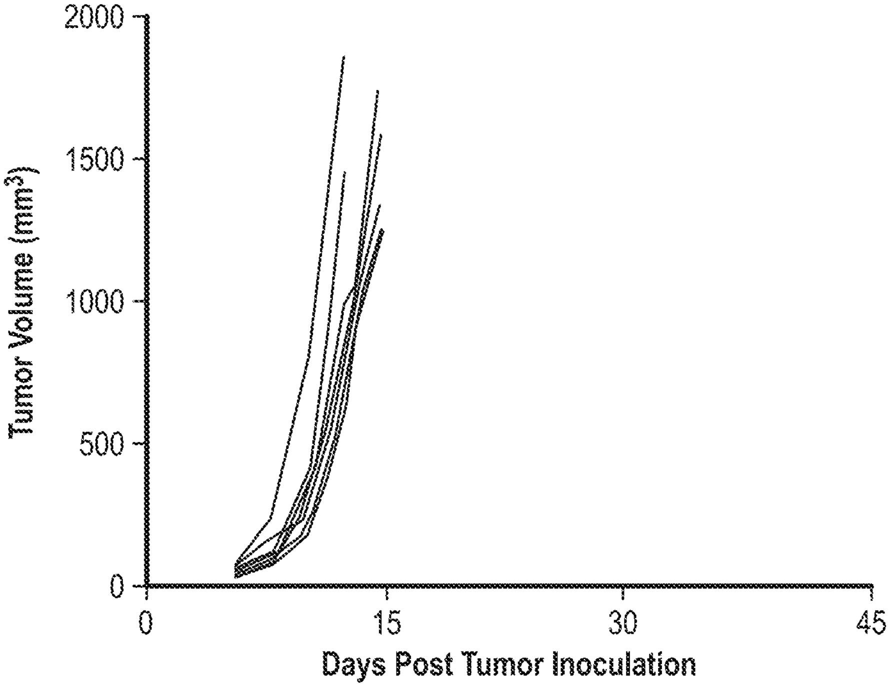
Figure 10F:
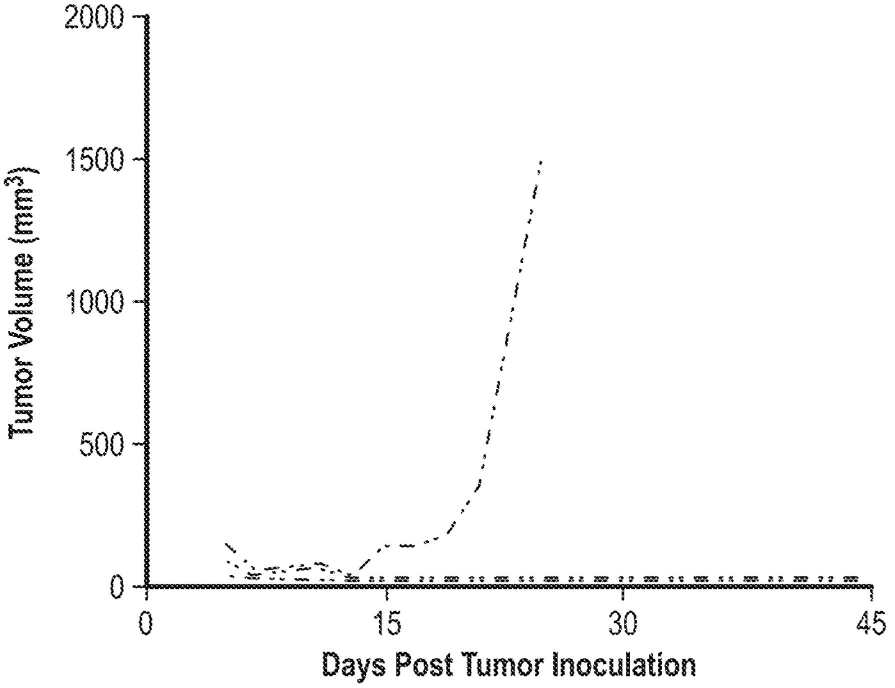
Figure 10G:
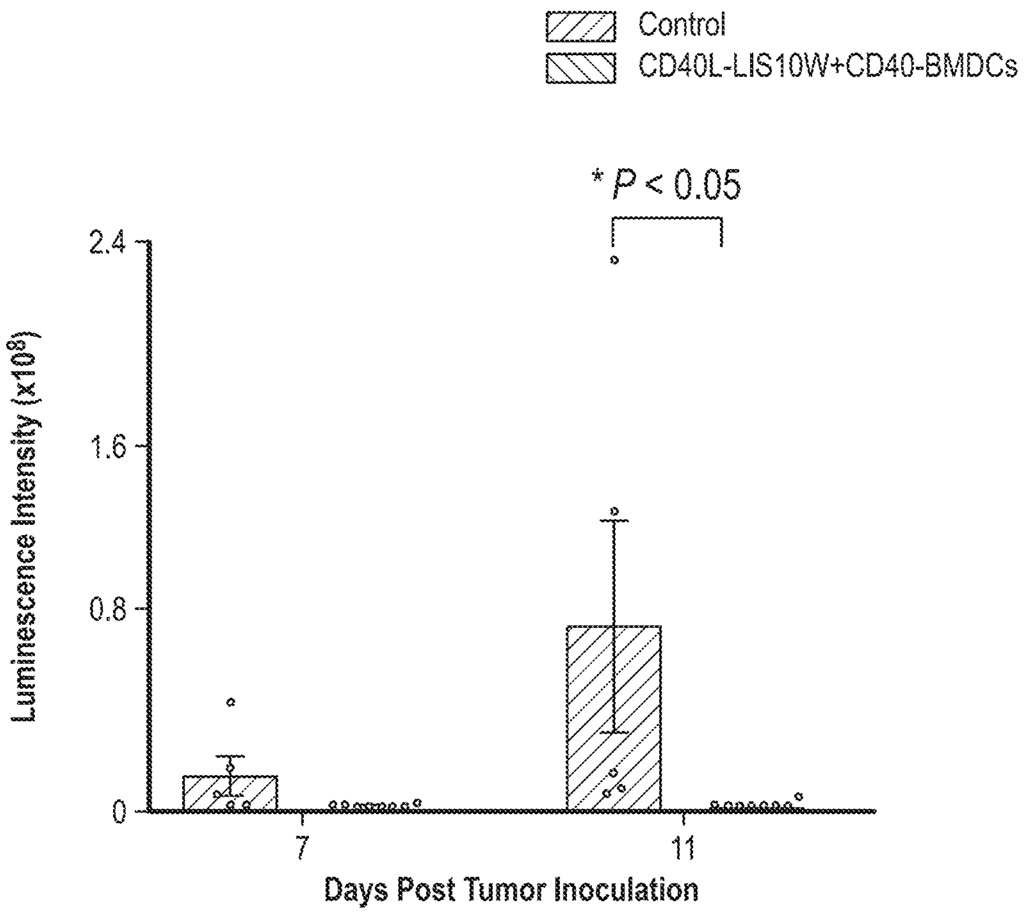

To evaluate the antitumor effects of the combination of cancer cell ICD and adoptive CD40-BMDC transfer, CD40-BMDCs were i.t. administrated 18 h after i.t. injection of CD40L-LIS10W (FIG. 3G). Four doses of this treatment regimen resulted in complete tumor regression in 83% B16F10 tumor bearing mice (FIG. 3H, FIG. 10A), which was significantly higher than CD40O-BMDCs+CD40 Ab treatment (0%, P<0.05) and CD40L-DIM7S+CD40-BMDCs treatment (17%, P<0.05). Importantly, all the responder mice in CD40L-LIS10W+CD40-BMDCs group were resistant to B16F10 tumor rechallenge on the opposite flank (FIG. 3I, FIG. 10B), indicating the development of antitumor memory. These results highlighted the crucial role of ICD in priming antitumor immunity in the CIC. To further confirm the function of CD40-BMDCs and CD40L-mediated activation in this treatment regimen, another two treatment groups were further studied, including FLuc-LIS10W+CD40-BMDCs and CD40L-LIS10W+CD40-DIM7S (FIG. 3J). Although FLuc-LIS10W and CD40L-LIS10W showed similar in vivo ICD effects (FIG. 3F), CD40L-LIS10W+CD40-BDMCs dramatically suppressed tumor growth by about 21 folds (P<0.05) and 7 folds (19 d post inoculation, P<0.05) in comparation with FLuc-LIS10W+CD40-BDMCs and CD40L-LIS10W+CD40-DIM7S, respectively (FIG. 5C, 5D), Furthermore, 83% mice survived from the CD40L-LIS10W+CD40-BDMCs group while none of the mice survived from the other two treatments 45 d after tumor inoculation (P<0.01, FIG. 3K). Additionally, upon rechallenge with B16F10 cells on the opposite flank, 100% responder mice were resistant to secondary tumor development (FIG. 3L, FIG. 10E). These findings implied that ICD treatment alone is not sufficient to eradicate tumoral lesions, emphasizing the importance of dendritic cell infiltration and activation. Long-term benefit of immunotherapy requires antitumor memory against tumor recurrence. Thus, the development of antitumor memory was further validated via an intracranially (i.c.) rechallenged mouse model (FIG. 3M). In this experiment, another melanoma cell line (B16F10-Luc2) was used containing a luciferase reporter, which facilitated monitoring brain tumor growth via bioluminescence imaging. CD40L-LIS10W+CD40-BDMCs treatment achieved about 88% complete regression of the primary s.c. tumor 45 d after tumor inoculation (FIG. 3N, FIG. 10F). Notably, the survived mice showed significantly delayed tumor growth in the brain (11 d post inoculation, P<0.05, FIG. 10G). Moreover, 38% of the responder mice remained tumor-free compared to 0% of naive controls (75 d post i.e. rechallenge, P<0.01, FIG. 3O). These data showed that a robust antitumor memory T cell population was generated from this local therapy.

Figure 4A:
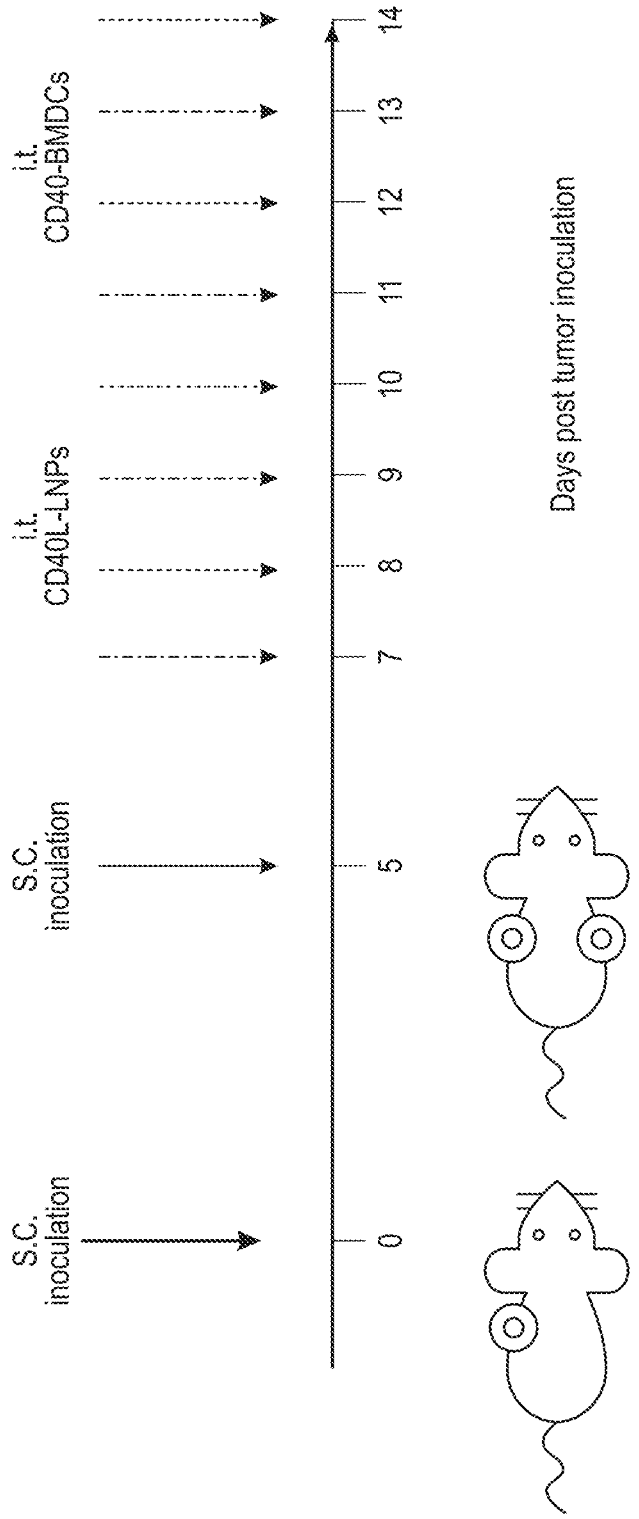
FIGS. 4A-4L. Therapeutic effects on two tumor or T cell depletion models, and the dynamic expression of cytokines and chemokines in tumoral tissues and blood. a, Schematic illustration of the B16F10 tumor model and the treatment regimen. b, c, Distal tumor volumes of individual mice (b) and mouse survival (c) over time; n=8 or 10. d, Schematic illustration of the B16F10-Luc2 tumor model and the treatment regimen. e, f, Brain tumor volumes (e) and mouse survival (f) over time; n=10. g, Schematic illustration of the B16F10 tumor model and the treatment regimen. h, i, Tumor volumes (h) and mouse survival (i) over time; n=6. j, Schematic illustration of the treatment regimen and sample collection. k, l, The dynamic expression of cytokines and chemokines in tumoral tissues (k) and blood (l); n=5. Data in b, e, and h are presented as mean±s.c.m. Statistical significance in b, e, and h was analyzed by two-tailed Student's t-test. Statistical significance in c, f, and i was analyzed by log-rank (Mantel-Cox) test. *P<0.05, P<0.01, *P<0.001, ****P<0.0001.
Figure 4B:
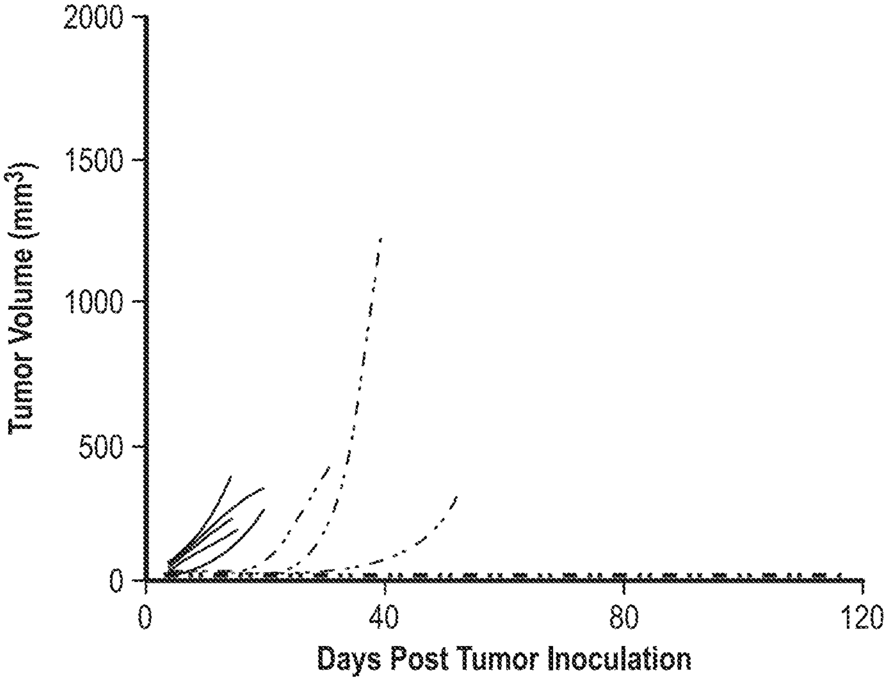
Figure 4C:
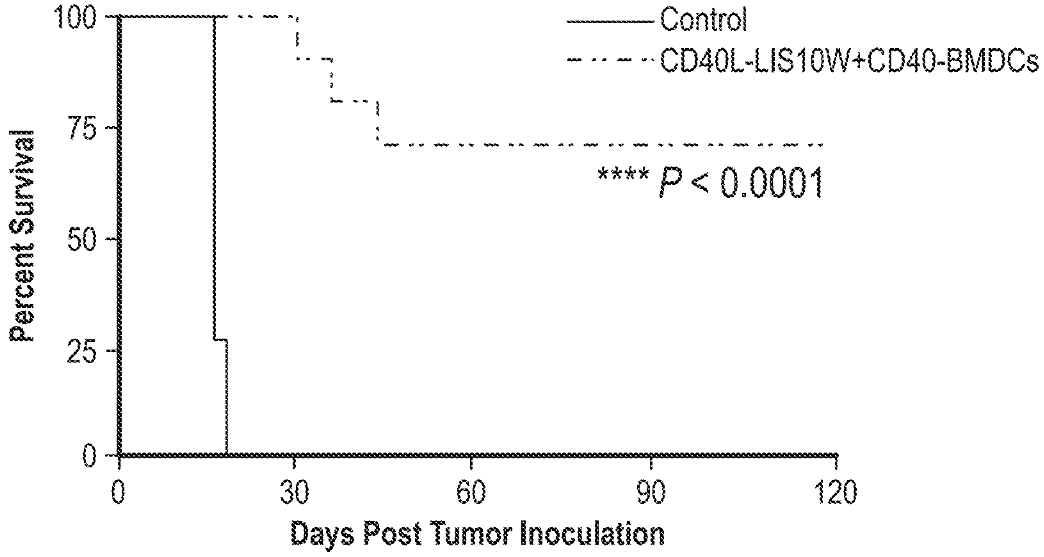
Figure 4D:
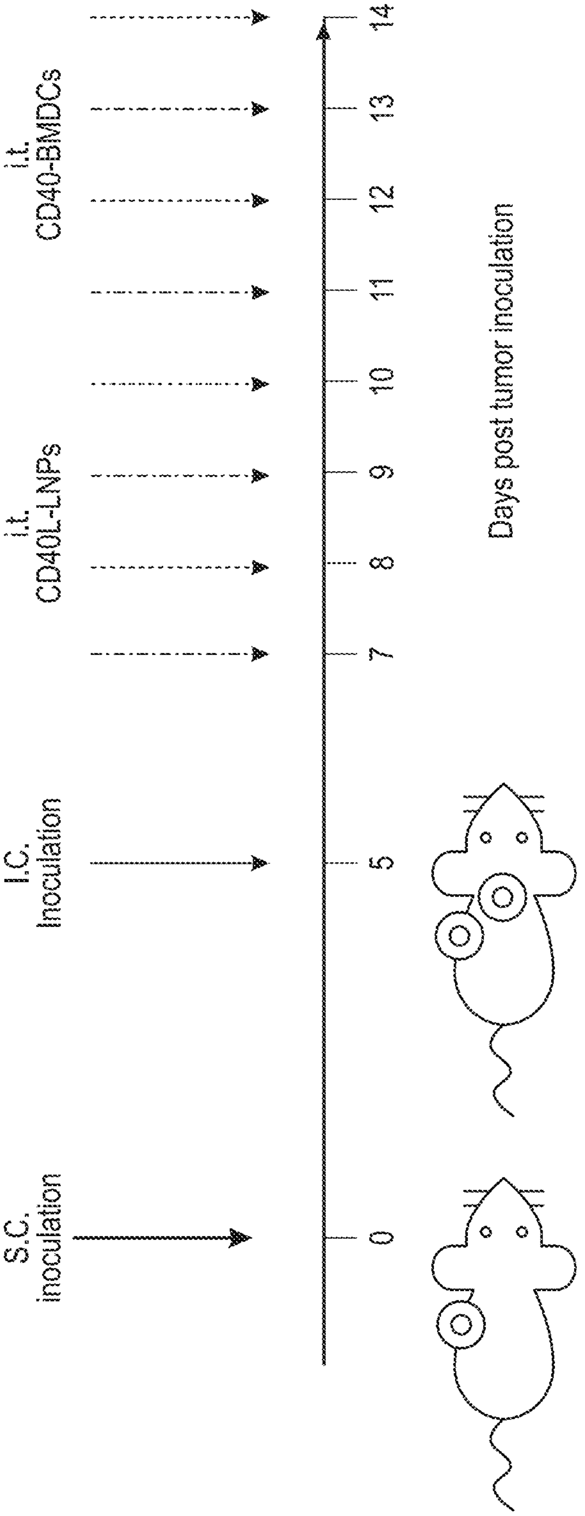
Figure 4E:
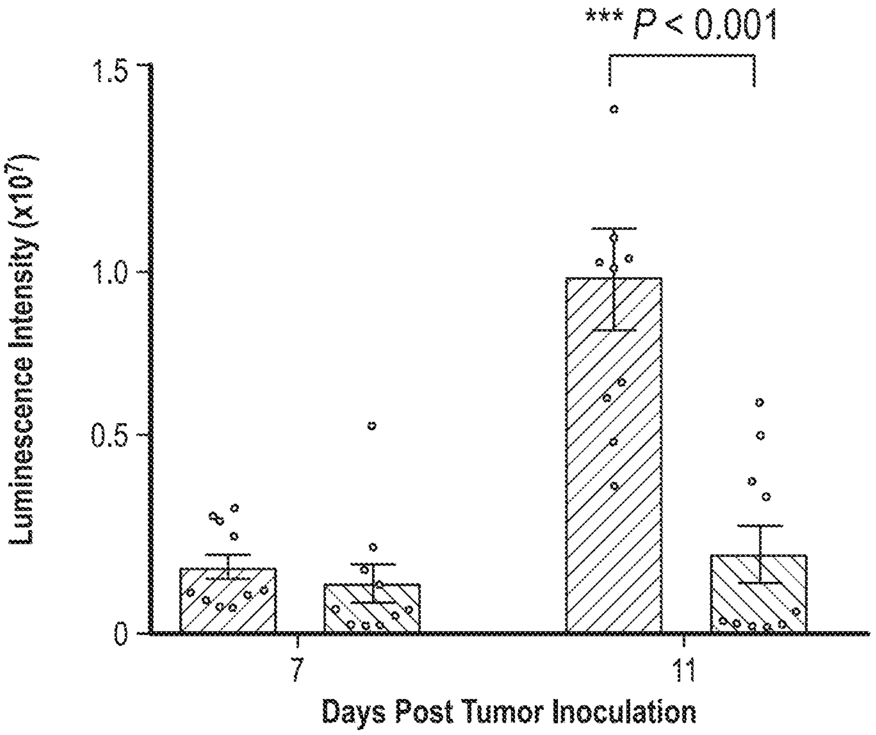
Figure 4F:
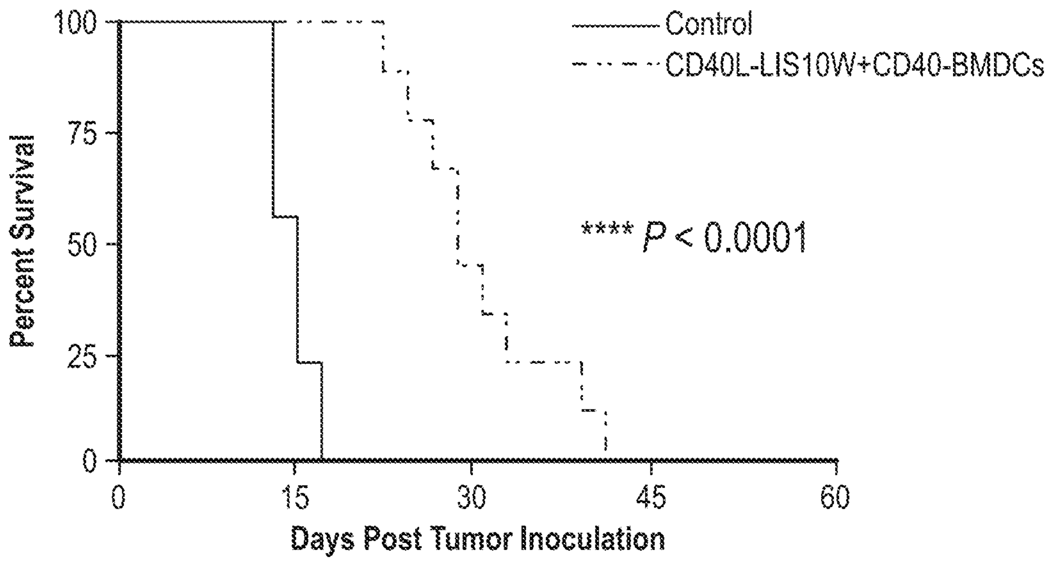
Figure 11A:
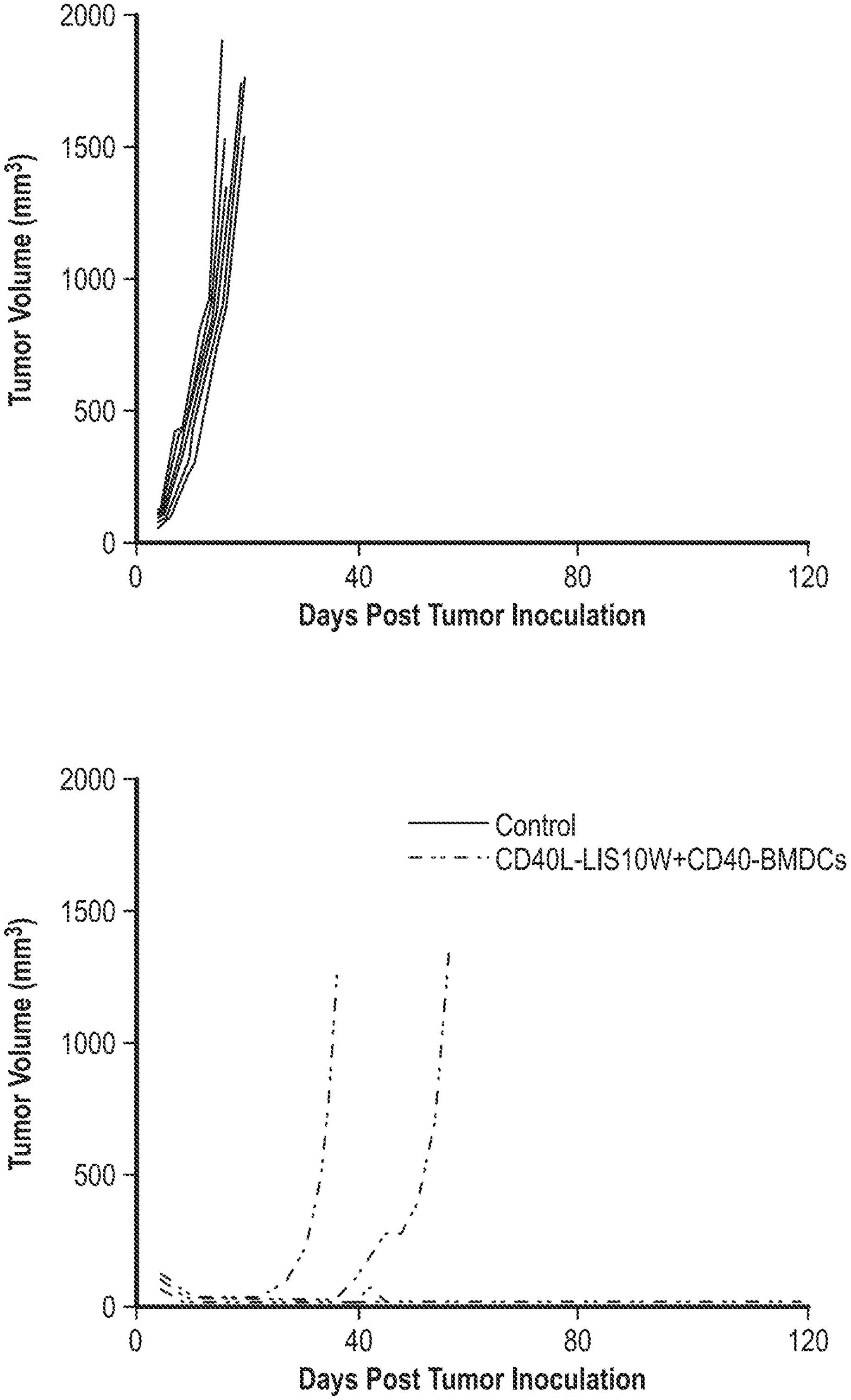
FIGS. 11A-11C. Tumor volume of individual mice. a, Tumor volume on the treated. side of individual mice; n=8 or 10. b, Tumor volume on the treated side of individual mice; n=10. c, Tumor volume of individual mice; n=6.
Figure 11B:
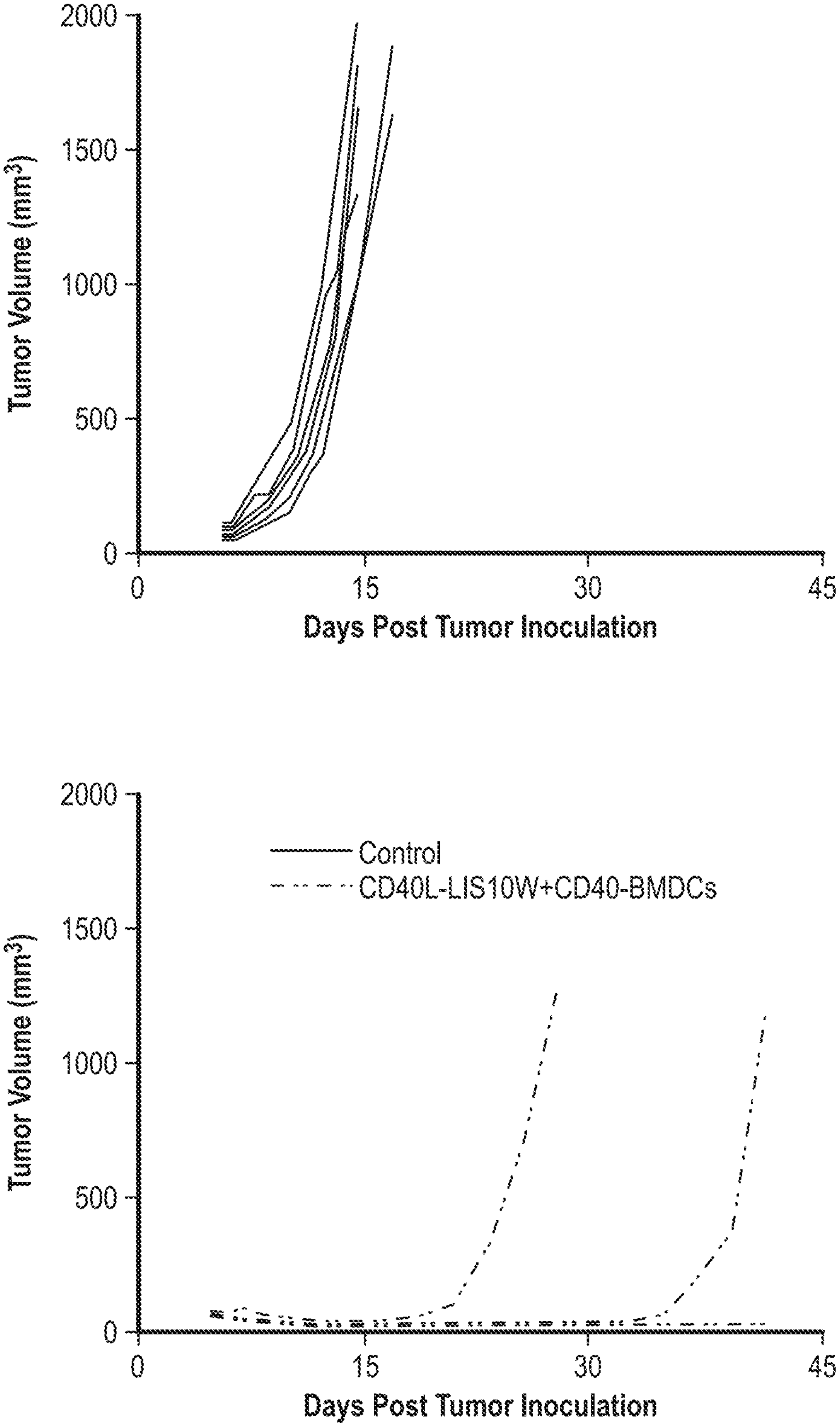

The efficacy of local immunotherapy in treating metastatic cancer is dependent on the development of a systemic antitumor immunity[5,7,10]. To evaluate this, B16F10 cells were inoculated on both flanks of each mouse, followed by CD40L-LIS10W+CD40-BDMCs treatment on one tumor site (FIG. 4A). The treatment eliminated 80% primary tumor (FIG. 11A) and 70% distal tumor (FIG. 4B), and the overall survival rate was around 70% (FIG. 4C). In another two-tumor model (skin+brain tumors), B16F10-Luc2 cells were s.c. and i.c. inoculated (FIG. 4D). CD40L-LIS10W+CD40-BDMCs treatment eradicated 80% s.c. tumor (FIG. 11B). Meanwhile, the treatment visibly regressed tumor growth in the brain (11 d post inoculation, P<0.001, FIG. 4E) and significantly prolonged the overall survival time (P<0.0001, FIG. 4F). Altogether, these results indicate that the local treatment resulted in systemic antitumor immunity.

Figure 4G:
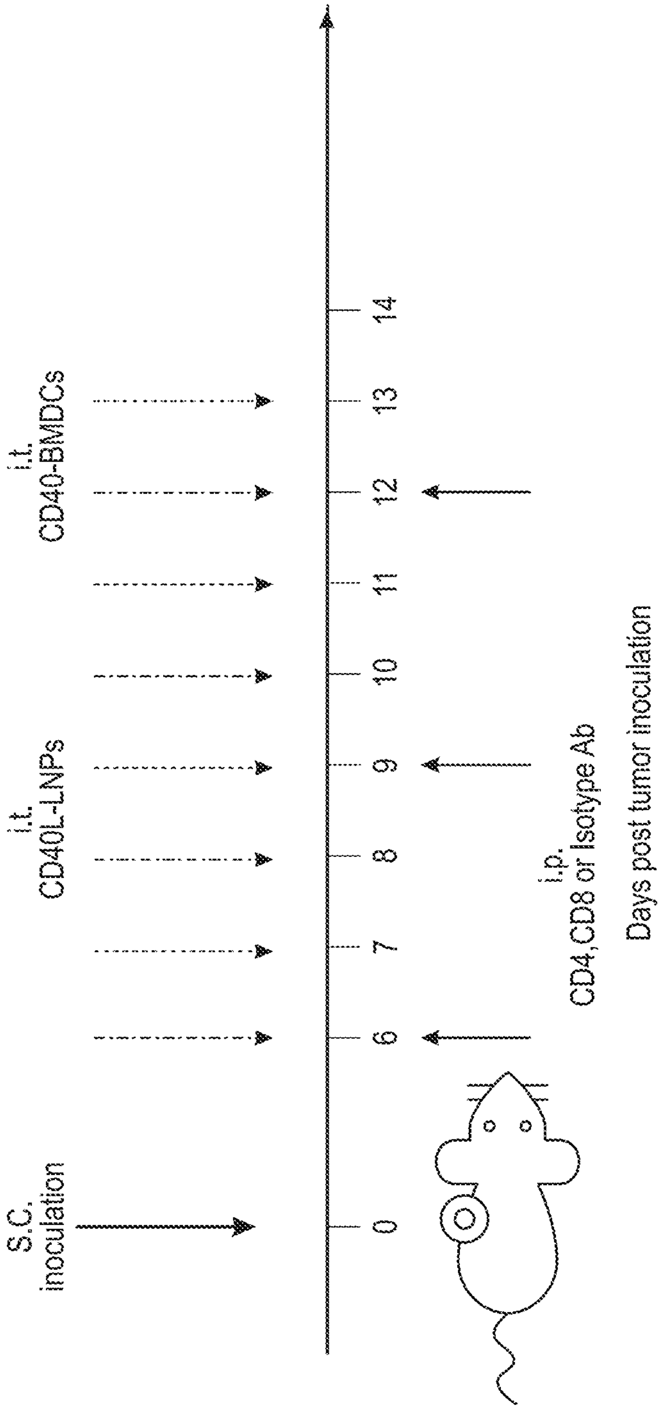
Figure 4H:
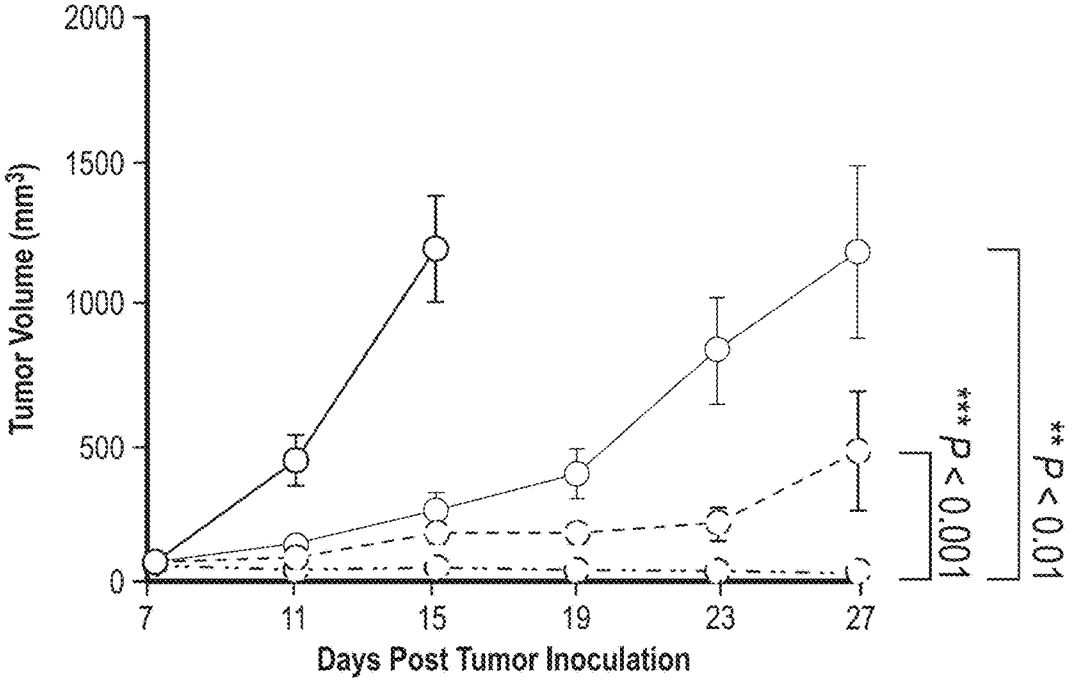
Figure 4I:
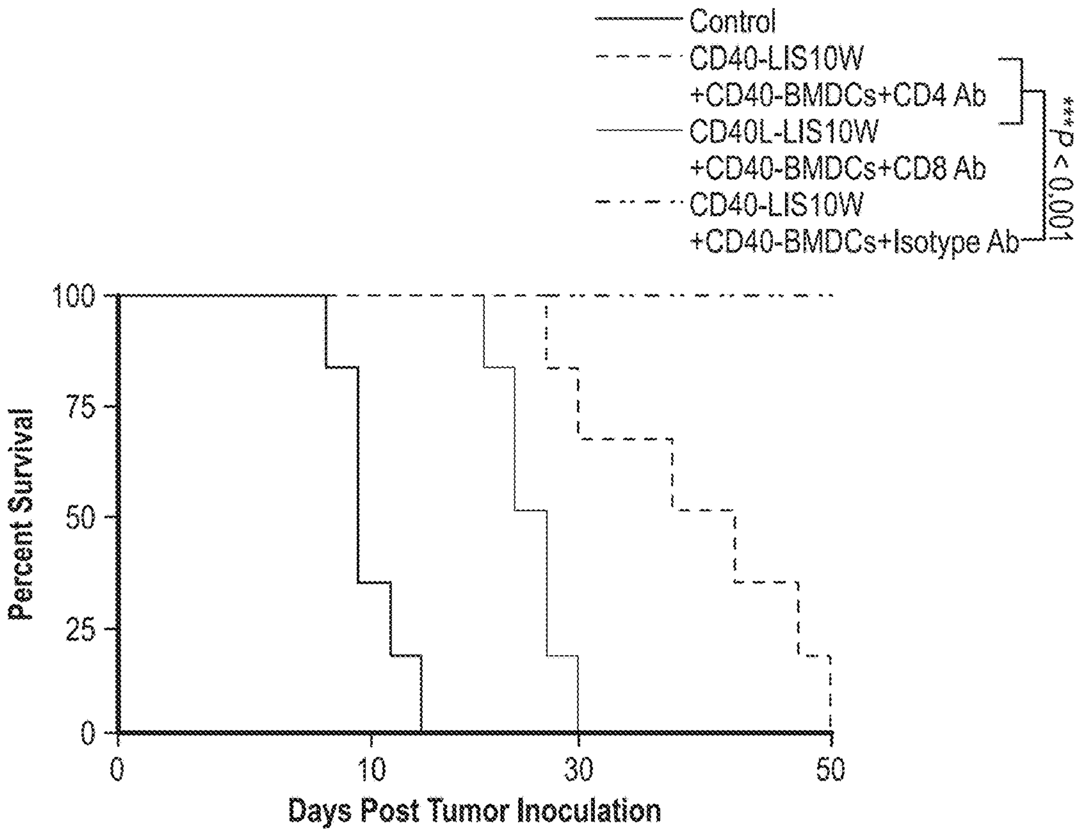
Figure 11C:
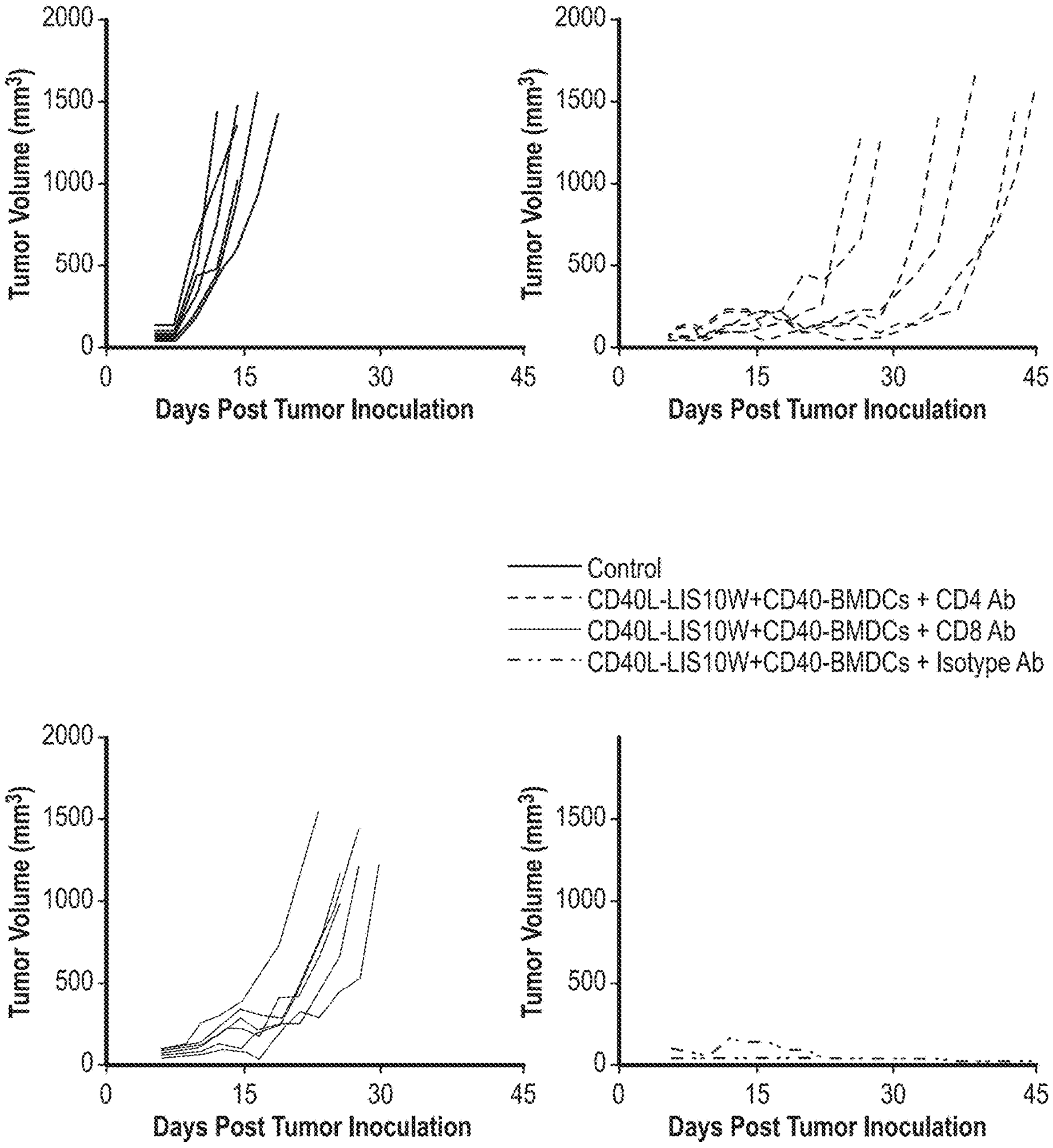

T cell-mediated cancer cell killing is an important step for eradicating tumoral lesions in the CIC. To evaluate the role of CD8 and CD4 T cells on the therapeutic efficacy, CD40L-LIS10W+CD40-BDMCs treatment was performed on mice receiving anti-CDS, anti-CD4, or isotype control Abs (FIG. 4G). Relative to the control group, the depletion of CD8 or CD4 T cells greatly compromised the tumor regression and mouse survival of CD40L-LIS10W+CD40-BDMCs treatment (FIG. 4H, 4I, FIG. 11C). Particularly, the depletion of CD8 T cells led to a more remarkably weakened therapeutic efficacy relative to the depletion of CD4 T cells (FIG. 4H, 4I, FIG. 11C), suggesting the crucial role of CD8 T cells in this treatment.

Figure 4J:
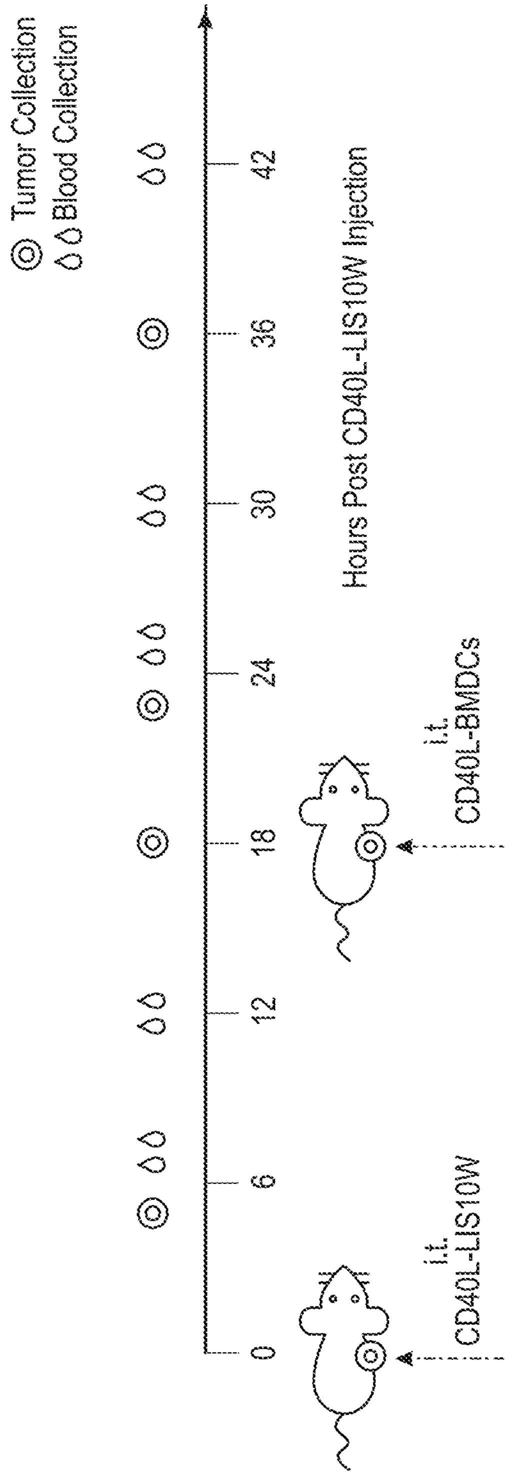
Figures 4K, 4L:
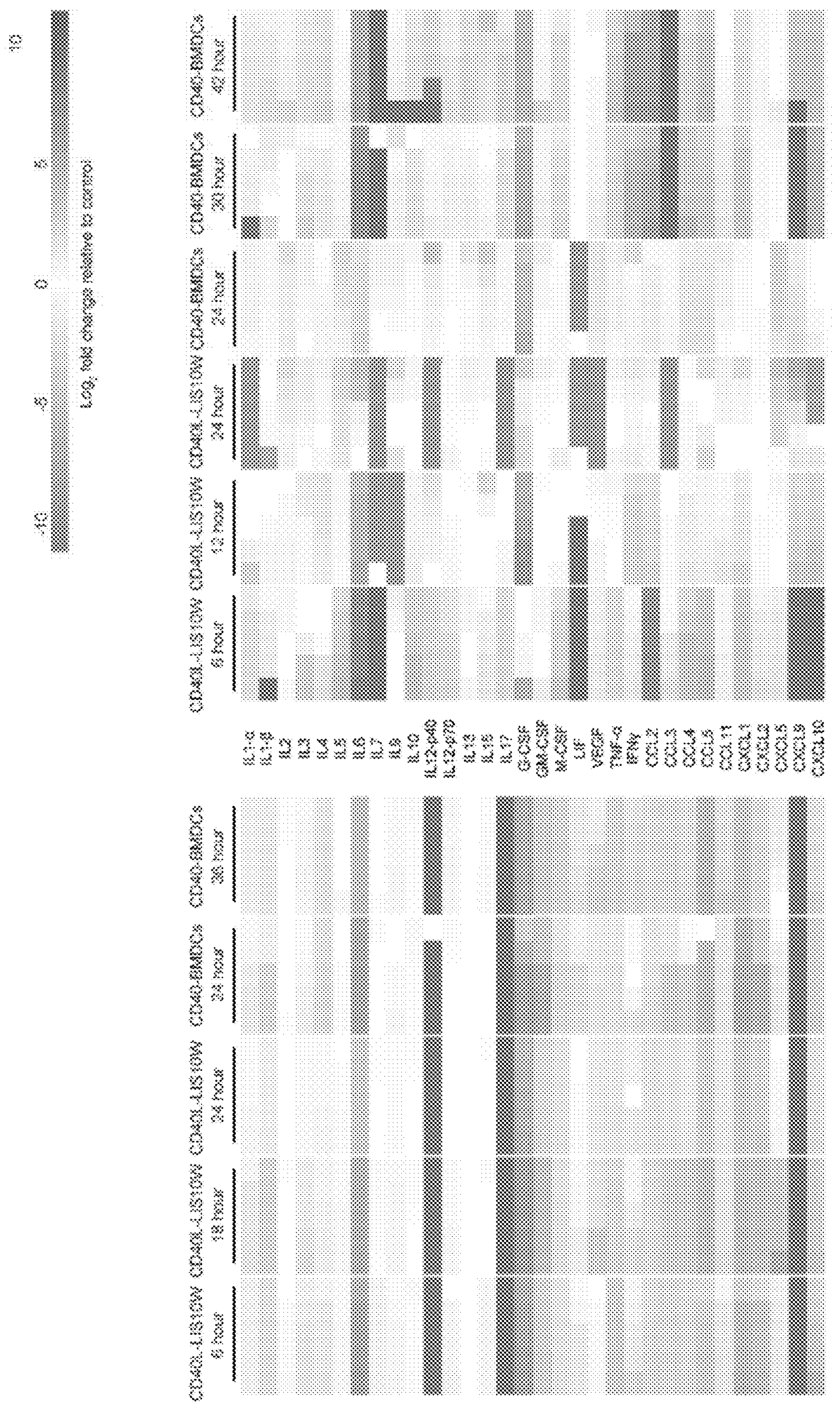
Figure 5A:
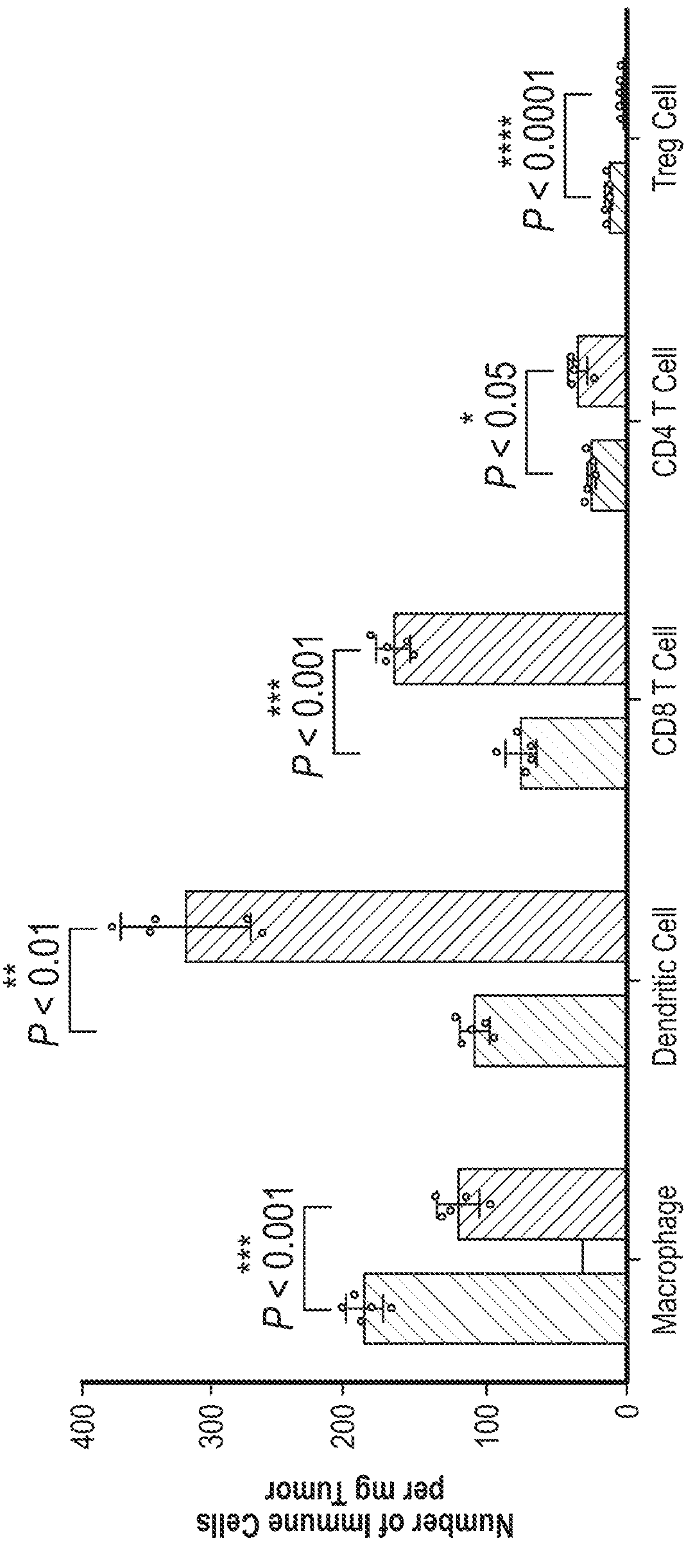
FIGS. 5A-5E. Immune cell infiltration in tumoral tissues. a, Immune cell populations in tumoral tissues; n=5. b, Percentage of activated macrophages and dendritic cells in in tumoral tissues; n=5. c, Percentage of primed CD8 T cells in tumoral tissues; n=5. d, e, Percentage of effector memory T cells and central memory T cells in the spleen (d) and blood (e); n=5.
Figure 5B:
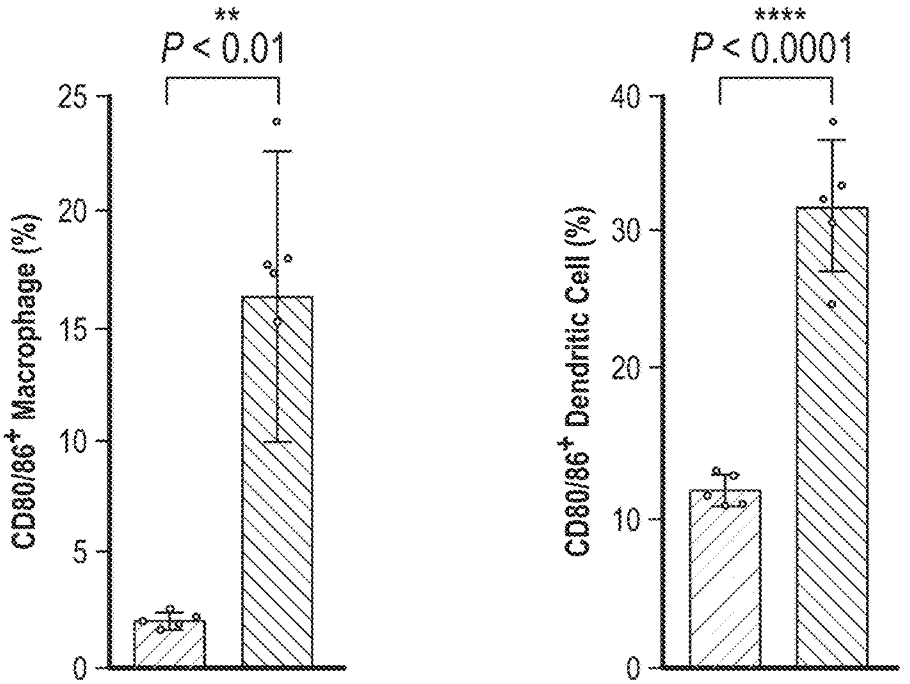
Figure 12:
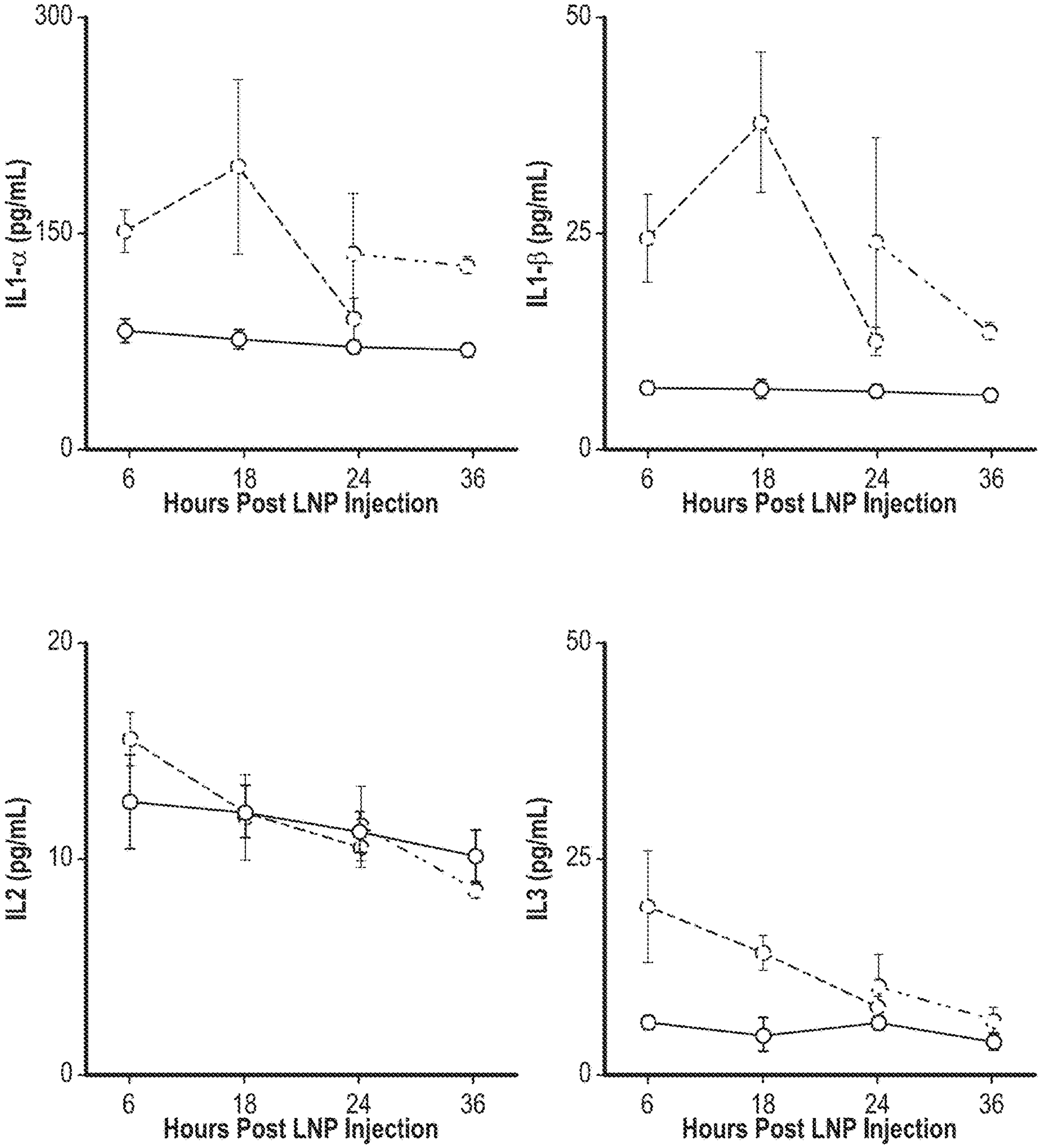
FIG. 12. The dynamic expression of cytokines and chemokines in mouse melanoma tissues; n=5.
Figure 13:
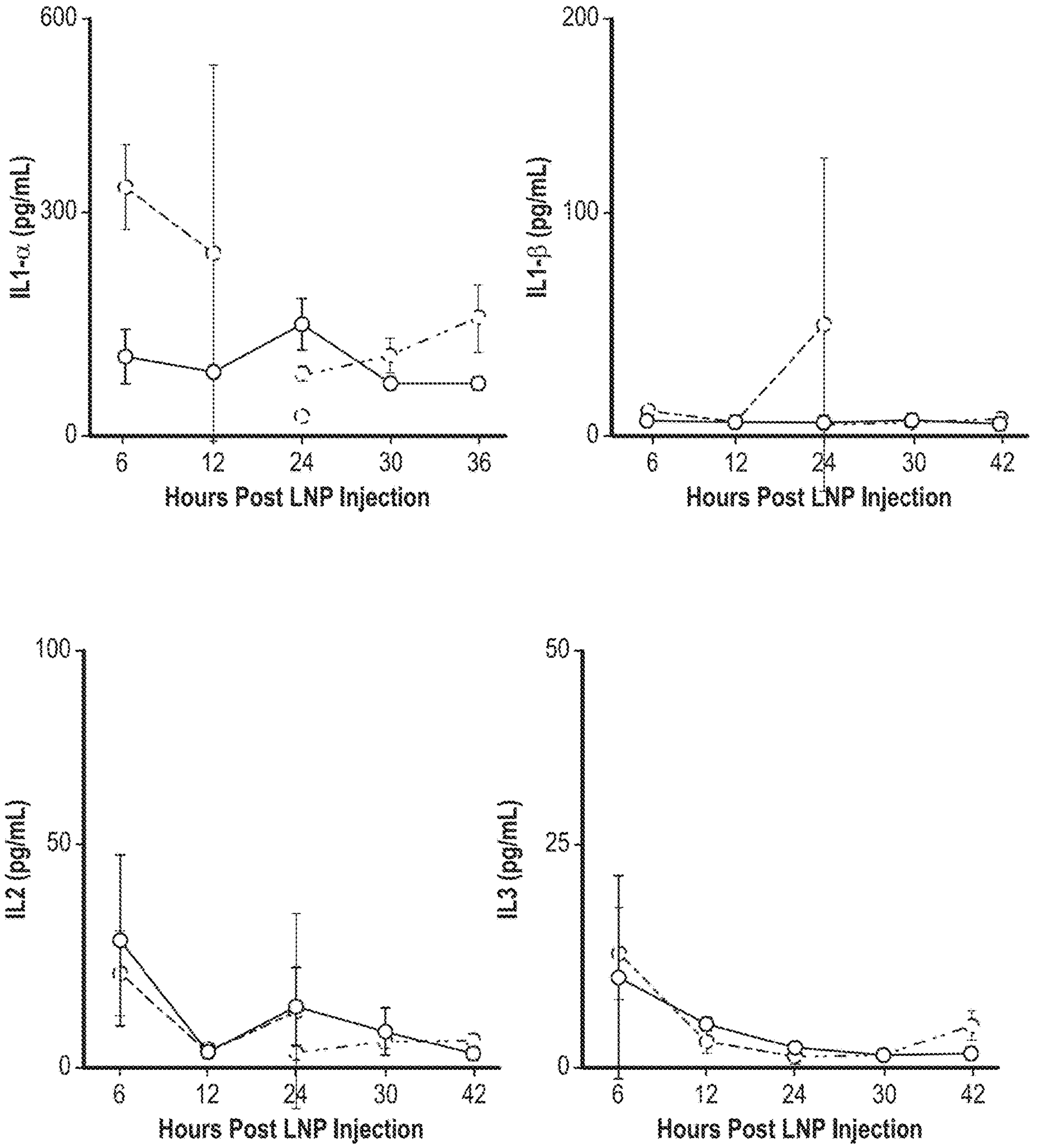
FIG. 13. The dynamic expression of cytokines and chemokines in mouse blood; n=5.

To uncover the underlying mechanisms of action for the treatment regimen of CD40L-LIS10W+CD40-BDMCs, the dynamic expression of cytokines and chemokines was used in mouse melanoma tissues and blood after the first injection (FIG. 4J). In tumoral tissues, CD40L-LIS10W elicited 29 cytokines and chemokines such as GM-CSF, IFN-γ, TNF-α, CCL5, and CXCL10 in a 32-plea panel from 6 to 24 h time course (FIG. 4K, FIG. 12). Moreover, their concentrations were further increased after i.t. administration of CD40-BDMCs (FIG. 4K, FIG. 12). In the blood, most of the cytokines and chemokines were upregulated 6 h post CD40L-LIS10W injection while their concentrations gradually decreased in the following 18 h (FIG. 4L, FIG. 13). However, CD40-BDMC administration re-stimulated the production of many cytokines and chemokines from 24 to 42 h time course (FIG. 4L, FIG. 13). These data indicate that CD40L-LIS10W+CD40-BDMCs better reprogrammed the immunosuppressive TME and induced stronger systemic immune responses than CD40L-LIS10W alone. The upregulation of these inflammatory cytokines and chemokines may not only enhance the recruitment and activation of immune cells, but also facilitate the development of immunological memory. Next, the changes of immune cell populations were profiled in tumoral tissues after CD40L-LIS10W+CD40-BDMCs treatment. In this experiment, CD40-BMDCs were labelled by CellTrace Blue before i.t. injection, which can distinguish the administrated dendritic cells from the endogenous dendritic cells via flow cytometry analysis. The treatment resulted in a massive influx of dendritic cells, CD8 T cells, and CD4 T cells while decreased the recruitment of macrophages and regulatory T (Treg) cells in tumoral tissues (FIG. 5A). Moreover, the treatment enhanced the percentage of antitumor phenotypes of APCs, including $CD80/86^+$ macrophages (P<0.01) and $CD80/86^+$ dendritic cells (P<0.0001, FIG. 5B). Importantly, the treatment stimulated the expression of Ki-67 (P<0.01), IFN-δ/TN-α (P<0.0001), and granzyme B (P<0.001, FIG. 5C) in CD8 T cells, indicating the generation of cytotoxic T cells. Memory T cells were also examined in the spleen and blood from the responder mice. Compared to naive controls, the numbers of effector memory and central memory T cells in both spleen and blood significantly increased, suggesting the development of long-term antitumor immunity.

Discussion

Figure 3O:
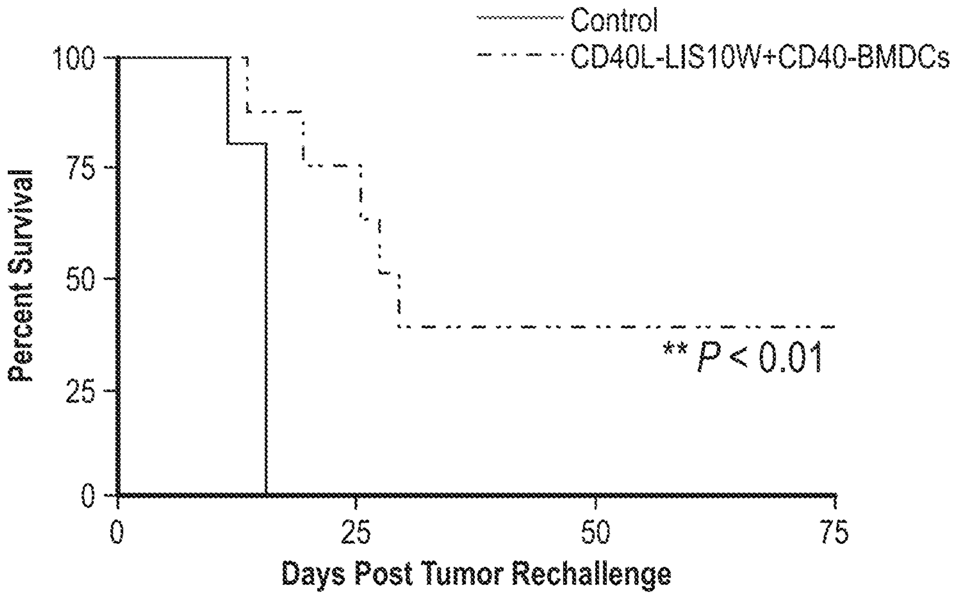
Figure 5C:
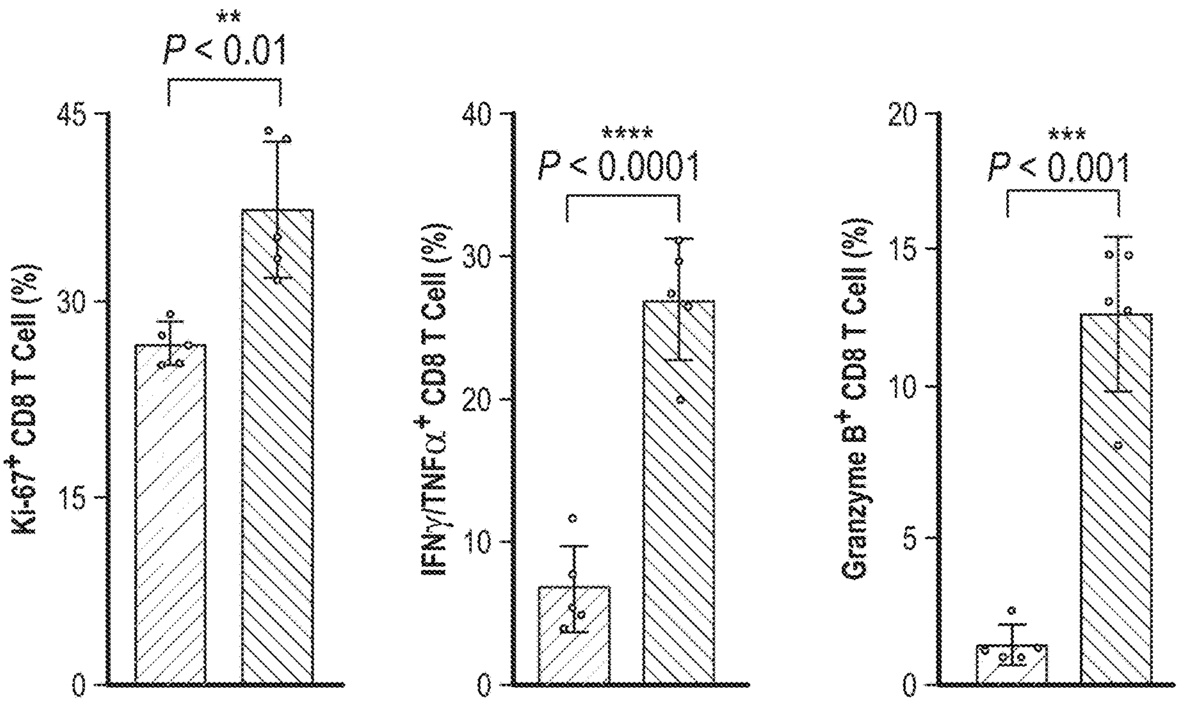
Figure 5D:
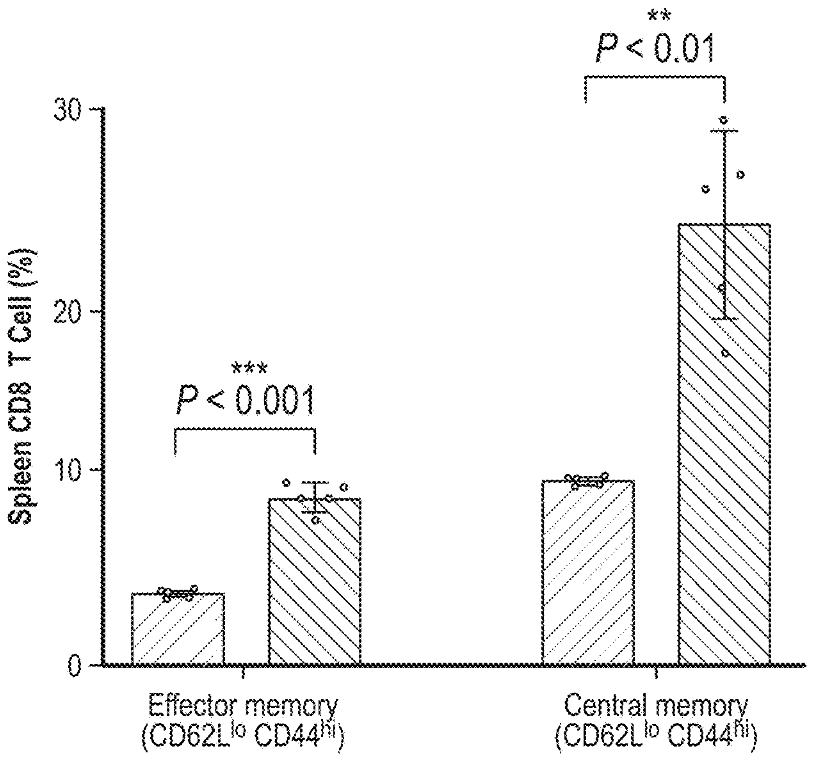
Figure 5E:
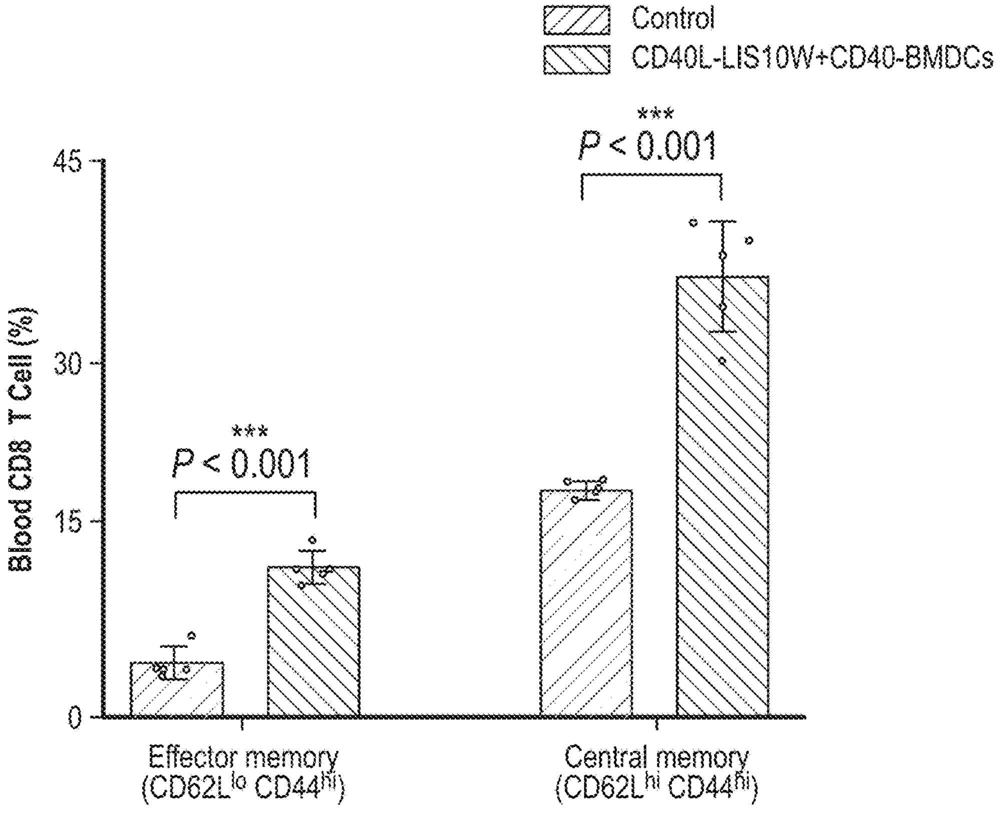

The immunosuppressive tumor microenvironment (TME) blocks the immune activation in the Cancer Immunity Cycle (CIC), leading to uncontrollable tumor growth, metastasis, and relapse. To overcome the incomplete activation, lipid nanoparticle (LNP)-induced immunogenic cell death (ICD) and dendritic cell therapy were combined to appropriately boost the CIC via comprehensive immune responses. A library of sugar alcohols-derived ionizable lipids was synthesized and two preferred LNP formulations were identified, DIM7S and LIS10W, for effective mRNA delivery. DIM7S showed 10-fold and 30-fold higher mRNA delivery efficacy in BMDCs than Lipo 3K and Electro, respectively (FIG. 7D). LIS10W induced robust ICD in melanoma tissues (FIG. 3F) and effectively delivered mRNA into melanoma cells (FIG. 9C, 9D). For CD40L-LIS10W+CD40-BMDCs treatment, CD40L, LIS10W was first i.t. administrated to induce cancer cell death. This caused the release of TAAs and DAMPs (e.g., HMGB1, extracellular ATP, and cellular surface calreticulin), and simultaneously resulted in CD40L expression in tumoral tissues. Next, CD40-BMDCs were i.t. adoptively transferred that were ex vivo engineered by CD40-DIM7S. Both in vitro and in vivo data showed that these activated dendritic cells upregulated the costimulatory molecules (FIG. 3A, FIG. 5B) and inflammatory cytokines (FIG. 3A, FIG. 4K, 4L), which together with presented TAAs stimulated the differentiation of naive T cells into cytotoxic CD8 T cells (FIG. 5C). On one hand, this benefits T cells-mediated cancer cell killing, an important step for eliminating tumoral lesions in the CIC. On the other hand, T cell priming facilitates their production of IFN-γ and TNF-α, which in turn activates APCs and elicits the production of chemokines (FIG. 4K, 4I), such as CCL3, CCL4, CCL5 and CXCL10. In response to these chemokines, additional APCs and T cells are recruited into tumoral tissues (FIG. 5A). All these events contribute to reprogramming the immunosuppressive TME, and continuously amplifying and broadening the CIC, ultimately leading to complete regression of over 80% primary cutaneous melanoma tumor (FIG. 3H, 3K, 3N). Importantly, the boosted CIC benefits the generation of memory CD8 T cells in the spleen and blood (FIG. 5D, 5E), resulting in nearly 100% and 38% protection from s.c. and i.c. melanoma rechallenge in responder mice, respectively (FIG. 3I, 3L, 3O). Lastly, this local treatment prevents about 70% distal cutaneous tumors and significantly regresses distal brain tumors, suggesting the effective suppression of metastatic cancers.

In summary, it was shown that synergistically inducing cancer cell immunogenic cell death (ICD) and dendritic cell activation, the first two steps in the Cancer Immunity Cycle (CIC), can reprogram the immunosuppressive TME and facilitate tumor antigen presentation. This strategy results in potent effector T cell responses and protective immune memory against cancer-specific antigens, which is reflected in the eradication of both local and distal tumors, and the prevention from tumor rechallenge. Overall, the combination of lipid-nanoparticle-mRNA formulations and dendritic cell therapy provides an important platform for cancer immunotherapy.

Materials and Methods

Antibodies

Antibodies used for flow cytometry: CD40-FITC (eBioscience, 11040285), CD40L-FITC (eBioscience, MA516506), CD80-FITC (eBioscience, 11080181), CD86-PE (eBioscience, 12086281), CD86-FITC (eBioscience, 11086281), MHCII-APC (eBioscience, 17532080), pro-form IL-1β-FITC (eBioscience, 11711480), calreticulin-Alexa Fluor 647 (Novus Biologicals, NBP1-47518AF647), Ki-67-FITC (eBioscience, 11569882), Granzyme B-FITC (eBioscience, 11889882), IFNγ-FITC (Biolegend, 505806), TNFα-FITC (eBioscience, 11732181), CD62L-FITC (eBioscience, 11-0621-81), CD44-Alexa Fluor 700 (eBioscience, 56044182)

Antibodies used for ELISA: rat anti-mouse IL-12 p70 (eBioscience, MM121), rat anti-mouse TNFα (eBioscience, 14732581), goat anti-rat IgG-HRP (Cell Signaling, 7077S), mouse anti-mouse HMGB1 (eBioscience, MA120338), goat anti-mouse IgG-HRP (Abeam, ab7068). Antibodies used for in vivo: anti-mouse CD40 antibody (CD40 Ab, BioXcell, BP00162), anti-mouse CD8α (Bioxcell, BE0004-1), anti-mouse CD4 (Bioxcell, BP0003-1), anti-rat IgG2b isotype (Bioxcell, BP0090)

Cell Culture

B16F10 melanoma cell line was obtained from Dr. Jianhua Yu's lab. B16F10-Luc2 melanoma cell line was purchased from American Type Culture Collection (ATCC). These two cell lines were cultured with Dulbecco's modified Eagle medium (ATCC, 302002) containing 10% fetal bovine serum (FBS, Gibco, 26140079) in an incubator at 37° C. in 5% CO2. Mouse bone marrow derived dendritic cells (BMDCs) were obtained by adaptation of previous procedures[19]. Briefly, monocytes were isolated from mouse bone marrow and cultured in RPMI 1640 medium containing 10% FBS, 50 ng/mL GM-CSF (Shenandoah Biotechnology, 20015) and 50 ng/mL IL4 (Shenandoah Biotechnology, 20018). After 8-day culture, BMDCs were purified with CD11c beads (Miltenyi Biotec, 130108338).

Flow Cytometry Gating

The gating strategies were based on previously reported methods[10,19].

B16F10 cells: $CD45^-$
Macrophages: $C45^+$, $CD11b^+$, $F4/80^+$
Activated macrophages: $CD45^+$, $CD11b^+$, $F4/80^{+,}$ $CD80^+/CD86^+$
Dendritic cells: $CD45^+$, $CD11b^+$, $CD11c^+$
Activated dendritic cells: $CD45^+$, $CD11b^+$, $CD11c^+$, $CD80^+/CD86^+$
CD4 T cells: $CD45^+$, $CD3e^+$, $CD4^+$, $FoxP3^-$
Regulatory T cells: $CD45^+$, $CD3e^+$, $CD4^+$, $FoxP3^+$
CD8 T cells: $CD45^+$, $CD3e^+$, $CD8a^+$
Effector memory T cells: $CD45^+$, $CD3e^+$, $CD8a^+$, $CD44^{hi}$, $CD62L^{lo}$
Central memory T cells: $CD45^+$, $CD3e^+$, $CD8a^+$, $CD44^{hi}$, $CD62L^{hi}$
Activated CD8 T cells: $CD45^+$, $CD3e^+$, $CD8a^+$, $Ki\text{-}67^+$/Granzyme $B^+/IFN\gamma^+/TNF\alpha^+$ mRNA Synthesis

The linear dsDNA of firefly luciferase (FLuc), mouse CD40, and mouse CD40L were obtained from Integrated DNA Technologies. The pUC19 vector was used for Golden Gate assembly to generate plasmids. mRNAs of FLuc, mouse CD40, and mouse CD40L were synthesized by previously reported methods[20].

Preparation and Characterization of Lipid Nanoparticles (LNPs)

mRNA LNPs were prepared by mixing an ethanol solution containing ionizable lipids, DOPE, cholesterol and DMG-PEG2000 and a citrate solution containing mRNA via NanoAssemblr (Precision NanoSystems, Canada)[19]. The size, polydispersity index (PDI) and zeta potential were measured by NanoZS Zetasizer (Malvern, USA). The encapsulation efficiency was detected by a Ribogreen assay. The morphology was observed on Glacios Cryo-TEM (Thermo Scientific, USA).

In the initial screening, newly synthesized ionizable lipids were formulated with DOPE, cholesterol and DMG-PEG2000 (Lipid:DOPE:Cholesterol=20:30:40:0.75, mole ratio) as well as FLuc mRNA (Lipid:mRNA=10:1, mass ratio)[21]. LNPs were formulated based on a L16 $(4)^4$ orthogonal table and the predicted formulations. Lipofectamine 3000/mRNA complex was prepared based on the recommended protocol. Electroporation for BMDCs was performed using mouse dendritic cell nucleofector kit (Lonza, VAPA1011). mRNA delivery efficacy was determined by a luciferase expression assay.

CD40 and CD40L Expression

About $1\times10^6$ BMDCs were seeded into each well of a 6-well plate and treated with 2.5 μg CD40-LNPs for 12 h. About $1\times10^5$ B16F10 cells were seeded into each well of a 24-well plate and were treated with 0.25 μg CD40L-LNPs for 18 h. Next, the cells were stained with the CD40-FITC or CD40L-FITC antibody and analyzed by LSRFortessa flow cytometer (Becton Dickinson, USA).

Mice with tumor volume about 500 $mm^2$ were i.t. injected with 10 μg FLuc-LNPs, CD40-LNPs, or CD40L-LNPs. After 6 h, the tumors were dissociated using mouse tumor dissociation kit (Miltenyi Biotec, 130-096-730). The infiltrating immune cells were isolated by Ficoll-Paque density gradient media (Cytiva, 17544602). After stained with antibody combinations based on above flow cytometry gating methods, the cells were analyzed by flow cytometry.

Dendritic Cell Activation and Analysis

CD40 overexpressed BMDCs (CD40-BMDCs) were incubated with 10 μg/mL anti-mouse CD40 antibody for 12 h. Next, some activation markers were stained by CD80, CD86, MHC-II and pro-form IL1-β antibodies and analyzed by flow cytometry. Other activation markers, including IL-12 and TNF-α were detected by ELISA.

LNPs-Induced Immunogenic Cell Death (ICD)

ICD markers were detected by adaptation of previous methods[5]. The cytotoxicity of LNPs in B16F10 cells was examined by a MTT assay. Extracellular ATP was measured by luminescent ATP detection kit (Abcam, ab113849). Extracellular HMGB1 level was detected by ELISA. Cell surface calreticulin was detected by flow cytometry.

Tumor Models and Treatment Regimens

C57BL/6 mice (male and female, 6-8 weeks) were purchased from the Jackson Laboratory and housed in The University Laboratory Animal Resources-Biomedical Research Tower of The Ohio State University. All mouse studies were approved by the Institutional Animal Care and Use Committee (IACUC) at The Ohio State University and complied with local, state, and federal regulations.

For one-side subcutaneous (s.c.) tumor model, about $1\times10^5$ B16F10 cells or $2\times10^5$ B16F10-Luc2 were s.c. injected on the right flank of mice. On day 7 post tumor inoculation, mice with tumor size about 0.5 cm of the largest diameter were randomized to different treatment groups. For two-side s.c. tumor model, about $1\times10^5$ B16F10 cells were s.c. injected on the right flank of mice. On day 5 post tumor inoculation on the right flank, about $1\times10^5$ B16F10 cells were s.c. injected on the left flank of mice. On day 7 post tumor inoculation on the right flank, mice with tumor size about 0.5 cm of the largest diameter were randomized to different treatment groups, For skin+brain two tumor model, about $2\times10^5$ B16F10-Luc2 cells were s.c. injected on the right flank of mice. On day 5 post tumor inoculation on the right flank, about $1\times10^4$ B16F10-Luc2 cells were intracranially (i.c.) injected with a depth of 3 mm. The injection site was 2 mm lateral to the sagittal suture and 1 mm anterior to the coronal suture. On day 7 post tumor inoculation on the right flank, mice with tumor size about 0.5 cm of the largest diameter were randomized to different treatment groups. For s.c. tumor rechallenge, on day 45 post tumor inoculation, about $1\times10^5$ B16F10 cells were s.c. injected on the left flank of completely responded mice. For brain tumor rechallenge, on day 45 post tumor inoculation, about $1\times10^4$ B16F10-Luc2 cells were i.c. injected in completely responded mice. For T cell depletion tumor models, $1\times10^5$ B16F10 cells were s.c. injected on the right flank of mice. On day 6 post tumor inoculation, mice were intraperitoneally treated with anti-mouse CD8α, anti-mouse CD4, or anti-rat IgG2b isotype antibody. Each antibody was given every 3 days for three doses with 200 μg per injection.

Treatment regimens in this study are as described below. In a single i.t. injection, the doses of CD40 Ab and LNPs were 50 μg and 5 μg, respectively; and the dose of dendritic cells was 2 million. For CD40-LNPs+CD40 Ab treatment, CD40 Ab was i.t. administrated 6 h post the i.t. injection of CD40-LNPs. For dendritic cells+CD40 Ab treatment, CD40 Ab was i.t. administrated 1 h post the i.t. injection of dendritic cells. For CD40-LNPs+CD40L-LNPs treatment, CD40-LNPs were i.t. administrated 18 h post the i.t. injection of CD40L-LNPs. For CD40L- or FLuc-LNPs+CD40-BMDCs treatment, CD40-BMDCs were i.t. administrated 18 h post the i.t. injection of CD40L- or FLuc-LNPs. All these treatment regimens included four doses.

The removal criteria in this study are as described below. Subcutaneous tumor size was measured every 2 to 4 days and calculated as the volume (length×width×width/2). Mice were sacrificed when the largest diameter of tumor reached 1.6 cm or they lost over 20% body weight. Brain tumor size was monitored by IVIS Lumina II (Caliper life sciences, USA). Mice were euthanized if they showed hunched posturing, had difficulty in ambulating and feeding, or they lost over 20% body weight.

Luminex Analysis of Cytokines and Chemokines

Mice with tumor volume about 500 $mm^2$ were i.t. injected with one dose of CD40L-LNPs+CD40-BMDCs. Mouse tumoral tissues and serum were collected from the 0 to 42 h time course post injection. Tumoral tissues were frozen in liquid nitrogen and pulverized tissues were extracted at 150 mg/ml in RIPA lysis buffer (Thermo Scientific, 89900) with protease inhibitors (Thermo Scientific, 87785). The whole blood was collected in tubes containing sodium citrate and serum was collected by centrifugation (10000 rpm) at 4° C. for 5 min. The tumoral lysate and serum were stored at −80° C. Mouse cytokines and chemokines were detected by mouse cytokine/chemokine discovery assay (Eve Technologies, Canada).

Analysis of Immune Cell Populations and Activation In Vivo

Mice with tumor volume about 250 $mm^2$ were i.t. treated with two doses of CD40L-LNPs+CD40-BMDCs. Next, tumoral tissues were collected and dissociated using mouse tumor dissociation kit (Miltenyi Biotec, 130-096-730). For profiling immune cell populations, total cells were stained with antibody combinations based on above flow cytometry gating methods, and then immune cell numbers were counted by flow cytometry. In this experiment, CD40-BMDCs were labelled by CellTrace Blue (Invitrogen, C34568) before i.t. injection, which can distinguish the administrated dendritic cells from the endogenous dendritic cells via flow cytometry. For evaluating immune cell activation, the infiltrating immune cells were isolated by Ficoll-Paque density gradient media (Cytiva, 17544602). After stained with antibody combinations based on above flow cytometry gating methods, T cell activation markers were detected by flow cytometry.

REFERENCES CITED

1 Chen, D. S, & Mellman, I. Oncology meets immunology: the cancer-immunity cycle. *Immunity* 39, 1-10, doi:10.1016/j.immuni.2013.07.012 (2013).

2 Wculek, S. K. et al. Dendritic cells in cancer immunology and immunotherapy. *Nature Reviews Immunology* 20, 7-24 (2020).

3 Galluzzi, L., Buqué, A., Kepp, O., Zitvogel, L. & Kroemer, G. Immunogenic cell death in cancer and infectious disease. *Nature Reviews Immunology* 17, 97-111 (2017).

4. Kroemer, G., Galluzzi, L., Kepp, O., & Zitvogel, L. Immunogenic cell death in cancer therapy. *Annual review of immunology* 31, 51-72 (2013).

5 Li, Y. et al. Multifunctional oncolytic nanoparticles deliver self-replicating IL-12 RNA to eliminate established tumors and prime systemic immunity. *Nature Cancer* 1, 882-893 (2020).

6 Vonderheide, R. H. CD40 agonist antibodies in cancer immunotherapy. *Annual review of medicine* 71, 47-58 (2020).

7 Melero, I., Castanon, E., Alvarez, M., Champiat, S. & Marabelle, A. Intratumoural administration and tumour tissue targeting of cancer immunotherapies. *Nature Reviews Clinical Oncology* 18, 558-576 (2021).

8 Hou, X., Zaks, T., Langer, R. & Dong, Y. Lipid nanoparticles for mRNA delivery. *Nature Reviews Materials* 6, 1078-1094 (2021).

9 Zhang, Y., Sun, C., Wang, C., Jankovic, K. E. & Dong, Y. Lipids and lipid derivatives for RNA delivery. *Chemical Reviews* 121, 12181-12277 (2021).

10 Hewitt, S. L. et al. Durable anticancer immunity from intratumoral administration of IL-23, IL-36γ, and OX40L mRNAs. *Science translational medicine* 11, eaat9143 (2019).

11 Ghosh, S. & Sudha, M. A review on polyols: new frontiers for health-based bakery products. *International journal of food sciences and nutrition* 63, 372-379 (2012).

12 Zada, B. et al. Recent advances in catalytic production of sugar alcohols and their applications. *Science China Chemistry* 60, 853-869 (2017).

13 Stoss, P. & Hemmer, R. 1, 4: 3,6-Dianhydrohexitols. *Advances in carbohydrate chemistry and biochemistry* 49, 93-173 (1991).

14 Spagnolo, F. et al. Survival of patients with metastatic melanoma and brain metastases in the era of MAP-kinase inhibitors and immunologic checkpoint blockade antibodies: a systematic review. *Cancer treatment reviews* 45, 38-45 (2016).

15 Wiggins, L. in *Advances in carbohydrate chemistry* Vol. 5 191-228 (Elsevier, 1950).

16 Fenouillot, F., Rousseau, A., Colomines, G., Saint-Loup, R. & Pascault, J. -P. Polymers from renewable 1, 4: 3,6-dianhydrohexitols (isosorbide, isomannide and isoidide): A review. *Progress in Polymer Science* 35, 578-622 (2010).

17 Aricò, F., Tundo, P., Maranzana, A. & Tonachini, G. Synthesis of five-membered cyclic ethers by reaction of 1,4-Diols with dimethyl carbonate. *ChemSusChem* 5, 1578-1586 (2012).

18 Kikuchi, T., Moore, M. A. & Crystal, R. G. Dendritic cells modified to express CD40 ligand elicit therapeutic immunity against preexisting murine tumors. *Blood, The Journal of the American Society of Hematology* 96, 91-99 (2000), 19 Li, W. et al. Biomimetic nanoparticles deliver mRNAs encoding costimulatory receptors and enhance T cell mediated cancer immunotherapy. *Nature communications* 12, 1-12 (2021).

20 Zeng, C. et al. Leveraging mRNA Sequences and Nanoparticles to Deliver SARS-CoV-2 Antigens In Vivo. *Advanced Materials* 32, 2004452 (2020).

21 Hou, X. et al. Vitamin lipid nanoparticles enable adoptive macrophage transfer for the treatment of multidrug-resistant bacterial sepsis. *Nature nanotechnology* 15, 41-46 (2020).

Example 2

Chemical Synthesis of Dianhydrohexitols-Derived Lipids

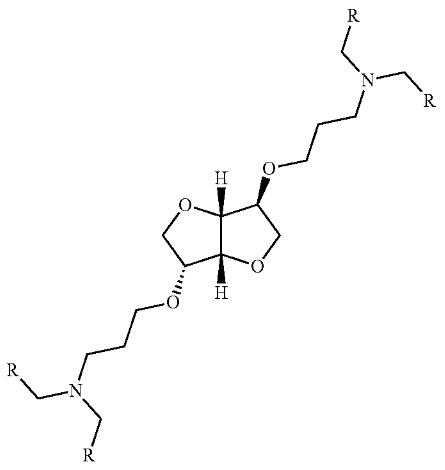

DIS-1 R = $R_1$ DIS-2 R = $R_2$
DIS-3 R = $R_3$ DIS-4 R = $R_4$
DIS-5 R = $R_5$ DIS-6 R = $R_6$
DIS-7 R = $R_7$ DIS-8 R = $R_8$
DIS-9 R = $R_9$ DIS-10 R = $R_{10}$

-continued

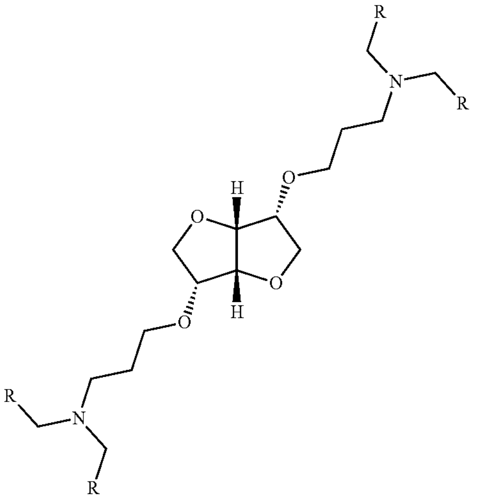

DIM-1 R = $R_1$ DIM-2 R = $R_2$
DIM-3 R = $R_3$ DIM-4 R = $R_4$
DIM-5 R = $R_5$ DIM-6 R = $R_6$
DIM-7 R = $R_7$ DIM-8 R = $R_8$
DIM-9 R = $R_9$ DIM-10 R = $R_{10}$

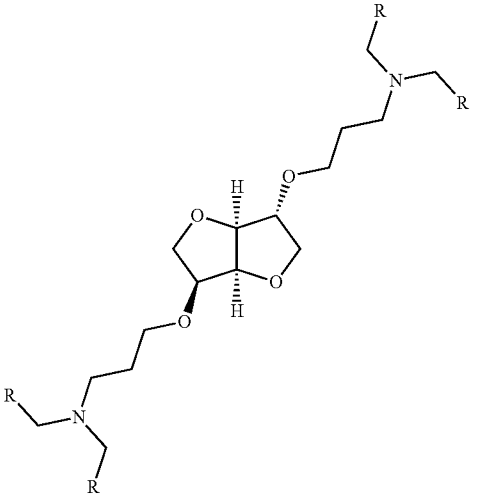

LIS-1 R = $R_1$ LIS-2 R = $R_2$
LIS-3 R = $R_3$ LIS-4 R = $R_4$
LIS-5 R = $R_5$ LIS-6 R = $R_6$
LIS-7 R = $R_7$ LIS-8 R = $R_8$
LIS-9 R = $R_9$ LIS-10 R = $R_{10}$

-continued

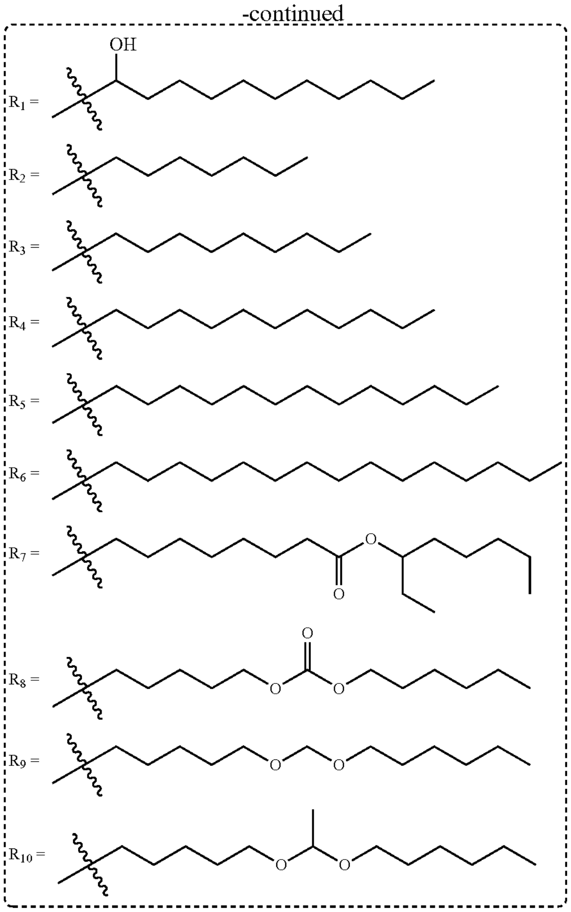

Chemical Structures of Dianhydrohexitols-Derived Ionizable Lipids

Synthesis of Aldehydes

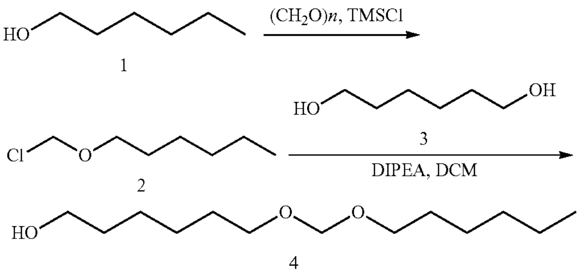

To a suspension of paraformaldehyde (1.5 g, 50 mmol) in TMSCl (25 mL, 197 mmol) was added 1-hexanol 1 (5.1 g, 50 mmol) dropwise at RT. The reaction mixture was allowed to stir for 2 h at room temperature. The clean solution was concentrated under reduce pressure to give 1-chloromethoxy-hexane 2 as a colorless oil that was used directly without further purification.

The above chloromethyl ether was added dropwise to a solution of 1,6-hexanediol 3 (11.8 g, 100 mmol) and i-$Pr_2NEt$ (17.45 mL, 100 mmol) in $CH_2Cl_2$ (150 mL). The reaction mixture was stirred at room temperature for 24 h and was subsequently quenched by the addition of a saturated solution of $NH_4Cl$ (80 mL). Extraction with $CH_2Cl_2$ (60 mL*2 times) was performed and the combined organic layers were washed with water (30 mL) and brine (30 mL) and dried over $Na_2SO_4$. The organic phase was filtered and concentrated under reduced pressure, the residue was purified via silica gel flash chromatography (20% EtOAc in hexane). 6.74 g of 4 was obtained as a colorless oil, yield 58.0%. $^1$H NMR (300 MHz, Chloroform-d) δ 4.65 (s, 2H), 3.63 (q, J=6.3 Hz, 2H), 3.51 (td, J=6.6, 2.9 Hz, 4H), 1.57 (dq, J=13.5, 6.9 Hz, 6H), 1.41-1.21 (m, 10H), 0.88 (t, J=3.6 Hz, 3H). HRMS (ESI, m/z): $[M+Na]^+$ calcd. For $C_{13}H_{28}N_aO_3$, 255.1931; found: 255.1941.

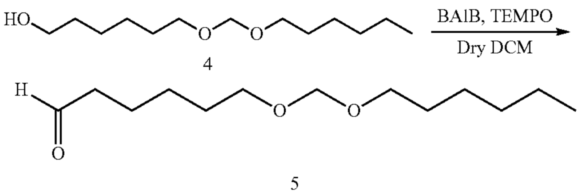

(Diacetoxyiodo)benzene (0.79 g, 2.45 mmol) was added to a suspension of 4 (518 mg, 2.23 mmol), TEMPO (34.9 mg, 0.22 mmol) and $NaHCO_3$ (412 mg, 4.9 mmol) in 20 mL of dry DCM at room temperature. The reaction mixture was stirred for 3 h and TLC showed 4 was totally consumed. Then the mixture was quenched with saturated aqueous solution of $Na_2S_2O_3$ (30 mL) and extracted with DCM (3*20 mL). The DCM phase was combined and washed with aqueous $NaHCO_3$ (20 mL) and brine (20 mL), dried over $Na_2SO_4$, filtrated and concentrated under reduced pressure. The residue was purified via silica gel flash chromatography (10% EtOAc in hexane). 510 mg of 5 was obtained as a colorless oil, quant. $^1$H NMR (300 MHz, Chloroform-d) δ 9.76 (s, 1H), 4.64 (s, 2H), 3.51 (q, J=6.09 Hz, 4H), 2.43 (t, J=7.2 Hz, 1H), 1.7-1.52 (m, 6H), 1.49-1.19 (m, 8H), 0.88 (t, J=6.3 Hz, 3H).

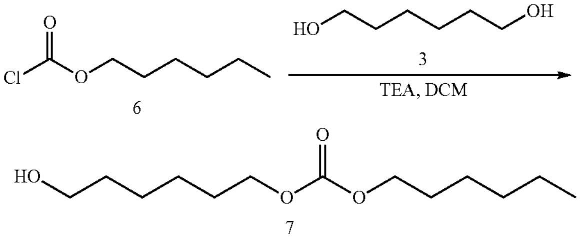

To a solution of 6 (5.0 g, 30.4 mmol) in DCM (30 mL) was added dropwise into a solution of 1,5-hexanediol 3 and TEA (16.9 mL, 121 mmol) in DCM (100 mL) at 0° C. over 30 min. After stirring for 3 h, the reaction was quenched with 50 mL of water and extracted with DCM (50 mL*3), then the organic phase was combined and washed with water, dried over $Na_2SO_4$ and concentrated under reduced pressure. The residue was purified via silica gel chromatography (20% EtOAc in hexanes). 3.2 g of 7 was obtained as a colorless oil, yield 45.3%. $^1$H NMR (300 MHz, Chloroform-d) δ 4.11 (td, J=6.6, 2.7 Hz, 4H), 3.62 (td, J=6.6, 3.3 Hz, 3H), 1.72-1.62 (m, 4H), 1.60-1.53 (m, 2H), 1.43-1.33 (m, 6H), 1.33-1.26 (m, 4H), 0.91-0.84 (t, J=6.6 Hz, 3H). HRMS (ESI, m/z): $[M+Na]^+$ calcd. For $C_{13}H_{26}N_aO_4$, 269.1723; found: 269.1735.

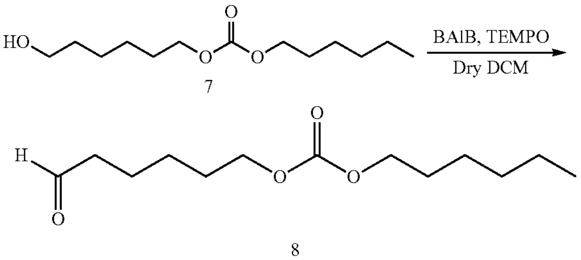

BAIB (1.41 g, 4.38 mmol) was added to a suspension of 7 (0.98 g, 3.98 mmol), TEMPO (62.2 mg, 0.4 mmol) and $NaHCO_3$ (736 mg, 8.6 mmol) in 20 mL of DCM. The reaction mixture was stirred for 3 h till TLC showed A was totally consumed. Then the mixture was quenched with saturated aqueous solution of $Na_2S_2O_3$ (30 mL) and extracted with DCM (3*20 mL). The DCM phase was combined and washed with aqueous $NaHCO_3$ (20 mL) and brine (20 mL), dried over $Na_2SO_4$, filtrated and concentrated under reduced pressure. The residue was purified via silica gel flash chromatography (10% EtOAc in hexane). 0.78 g of 8 was obtained as a light yellow oil, yield 80.2%. $^1$H NMR (300 MHz, Chloroform-d) δ 9.77 (t, J=1.5 Hz, 1H), 4.13 (td, J=6.6, 2.7 Hz, 4H), 2.45 (td, J=7.2, 1.8 Hz, 2H), 1.76-1.58 (m, 6H), 1.48-1.25 (m, 8H), 0.89 (t, J=6.6 Hz, 3H).

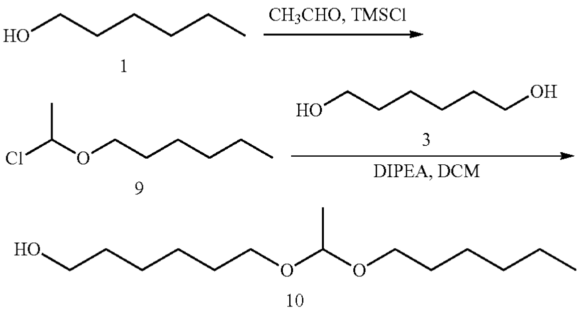

To a solution of acetaldehyde (1.76 g, 40 mmol) in TMSCl (20 mL, 157 mmol) was added 1-hexanol 1 (5.1 g, 50 mmol) dropwise at RT. The reaction mixture was allowed to stir for 2 h at room temperature. The clean solution was concentrated under reduce pressure to give 9 as a colorless oil that was used directly without further purification.

The above chloromethyl ether was added dropwise to a solution of 1,6-hexanediol 3 (9.44 g, 80 mmol) and i-$Pr_2NEt$ (13.96 mL, 80 mmol) in $CH_2Cl_2$ (150 mL). The reaction mixture was stirred at room temperature for 24 h and was subsequently quenched by the addition of a saturated solution of $NH_4Cl$ (80 mL). Extraction with $CH_2Cl_2$ (60 mL*2 times) was performed and the combined organic layers were washed with water (30 mL) and brine (30 mL) and dried over $Na_2SO_4$. The organic phase was filtered and concentrated under reduced pressure, the residue was purified via silica gel flash chromatography (20% EtOAc in hexane). 3.45 g of 10 was obtained as a colorless oil, yield 35.0%. $^1$H NMR (300 MHz, Chloroform-d) δ 4.64 (q, J=5.4 Hz, 1H), 3.68-3.48 (m, 4H), 3.38 (dtd, J=9.3, 6.6, 2.4 Hz, 2H), 1.65-1.47 (m, 7H), 1.43-1.23 (m, 13H), 0.87 (t, J=6.6 Hz, 3H). HRMS (ESI, m/z): $[M+Na]^+$ calcd. For $C_{14}H_{30}N_aO_3$, 269.2087; found: 269.2075.

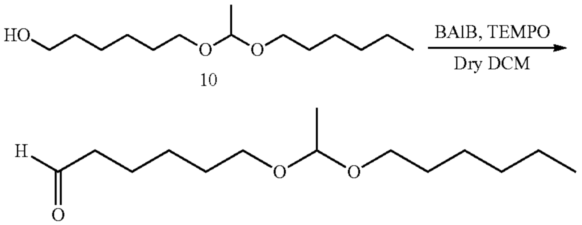

10

11

BAIB (1.77 g, 5.5 mmol) was added to a suspension of 10 (1.23 g, 5.0 mmol), TEMPO (78.2 mg, 0.5 mmol) and $NaHCO_3$ (924 mg, 11.0 mmol) in 20 mL of DCM. The reaction mixture was stirred for 3 h till TLC showed A was totally consumed. Then the mixture was quenched with saturated aqueous solution of $Na_2S_2O_3$ (30 mL) and extracted with DCM (3*20 mL). The DCM phase was combined and washed with aqueous $NaHCO_3$ (20 mL) and brine (20 mL), dried over $Na_2SO_4$, filtrated and concentrated under reduced pressure. The residue was purified via silica gel flash chromatography (10% EtOAc in hexane). 1.0 g of 11 was obtained as a light yellow oil, yield 81.8%. $^1H$ NMR (300 MHz, Chloroform-d) δ 9.78 (s, 1H), 4.66 (q, J=5.4 Hz, 1H), 3.57 (dq, J=9.2, 6.8 Hz, 2H), 3.41 (dtd, J=9.8, 6.6, 3.3 Hz, 2H), 2.45 (td, J=7.2, 1.8 Hz, 2H), 1.73-1.51 (m, 6H), 1.48-1.25 (m, 11H), 0.990 (t, J=6.6 Hz, 3H). HRMS (ESI, m/z): $[M+Na]^+$ calcd. For $C_{13}H_{28}N_aO_3$, 255.1931; found: 255.1941.

Synthesis of Sugar Alcohol-Derived Diamines

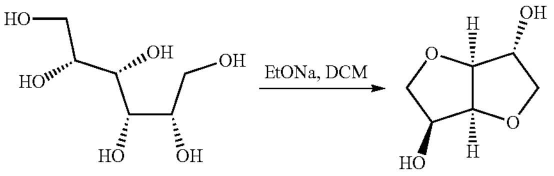

L-Sorbitol
12

L-Isosorbide
13

To a solution of L-isosorbide (2.0 g, 10.98 mmol) and Diethyl Carbonate (DMC) (3.96 g, 43.9 mmol) in 12 mL of MeOH was added EtONa (75 mg, 1.1 mmol), the resulting mixture was allowed to reflux for 48 h. Then the reaction was stopped, cooled at room temperature, and diethyl ether (15 mL) was added to the mixture. The reaction mixture was then filtered through a pad of Celite and the solvent evaporated. Finally, the product was purified by silica gel chromatography using dichloromethane/methanol (9:1) as eluent, 1.2 g of desired product was obtained as a white solid, yield 75%.

$^1$NMR (400 MHz, Deuterium Oxide) δ 4.68 (t, J=4.7 Hz, 1H), 4.52 (d, J=4.3 Hz, 1H), 4.43 (td, J=6.9, 5.0 Hz, 1H), 4.36 (d, J=3.2 Hz, 1H), 4.02-3.94 (m, 2H), 3.90 (dd, J=10.5, 3.2 Hz, 1H), 3.52 (dd, J=9.1, 7.4 Hz, 1H). $^{13}C$ NMR (75 MHz, Deuterium Oxide) δ 87.33, 81.40, 75.46, 75.07, 71.76, 71.09. MS (ESI, m/z): $[M+H]^+$ calcd. For $C_6H_{11}O_4$, 147.1; found: 147.1.

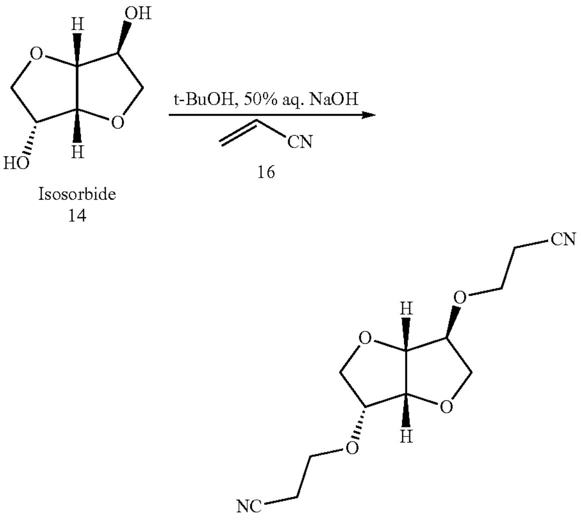

Isosorbide
14

16

17

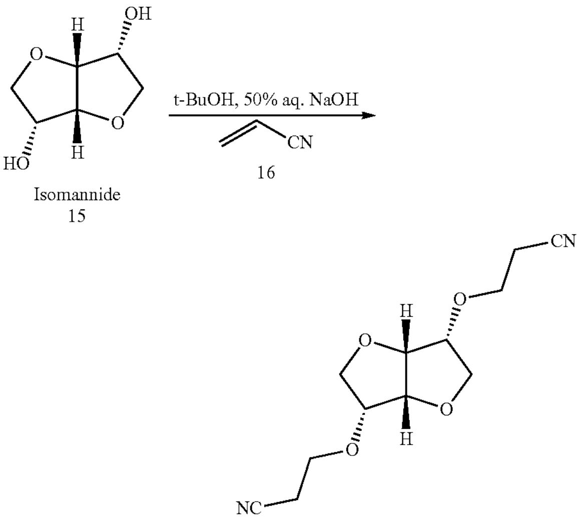

Isomannide
15

16

18

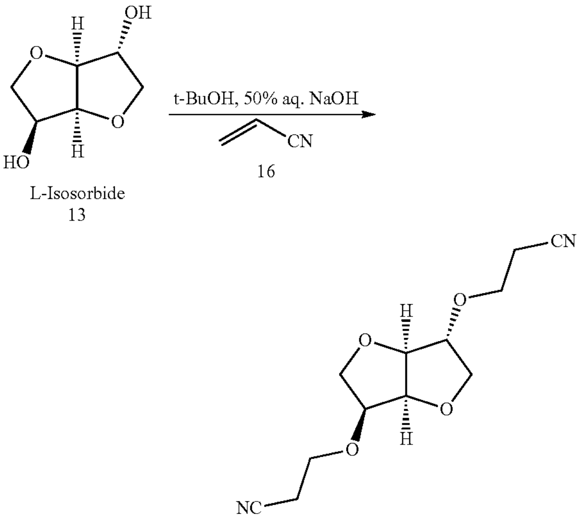

L-Isosorbide
13

16

19

Dicyanoethylation of diols were carried out according to a previously reported method[1]. To a solution of diol (7.3 g, 50 mmol) in tert-butanol and 50% aqueous NaOH solution (2.0 g, 0.5mol %) was add acrylonitrile 16 (7.96 g, 150 mmol) dropwise over 30 min at 60° C. The reaction was continued over a total period of 6 hours. Tert-Butanol and the excess acrylonitrile were removed via rotate evaporation under reduced pressure. The residue was dissolved in 100 mL of DCM, unreacted isosorbide and monocyanoethylated isosorbide were removed by triple water washing. The organic layer was dried over anhydrous $Na_2SO_4$, the solution was filtered and the solvent was removed under reduced pressure. The residue was purified by silica gel chromatography (0%-100% Hexane in Dichloromethane) to corresponding product as a yellow oil.

Compound 17: yield 70.5%, $^1H$ NMR (400 MHz, DMSO-$d_6$) δ 4.60 (t, J=4.8 Mz, 1H), 4.42 (dt, J=4.4, 1.2 Hz, 1H), 4.06 (td, J=6.4, 4.8 Hz, 1H), 4.02-3.98 (m, 1H), 3.89-3.72 (m, 4H), 3.67-3.60 (m, 3H), 3.47 (dd, J=8.8, 6.8 Hz, 1H), 2.78-2.72 (m, 4H). MS (ESI, m/z): $[M+Na]^+$ calcd. For $C_{12}H_{17}N_2O_4$, 275.1002; found: 275.1007.

Compound 18: yield 68%. $^1H$ NMR (300 MHz, DMSO-$d_6$) δ 4.52 (dt, J=4.7, 2.4 Hz, 2H), 4.07 (tdd, J=8.0, 3.6, 1.6 Hz, 2H), 3.89 (dd, J=8.5, 6.7 Hz, 2H), 3.79-3.73 (m, 1H), 3.71 (d, J=6.1 Hz, 1H), 3.62 (ddd, J=9.7, 6.5, 5.7 Hz, 2H), 3.50 (t, J=8.2 Hz, 2H), 2.75 (ddd, J=6.6, 5.7, 1.1 Hz, 4H). MS (ESI, m/z): $[M+Na]^+$ calcd. For $C_{12}H_{17}N_2O_4$, 275.1; found: 275.1.

Compound 19: yield 93%. $^1H$ NMR (300 MHz, DMSO-$d_6$) δ 4.61 (t, J=4.8 Hz, 1H), 4.43 (dt, J=4.8, 0.9 Hz, 1H), 4.07 (td, J=6.6, 4.8 Hz, 1H), 4.03-3.97 (m, 1H), 3.90-3.72 (m, 4H), 3.70-3.59 (m, 3H), 3.48 (dd, J=8.7, 6.6 Hz, 1H), 2.82-2.71 (m, 4H). $^{13}C$ NMR (75 MHz, DMSO-$d_6$) δ 120.07, 120.06, 86.42, 84.49, 80.89, 80.46, 73.44, 70.70, 65.47, 64.54, 19.19, 19.14. MS (ESI, m/z): $[M+Na]^+$ calcd. For $C_{12}H_{17}N_2O_4$, 275.1; found: 275.0.

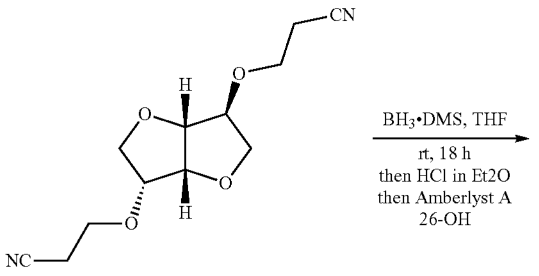

17

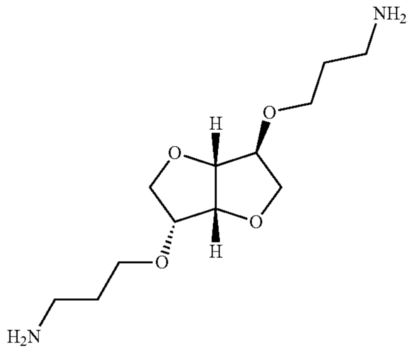

20
Isosorbide derived diamine

-continued

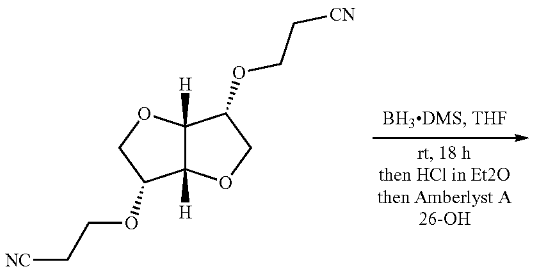

18

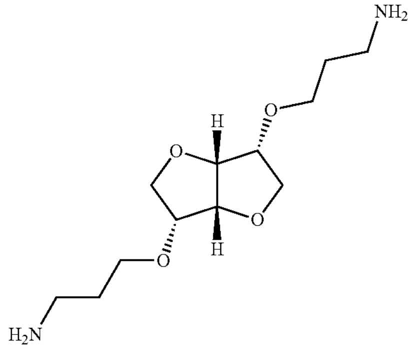

21
Isomannide derived diamine

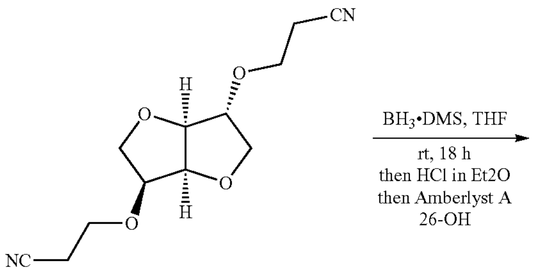

19

-continued

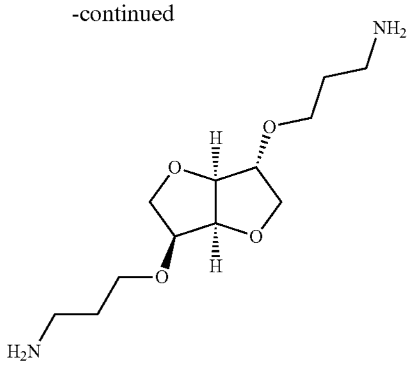

22
L-Isosorbide derived diamine

Diamines were synthesized according to methods reported previously[2]. To a solution of $BH_3$·THF complex in THF (2.0 M, 29.7 mL, 59.4 mmol) was added a solution of dinitrile compound (3.0 g, 11.89 mmol) in THF (25 mL) dropwise over 1 h at room. After the addition was completed, the reaction was stirred for 48 h. Then, methanol (30 mL) was added carefully to quench the reaction, during which hydrogen gas evolved vigorously. After stirring for 3 h, the solvent was removed under reduced pressure, then 40 mL of THF was added to dissolve the residue followed by the addition of hydrochloric acid in diethyl ether solution (2.0 M, 29.7 mL) dropwise upon which a white precipitate formed. The suspension was then filtered to give the crude diamine·HCl salt as a white powder. Then the diamine 2HCl salt was dissolved in deionized water (30 mL) to give a light yellow solution. To this solution freshly washed Amberlyst A 26-OH (17 g) was added. The resulting suspension was sonicated in an ultrasonic bath for 1.5 h at 30° C. The suspension was filtered through a pad of Celite and the resin was washed thoroughly with water (3×4 mL). The combined clear colorless solutions were evaporated to dryness using a rotary evaporator (or freeze-dried) to afford the extended diamine as a light yellow oily liquid.

Isosorbide derived diamine 20: yield 70%. $^1H$ NMR (300 MHz, Methanol-$d_4$) δ 4.64 (t, J=4.5 Hz, 1H), 4.54-4.45 (m, 1H), 4.11-4.00 (m, 1H), 3.98-3.84 (m, 4H), 3.80-3.69 (m, 1H), 3.66-3.43 (m, 4H), 2.86-2.61 (m, 4H), 1.83-1.67 (m, 4H). HRMS (ESI, m/z): $[M+H]^+$ calcd. For $C_{12}H_{25}N_2O_4$, 261.1809; found: 261.1819.

Isomannide derived diamine 21: yield 68%. HRMS (ESI, m/z): $[M+H]^+$ calcd. For $C_{12}H_{25}N_2O_4$, 261.1809; found: 261.1817.

L-Isosorbide derived diamine 22: yield 71%. $^1H$ NMR (400 MHz, Methanol-$d_4$) δ 4.67 (t, J=4.4 Hz, 1H), 4.56-4.54 (m, 1H), 4.13-4.10 (m, 1H), 3.98-3.92 (m, 2H), 3.92-3.86 (m, 2H). 3.78-3.68 (m, 1H), 3.68-3.50 (m, 4H), 2.94-2.71 (m, 4H), 1.85-1.73 (m, 4H). MS (ESI, m/z): $[M+H]^+$ calcd. For $C_{12}H_{25}N_2O_4$, 261.2; found: 261.2.

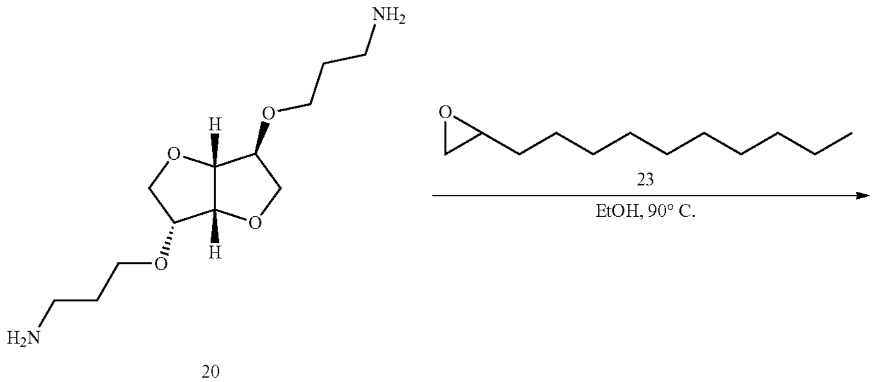

20

-continued
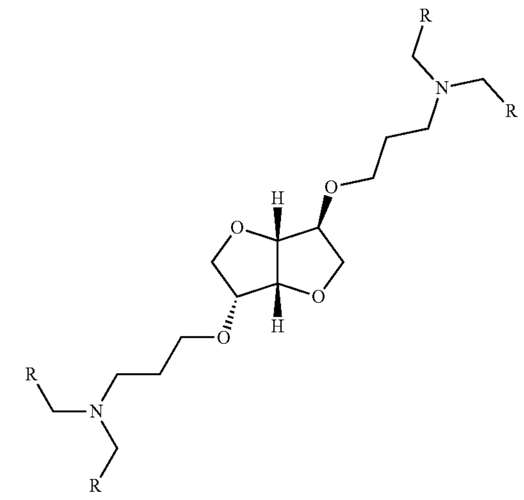
R = 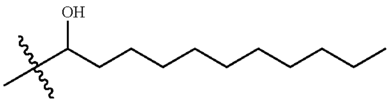
DIS-1
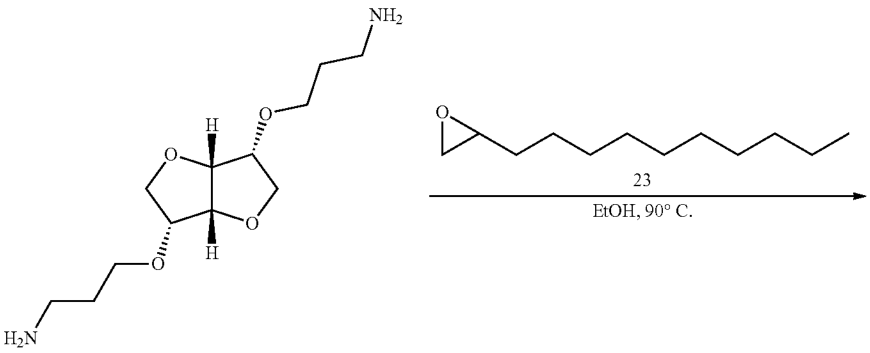
21

-continued
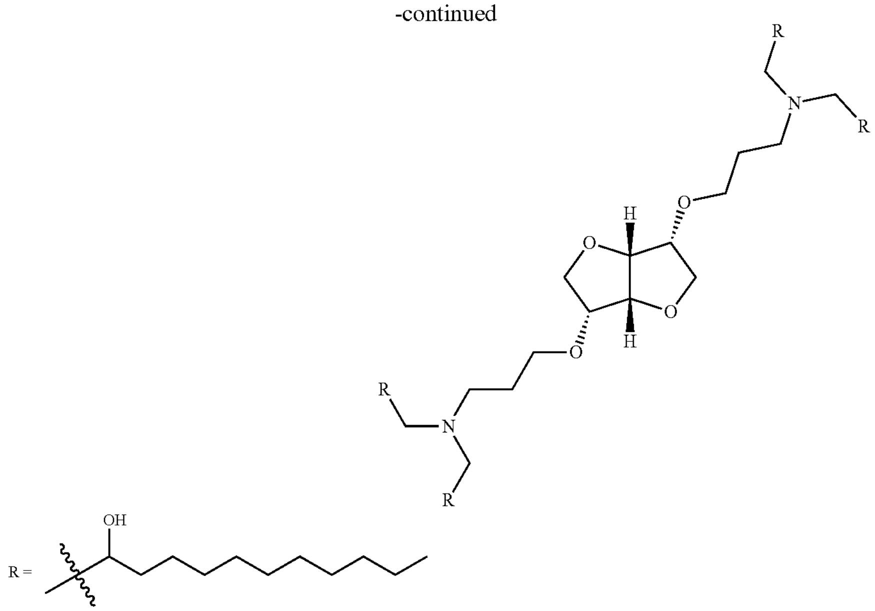
DIM-1
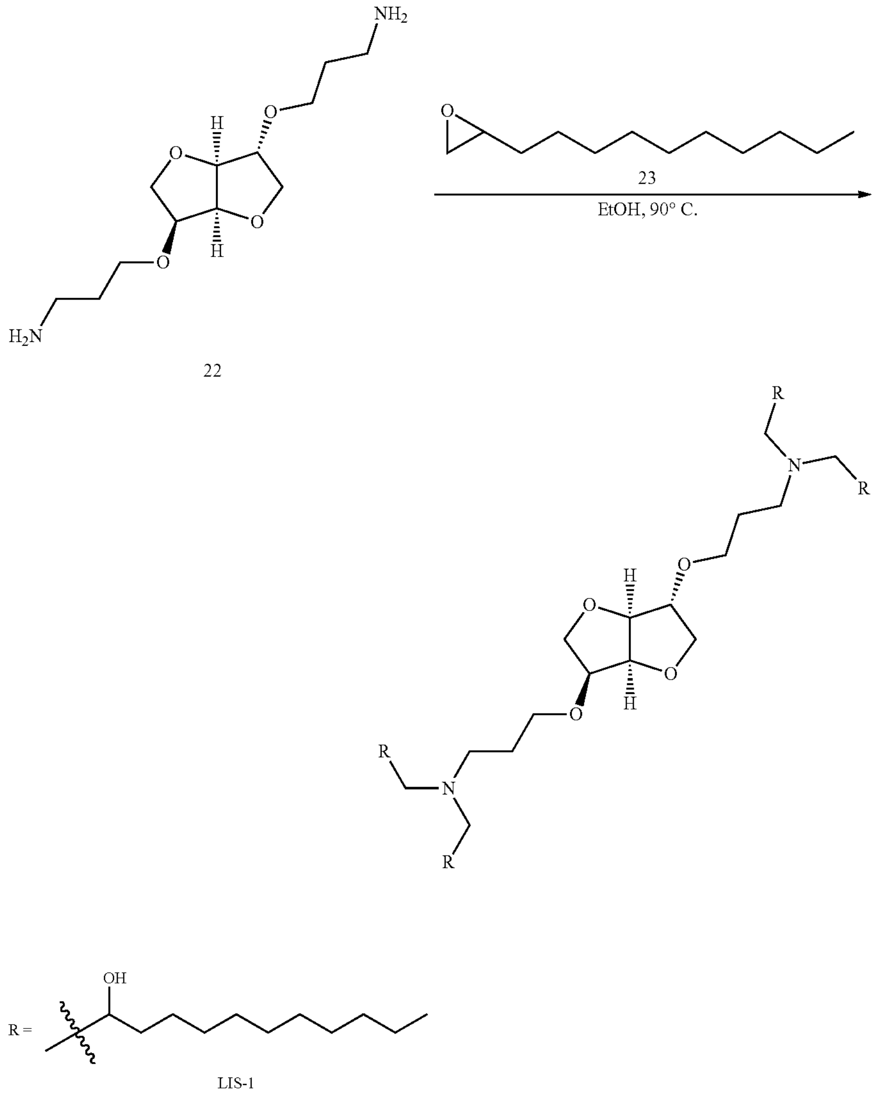
LIS-1

Synthesis of β-Aminoalcohols

To a solution of diamine (52 mg, 0.2 mmol) in 2 mL of dry EtOH was added epoxide 23 (184 mg, 1.0 mmol). Then the mixture was warmed to 90° C. and kept stirring for 12 h. TLC showed totally consumed of A, EtOH was removed under reduced pressure. The residue was purified via silica gel chromatography (0%-100% [mixture of 3% NH4OH, 22% MeOH in dichloromethane] in dichloromethane) to give desire products.

DIS-1: yield 61.2%. $^1$H NMR (300 MHz, Chloroform-d) δ 4.66-4.60 (m, 1H), 4.51 (d, J=3.9 Hz, 1H), 3.95 (qd, J=7.5, 3.9 Hz, 5H), 3.88-3.05 (m, 11H), 2.97-2.05 (m, 12H), 1.82-1.60 (m, 4H), 1.50-1.19 (m, 72H), 0.99-0.78 (m, 12H). HRMS (ESI, m/z): $[M+H]^+$ calcd. For $C_{60}H_{121}N_2O_8$, 997.9118; found: 997.9118.

DIM-1: yield 69.2%. $^1$H NMR (300 Chloroform-d) δ 4.56 (dd, J=4.5, 2.7 Hz, 2H), 4.11-3.89 (m, 4H), 3.89-3.49 (m, 9H), 3.49-3.23 (m, 5H), 2.86-2.14 (m, 12H), 1.85-1.65 (m, 4H), 1.50-1.17 (m, 72H), 0.91-0.80 (m, 12H). MS (ESI, m/z): $[M+H]^+$ calcd. For $C_{60}H_{121}N_2O_8$, 997.9; found: 998.0.

LIS-1: yield 38.1%. $^1$H NMR (300 MHz, Chloroform-d) δ 4.67-4.61 (m, 1H), 4.55-4.39(m, 1H), 4.03-3.80 (m, 5H), 3.55 (tdd, J=34.4, 30.2, 12.9, 6.2 Hz, 12H), 2.90-2.08 (m, 12H), 1.86-1.61 (m, 4H), 1.47-1.19 (m, 72H), 0.87 (t, J6.5 Hz, 12H). MS (ESI, m/z): $[M+H]^+$ calcd. For $C_{60}H_{121}N_2O_8$, 997.9; found: 998.0.

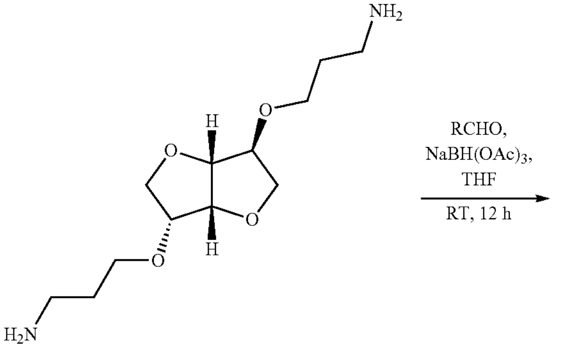

20

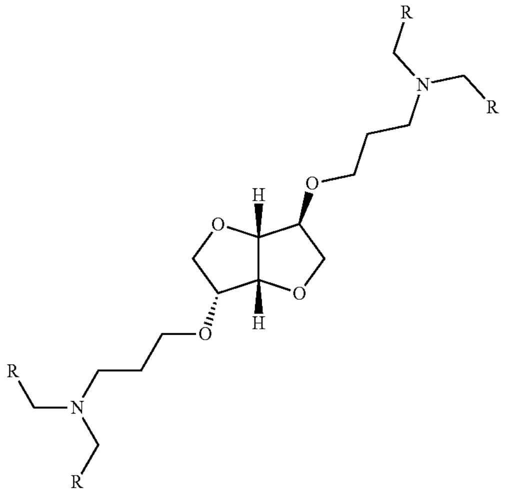

-continued

R = 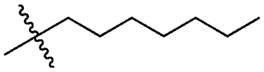

DIS-2

R = 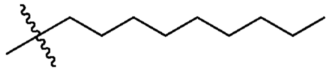

DIS-3

R = 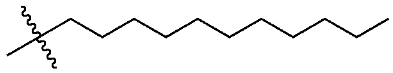

DIS-4

R = 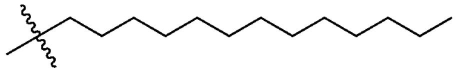

DIS-5

R = 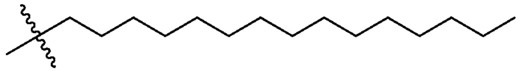

DIS-6

R = 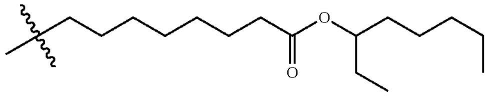

DIS-7

R = 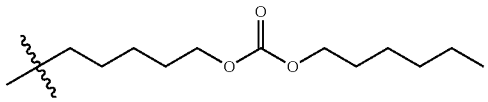

DIS-8

R = 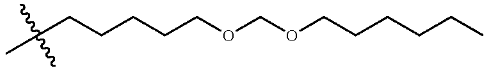

DIS-9

R = 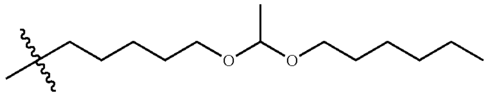

DIS-10

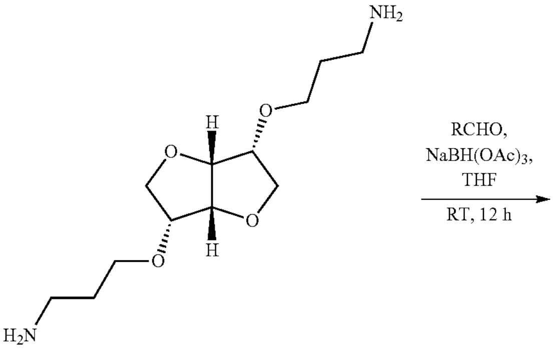

21

-continued
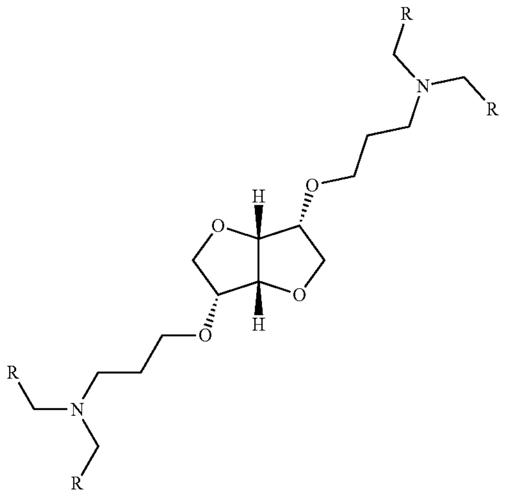
R = 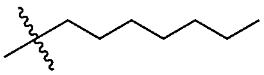
DIM-2
R = 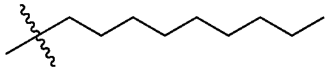
DIM-3
R = 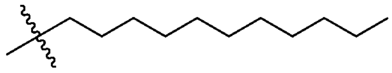
DIM-4
R = 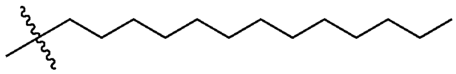
DIM-5
R = 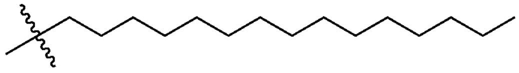
DIM-6
R = 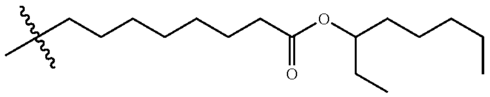
DIM-7
R = 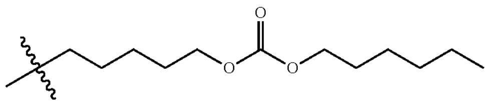
DIM-8
R = 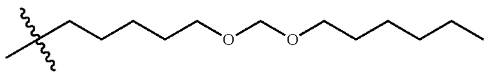
DIM-9
R = 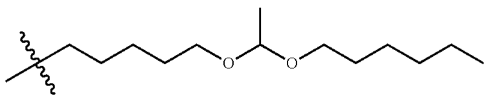
DIM-10
-continued
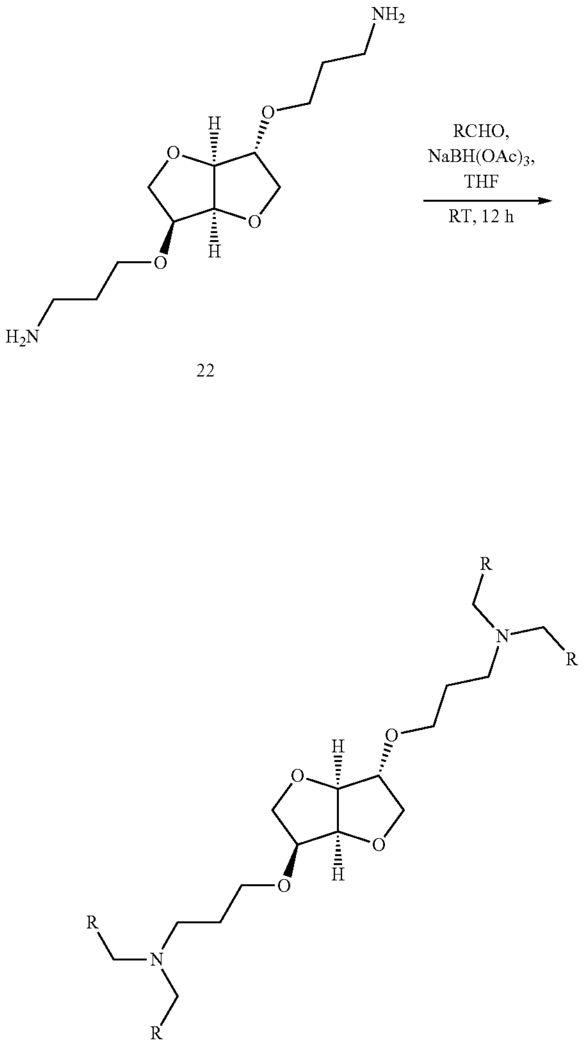
22
R = 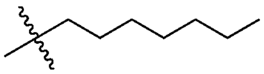
LIS-2
R = 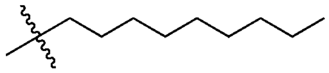
LIS-3
R = 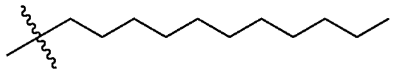
LIS-4
R = 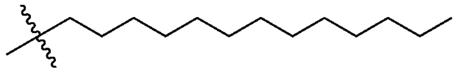
LIS-5
R = 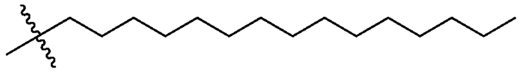
LIS-6

-continued

R =
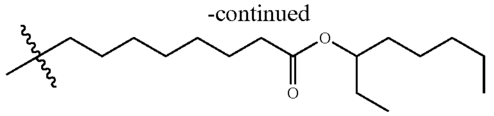

LIS-7

R =
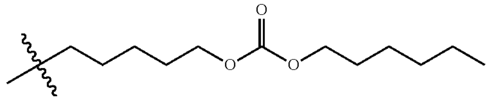

LIS-8

R =
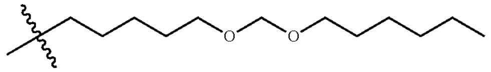

LIS-9

R =
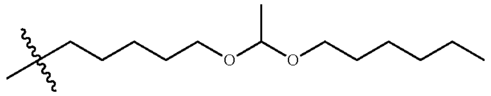

LIS-10

General synthetic procedure for the reductive amination of diamines: To a solution of diamine (52 mg, 0.2 mmol) in THF (4 mL) was added aldehyde (1.0 mmol), the mixture was kept stirring for 30 min at RT. Then $NaBH(OAc)_3$ (254 mg, 1.2 mmol) was added to the above solution, and the resulting mixture was stirred for 12 h. Aq. $NaHCO_3$ solution (15 mL) was added to quench the reaction. The aqueous solution was extracted with DCM (15 mL*3 times), the organic phase was combined and dried over anhydrous $Na_2SO_4$, filtered and concentrated under reduced pressure. The residue was purified via silicon gel chromatography (0%-100% [mixture of 3% $NH_4OH$, 22% MeO in Dichloromethane] in Dichloromethane) to give desired compounds.

Compound DIS-2: yield 37.0%. $^1$H NMR (300 MHz, Chloroform-d) δ 4.60 (t, J=4.2 Hz, 1H), 4.48 (d, J=4.2 Hz, 1H), 4.02-3.84 (m, 5H), 3.68 (dt, J=9.3, 6.6 Hz, 1H), 3.62-3.33 (m, 4H), 2.63-2.18 (m, 12H), 1.79-1.60 (m, 4H), 1.49-1.15 (m, 48H), 0.88 (t, J=6.6 Hz, 12H). MS (ESI, m/z): $[M+H]^+$ calcd. For $C_{44}H_{89}N_2O_4$, 709.7; found: 709.9.

Compound DIS-3: yield 37.0%. $^1$H NMR (300 MHz, Chloroform-d) δ 4.60 (t, J=4.2 Hz, 1H), 4.48 (d, J=4.2 Hz, 1H), 4.03-3.87 (m, 5H), 3.75-3.62 (m, 1H), 3.62-3.38 (m, 4H), 2.61-2.40 (m, 4H), 2.40-2.25 (m, 8H), 1.76-1.65 (m, 4H), 1.48-1.15 (m, 64H), 0.88 ((t, J=6.6 Hz, 12H). MS (ESI, m/z): $[M+H]^+$ calcd. For $C_{52}H_{105}N_2O_4$, 821.8; found: 821.9.

Compound MS-4: yield 49.3%. $^1$H NMR (300 MHz, Chloroform-d) δ 4.59 (t, J=4.5 Hz, 1H), 4.48 (d, J=4.2 Hz, 1H), 4.01-3.85 (m, 5H), 3.72-3.65 (m, 1H), 3.62-3.37 (m, 4H), 2.60-2.28 (m, 12H), 1.83-1.55 (m, 4H), 1.48-1.32 (m, 8H), 1.30-1.17 (s, 72H), 0.97-0.74 (m, 12H). MS (ESI, m/z): $[M+H]^+$ calcd. For $C_{60}H_{121}N_2O_4$, 933.9321; found: 933.9320.

Compound DIS-5: yield 33.0%. $^1$H NMR (300 MHz, Chloroform-d) δ 4.60 (t, J=4.2 Hz, 1H), 4.48 (d, J=4.2 Hz, 1H), 4.02-3.85 (m, 5H), 3.72-3.64 (m, 1H), 3.62-3.38 (m, 4H), 2.54-2.25 (m, 12H), 1.79-1.61 (m, 4H), 1.50-1.15 (m, 96H), 0.98-0.81 (m, 12H). MS (ESI, m/z): $[M+H]^+$ calcd. For $C_{68}H_{137}N_2O_4$, 1046.1; found: 1046.0.

Compound DIS-6: yield 19.1%, $^1$H NMR (300 MHz, Chloroform-d) δ 4.59 (t, J=4.2 Hz, 1H), 4.48 (d, J=4.2 Hz, 1H), 4.02-3.85 (m, 5H), 3.72-3.65 (m, 1H), 3.63-3.41 (m, 4H), 2.73-2.30 (m, 12H), 1.84-1.65 (m, 4H), 1.50-1.35 (m, 8H), 1.35-1.17 (m, 104H), 0.92-0.80 (m, 12H). MS (ESI m/z): $[M+H]^+$ calcd. For $C_{76}H_{153}N_2O_4$, 1158.2; found: 1158.2.

Compound DIS-7: yield 45.7%. $^1$H NMR (400 MHz, Chloroform-d) δ 4.81 (ddd, J=12.4, 6.8, 5.6 Hz, 4H), 4.59 (t, J=4.0 Hz, 1H), 4.48 (d, J=4.2 Hz, 1H), 4.02-3.80 (m, 5H), 3.68 (dt, J=9.1, 6.5 Hz, 1H), 3.70-3.63 (m, 1H), 3.52-3.40 (m, 3H), 2.54-2.39 (m, 4H), 2.35 (tt, J=7.2, 3.2 Hz, 8H), 2.28 (t, J=7.6 Hz, 8H), 1.86-1.41 (m, 28H), 1.41-1.05 (m, 64H), 0.94-0.79 (m, 24H). HRMS (ESI, m/z): $[M+H]^+$ calcd. For $C_{80}H_{153}N_2O_{12}$, 1334.1418; found: 1334.1404.

Compound DIS-8: yield 35.0%. $^1$H NMR (300 MHz, Chloroform-d) δ 4.59 (t, J=4.2 Hz, 1H), 4.47 (d, J=4.2 Hz, 1H), 4.11 (t, J=6.9 Hz, 16H), 4.01-3.86 (m, 5H), 3.74-3.62 (m, 1H), 3.60-3.46 (m, 4H), 2.47-2.30 (m, 12H), 1.77-1.61 (m, 20H), 1.43-1.24 (m, 48H), 1.01-0.79 (m, 12H). MS (ESI, m/z): $[M-H]^+$ calcd. For $C_{64}H_{121}N_2O_{16}$, 1173.9; found: 1174.0.

Compound DIS-9: yield 31.0%. $^1$H NMR (300 MHz, Chloroform-d) δ 4.66 (s, 8H), 4.60 (t, J=4.2 Hz, 1H), 4.48 (d, J=4.2 Hz, 1H), 4.01-3.85 (m, 4H), 3.72-3.64 (m, 1H), 3.60-3.38 (m, 20H), 2.60-2.30 (m, 12H), 1.79-1.52 (m, 20H), 1.49-1.22 (m, 48H), 0.95-0.80 (m, 12H). MS (ESI, m/z): $[M+H]^+$ calcd. For $C_{64}H_{129}N_2O_{12}$, 1118.0; found: 1118.1.

Compound DIS-10: yield 54.5%. $^1$H NMR (300 MHz, Chloroform-d) δ 4.65 (d, J=5.2 Hz, 4H), 4.58 (t, J=4.2 Hz, 1H), 4.47 (d, J=4.2 Hz, 1H), 4.02-3.83 (m, 5H), 3.67-3.46 (m, 12H), 3.47-3.30 (m, 9H), 2.53-2.26 (m, 12H), 1.84-1.47 (m, 30H), 1.46-1.14 (m, 50H), 0.86 (d, J=6.9 Hz, 12H). MS (ESI, m/z): $[M+H]^+$ calcd. For $C_{68}H_{137}N_2O_{12}$, 1174.0; found: 1174.2.

Compound DIM-2: yield 54.5%. $^1$H NMR (300 MHz, Chloroform-d) δ 4.59-4.49 (m, 2H), 4.11-3.92 (m, 4H), 3.75-3.61 (m, 4H), 3.51 (dt, J=9.0, 6.6 Hz, 2H), 2.48 (td, J=6.9, 2.1 Hz, 4H), 2.43-2.33 (m, 8H), 1.76 (p, J=6.9 Hz, 4H), 1.50-1.36 (m, 8H), 1.35-1.15 (d, J=2.6 Hz, 40H), 0.89 (t, J=6.9 Hz, 12H). MS (ESI, m/z): $[M+H]^+$ calcd. For $C_{44}H_{89}N_2O_4$, 709.7; found: 709.8.

Compound DIM-3: yield 31.7%. $^1$H NMR (300 MHz, Chloroform-d) δ 4.52 (dd, J=3.0, 1.2 Hz, 2H), 4.07-3.93 (m, 4H), 3.75-3.58 (m, 4H), 3.49 (dt, J=9.0, 6.6 Hz, 2H), 2.46 (td, J=6.9, 1.8 Hz, 4H), 2.41-2.27 (m, 8H), 1.74 (p, J=6.9 Hz, 4H), 1.39 (p, J=6.8, 6.2 Hz, 8H), 1.32-1.15 (m, 56H), 0.87 (t, J=6.6 Hz, 12H). MS (ESI, m/z): $[M+H]^+$ calcd. For $C_{52}H_{105}N_2O_4$, 821.8; found: 821.9.

Compound DIM-4: yield 49.3%. $^1$H NMR (400 MHz, Chloroform-d) δ 4.53 (dt, J=4.4, 2.0 Hz, 2H), 4.08-3.94 (m, 4H), 3.72-3.60 (m, 4H), 3.49 (dt, J=9.2, 6.8 Hz, 2H), 2.60-2.46 (m, 4H), 2.47-2.30 (m, 8H), 1.76 (p, J=7.0 Hz, 4H), 1.49-1.35 (m, 8H), 1.31-1.20 (m, 72H), 0.88 (t, J=6.8 Hz, 12H). HRMS (ESI, m/z): $[M+H]^+$ calcd. For $C_{60}H_{121}N_2O_4$, 933.9321; found: 933.9321.

Compound DIM-5: yield 22.0%, $^1$H NMR (300 MHz, Chloroform-d) δ 4.52 (d, J=3.0 Hz, 2H), 4.09-3.93 (m, 4H), 3.75-3.59 (m, 4H), 3.49 (dt, J=9.0, 6.6 Hz, 2H), 2.46 (td, J=6.9, 1.8 Hz, 4H), 2.41-2.27 (m, 8H), 1.74 (p, J=6.9 Hz, 4H), 1.50-1.15 (m, 96H), 0.88 (t, J=6.6 Hz, 12H). MS (ESI, m/z): $[M+H]^+$ calcd. For $C_{68}H_{137}N_2O_4$, $11137N_2O_4$, 1046.1; found: 1046.0.

Compound DIM-6: yield 37.3%, $^1$H NMR (300 MHz, Chloroform-d) δ 4.55 (dd, J=3.3, 1.5 Hz, 2H), 4.10-3.93 (m, 4H), 3.74-3.58 (m, 4H), 3.49 (dt, J=9.0, 6.6 Hz, 2H), 2.46 (td, J=6.9, 1.8 Hz, 4H), 2.35 (dd, J=8.5, 6.3 Hz, 8H), 1.74 (p, J=6.9 Hz, 4H), 1.45-1.15 (m, 112H), 0.88 (t, J=6.6 Hz, 12H). MS (ESI, m/z): $[M+H]^+$ calcd. For $C_{76}H_{153}N_2O_4$, 1158.2; found: 1158.0.

Compound DIM-7: yield 36.0%. $^1$H NMR (400 MHz, Chloroform-d) δ 4.81 (p, J=6.4 Hz, 4H), 4.53 (d, J=2.8 Hz, 2H), 4.08-3.94 (m, 4H), 3.75-3.60 (m, 4H), 3.48 (dt, J=9.0, 6.6 Hz, 2H), 2.51 (t, J=7.2 Hz, 4H), 2.39 (t, 7.6 Hz, 8H), 2.27

(t, J=7.6 Hz, 8H), 1.76 (p, J=6.8 Hz, 4H), 1.66-1.46 (m, 24H), 1.45-1.35 (m, 8H), 1.33-1.19 (m, 56H), 0.91-0.82 (m, 24H).

Compound DIM-8: yield 32.5%. $^1$H NMR (300 MHz, Chloroform-d) δ 4.52 (d, J=3.0 Hz, 2H), 4.11 (t, J=6.6 Hz, 15H), 4.04-3.91 (m, 4H), 3.74-3.57 (m, 4H), 3.54-3.40 (m, 2H), 2.45 (t, J=7.2 Hz, 4H), 2.35 (t, J=7.2 Hz, 8H), 1.80-1.60 (m, 20H), 1.46-1.19 (m, 48H), 0.88 (t, J=6.6 Hz, 12H). MS (ESI, m/z): $[M+H]^+$ calcd. For $C_{64}H_{121}N_2O_{16}$, 1173.9; found: 1174.0.

Compound DIM-9: yield 26.2%. $^1$H NMR (400 MHz, Chloroform-d) δ 4.65 (s, 8H), 4.52 (d, J=3.6 Hz, 2H), 4.10-3.90 (m, 4H), 3.69-3.61 (m, 4H), 3.53-3.45 (m, 18H), 2.55-2.30 (m, 12H), 1.80-1.65 (m, 4H), 1.56 (p, J=6.8 Hz, 16H), 1.49-1.14 (m, 48H), 0.88 (t, J=6.8 Hz, 12H). MS (ESI, m/z): $[M+H]^+$ calcd. For $C_{64}H_{129}N_2O_4$, 1118.0; found: 1118.2.

Compound DIM-10: yield 29.4%. $^1$H NMR (300 MHz, Chloroform-d) δ 4.64 (q, J=5.4 Hz, 4H), 4.51 (d, J=3.0 Hz, 2H), 4.10-3.90 (m, 4H), 3.73-3.25 (m, 22H), 2.44 (t, J=7.2 Hz, 4H), 2.35 (t, J=7.2 Hz, 8H), 1.80-1.65 (m, 4H), 1.54 (p, J=6.9 Hz, 16H), 1.45-1.20 (m, 60H), 0.87 (t, J=6.6 Hz, 12H). MS (EST, m/z): calcd. For $C_{68}H_{137}N_2O_4$, 1174.0; found: 1174.3.

Compound LIS-2: yield 31.0%. $^1$H NMR (400 MHz, Chloroform-d), δ 4.60 (t, J=4.4 Hz, 1H), 4.48 (d, J=4.4 Hz, 1H), 4.01-3.88 (m, 5H), 3.68 (dt, J=9.2, 6.8 Hz, 11H), 3.57 (t, J=8.0 Hz, 1H), 3.53-3.45 (m, 3H), 2.55-2.32 (m, 12H), 1.81-1.65 (m, 4H), 1.45-1.35 (m, 8H), 1.33-1.20 (s. 40H), 0.87 (t, J=6.8 Hz, 12H). MS (ESI, m/z): $[M+H]^+$ calcd. For $C_{44}H_{89}N_2O_4$, 709.7; found: 709.8.

Compound LIS-3: yield 29.2%. $^1$H NMR (400 MHz, Chloroform-d), δ 4.60 (t, J=4.4 Hz, 1H), 4.48 (d, J=4.0 Hz, 1H), 4.03-3.86 (m, 5H), 3.69 (dt, J=9.4, 6.4 Hz, 1H), 3.62-3.45 (m, 4H), 2.77-2.20 (m, 12H), 1.85-1.69 (m, 4H), 1.52-1.36 (m, 8H), 1.35-1.15 (s, 56H), 0.88 (t, J=6.4 Hz, 12H). MS (ESI, m/z): calcd. For $C_{52}H_{105}N_2O_4$, 821.8; found: 822.0.

Compound LIS-4: yield 30.3%. $^1$H NMR (300 MHz, Chloroform-d) δ 4.60 (t, J=4.2 Hz, 1H), 4.48 (d, J=4.2 Hz, 1H), 4.00-3.85 (m, 5H), 3.68 (dt, J=9.0, 6.3 Hz, 1H), 3.63-3.43 (m, 4H), 2.55-2.30 (m, 12H), 1.80-1.64 (m, 4H), 1.50-1.15 (m, 80H), 0.87 (t, J=6.6 Hz, 12H). MS (ESI, m/z): $[M+H]^+$ calcd. For $C_{60}H_{121}N_2O_4$, 933.9; found: 934.2.

Compound LIS-5: yield 30.6%. $^1$H NMR (300 MHz, Chloroform-d) δ 4.63 (t, J=4.2 Hz, 1H), 4.51 (d, J=4.2 Hz, 1H), 4.14-3.85 (m, 5H), 3.80-3.65 (m, 11H), 3.64-3.45 (m, 4H), 2.70-2.30 (m, 12H), 1.89-1.62 (m, 4H), 1.55-1.40 (m, 8H), 1.40-1.15 (m, 88H), 0.90 (d, J=6.3 Hz, 12H), MS (ESI, m/z): $[M+H]^+$ calcd. For $C_{68}H_{137}N_2O_4$, 1046.1; found: 1046.3.

Compound LIS-6: yield 29.4%. $^1$H NMR (400 MHz, Chloroform-d) δ 4.60 (t, J=4.4 Hz, 1H), 4.48 (d, J=4.4 Hz, 1H), 4.07-3.83 (m, 5H), 3.75-3.65 (m, 1H), 3.62-3.43 (m, 4H), 2.88-2.12 (m, 12H), 1.85-1.65 (m, 4H), 1.55-1.15 (m, 112H), 0.88 (t, J=6.8 Hz, 12H).

Compound LIS-7: yield 20.2%. $^1$H NMR (400 MHz, Chloroform-d) δ 4.80 (p, J=6.4 Hz, 4H), 4.59 (t, J=4.4 Hz, 1H), 4.47 (d, J=4.4 Hz, 1H), 4.08-3.82 (m, 5H), 3.75-3.65 (m, 1H), 3.61-3.42 (m, 4H), 2.58-2.30 (m, 12H), 2.27 (t, J=7.6 Hz, 8H) 1.77-1.48 (m, 28H), 1.42-1.18 (m, 64H), 0.92-0.82 (m, 24H). MS (ESI, m/z): $[M+H]^{2+}$ calcd. For $C_{80}H_{154}N_2O_{12}$, 667.6; found: 668.0.

Compound LIS-8: yield 25.6%. $^1$H NMR (400 MHz, Chloroform-d) δ 4.61 (d, J=4.4 Hz, 1H), 4.50 (d, J=4.4 Hz, 1H), 4.13 (t, J=6.8 Hz, 16H), 4.02-3.90 (m, 5H), 3.75-3.65 (m, 1H), 3.60-3.45 (m, 4H), 2.65-2.28 (m, 12H), 1.80-1.60 (m, 20H), 1.55-1.20 (m, 48H), 0.91 (d, J=6.4 Hz, 12H). MS (ESI, m/z): $[M+H]^+$ calcd. For $C_{64}H_{121}N_2O_{16}$, 1173.9; found: 1174.0.

Compound LIS-9: yield 26.4%. $^1$H NMR (400 MHz, Chloroform-d) δ 4.66 (s, 8H), 4.59 (t, J=4.0 Hz, 1H), 4.46 (d, J=4.0 Hz, 1H), 4.03-3.83 (m, 4H), 3.76-3.63 (m, 1H), 3.60-3.45 (m, 20H), 2.60-2.25 (m, 12H), 1.79-1.22 (m, 68H), 0.89-6.8 Hz, 12H). MS (ESI, m/z): $[M+H]^+$ calcd. For $C_{64}H_{129}N_2O_{12}$, 1118.0; found: 1118.0.

Compound LIS-10: yield 25.9%. $^1$H NMR (400 MHz, Chloroform-d) δ 4.65 (q, J=5.2 Hz, 4H), 4.59 (t, J=4.4 Hz, 1H), 4.47 (d, J=4.4 Hz, 1H), 4.03-3.84 (m, 5H), 3.67 (dt, J=9.2, 6.4 Hz, 1H), 3.61-3.30 (m, 20H), 2.62-2.28 (m, 12H), 1.80-1.63 (m, 6H), 1.60-1.50 (m, 16H), 1.49-1.18 (m, 58H), 0.88 (t, J=6.8 Hz, 12H). MS (ESI, m/z): $[M+H]^+$ calcd. For $C_{68}H_{137}N_2O_{12}$, 1174.0; found: 1174.1.

REFERENCES

1 Hong, J., Radojcic, D., Ionescu, M., Petrovic, Z. S., Eastwood, E. Advanced Materials from Corn: Isosorbide-Based Epoxy Resins. *Polym. Chem.* 5, 5360-5368 (2014).

2 Wroblewska, A., Zych, A., Thiyagarajan, S., Dudenko, D., van Es, :D., Hansen, M. R., Koning, C., Duchateau, R., Jasinska-Walc, L. Towards Sugar-Derived Polyamides as Environmentally Friendly Materials. *Polym. Chem.* 6, 4133-4143 (2015), Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A compound having Formula I, II, or III:

Formula I

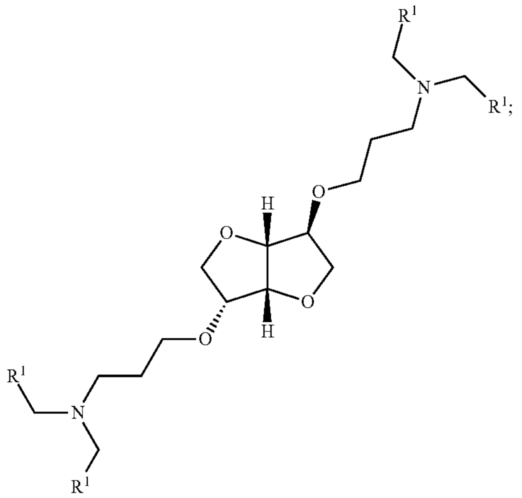

-continued

Formula II

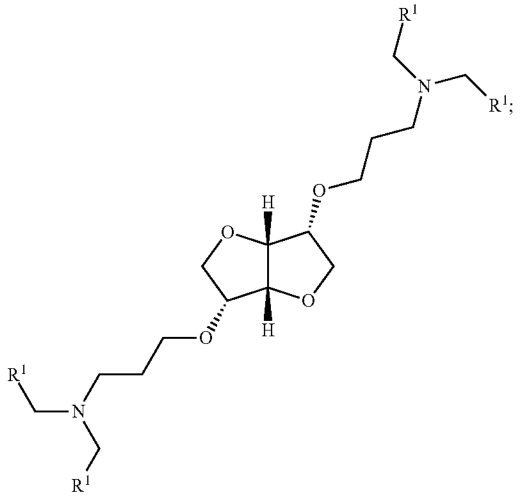

2. The compound of claim 1, wherein the compound has the formula:

Formula I

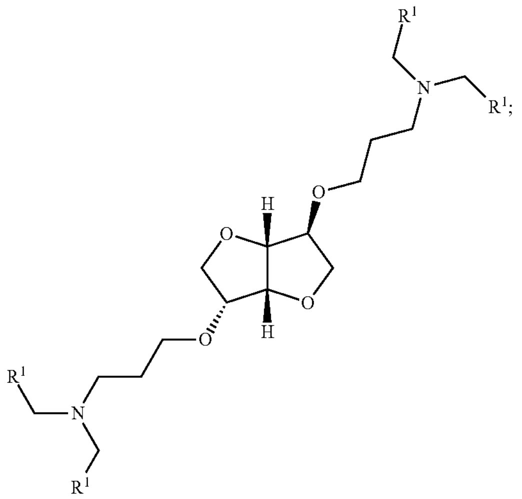

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

3. The compound of claim 1, wherein the compound has the formula:

Formula III

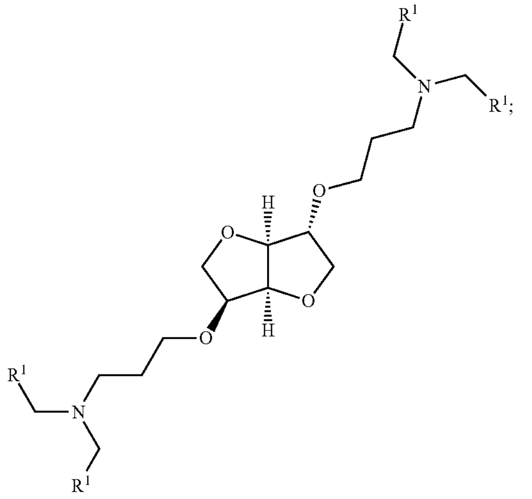

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

Formula II

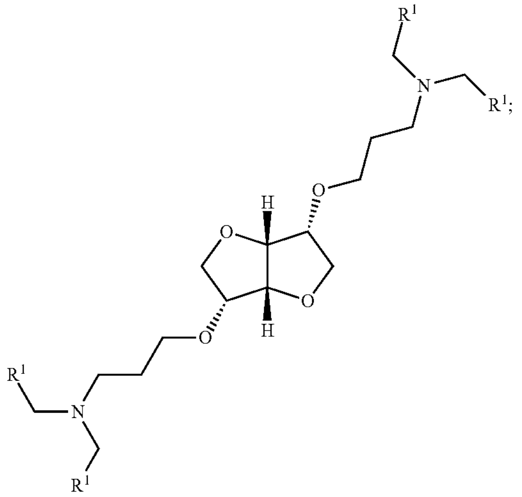

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

4. The compound of claim 1, wherein the compound has the formula:

Formula III

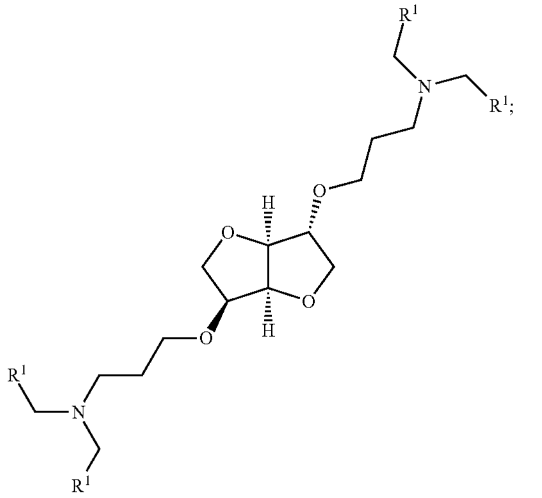

or a salt thereof, wherein:

$R^1$ is independently selected from alkyl, alkenyl, alkynyl, hydroxyl, ester, ether, carbonate, alkylalcohol, alkylether, alkylester, carbamate, urea, guanidine, disulfide, amide, acetal, ketal, thioketal, trisulfide, and oxime ether.

5. The compound of claim 1, wherein $R^1$ is selected from the following:

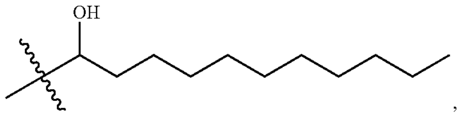
,
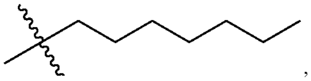
,
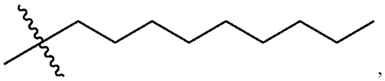
,
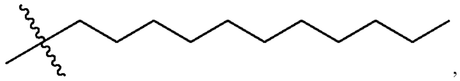
,
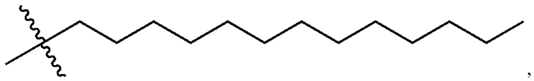
,
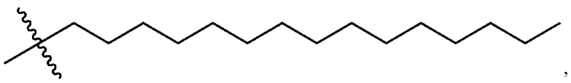
,
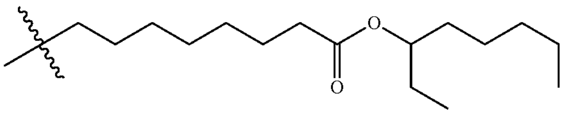
,
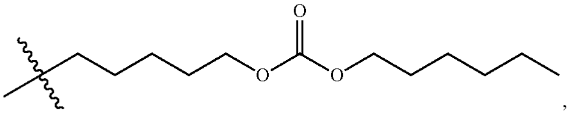
, -continued

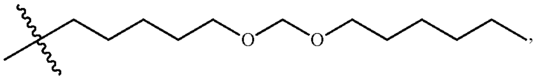
, and

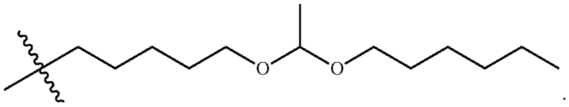
.

6. The compound of claim 5, wherein $R^1$ is

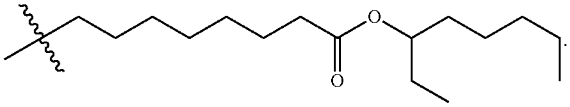 [SMILES: *CCCCCCCC(=O)OC(CC)CCCCC]
.

7. The compound of claim 5, wherein $R^1$ is

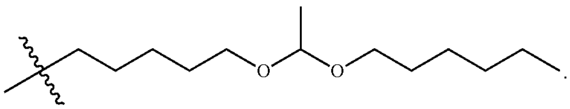 [SMILES: *CCCCCOC(C)OCCCCCC]
.

8. The compound of claim 1, wherein the compound is

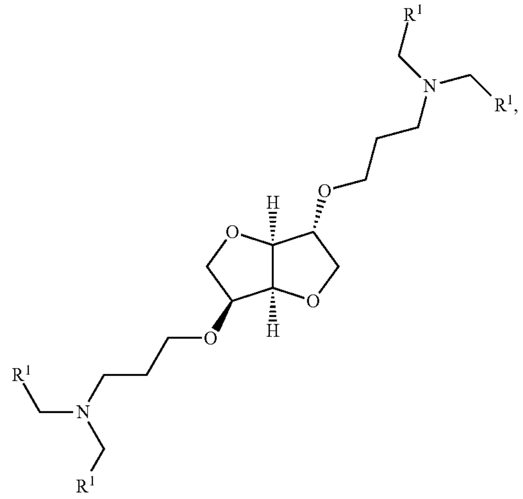

wherein $R^1$ is

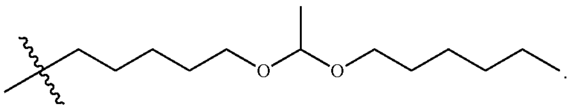 [SMILES: *CCCCCOC(C)OCCCCCC]
.

9. The compound of claim 1, wherein the compound is
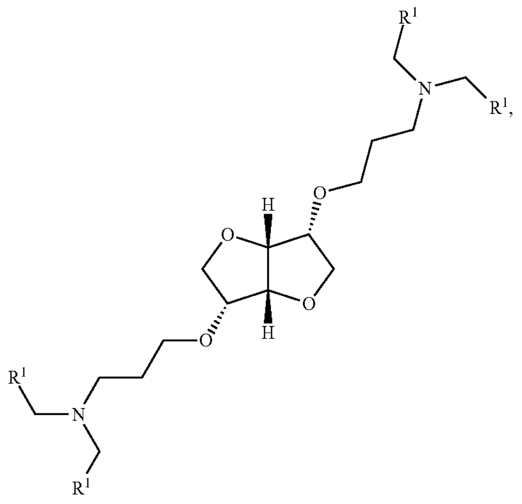
wherein $R^1$ is
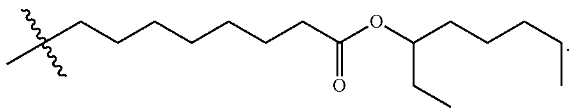 [SMILES: *CCCCCCCC(=O)OC(CC)CCCCC]
* * * * *